United States Patent
Valamehr et al.

(10) Patent No.: US 10,947,505 B2
(45) Date of Patent: Mar. 16, 2021

(54) METHODS AND COMPOSITIONS FOR INDUCING HEMATOPOIETIC CELL DIFFERENTIATION

(71) Applicant: FATE THERAPEUTICS, INC., San Diego, CA (US)

(72) Inventors: Bahram Valamehr, San Diego, CA (US); Raedun Clarke, San Diego, CA (US); Ryan Bjordahl, San Diego, CA (US)

(73) Assignee: Fate Therapeutics, Inc., San Diego, CA (US)

( * ) Notice: Subject to any disclaimer, the term of this patent is extended or adjusted under 35 U.S.C. 154(b) by 0 days.

(21) Appl. No.: 17/062,478

(22) Filed: Oct. 2, 2020

(65) Prior Publication Data

US 2021/0024891 A1 Jan. 28, 2021

Related U.S. Application Data

(60) Division of application No. 15/773,519, filed as application No. PCT/US2016/044122 on Jul. 26, 2016, which is a continuation-in-part of application No. PCT/US2016/014918, filed on Jan. 26, 2016.

(60) Provisional application No. 62/337,093, filed on May 16, 2016, provisional application No. 62/251,016, filed on Nov. 4, 2015.

(51) Int. Cl.
| | |
|---|---|
| *C12N 5/0789* | (2010.01) |
| *G01N 33/50* | (2006.01) |
| *A61K 39/00* | (2006.01) |
| *A61K 35/28* | (2015.01) |
| *A61K 35/545* | (2015.01) |

(52) U.S. Cl.
CPC .......... *C12N 5/0647* (2013.01); *A61K 35/28* (2013.01); *A61K 39/0011* (2013.01); *G01N 33/5073* (2013.01); *A61K 35/545* (2013.01); *A61K 2039/5158* (2013.01); *C12N 2501/115* (2013.01); *C12N 2501/125* (2013.01); *C12N 2501/14* (2013.01); *C12N 2501/145* (2013.01); *C12N 2501/155* (2013.01); *C12N 2501/165* (2013.01); *C12N 2501/22* (2013.01); *C12N 2501/2302* (2013.01); *C12N 2501/2303* (2013.01); *C12N 2501/235* (2013.01); *C12N 2501/2306* (2013.01); *C12N 2501/2311* (2013.01); *C12N 2501/415* (2013.01); *C12N 2501/727* (2013.01); *C12N 2501/999* (2013.01); *C12N 2506/45* (2013.01); *C12N 2510/00* (2013.01); *C12N 2533/90* (2013.01); *Y02A 50/30* (2018.01)

(58) Field of Classification Search
CPC .................................................. C12N 5/0647
See application file for complete search history.

(56) References Cited

U.S. PATENT DOCUMENTS

| | | |
|---|---|---|
| 5,780,300 A | 7/1998 | Artavanis-Tsakonas et al. |
| 5,858,358 A | 1/1999 | June et al. |
| 5,883,223 A | 3/1999 | Gray |
| 5,942,435 A | 8/1999 | Wheeler |
| 6,140,081 A | 10/2000 | Barbas |
| 6,352,694 B1 | 3/2002 | June et al. |
| 6,453,242 B1 | 9/2002 | Eisenberg et al. |
| 6,534,055 B1 | 3/2003 | June et al. |
| 6,534,261 B1 | 3/2003 | Cox et al. |
| 6,534,476 B2 | 3/2003 | Miyazono et al. |
| 6,689,744 B2 | 2/2004 | Gao et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |

(Continued)

FOREIGN PATENT DOCUMENTS

| | | |
|---|---|---|
| EP | 1992360 A1 | 11/2008 |
| EP | 2606884 A1 | 6/2013 |

(Continued)

OTHER PUBLICATIONS

Ameri et al., "FGF2 specifies hESC-derived definitive endoderm into foregut/midgut cell lineages in a concentration-dependent manner," *Stem Cells*, 28(1):45-56 (2010).
Ansari et al., "The programmed death-1 (PD-1) pathway regulates autoimmune diabetes in nonobese diabetic (NOD) mice," *J. Exp. Med.*, 198(1):63-69 (2003).
Beilhack et al., "Purified allogeneic hematopoietic stem cell transplantation blocks diabetes pathogenesis in NOD mice," *Diabetes*, 52:59-68 (2003).
Birch et al., "Suspension culture of mammalian cells," Bioprocess Technol., 10:251-270 (1990).
Brentjens et al., "Genetically targeted T cells eradicate systemic acute lymphoblastic leukemia xenografts," Clin. Cancer Res., 13(18Pt 1):5426-5435 (2007).

(Continued)

*Primary Examiner* — Scott Long

(74) *Attorney, Agent, or Firm* — Mintz Levin Cohn Ferris Glovsky and Popeo, P.C.

(57) ABSTRACT

The invention provides culture platforms, cell media, and methods of differentiating pluripotent cells into hematopoietic cells. The invention further provides pluripotent stem cell-derived hematopoietic cells generated using the culture platforms and methods disclosed herein, which enable feed-free, monolayer culturing and in the absence of EB formation. Specifically, pluripotent stem cell-derived hematopoietic cell of this invention include, and not limited to, iHSC, definitive hemogenic endothelium, hematopoietic multipotent progenitors, T cell progenitors, NK cell progenitors, T cells, NK cells, NKT cells and B cells.

20 Claims, 61 Drawing Sheets

(56) References Cited

U.S. PATENT DOCUMENTS

| | | | |
|---|---|---|---|
| 7,888,121 | B2 | 2/2011 | Urnov et al. |
| 7,972,854 | B2 | 7/2011 | Miller et al. |
| 8,044,201 | B2 | 10/2011 | Xu et al. |
| 8,168,428 | B2 | 5/2012 | Zon et al. |
| 8,389,282 | B2 | 3/2013 | Sadelain et al. |
| 8,652,845 | B2 | 2/2014 | Niwa et al. |
| 9,220,728 | B2 | 12/2015 | Sadelain et al. |
| 9,382,531 | B2 * | 7/2016 | Slukvin .................. C12N 15/00 |
| 9,452,186 | B2 | 9/2016 | Shoemaker et al. |
| 9,889,160 | B2 | 2/2018 | Jantz et al. |
| 10,287,606 | B2 | 5/2019 | Valamehr et al. |
| 10,464,989 | B2 | 11/2019 | Walcheck et al. |
| 10,626,372 | B1 | 4/2020 | Valamehr et al. |
| 10,858,628 | B2 | 12/2020 | Valamehr et al. |
| 2004/0067583 | A1 | 4/2004 | Bernstein et al. |
| 2004/0101519 | A1 | 5/2004 | June et al. |
| 2004/0171148 | A1 | 9/2004 | Schmitt et al. |
| 2005/0119203 | A1 | 6/2005 | Steinbrecher et al. |
| 2006/0034810 | A1 | 2/2006 | Riley et al. |
| 2006/0121005 | A1 | 6/2006 | Berenson et al. |
| 2011/0027235 | A1 | 2/2011 | Gregory et al. |
| 2011/0027886 | A1 | 2/2011 | Han et al. |
| 2011/0145940 | A1 | 6/2011 | Voytas et al. |
| 2012/0009676 | A1 | 1/2012 | Mack |
| 2012/0039911 | A1 | 2/2012 | Park et al. |
| 2012/0129211 | A1 | 5/2012 | Kattman et al. |
| 2012/0202291 | A1 | 8/2012 | Chen et al. |
| 2012/0264218 | A1 | 10/2012 | Lin et al. |
| 2013/0071414 | A1 | 3/2013 | Dotti et al. |
| 2013/0078226 | A1 | 3/2013 | Nakauchi et al. |
| 2013/0280222 | A1 | 10/2013 | Kay et al. |
| 2014/0155468 | A1 | 6/2014 | Gregory et al. |
| 2014/0171148 | A1 | 9/2014 | Hillbrink et al. |
| 2014/0273211 | A1 | 9/2014 | Slukvin et al. |
| 2014/0349402 | A1 | 11/2014 | Cooper et al. |
| 2014/0369973 | A1 | 12/2014 | Bernstein et al. |
| 2015/0140665 | A1 | 5/2015 | Calos et al. |
| 2015/0174169 | A1 | 6/2015 | Genovese et al. |
| 2015/0342993 | A1 | 12/2015 | Kloss et al. |
| 2015/0376296 | A1 | 12/2015 | Fedorov et al. |
| 2016/0009813 | A1 | 1/2016 | Themeli et al. |
| 2017/0020922 | A1 | 1/2017 | Wagner et al. |
| 2017/0073643 | A1 | 3/2017 | Valamehr et al. |
| 2018/0008640 | A1 * | 1/2018 | Feng .................. A61P 33/06 |
| 2018/0072992 | A1 | 3/2018 | Valamehr et al. |
| 2018/0112180 | A1 | 4/2018 | Robbins et al. |
| 2018/0155717 | A1 | 6/2018 | Valamehr et al. |
| 2018/0320137 | A1 * | 11/2018 | Valamehr .................. A61P 7/00 |
| 2019/0071636 | A1 * | 3/2019 | Eto .................. A61P 7/08 |
| 2019/0119638 | A1 | 4/2019 | Sadelain et al. |
| 2019/0271005 | A1 | 9/2019 | Valamehr et al. |
| 2020/0095604 | A1 | 3/2020 | Valamehr et al. |
| 2020/0248142 | A1 | 8/2020 | Valamehr et al. |

FOREIGN PATENT DOCUMENTS

| | | |
|---|---|---|
| EP | 2853590 A1 | 4/2015 |
| EP | 2853590 B1 | 4/2015 |
| WO | WO 1998/53058 A1 | 11/1998 |
| WO | WO 1998/53059 A1 | 11/1998 |
| WO | WO 1998/53060 A1 | 11/1998 |
| WO | WO 1999/001426 A1 | 1/1999 |
| WO | WO 2002/006213 A2 | 1/2002 |
| WO | WO 2002/016536 A1 | 2/2002 |
| WO | WO 2003/016496 A2 | 2/2003 |
| WO | WO 2003/077914 A1 | 9/2003 |
| WO | WO 2005/051301 A2 | 6/2005 |
| WO | WO 2005/117994 A2 | 12/2005 |
| WO | WO 2007/044084 A2 | 4/2007 |
| WO | WO 2008/006583 A1 | 1/2008 |
| WO | WO 2008/094597 A2 | 8/2008 |
| WO | WO 2009/091826 A2 | 7/2009 |
| WO | WO 2009/091826 A3 | 7/2009 |
| WO | WO 2009/091826 A9 | 7/2009 |
| WO | WO 2009/097140 A1 | 8/2009 |
| WO | WO 2010/096746 A1 | 8/2010 |
| WO | WO 2010/099539 A1 | 9/2010 |
| WO | WO 2011/096482 A1 | 8/2011 |
| WO | WO 2011/115308 A1 | 9/2011 |
| WO | WO 2011/159726 A2 | 12/2011 |
| WO | WO 2012/012667 A2 | 1/2012 |
| WO | WO 2012/021845 A2 | 2/2012 |
| WO | WO 2012/087965 A2 | 6/2012 |
| WO | WO 2013/009825 A1 | 1/2013 |
| WO | WO 2013/074916 A1 | 5/2013 |
| WO | WO 2013/075222 A1 | 5/2013 |
| WO | WO 2013/086029 A1 | 6/2013 |
| WO | WO 2013/126794 A1 | 8/2013 |
| WO | WO 2013/158292 A1 | 10/2013 |
| WO | WO 2013/163171 A1 | 10/2013 |
| WO | WO 2013/176197 A1 | 11/2013 |
| WO | WO 2013/176916 A1 | 11/2013 |
| WO | WO 2014/011540 A1 | 1/2014 |
| WO | WO 2014/062138 A1 | 4/2014 |
| WO | WO 2014/152603 A1 | 9/2014 |
| WO | WO 2014/165131 A1 | 10/2014 |
| WO | WO 2014/165825 A2 | 10/2014 |
| WO | WO 2014/165825 A3 | 10/2014 |
| WO | WO 2016/123100 A1 | 8/2016 |
| WO | WO 2016/123117 A1 | 8/2016 |
| WO | WO 2017/079673 A1 | 5/2017 |
| WO | WO 2017/180989 A2 | 10/2017 |

OTHER PUBLICATIONS

Brentjens et al., "Treatment of chronic lymphocytic leukemia with genetically targeted autologous T cells: case report of an unforeseen adverse event in a phase I clinical trial," Mol. Ther., 18(4):666-668 (2010).

Brevini et al., "No shortcuts to pig embryonic stem cells," *Theriogenology*, 74(4):544-550 (2010).

Brown et al., "Derivation of induced pluripotent stem cells from human peripheral blood T lymphocytes," PLoSOne, 5(6):e11373 (2010).

Bykovskaia, S.N. et al. (Oct. 1999). "The generation of human dendritic and NK cells from hemopoietic progenitors induced by interleukin-15," J Leukoc Biol 66(4):659-666.

Chang et al., "Transforming growth factor-beta signaling in breast cancer", Frontiers in Bioscience, 12: 4393-4401 (2007).

Chen, W. et al. (Jun. 2014). "Generation of the SCN1A epilepsy mutation in hiPS cells using the TALEN technique," Scientific Reports 4:5404, pp. 1-7.

Chiang et al., "Differentiation of an embryonic stem cell to hemogenic endothelium by defined factors: essential role of bone morphogenetic protein 4," Development, 138(13):2833-2843 (2011).

Choi et al., "Identification of the hemogenic endothelial progenitor and its direct precursor in human pluripotent stem cell differentiation cultures," Cell Rep., 2(3):553-567 (2012).

Cui et al., "Selective inhibition of TGF-β responsive genes by Smad-interacting peptide aptamers from FoxH1, Lef1 and CBP", Oncogene, 24: 3864-3874 (2005).

Dacosta et al., "SB-505124 is a selective inhibitor of transforming growth factor-beta type I receptors ALK4, ALK5, and ALK7," Mol. Pharmacol., 65(3):744-752 (2004).

D'Addio et al., "Autologous nonmyeloablative hematopoietic stem cell transplantation in new-onset type 1 diabetes: a multicenter analysis," *Diabetes*, 63:3041-3046 (2014).

De Gouville and Huet, "Inhibition of ALK5 as a new approach to treat liver fibrotic diseases", Drug News Perspective, 19(2): 85-90 (2006).

Dravid, G. (Nov.-Dec. 2005, e-published Jul. 7, 2005). "Defining the role of Wnt/β-catenin signaling in the survival, proliferation, and self-renewal of human embryonic stem cells," Stem Cells 23(10):1489-1501.

Ducy, P. et al. (Jun. 2000). "The family of bone morphogenetic proteins," Kidney Int 57(6):2207-2214.

Eiselleova et al., "A complex role for FGF-2 in self-renewal, survival, and adhesion of human embryonic stem cells," *Stem Cells*, 27(8):1847-1857 (2009).

(56) References Cited

OTHER PUBLICATIONS

Eyquem, J. et al. (Mar. 2, 2017, e-published Feb. 22, 2017). "Targeting a CAR to the TRAC locus with CRISPR/Cas9 enhances tumour rejection," Nature 543(7643):113-117.
Figueiredo et al., "Class-, gene-, and group-specific HLA silencing by lentiviral shRNA delivery," J. Mol. Med., 84(5):425-437 (2006).
Fiorina et al., "Targeting the CXCR4-CXCL12 axis mobilizes autologous hematopoietic stem cells and prolongs islet allograft survival via programmed death ligand 1,"*J. Immunol.*, 186:121-131 (2011).
French et al., "Human induced pluripotent stem cell-derived B lymphocytes express sIgM and can be generated via a hemogenic endothelium intermediate," Stem Cells and Development, 24(9):1082-1095 (2015).
Gellibert et al., "Discovery of 4-{4-[3-(Pyridin-2-yl)-1H-pyrazol-4-yl]pyridin-2-yl}-N-(tetrahydro-2H- pyran-4-yl)benzamide (GW788388): A Potent, Selective, and Orally Active Transforming Growth Factor-β Type I Receptor Inhibitor", Journal Medicinal Chemistry, 49(7): 2210-2221 (2006).
Gong et al., "Cancer patient T cells genetically targeted to prostate-specific membrane antigen specifically lyse prostate cancer cells and release cytokines in response to prostate-specific membrane antigen," Neoplasia, 1(2):123-127 (1999).
Hoffman, L.M. et al. (Jun. 2005). "Characterization and culture of human embryonic stem cells," Nat Biotechnol 23(6):699-708.
Hoggatt et al., "Prostaglandin E2 enhances hematopoietic stem cell homing, survival, and proliferation," *Blood*, 113(22):5444-5455 (2009).
Hu et al., "Large-scale mammalian cell culture," Curr. Opin. Biotechnol., 8(2):148-153 (1997).
Huang et al., "Pivotal role for glycogen synthase kinase-3 in hematopoietic stem cell homeostasis in mice," J. Clin. Invest., 119(12):3519-3529 (2009).
Inman et al., "SB-431542 is a potent and specific inhibitor of transforming growth factor-β Superfamily Type I Activin Receptor-Like Kinase (ALK) Receptors ALK4, ALK5, and ALK7", Molecular Pharmacology, 62(1): 65-74 (2002).
Joo et al., "Rock suppression promotes differentiation and expansion of endothelial cells from embryonic stem cell-derived Flk1(+) mesodermal precursor cells," Blood, 120(13):2733-2744 (2012).
Kaminska, et al., "TGF beta signalling and its role in tumour pathogenesis", Acta Biochimica Polonica, 52(2): 329-337 (2005).
Kennedy et al., "T lymphocyte potential marks the emergence of definitive hematopoietic progenitors in human pluripotent stem cell differentiation cultures," Cell Rep., 2(6):1722-1735 (2012).
Kim, et al., "Pharmacokinetics and tissue distribution of 3-((5-(6-methylpyridin-2-yl)-4-(quinoxalin-6-yl)-1H-imidazol-2-yl)methyl)benzamide; a novel ALK5 inhibitor and a potential anti-fibrosis drug", Xenobiotica, 38(3): 325-339 (2008).
Kitano, "Serum-free media," in Animal Cell Bioreactors, eds. Ho and Wang, Butterworth-Heinemann, Stoneham, MA, Chapter 4, pp. 73-106 (1991).
Knorr et al., "Clinical-scale derivation of natural killer cells from human pluripotent stem cells for cancer therapy," Stem Cells Transl. Med., 2(4):274-283 (2013).
Knorr et al., "Engineering Human Pluripotent Stem Cells for Enhanced Lymphocyte Development and Function a Dissertation Submitted to the Faculty of the Graduate School of the University of Minnesota by," Oct. 2012, Retrieved from the Internet: URL:http://conservancy.umn.edu/bitstream/handle/11299/142741/Knorr_umn_0130E_13251.pdf? segue nce=1&isAllowed=y [retrieved on Oct. 5, 2015].
Knorr et al., "Pluripotent stem cell-derived natural killer cells for cancer therapy," Transl. Res., 156(3):147-154 (2010).
Krawetz et al., "Inhibition of Rho kinase regulates specification of early differentiation events in P19 embryonal carcinoma stem cell," PLoS One, 6(11):e26484 (2011).
Kumar, D. et al. (Mar. 26, 2015,). "Induced Pluripotent Stem Cells: Mechanisms, Achievements and Perspectives in Farm Animals," World J Stem Cells 7(2):315-328.

Li, W. et al. (Dec. 2009). "Generation of human-induced pluripotent stem cells in the absence of exogenous Sox2," Stem Cells 27(12):2992-3000.
Lian et al., "Efficient differentiation of human pluripotent stem cells to endothelial progenitors via small-molecule activation of WNT signaling," Stem Cell Reports, 3(5):804-816 (2014).
Lu, Y. et al. (Aug. 2012). "Livestock Induced Pluripotent Stem Cells," Reprod Domest Anim 47(Suppl 4):72-76.
Macleod, D.T. et al. (Apr. 5, 2017, e-published Feb. 23, 2017). "Integration of a CD19 CAR into the TCR Alpha Chain Locus Streamlines Production of Allogeneic Gene-Edited CAR T Cells," Mol Ther 25(4):949-961.
Maher et al., "Human T-lymphocyte cytotoxicity and proliferation directed by a single chimeric TCRzeta /CD28 receptor," Nat. Biotechnol., 20(1):70-75 (2002).
Meijer, L. et al. (Sep. 2004). "Pharmacological inhibitors of glycogen synthase kinase 3," Trends Pharmacol Sci 25(9):471-480.
Menon et al., "Lymphoid regeneration from gene-corrected SCID-X1 subject-derived iPSCs," Cell Stem Cell, 16(4):367-372 (2015).
Mikels, A.J. et al. (Dec. 4, 2006). "Wnts as ligands: processing, secretion and reception," Oncogene 25(57):7461-7468.
Munoz et al., "Constraints to progress in embryonic stem cells from domestic species," Stem Cell Rev. Rep., 5:6-9 (2009).
Munoz et al., "Conventional pluripotency markers are unspecific for bovine embryonic-derived cell-lines," *Theriogenology*, 69(9):1159-1164 (2008).
Nazareth, E.J. et al. (Dec. 2010, e-published Oct. 20, 2013). "High-throughput fingerprinting of human pluripotent stem cell fate responses and lineage bias," Nat Methods 10(12):1225-1231.
Ninomiya, H. et al. (Jan. 2015, e-published Aug. 15, 2014). "Improved efficiency of definitive endoderm induction from human induced pluripotent stem cells in feeder and serum-free culture system," In Vitro Cell Dev Biol Anim 51(1):1-8.
Nishimura et al., "Generation of rejuvenated antigen-specific T cells by reprogramming to pluripotency and redifferentiation," Cell Stem Cell, 12(1):114-126 (2013).
Ogorevc, J. et al. (Feb. 19, 2016). "Cellular reprogramming in farm animals: an overview of iPSC generation in the mammalian farm animal species," J Anim Sci Biotechnol 7:10.
Ozkaynak et al., "Programmed death-1 targeting can promote allograft survival," *J. Immunol.*, 169:6546-6553 (2002).
Papapetrou et al., "Genomic safe harbors permit high β-globin transgene expression in thalassemia induced pluripotent stem cells," Nat. Biotechnol., 29(1):73-78 (2011).
Paris et al., "Equine embryos and embryonic stem cells: defining reliable markers of pluripotency," *Theriogenology*, 74:516-524 (2010).
Paterson, Y.Z. et al. (Jan. 2018, e-published Jul. 5, 2017). "Characterization of companion animal pluripotent stem cells," Cytometry A 93(1):137-148.
Pearson et al., "The stepwise specification of embryonic stem cells to hematopoietic fate is driven by sequential exposure to Bmp4, activin A, bFGF and VEGF," Development, 135:1525-1535 (2008).
Poirot et al., "Multiplex genome-edited T-cell manufacturing platform for "off-the-shelf" adoptive T-cell immunotherapies," Cancer Res., 75(18):3853-3864 (2015).
Rahman et al., "Rescue of DNA-PK Signaling and T-Cell Differentiation by Targeted Genome Editing in a prkdc Deficient iPSC Disease Model," *PLoS Genet.*, 11(5):e1005239 (2015).
Rathjen et al., "Properties and uses of embryonic stem cells: prospects for application to human biology and gene therapy," Reprod. Fertil. Dev., 10:31-47 (1998).
Riella et al., "Role of the PD-1 pathway in the immune response," *Am. J. Transplant.*, 12:2575-2587 (2012).
Robertston, "Derivation and maintenance of embryonic stem cell cultures," Methods Mol. Biol., 75:173-184 (1997).
Sadelain et al., "The promise and potential pitfalls of chimeric antigen receptors," Curr. Opin. Immunol.21(2):215-223 (2009).
Sato, T. et al. (Nov. 2007). "High-level expression of CD109 is frequently detected in lung squamous cell carcinomas," Pathology International 57(11):719-724.
Schmitt et al., "Induction of T cell development and establishment of T cell competence from embryonic stem cells differentiated in vitro," Nat. Immunol., 5(4):410-417 (2004).

(56) References Cited

OTHER PUBLICATIONS

Schmitt et al., "Induction of T cell development from hematopoietic progenitor cells by delta-like-1 in vitro," Immunity, 17(6):749-756 (2002).
Shimanuki et al., "Modulation of the functional binding sites for TGF-beta on the type II receptor leads to suppression of TGF-beta signaling", Oncogene, 26: 3311-3320 (2007).
Shimasaki, S. et al. (Feb. 2004). "The bone morphogenetic protein system in mammalian reproduction," Endocr Rev 25(1):72-101.
Smith, C. et al. (Mar. 2015, e-published Nov. 24, 2014). "Efficient and allele-specific genome editing of disease loci in human iPSCs," Mol Ther 23(3):570-577.
Song et al., "Improved hematopoietic differentiation efficiency of gene-corrected beta-thalassemia induced pluripotent stem cells by CRISPR/Cas9 system," *Stem Cells Dev.*, 24(9):1053-1065 (2015).
Spier, "Large-scale mammalian cell culture: methods, applications and products," Curr. Opin. Biotechnol. 2(3):375-379 (1991).
Suzuki et al., "A novel small-molecule inhibitor of transforming growth factor beta type I receptor kinase (SM16) inhibits murine mesothelioma tumor growth in vivo and prevents tumor recurrence after surgical resection", Cancer Research, 67(5): 2351-2359 (2007).
Themeli, M. et al. (Oct. 2013, e-published Aug. 11, 2013). "Generation of tumor-targeted human T lymphocytes from induced pluripotent stem cells for cancer therapy," Nat Biotechnol 31(10):928-933.
Themeli, M. et al. (Apr. 2, 2015). "New cell sources for T cell engineering and adoptive immunotherapy," Cell Stem Cell 16(4):357-366.
Tojo, et al., "The ALK-5 inhibitor A-83-01 inhibits Smad signaling and epithelia-to-mesenchymal transition by transforming growth factor-β," Cancer Sci, 96(11): 791-800 (2005).
Torikai et al., "A foundation for universal T-cell based immunotherapy: T cell engineered to express a CD19-specific chimeric-antigen-receptor and eliminate expression of endogenous TCR," Blood, 119(24):5697-5705 (2012).
Tsutsui, H. et al. (Jan. 2011). "An optimized small molecule inhibitor cocktail supports long-term maintenance of human embryonic stem cells," Nat Commun 2:167.
Valamehr, B. et al. (Sep. 2011). "Developing defined culture systems for human pluripotent stem cells," Regen Med 6(5):623-634.
Valamehr et al., "A novel platform to enable the high-throughput derivation and characterization of feeder-free human iPSCs," Sci. Rep., 2:213:1-11 (2012).
Valamehr et al., "Platform for induction and maintenance of transgene-free hiPSCs resembling ground state pluripotent stem cells," Stem Cell Reports, 2:366-381 (2014).
Verfaillie, C.M. et al. (2002). "Stem cells: hype and reality," Hematology Am Soc Hematol Educ Program 369-391.
Vijayaragavan et al., "Noncanonical Wnt signaling orchestrates early developmental events toward hematopoietic cell fate from human embryonic stem cells," Cell Stem Cell, 4:248-262 (2009).
Vizcardo, R. et al. (Jan. 3, 2013). "Regeneration of human tumor antigen-specific T cells from iPSCs derived from mature CD8(+) T cells," Cell Stem Cell 12(1):31-36.
Vodyanik et al., "Leukosialin (CD43) defines hematopoietic progenitors in human embryonic stem cell differentiation cultures," *Blood*, 108:2095-2105 (2006).
Voltarelli et al., "Autologous nonmyeloablative hematopoietic stem cell transplantation in newly diagnosed type 1 diabetes mellitus," *JAMA*, 297(14):1568-1576 (2007).
Wang et al., "WNT and BMP signaling are both required for hematopoietic cell development from human ES cells," Stem Cell Res., 3(2-3):113-125 (2009).
Wiles, "Embryonic stem cell differentiation in vitro," Methods Enzymol., 225:900-918 (1993).
Wrzesinski, et al., "Transforming growth factor-beta and the immune response: implications for anticancer therapy", Clinical Cancer Research, 13(18): 5262-5270 (2007).
Xu et al., "BMP4 initiates human embryonic stem cell differentiation to trophoblast," *Nat. Biotechnol.*, 20:1261-1264 (2002).
Yamane et al., "Expression of AA4.1 marks lymphohematopoietic progenitors in early mouse development," Proc. Natl. Acad. Sci. USA, 106(22):8953-8958 (2009).
Zhao et al., "Inhibition of transforming growth factor-beta1-induced signaling and epithelial-to-mesenchymal transition by the Smad-binding peptide aptamer Trx-SARA", Molecular Biology of the Cell, 17(9): 3819-3831 (2006).
Zheng et al., "Ex vivo expanded hematopoietic stem cells overcome the MHC barrier in allogeneic transplantation," Cell Stem Cell, 9:119-130 (2011).

* cited by examiner

Platforms for CD34+ hemogenic endothelium (HE) and T cell progenitors

| Naive hiPSC | | Mesoderm | | Sort CD34+HE Definitive Hemogenic Endothelium | Pre-T cell progenitors | T cell progenitors or T cell |
|---|---|---|---|---|---|---|
| -Matrigel<br>-DMEM/F12<br>-KOSR<br>-Glut & NEAA & ITS<br>-bME<br>-CHIR99021<br>-Thiazovivin<br>-PD0325901<br>-LIF<br>-bFGF | -Matrigel<br>-StemPro 34<br>-Glut & ITS<br>-AA<br>-MTG<br>-BMP4 | -Matrigel<br>-StemPro 34<br>-Glut & ITS<br>-AA<br>-MTG<br>-BMP4<br>-bFGF | -Matrigel<br>-StemPro 34<br>-Glut & ITS<br>-AA<br>-MTG<br>-BMP4<br>-bFGF<br>-CHIR99021 | -Matrigel<br>-StemPro 34<br>-Glut & ITS<br>-AA<br>-MTG<br>-VEGF<br>-bFGF<br>-SCF<br>-IL6<br>-IL11<br>-Y27632 | -StemPro 34<br>-Glut & ITS<br>-AA<br>-MTG<br>-VEGF<br>-bFGF<br>-SCF<br>-BMP4<br>-Flt3L<br>-IL7<br>-Y27632 | -Matrigel, FF or Stromal<br>-αMEM<br>-FBS<br>-Glut<br>-SCF<br>-Flt3L<br>-IL7 |

FIG. 2

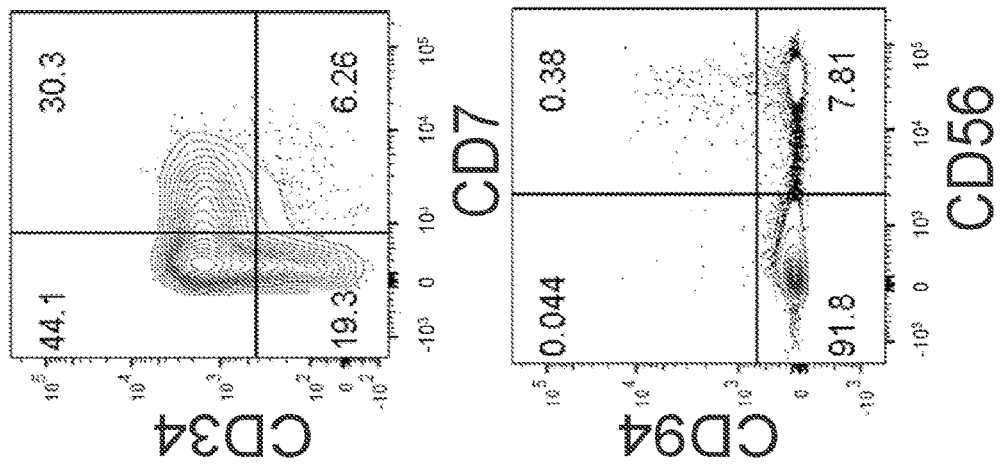
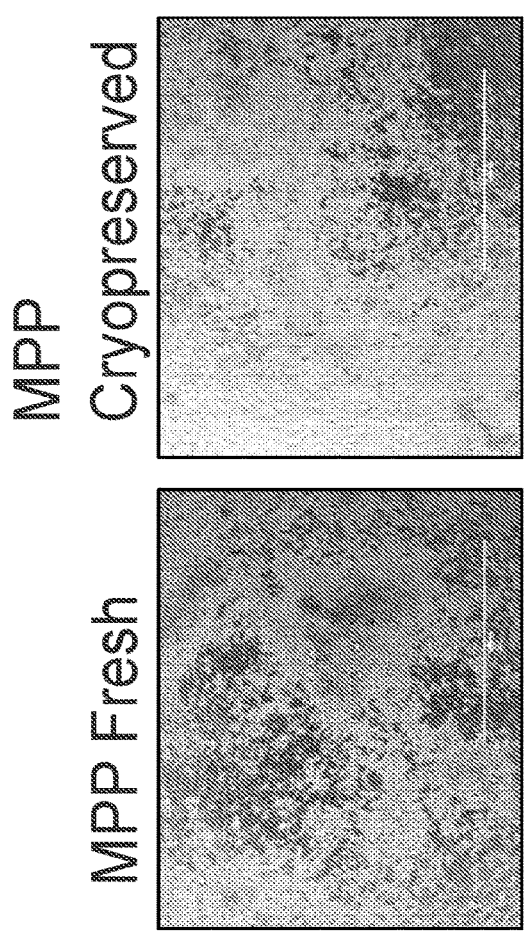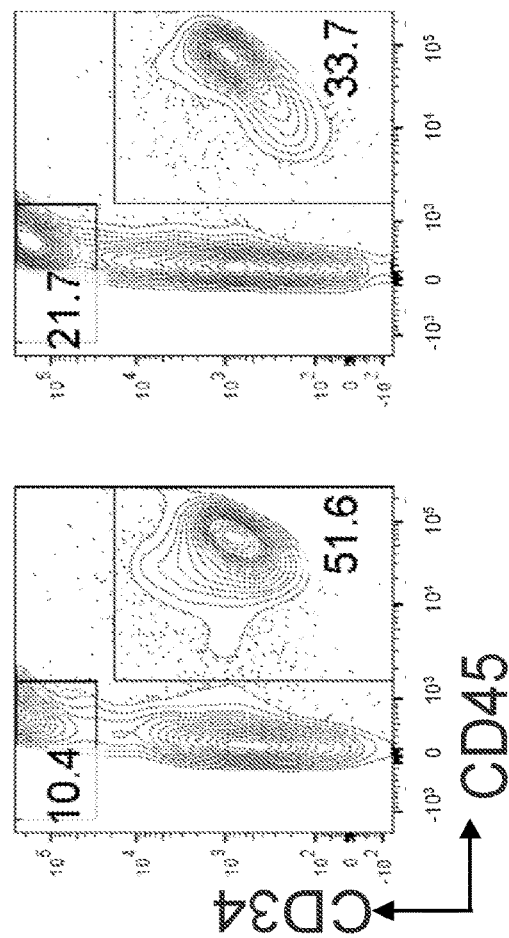
FIG. 8C
FIG. 8D

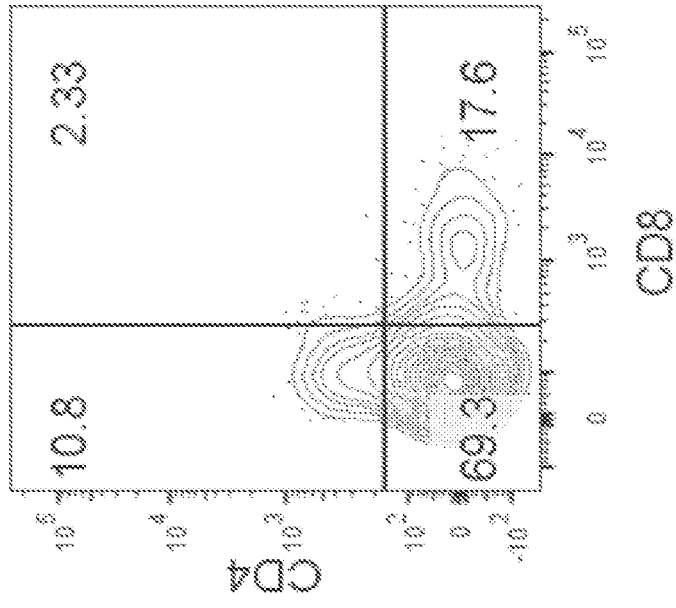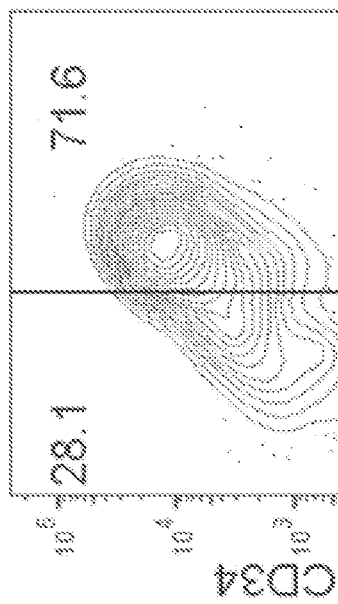
FIG. 10A
FIG. 10B iPSC-derived, iCD34 differentiated towards NK cells.
Early NK lineage markers
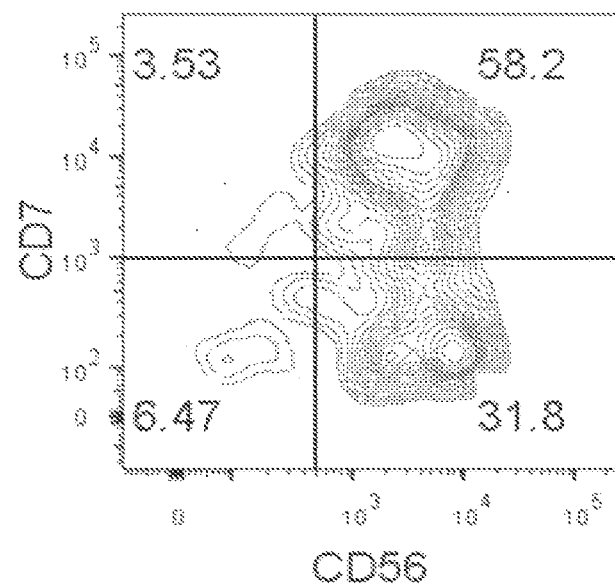
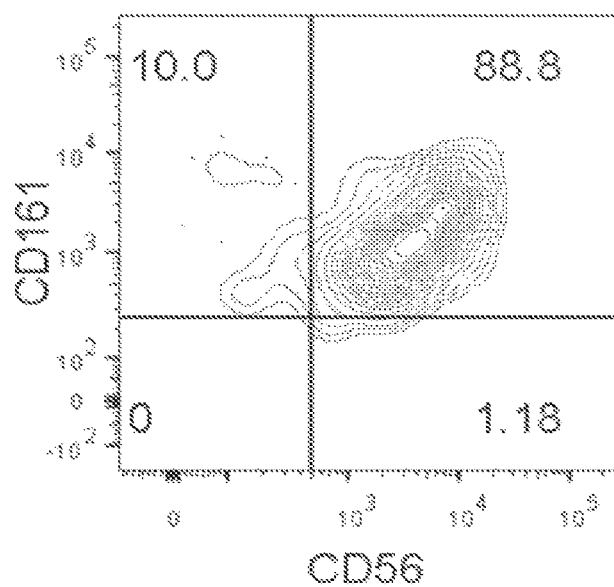
FIG. 11A CD34 positive cells were counted and plotted over time for both monolayer and EB mediated hematopoietic differentiation.

| Name | Clone | CD34+ CD43- Marker+ | CD34+ CD43+ Marker+ | Name | Clone | CD34+ CD43- Marker+ | CD34+ CD43+ Marker+ | Name | Clone | CD34+ CD43- Marker+ | CD34+ CD43+ Marker+ |
|---|---|---|---|---|---|---|---|---|---|---|---|
| CD29 | TS2/16 | 100 | 0 | CD44 | B18 | 51.7 | 44.7 | CD97 | VIM3b | 4.26 | 93.9 |
| CD49e | NKI-SAM-1 | 100 | 0 | CD82 | ASL-24 | 45.7 | 47.2 | CD319 | 162.1 | 3.95 | 95.7 |
| CD59 | p282 (H19) | 100 | 0.027 | CD54 | HA58 | 42 | 51.2 | CD69 | FN50 | 3.34 | 94.2 |
| CD34 | 581 | 99.9 | 0.1 | SSEA-5 | 8E11 | 41.2 | 51.2 | CD338 | 503 | 3.29 | 95.7 |
| CD24 | ML5 | 99.9 | 0.12 | CD56 | HCD56 | 39.3 | 51.4 | Podoplanin | NC-03 | 3.16 | 95.5 |
| CD90 | 5E10 | 99.7 | 0.2 | CD206 | 15-2 | 39.7 | 52 | CD111 | R1.302 | 2.78 | 93.3 |
| CD276 | MIH42 | 99.7 | 0.23 | CD73 | AD2 | 42.3 | 52.8 | CD304 | 12C2 | 2.37 | 94.6 |
| CD298 | LNH-94 | 99.7 | 0.28 | CCR10 | 6588-5 | 3.3 | 55.9 | CD326 | 9C4 | 2.49 | 95.2 |
| | | | | | | | | | | | |
| CD81 | 5A6 | 99.5 | 0.31 | CD164 | 67D2 | 32.1 | 59.7 | CD257 | T7-241 | 2.14 | 97.4 |
| CD112 | TX31 | 99.6 | 0.34 | CD95 | DX2 | 30.5 | 61.2 | CD100 | A8 | 2.08 | 96.4 |
| CD156c | SHM14 | 99.4 | 0.43 | CD144 | BV9 | 35.1 | 66.1 | CD32 | FUN-2 | 2.02 | 97.5 |
| CD63 | H5C6 | 99 | 0.76 | CD166 | 3A6 | 21.4 | 74.5 | CD253 | RIK-2 | 1.71 | 97.8 |
| | | | | Lymphotoxin β Receptor | 31G4D8 | | | | | | |
| CD99 | HCD99 | 99.1 | 0.78 | | | 21.2 | 67.5 | CD79b | CB3-1 | 1.59 | 98.3 |
| CD31 | WM59 | 98.8 | 1 | CD252 | 11C3.1 | 19.7 | 74 | CD33 | WM53 | 1.35 | 97.8 |
| CD165 | SN2 (N6-D11) | 98.4 | 1.37 | CD55 | JS11 | 19 | 73.8 | CD83 | HB15e | 1.37 | 98.5 |
| CD102 | CBR-IC2/2 | 98.3 | 1.54 | HLA-A,B,C | W6/32 | 17.5 | 74.9 | GARP | 7B11 | 1.34 | 95.6 |
| CD146 | SHM-57 | 97.5 | 1.82 | CD40 | HB14 | 17.1 | 78.5 | CD183 | G025H7 | 1.33 | 98.5 |
| CD49c | ASC-1 | 96.5 | 2.62 | CD46 | MEM-55 | 13.7 | 75.3 | CD357 | 621 | 1.03 | 98.9 |
| CD13 | WM15 | 94.6 | 4.16 | CD340 | TRA-2-10 | 17 | 74.9 | CD261 | DJR1 | 0.98 | 98.8 |
| CD58 | TS2/9 | 92.7 | 4.24 | CD119 | GIR-208 | 15.7 | 76.3 | CD196 | G034E3 | 0.97 | 98.9 |
| β2-microglobulin α681 | 2M2 | 90.9 | 5.66 | CD106 | STA | 14.8 | 80 | MSC, NPC | W4A5 | 0.97 | 99 |
| Integrin α9β1 | Y9A2 | 91.5 | 5.94 | CD66a/c/e | ASL-32 | 14 | 82.5 | CD218a | H44 | 0.96 | 98.9 |
| CD51 | NKI-M9 | 90.7 | 6.46 | CD49d | 9F10 | 13.5 | 79.6 | CD115 | 9-4D2-1E4 | 0.94 | 99 |
| CD10 | H110a | 91.4 | 6.53 | CD45RB | MEM-55 | 13.7 | 81 | CD266 | ITEM-1 | 0.9 | 98.6 |
| CD202b | 33.1 (Ab33) | 91.1 | 7.59 | DLL4 | MHD4-46 | 13.5 | 87.6 | EGFR | AY13 | 0.84 | 98.9 |
| CD141 | M80 | 88.6 | 9.28 | CD107a | H4A3 | 12.7 | 87.8 | HVEM | 122 | 0.8 | 99 |
| CD49a | TS2/7 | 87 | 9.66 | CD116 | 4H1 | 9.98 | 89.2 | CD271 | ME20.4 | 0.79 | 98.8 |
| CD9 | H19a | 85.6 | 11.9 | CD324 | 67A4 | 9.41 | 87.4 | CX3CR1 | 2A9-1 | 0.79 | 99 |
| | | | | | | | | | | | |
| CD201 | RCR-401 | 77.9 | 17.2 | CD123 | 6H6 | 9.18 | 87.5 | C5L2 | 1D9-M12 | 0.78 | 98.9 |
| CD47 | CC2C6 | 74.5 | 18.1 | CD49f | GoH3 | 9.17 | 86.8 | NPC | 57D2 | 0.76 | 99.2 |
| CD262 | DJR2-4 (7-8) | 73.5 | 18.2 | CD200 | OX-104 | 8.12 | 87.8 | CD244 | C1.7 | 0.75 | 99.1 |
| CD109 | W7C5 | 74.2 | 20.3 | CD71 | CY1G4 | 13.7 | 87.6 | CD301 | H037G3 | 0.75 | 99.1 |
| CD39 | A1 | 74.2 | 23 | CD172a | SE5A5 | 7.44 | 87.8 | CD226 | 11A8 | 0.69 | 98.9 |
| CD317 | RS38E | 69.1 | 26.4 | CD21 | Bu32 | 7.35 | 89.2 | CD337 | P30-15 | 0.68 | 99.3 |
| CD143 | 5-369 | 67.9 | 26.5 | CD184 | 12G5 | 7.16 | 91.9 | SUSD2 | W3D5 | 0.62 | 99.1 |
| Integrin β5 | AST-3T | 65.4 | 27.1 | CD263 | DJR3 | 6.18 | 91.1 | CD138 | DL-101 | 0.6 | 99.3 |
| CD105 | 43A3 | 67.4 | 27.2 | HLA-A2 | BB7.2 | 5.98 | 89.6 | CD181 | 8F1/CXCR1 | 0.6 | 99.2 |
| CD155 | SKII.4 | 61.2 | 28.3 | CD221 | 1H7/CD221 | 5.74 | 89.9 | CD167a | 51D6 | 0.58 | 99.2 |
| CD93 | VIMD2 | 62.4 | 32.6 | Notch 4 | MHN4-2 | 5.44 | 91 | CD158d | mAb 33 (33) | 0.56 | 99.2 |
| SSEA-4 | MC-813-70 | 59.2 | 34.3 | MSC | W7C6 | 4.53 | 92.3 | CD352 | NT-7 | 0.56 | 99.3 |

| Name | Clone | CD34+ CD43- Marker+ | CD34+ CD43+ Marker+ |
|---|---|---|---|
| CXCR7 | 8F11-M16 | 0.53 | 99.3 |
| CD74 | LN2 | 0.51 | 99.3 |
| CD274 | 29E.2A3 | 0.48 | 99.1 |
| 4-1BB Ligand | 5F4 | 0.46 | 99.3 |
| CD215 | IM7A4 | 0.46 | 99.4 |
| Tim-1 | 1D12 | 0.45 | 99.6 |
| CD140b | 18A2 | 0.44 | 99.4 |
| CD277 | BT3.1 | 0.41 | 98.8 |
| CD231 | SN1a (M3 3D9) | 0.4 | 99.4 |
| CD179b | HSL11 | 0.35 | 99 |
| CD344 | CH3A4A7 | 0.35 | 99.5 |
| TNAP | W8B2 | 0.32 | 99.7 |
| CD278 | C398.4A | 0.31 | 99.5 |
| TCR gamma/delta | B1 | 0.31 | 99.6 |
| CD220 | B6.220 | 0.3 | 99.5 |
| CD158b | DX27 | 0.28 | 99.2 |
| CD197 | G043H7 | 0.28 | 99.6 |
| MICA/MICB | 6D4 | 0.28 | 99 |
| CD84 | CD84.1.21 | 0.27 | 99.6 |
| Jagged 2 | MHJ2-523 | 0.27 | 99.6 |
| CD124 | G077F6 | 0.26 | 99.6 |
| CD1d | 51.1 | 0.25 | 99.7 |
| CD48 | BJ40 | 0.25 | 99.6 |
| CD158f | JP-R1 | 0.24 | 99.7 |
| CD62L | DREG-56 | 0.23 | 99.5 |
| CD80 | 2D10 | 0.23 | 99.7 |
| CD85d | 42D1 | 0.23 | 99.6 |
| CD210 | 3F9 | 0.23 | 99.7 |
| IFN-γ R b chain | 2HUB-159 | 0.23 | 99.6 |
| SUSD2 | W5C5 | 0.23 | 99.3 |
| TCR α/β | IP26 | 0.23 | 99.8 |
| CD1a | HI149 | 0.22 | 99.6 |
| CD28 | CD28.2 | 0.22 | 99.6 |
| CD85 | GHI/75 | 0.22 | 99.5 |
| CD108 | MEM-150 | 0.22 | 99.7 |
| HLA-E | 3D12 | 0.22 | 99.7 |
| CD64 | 10.1 | 0.21 | 99.7 |
| DR3 | JD3 | 0.21 | 99.7 |
| Siglec-9 | K8 | 0.21 | 99.8 |
| Tim-3 | F38-2E2 | 0.21 | 99.8 |

FIG. 26

| Name | Clone | CD34+ CD43- Marker+ | CD34+ CD43+ Marker+ | Name | Clone | CD34+ CD43- Marker+ | CD34+ CD43+ Marker+ | Name | Clone | CD34+ CD43- Marker+ | CD34+ CD43+ Marker+ |
|---|---|---|---|---|---|---|---|---|---|---|---|
| CD61 | VI-PL2 | 0.2 | 99.8 | CD170 | 1A5 | 0.1 | 99.8 | CD38 | HIT2 | 0.048 | 99.9 | CD5 | UCHT2 | 0 | 100 |
| CD158a/h | HP-MA4 | 0.2 | 99.3 | CD200R | OX-108 | 0.1 | 99.8 | CD148 | A3 | 0.048 | 99.8 | CD6 | BL-CD6 | 0 | 100 |
| CD161 | HP-3G10 | 0.2 | 99.8 | CD104 | 58X84 | 0.098 | 99.9 | CLEC9A | 8F9 | 0.048 | 99.9 | CD11b | ICRF44 | 0 | 99.9 |
| CD205 | HD30 | 0.2 | 99.8 | Integrin β7 | FIB504 | 0.098 | 99.9 | CD85 | 17G10.2 | 0.046 | 99.8 | CD16 | 3G8 | 0 | 100 |
| CD255 | CARL-1 | 0.2 | 99.7 | Notch 1 | MHN1-519 | 0.092 | 99.9 | CD3 | HIT3a | 0.045 | 99.9 | CD19 | HIB19 | 0 | 100 |
| CD300f | UP-D2 | 0.2 | 99.4 | IgG2a_Ctrl | RTK2758 | 0.091 | 99.8 | CD131 | 1C1 | 0.045 | 99.9 | CD22 | HIB22 | 0 | 100 |
| TCR Vβ23 | αHUT7 | 0.2 | 99.8 | CD43 | CD43-10G7 | 0.089 | 99.9 | IgLC-κ | MHK-49 | 0.045 | 99.9 | CD23 | EBVCS-5 | 0 | 100 |
| CD62E | HAE-1f | 0.19 | 99.7 | CD180 | MHR73-11 | 0.087 | 99.8 | CD85 | MKT5.1 | 0.044 | 99.8 | CD42b | HIP1 | 0 | 100 |
| CD62P | AK4 | 0.19 | 99.6 | N/A | 2H3 | 0.085 | 99.9 | CD229 | HLy-9.1.25 | 0.044 | 100 | CD5D | CBR-IC3/1 | 0 | 99.9 |
| CD213a2 | SHM38 | 0.19 | 99.7 | CD35 | 5D12 | 0.084 | 99.9 | CD35 | E11 | 0.042 | 99.9 | CD53 | HI29 | 0 | 100 |
| CD258 | T5-39 | 0.19 | 99.7 | CD284 | HTA125 | 0.083 | 99.8 | CD235ab | HIR2 | 0.042 | 99.9 | CD89 | A59 | 0 | 99.9 |
| CD45RO | UCHL1 | 0.18 | 99.7 | CD314 | 1D11 | 0.082 | 99.9 | CD360 | 2G1-K12 | 0.042 | 99.9 | CD94 | DX22 | 0 | 100 |
| CD132 | TUGh4 | 0.18 | 99.7 | CD272 | MIH26 | 0.082 | 99.9 | CD27 | O323 | 0.038 | 100 | N/A | 8827 | 0 | 100 |
| CD85h | 24 | 0.17 | 99.7 | CD179a | HSL96 | 0.081 | 99.9 | Pre-BCR | HSL2 | 0.035 | 99.9 | CD103 | Ber-ACT8 | 0 | 99.9 |
| N/A | DY12 | 0.17 | 99.7 | IgM_Ctrl | MM-30 | 0.081 | 99.9 | CD127 | A019D5 | 0.034 | 99.9 | CD154 | 24-31 | 0 | 99.9 |
| SSEA-1 | MC-480 | 0.17 | 99.8 | CD303 | 201A | 0.08 | 99.8 | CD262 | TL2.1 | 0.033 | 100 | CD162 | KPL-1 | 0 | 100 |
| CD20 | 2H7 | 0.16 | 99.8 | CD7 | CD7-6B7 | 0.079 | 99.8 | CD158e1 | DX9 | 0.032 | 100 | CD169 | 7-239 | 0 | 99.9 |
| CD26 | BA5b | 0.16 | 99.6 | CD135 | BV10A4H2 | 0.078 | 99.9 | CD300e | UP-H2 | 0.032 | 99.7 | CD207 | 10E2 | 0 | 100 |
| CD117 | 104D2 | 0.16 | 99.5 | CD52 | HI186 | 0.077 | 99.8 | HLA-G | 87G | 0.032 | 99.9 | CD243 | UIC2 | 0 | 99.9 |
| CD273 | 24F.10C12 | 0.16 | 99.8 | CD318 | CUB1 | 0.077 | 99.8 | CD334 | 4FR6D3 | 0.031 | 100 | CD267 | 1A1 | 0 | 99.9 |
| CD66b | G10F5 | 0.15 | 99.7 | CD351 | TX01 | 0.077 | 99.9 | CD126 | UV4 | 0.03 | 99.9 | CD279 | EH12.2H7 | 0 | 99.8 |
| CD70 | 113-16 | 0.15 | 99.8 | CD172g | L5b2.20 | 0.073 | 99.9 | CD140a | 16A1 | 0.03 | 100 | CD307e | 509f6 | 0 | 100 |
| CD85k | ZM4.1 | 0.14 | 99.8 | CD203c | NP4D6 | 0.073 | 99.8 | CD336 | P44-8 | 0.029 | 99.9 | CD335 | 9E2 | 0 | 100 |
| CD88 | S5/1 | 0.14 | 99.7 | IgM_Ctrl | RTK2118 | 0.072 | 99.9 | erbB3 | 1B4C3 | 0.029 | 99.9 | CD354 | TREM-26 | 0 | 99.9 |
| Siglec-8 | 7C9 | 0.14 | 99.9 | CD11a | HI111 | 0.071 | 99.8 | Siglec-10 | 5G6 | 0.029 | 99.9 | FcεRIα | AER-37 | 0 | 100 |
| IgG2a_Ctrl | MOPC-173 | 0.14 | 99.7 | CD15 | W6D3 | 0.071 | 99.9 | CD14 | M5E2 | 0.028 | 99.9 | HLA-DQ | HLADQ1 | 0 | 100 |
| CD129 | AH9R7 | 0.13 | 99.7 | TCR Vβ2 | B6 | 0.071 | 99.9 | CD193 | 5E8 | 0.028 | 99.9 | HLA-DR | L243 | 0 | 99.9 |
| CD163 | GHI/61 | 0.13 | 99.8 | CD41 | HIP8 | 0.069 | 99.9 | DLL1 | MHD1-314 | 0.028 | 100 | IgLC-λ | MHL-38 | 0 | 100 |
| CD209 | 9E9A8 | 0.13 | 99.8 | CD254 | MIH24 | 0.069 | 99.8 | CD11c | 3.9 | 0.027 | 99.9 | IgM | MHM-88 | 0 | 100 |
| LAP | TW4-6H10 | 0.13 | 99.7 | IgG1_Ctrl | RTK2071 | 0.068 | 99.9 | CD137 | 4B4-1 | 0.027 | 99.9 | Notch 2 | MHN2-25 | 0 | 100 |
| CD114 | LMM741 | 0.12 | 99.8 | CD18 | TS1/18 | 0.067 | 99.9 | CD286 | TLR6.127 | 0.027 | 99.9 | Notch3 | MHN3-21 | 0 | 100 |
| FcRL4 | 413D12 | 0.12 | 99.9 | TCR Vβ7.2 | 3C10 | 0.067 | 99.9 | CD325 | 8C11 | 0.027 | 99.8 | PSMA | LN1-17 | 0 | 100 |
| C3aR | hC3aR28 | 0.12 | 99.7 | CD328 | 6-434 | 0.061 | 99.9 | CLEC12A | 50C1 | 0.027 | 99.9 | SSEA-3 | MC-631 | 0 | 99.9 |
| IgD | IA6-2 | 0.12 | 99.9 | IgG3_Ctrl | MG3-35 | 0.06 | 99.9 | DOR | DOR7D2A4 | 0.026 | 100 | TCR Vβ13.2 | H132 | 0 | 100 |
| Mac-2 | Gal397 | 0.12 | 99.9 | IgG_Ctrl | HTK888 | 0.059 | 99.9 | CD6a | HIT8a | 0.025 | 100 | TCR Vβ8 | JR2 (JR.2) | 0 | 100 |
| IgG2b_Ctrl | MPC-11 | 0.12 | 99.8 | CD182 | 5E8/CXCR2 | 0.058 | 99.8 | CD86 | IT2.2 | 0.024 | 100 | TCR Vβ9 | MKB1 | 0 | 100 |
| CD1b | SN13 (K5-1B8) | 0.11 | 99.9 | Blank | | 0.057 | 99.9 | CD11b | CBRM1/5 | 0.023 | 99.9 | Vγ9 | 83 | 0 | 100 |
| CD57 | HCD57 | 0.11 | 99.8 | CD4 | RPA-T4 | 0.056 | 99.9 | CD290 | 3C10C5 | 0.023 | 99.9 | Vα24-Jα18 | 6B11 | 0 | 99.9 |
| CD178 | NOK-1 | 0.11 | 99.7 | CD25 | BC96 | 0.056 | 99.9 | CD268 | 11C1 | 0.022 | 100 | Trm-4 | 9F4 | 0 | 100 |
| CD355 | C.24.1 | 0.11 | 99.9 | CD30 | BY88 | 0.053 | 99.9 | CD45 | HI30 | 0.022 | 100 | TLT-2 | MIH61 | 0 | 100 |
| IgG1_Ctrl | MOPC-21 | 0.11 | 99.9 | CD150 | A12 (7D4) | 0.052 | 99.9 | CD45RA | HI100 | 0.02 | 99.8 | TRA-1-81 | TRA-1-81 | 0 | 100 |
| CD36 | 5-271 | 0.1 | 99.9 | CD152 | L3D10 | 0.051 | 99.9 | CD172b | B4B6 | 0.019 | 100 | TSLPR | 1B4 | 0 | 100 |
| CD96 | NK92.39 | 0.1 | 99.9 | IL-28RA | MHLICR2a | 0.051 | 99.9 | CD1c | L161 | 0 | 100 | IgG2b_Ctrl | RTK4530 | 0 | 100 |
| CD122 | TU27 | 0.1 | 99.9 | TRA-1-60-R | TRA-1-60-R | 0.049 | 100 | CD2 | RPA-2.10 | 0 | 100 | | | | |

FIG. 26 (Continued)

HLA class I null iPSCs differentiate into iCD34 HE and can be further differentiated into pan-hematopoietic and lymphoid progenitors HLA class I null iPSCs differentiate into iCD34 HE and can be further differentiated into pan-hematopoietic and lymphoid progenitors HLA class I modulated iPSC can generate functional CD34+HE iPSC genetically engineered to express the high-affinity CD16 receptor and 41BBL costimulatory molecule retain expression throughout differentation to iCD34 cells

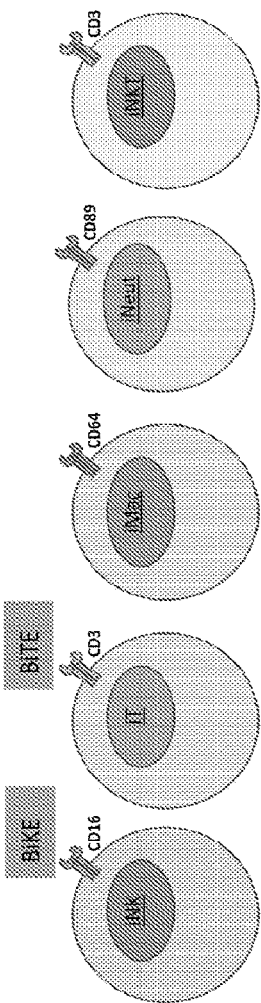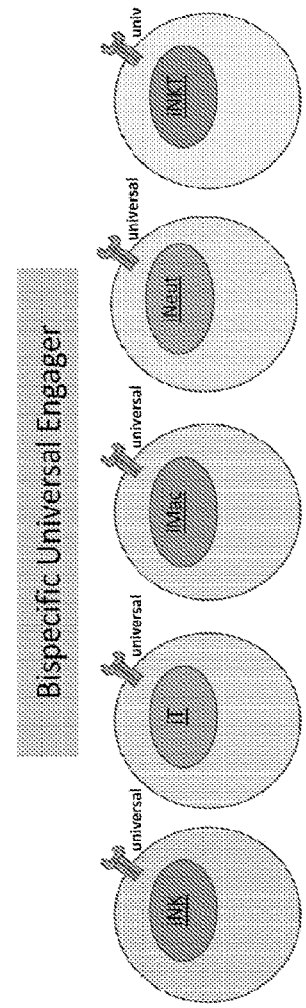
FIG. 40A
FIG. 40B

METHODS AND COMPOSITIONS FOR INDUCING HEMATOPOIETIC CELL DIFFERENTIATION

RELATED APPLICATION

This application claims priority to U.S. Provisional Application Ser. No. 62/251,016, filed Nov. 4, 2015; International Application Number PCT/US16/14918, filed Jan. 26, 2016; and U.S. Provisional Application Ser. No. 62/337,093, filed May 16, 2015, and the disclosures of which are hereby incorporated by reference in their entirety.

FIELD OF INVENTION

The invention relates generally to compositions and methods for manufacturing cells of all hematopoietic lineages from pluripotent stem cells. In particular, the invention relates to improved culture platforms for manufacturing cells of all hematopoietic lineages from pluripotent stem cells including human induced pluripotent stem cells.

BACKGROUND

Human induced pluripotent stem cell (hiPSC) technology represents a highly promising and potentially unlimited source of therapeutically viable hematopoietic cells for the treatment of numerous hematological and non-hematological malignancies including cancer. To advance the promise of hiPSC and genomically engineered hiPSC technology as an allogeneic source of hematopoietic cellular therapeutics, it is essential to be able to efficiently and reproducibly generate not only hematopoietic stem and progenitor cells (HSCs) but also immune effector populations, including the diverse subsets of T, B, NKT, and NK lymphoid cells, and progenitor cells thereof.

The in vitro derivation of HSCs with the potential to generate lymphocytes is complicated by the existence of at least two temporally and spatially distinct waves of blood formation during embryonic development: primitive and definitive hematopoiesis. Primitive hematopoiesis initiates in the extraembryonic yolk sac and generates a transient and restricted hematopoietic repertoire mainly including primitive erythroid and myeloid cells, but not HSCs. Nascent HSCs only emerge later during the definitive wave from a specialized endothelial progenitor within the arterial vasculature termed definitive hemogenic endothelium (HE). Definitive HE then undergoes an endothelial-to-hematopoietic transition to give rise to HSCs, which then ultimately migrate to the bone marrow where they sustain multi-lineage hematopoiesis, including T, B, NKT, and NK lymphoid cells, throughout adult life. Therefore the generation of HSCs and lymphoid effector cells from pluripotent stem cells is dependent upon the ability to accurately recapitulate the intricate stages of early embryonic hematopoietic development towards the definitive program through well-designed and validated methods and compositions.

A limited number of studies have described the directed differentiation of hiPSCs to definitive HE in vitro. A major hurdle in utilizing hiPSCs for therapeutic purposes has been the requirement to initially co-culture such cells with murine- or human-derived stromal cells in the presence of ill-defined serum-containing media in order to maintain pluripotency and induce differentiation. In addition, the existing protocols have also employed a strategy consisting of culturing iPSC to form an embryoid body (EB), which is a heterogeneous aggregate of cells comprising various differentiated cells including ectoderm, mesoderm, and endoderm cells. Those procedures either require aggregating pluripotent cells by for example spinning to form clumps, allowing the cells to settle and aggregate in wells or allowing for passive aggregation and clump formation in suspension culture. The formed EBs are maintained for certain duration in differentiation inducing culture systems, typically seven to ten days, to allow for proper differentiation, then the EBs are either transferred to adherent culture for further maturation or dissociated into single cells for cell type selection in order to proceeding to the subsequent differentiation steps. (Kennedy et al., Cell Reports 2012:1722-1735; Knorr, et al., Stem Cells Translational Medicine 2013 (2):274-283). For example, Kennedy et al. teach to generate EBs for iPSCs differentiation, where pluripotent cells were treated with collagenase and trypsin to allow for scraping of the cells to form small aggregates which were then cultured to form EBs. EB formation has been shown to facilitate pluripotent stem cell differentiation, however the requirement of forming aggregates and subsequent EBs is labor intensive, the cell numbers minimally increase in this process, the cellular content in the three dimensional EB aggregates are exposed to the media factors inconsistently and unevenly, which leads to heterogeneous cells products that are in variable differentiation stages, and greatly hinders the scalability and reproducibility of a manufacturing process that is required to be efficient and streamlined.

Therefore, there is a need for methods and compositions of differentiating stem cell to definitive hematopoiesis without relying on co-culturing or serum-containing media, and without requiring the formation of embryoid body aggregates as intermediates.

SUMMARY OF THE INVENTION

The present invention relates generally to cell culture conditions, media, culture platforms, and methods for culturing and differentiating stem cells to a hematopoietic cell fate.

Specifically, the present invention provides methods and compositions for the generation of hematopoietic cell lineages through definitive hemogenic endothelium (HE) derived from pluripotent stem cells, including hiPSCs under serum/feeder-free conditions and in a scalable and monolayer culturing platform without the need of EB formation. Cells that may be differentiated according to the methods of the invention range from pluripotent stem cells, to progenitor cells that are committed to a particular terminally differentiated cell and transdifferentiated cells, cells of various lineages directly transitioned to hematopoietic fate without going through a pluripotent intermediate. Similarly, the cells produced by differentiation of stem cells range from multipotent stem or progenitor cells to terminally differentiated stem cells, and all intervening hematopoietic cell lineages.

The present invention provides methods and compositions for differentiating and expanding cells of the hematopoietic lineage from pluripotent stem cells in monolayer culturing, which comprises contacting the pluripotent stem cells with a BMP pathway activator, and optionally, bFGF. As such, pluripotent stem cell-derived mesodermal cells are obtained and expanded without forming embryoid bodies from pluripotent stem cells. The mesodermal cells are then subjected to contact with a BMP pathway activator, bFGF, and a WNT pathway activator to obtain expanded mesodermal cells having definitive hemogenic endothelium (IE) potential without forming embryoid bodies from the pluripotent stem cells. By subsequent contact with bFGF, and optionally, a ROCK inhibitor, and/or a WNT pathway activator, the mesodermal cells having definitive HE potential are differentiated to definitive HE cells, which are also expanded during differentiation.

The methods provided herein for obtaining cells of the hematopoietic lineage are superior to EB-mediated pluripotent stem cell differentiation, because EB formation leads to modest to minimal cell expansion, does not allow monolayer culturing which is important for many applications requiring homogeneous expansion, and homogeneous differentiation of the cells in a population, and is laborious and low efficiency.

Provided herein is a monolayer differentiation platform that facilitates differentiation towards definitive hemogenic endothelium resulting in the derivation of hematopoietic stem cells and differentiated progeny such as T, B, NKT and NK cells. The demonstrated monolayer differentiation strategy combines enhanced differentiation efficiency with large-scale expansion enables the delivery of therapeutically relevant number of pluripotent stem cell-derived hematopoietic cells for various therapeutic applications. Further, the present invention disclosed that monolayer culturing using the methods provided herein leads to functional hematopoietic lineage cells that enable full range of in vitro differentiation, ex vivo modulation, and in vivo long term hematopoietic self-renewal, reconstitution and engraftment. As used herein, the iPSC derived hematopoietic lineage cells include, but not limited to, definitive hemogenic endothelium, hematopoietic multipotent progenitor cells, hematopoietic stem and progenitor cells, T cell progenitors, NK cell progenitors, T cells, NK cells, NKT cells, B cells, macrophages, and neutrophils.

One aspect of the present invention provides a culture platform for obtaining pluripotent stem cell-derived hematopoietic lineage cells, which comprises: (i) a culture medium comprising a ROCK inhibitor; one or more growth factors and cytokines selected from the group consisting of bFGF, VEGF, SCF, IGF, EPO, IL6, and IL11; and optionally a Wnt pathway activator; and is optionally free of TGFβ receptor/ALK inhibitor, wherein the medium is suitable for differentiating and expanding definitive hemogenic endothelium from mesodermal cells having definitive hemogenic endothelium potential; (ii) a culture medium comprising a BMP activator, bFGF, and a GSK3 inhibitor, and is optionally free of TGFβ receptor/ALK inhibitor, wherein the medium is suitable for obtaining mesodermal cell having definitive hemogenic endothelium potential; and (iii) a culture medium that comprises a BMP activator, and optionally bFGF, wherein the medium is suitable for differentiating and expanding mesodermal cells from pluripotent stem cells. In some embodiments, the pluripotent stem cells of the above culture platform are iPSCs. In some embodiments, the iPSCs are naïve iPSCs. In some embodiments, the above culture platform further comprises: (iv) a culture medium that comprises a MEK inhibitor, a GSK3 inhibitor, and a ROCK inhibitor, and is free of TGFβ receptor/ALK inhibitors, wherein the medium is suitable for seeding and expanding pluripotent stem cells.

In some embodiments of the above culture platform, the culture platform further comprises additional culture media: (i) a culture medium comprising one or more growth factors and cytokines selected from the group consisting of SCF, Flt3L, and IL7, but free of one or more of VEGF, bFGF, TPO, BMP activators and ROCK inhibitors, wherein the culture medium is suitable for differentiating pluripotent stem cell-derived pre-T cell progenitors to T cell progenitor or T cells; or (ii) a culture medium comprising a ROCK inhibitor; one or more growth factors and cytokines selected from the group consisting of VEGF, bFGF, SCF, Flt3L, TPO, and IL7; and optionally a BMP activator, wherein the culture medium is suitable for differentiating pluripotent stem cell-derived definitive hemogenic endothelium to pre-T cell progenitor; and these additional culture media are suitable for generating pluripotent stem cell-derived T lineage cells.

In some embodiments of the above culture platform, the culture platform may further comprise: (i) a medium comprising one or more growth factors and cytokines selected from the group consisting of SCF, Flt3L, IL3, IL7, and IL15, wherein the medium is free of one or more of VEGF, bFGF, TPO, BMP activators and ROCK inhibitors and is suitable for differentiating pluripotent stem cell-derived pre-NK cell progenitors to NK cell progenitors or NK cells; or (ii) a medium comprising a ROCK inhibitor; one or more growth factors and cytokines selected from the group consisting of VEGF, bFGF, SCF, Flt3L, TPO, IL3, IL7, and IL15; and optionally a BMP activator; wherein the medium is suitable for differentiating pluripotent stem cell-derived definitive hemogenic endothelium into pre-NK cell progenitors; and these additional media are suitable for generating pluripotent stem cell-derived NK lineage cells.

In one embodiment, the above provided culture platform further comprises: (i) a culture medium comprising a BMP activator, one or more growth factors and cytokines selected from the group consisting of TPO, IL3, GMCSF, EPO, bFGF, VEGF, SCF, IL6, and IL11, but free of ROCK inhibitor, wherein the culture medium is suitable for differentiating pluripotent stem cell-derived pre-HSCs to hematopoietic multipotent progenitors; (ii) a culture medium comprising a BMP activator, a ROCK inhibitor, and one or more growth factors and cytokines selected from the group consisting of TPO, IL3, GMCSF, EPO, bFGF, VEGF, SCF, IL6, Flt3L and IL11, a wherein the culture medium is suitable for differentiating pluripotent stem cell-derived definitive hemogenic endothelium to pre-HSCs; and these culture media are provided for generating pluripotent stem cell-derived hematopoiesis multipotent progenitors.

Another aspect of the present invention provides a composition for differentiating and expanding pluripotent stem cell-derived hematopoietic cells, which comprises one or more of the following: (i) a culture medium comprising a ROCK inhibitor; one or more growth factors and cytokines selected from the group consisting of bFGF, VEGF, SCF, IGF, EPO, IL6, and IL11; optionally, a Wnt pathway activator; and pluripotent stem cell-derived mesodermal cells with definitive hemogenic endothelium potential, wherein the medium is optionally free of TGFβ receptor/ALK inhibitor, wherein the medium is suitable for differentiating and expanding definitive hemogenic endothelium from the pluripotent stem cell-derived mesodermal cells with hemogenic endothelium potential; (ii) a culture medium comprising a BMP activator, bFGF, and a GSK3 inhibitor, but free of TGFβ receptor/ALK inhibitor; and pluripotent stem cell-derived mesodermal cells, wherein the medium is suitable for differentiating and expanding mesodermal cells having definitive hemogenic endothelium potential from pluripotent stem cell-derived mesodermal cells; and (iii) a culture medium that comprises a BMP activator, and optionally bFGF; and iPSCs, wherein the medium is suitable for differentiating and expanding mesodermal cells from pluripotent stem cells.

In some embodiments of the composition for differentiating and expanding pluripotent stem cell-derived hematopoietic cells, the pluripotent stem cells are iPSCs. In some embodiments, the iPSCs are naïve iPSCs. In some embodiments, the iPSC comprises one or more genetic imprints, and wherein the one or more genetic imprints comprised in the iPSC are retained in the hematopoietic lineage cells differentiated therefrom.

In some embodiments of the composition for differentiating and expanding pluripotent stem cell-derived hematopoietic cells, the composition comprises an additional culture medium, such as: (vi) a culture medium that comprises a MEK inhibitor, a GSK3 inhibitor, and a ROCK inhibitor, and is free of TGFβ receptor/ALK inhibitors; and pluripotent stem cells; wherein the medium is suitable for seeding and expanding the pluripotent stem cells. In some embodiments, the pluripotent stem cells are iPSCs. In some embodiments, the iPSCs are naïve iPSCs. In some embodiments, the iPSC comprises one or more genetic imprints, and wherein the one or more genetic imprints comprised in the iPSC are retained in the hematopoietic lineage cells differentiated therefrom.

In some embodiments of the above composition for differentiating and expanding pluripotent stem cell-derived hematopoietic cells the composition additionally comprises: (i) a culture medium comprising one or more growth factors and cytokines selected from the group consisting of SCF, Flt3L, and IL7, but free of one or more of VEGF, bFGF, TPO, BMP activators and ROCK inhibitors; and pluripotent stem cell-derived pre-T cell progenitors, wherein the culture medium is suitable for differentiating the pluripotent stem cell-derived pre-T cell progenitors to T cell progenitors or T cells; or (ii) a culture medium comprising a ROCK inhibitor; one or more growth factors and cytokines selected from the group consisting of VEGF, bFGF, SCF, Flt3L, TPO, and IL7; and optionally a BMP activator; and pluripotent stem cell-derived definitive hemogenic endothelium, wherein the culture medium is suitable for differentiating the definitive hemogenic endothelium into pre-T cell progenitor. These additional media are suitable for generating pluripotent stem cell-derived T lineage cells.

In one embodiment of the above composition for differentiating and expanding pluripotent stem cell-derived hematopoietic cells, the composition further comprises one or more medium for generating pluripotent stem cell-derived hematopoiesis multipotent progenitors, wherein the medium comprises: (i) a culture medium comprising a BMP activator, one or more growth factors and cytokines selected from the group consisting of TPO, IL3, GMCSF, EPO, bFGF, VEGF, SCF, IL6, and IL11, but free of ROCK inhibitor, and pluripotent stem cell-derived pre-HSC, wherein the culture medium is suitable for differentiating the pre-HSC to hematopoietic multipotent progenitors; and/or (ii) a culture medium comprising a BMP activator, a ROCK inhibitor, one or more growth factors and cytokines selected from the group consisting of TPO, IL3, GMCSF, EPO, bFGF, VEGF, SCF, IL6, Flt3L and IL11, and pluripotent stem cell-derived definitive hemogenic endothelium, wherein the culture medium is suitable for differentiating the definitive hemogenic endothelium to pre-HSC.

One aspect of the present invention provides a culture platform for generating pluripotent stem cell-derived T lineage cells, which comprises: (i) a culture medium that comprises a BMP activator, and optionally bFGF, wherein the medium is suitable for differentiating and expanding pluripotent stem cell-derived mesodermal cells from pluripotent stem cells; (ii) a culture medium comprising a BMP activator, bFGF, and a GSK3 inhibitor, and optionally free of TGFβ receptor/ALK inhibitor, wherein the medium is suitable for obtaining mesodermal cells having definitive HE potential from the mesodermal cells; (iii) a culture medium comprising a ROCK inhibitor, one or more growth factors and cytokines selected from the group consisting of bFGF, VEGF, SCF, IGF, EPO, IL6, and IL11; optionally, a Wnt pathway activator; and optionally free of TGFβ receptor/ALK inhibitor, wherein the medium is suitable for differentiating and expanding definitive hemogenic endothelium from the mesodermal cells with definitive hemogenic endothelium potential; (iv) a culture medium comprising a ROCK inhibitor; one or more growth factors and cytokines selected from the group consisting of VEGF, bFGF, SCF, Flt3L, TPO, and IL7; and optionally a BMP activator; and pluripotent stem cell-derived definitive hemogenic endothelium, wherein the culture medium is suitable for differentiating the definitive hemogenic endothelium into pre-T cell progenitor; and (v) a culture medium comprising one or more growth factors and cytokines selected from the group consisting of SCF, Flt3L, and IL7, but free of one or more of VEGF, bFGF, TPO, BMP activators and ROCK inhibitors; and pluripotent stem cell-derived pre-T cell progenitors, wherein the culture medium is suitable for differentiating the pre-T cell progenitors to T cell progenitors or T cells.

In some embodiments of the above culture platform for generating pluripotent stem cell-derived T lineage cells, the culture platform further comprises: (vi) a culture medium that comprises a MEK inhibitor, a GSK3 inhibitor, and a ROCK inhibitor, and is optionally free of TGFβ receptor/ALK inhibitors, wherein the medium is suitable for seeding and expanding pluripotent stem cells. In some embodiments, the pluripotent stem cells are iPSCs. In some embodiments, the iPSCs are naïve iPSCs. In some embodiments, the iPSC comprises one or more genetic imprints, and wherein the one or more genetic imprints comprised in the iPSC are retained in the pluripotent stem cell derived T lineage cells differentiated therefrom.

Another aspect of the present invention provides a culture platform for generating pluripotent stem cell-derived NK cells, which comprises: (i) a culture medium that comprises a BMP activator, and optionally bFGF, wherein the medium is suitable for differentiating and expanding mesodermal cells from pluripotent stem cells; (ii) a culture medium comprising a BMP activator, bFGF, and a GSK3 inhibitor, and optionally free of TGFβ receptor/ALK inhibitor, wherein the medium is suitable for obtaining mesodermal cells having definitive hemogenic endothelium potential from mesodermal cells; (iii) a culture medium comprising a ROCK inhibitor; one or more growth factors and cytokines selected from the group consisting of bFGF, VEGF, SCF, IGF, EPO, IL6, and IL11; optionally a Wnt pathway activator; and optionally free of TGFβ receptor/ALK inhibitor, wherein the medium is suitable for differentiating definitive hemogenic endothelium from mesodermal cells having definitive hemogenic endothelium potential; (iv) a culture medium comprising a ROCK inhibitor; one or more growth factors and cytokines selected from the group consisting of VEGF, bFGF, SCF, Flt3L, TPO, IL3, IL7, and IL15; and optionally, a BMP activator, wherein the medium is suitable for differentiating definitive hemogenic endothelium into pre-NK cell progenitor; and (v) a medium comprising one or more growth factors and cytokines selected from the group consisting of SCF, Flt3L, IL3, IL7, and IL15, wherein the medium is free of one or more of VEGF, bFGF, TPO, BMP activators and ROCK inhibitors and is suitable for differentiating pre-NK cell progenitors to NK cell progenitors or NK cells.

In some embodiment of the above culture platform for generating pluripotent stem cell-derived NK cells, the culture platform further comprises: (vi) a culture medium that comprises a MEK inhibitor, a GSK3 inhibitor, and a ROCK inhibitor, and is free of TGFβ receptor/ALK inhibitors, wherein the medium is suitable for seeding and expanding pluripotent stem cells. In some embodiments, the pluripotent stem cells are iPSCs. In some embodiments, the iPSCs are naïve iPSCs. In some embodiments, the iPSC comprises one or more genetic imprints, and wherein the one or more genetic imprints comprised in the iPSC are retained in the pluripotent stem cell derived NK lineage cells differentiated therefrom Yet another aspect of the present invention provides a culture platform for generating pluripotent stem cell-derived definitive hemogenic endothelium (iHE), which comprises: (i) a culture medium that comprises a BMP activator, and optionally bFGF, wherein the medium is suitable for differentiating and expanding mesodermal cells from pluripotent stem cells; (ii) a culture medium comprising a BMP activator, bFGF, and a GSK3 inhibitor, and optionally free of TGFβ receptor/ALK inhibitor, wherein the medium is suitable for obtaining mesodermal cells having definitive hemogenic endothelium potential from the pluripotent stem cell-derived mesodermal cells; and (iii) a culture medium comprising a ROCK inhibitor, and one or more growth factors and cytokines selected from the group consisting of bFGF, VEGF, SCF, IL6, IL11, wherein the medium is optionally free of TGFβ receptor/ALK inhibitor, and wherein the medium is suitable for differentiating and expanding definitive hemogenic endothelium from the mesodermal cells having definitive hemogenic endothelium potential.

In some embodiments of the culture platform for generating pluripotent stem cell-derived definitive hemogenic endothelium (iHE), the culture platform further comprises (iv) a culture medium that comprises a MK inhibitor, a GSK3 inhibitor, and a ROCK inhibitor, and is free of TGFβ receptor/ALK inhibitors, wherein the medium is suitable for seeding and expanding pluripotent stem cells.

Still another aspect of the invention provides a culture platform for generating pluripotent stem cell-derived hematopoiesis multipotent progenitors, which comprises: (i) a culture medium that comprises a BMP activator, and optionally bFGF, wherein the medium is suitable for differentiating and expanding pluripotent stem cell-derived mesodermal cells from pluripotent stem cells; (ii) a culture medium comprising a BMP activator, bFGF, and a GSK3 inhibitor, and optionally free of TGFβ receptor/ALK inhibitor, wherein the medium is suitable for obtaining mesodermal cells having definitive hemogenic endothelium potential from the pluripotent stem cell-derived mesodermal cells; (iii) a culture medium comprising a ROCK inhibitor; one or more growth factors and cytokines selected from the group consisting of bFGF, VEGF, SCF, IGF, EPO, IL6, and IL1; and optionally, a Wnt pathway activator, wherein the medium is optionally free of TGFβ receptor/ALK inhibitor, wherein the medium is suitable for differentiating and expanding definitive hemogenic endothelium from mesodermal cells having definitive hemogenic endothelium potential; (iv) a culture medium comprising a BMP activator, a ROCK inhibitor, one or more growth factors and cytokines selected from the group consisting of TPO, IL3, GMCSF, EPO, bFGF, VEGF, SCF, IL6, Flt3L and IL11; wherein the culture medium is suitable for differentiating definitive hemogenic endothelium to pre-HSC; and (v) a culture medium comprising a BMP activator, one or more growth factors and cytokines selected from the group consisting of TPO, IL3, GMCSF, EPO, bFGF, VEGF, SCF, IL6, and IL11, wherein the medium is free of ROCK inhibitor, wherein the culture medium is suitable for differentiating pre-HSC to hematopoietic multipotent progenitors. In some embodiments, the culture platform further comprises (vi) a culture medium that comprises a MEK inhibitor, a GSK3 inhibitor, and a ROCK inhibitor, and is free of TGFβ receptor/ALK inhibitors, wherein the medium is suitable for seeding and expanding pluripotent stem cells. In some embodiments, the pluripotent stem cells are iPSCs. In some embodiments, the iPSCs are naïve iPSCs. In some embodiments, the iPSC comprises one or more genetic imprints, and wherein the one or more genetic imprints comprised in the iPSC are retained in the pluripotent stem cell derived hematopoietic cells differentiated therefrom.

Another aspect of the invention provides a method for directing differentiation of pluripotent stem cells into cells of a definitive hematopoietic lineage, which comprises: (i) contacting pluripotent stem cells with a composition comprising a BMP activator, and optionally bFGF, to initiate differentiation and expansion of mesodermal cells from the pluripotent stem cells; (ii) contacting the mesodermal cells with a composition comprising a BMP activator, bFGF, and a GSK3 inhibitor, wherein the composition is optionally free of TGFβ receptor/ALK inhibitor, to initiate differentiation and expansion of mesodermal cells having definitive HE potential from the mesodermal cells; (iii) contacting the mesodermal cells having definitive HE potential with a composition comprising a ROCK inhibitor; one or more growth factors and cytokines selected from the group consisting of bFGF, VEGF, SCF, IGF, EPO, IL6, and IL11; and optionally, a Wnt pathway activator, wherein the composition is optionally free of TGFβ receptor/ALK inhibitor, to initiate differentiation and expansion of definitive hemogenic endothelium from pluripotent stem cell-derived mesodermal cells having definitive hemogenic endothelium potential; and optionally, subjecting pluripotent stem cells, pluripotent stem cell-derived mesodermal cells, mesodermal cells having hemogenic endothelium, and/or definitive hemogenic endothelium under low oxygen tension between about 2% to about 10%.

In some embodiments of the method for directing differentiation of pluripotent stem cells into cells of a hematopoietic lineage, the method further comprises contacting pluripotent stem cells with a composition comprising a MEK inhibitor, a GSK3 inhibitor, and a ROCK inhibitor, wherein the composition is free of TGFβ receptor/ALK inhibitors, to seed and expand the pluripotent stem cells. In some embodiments, the pluripotent stem cells are iPSCs. In some embodiments, the iPSCs are naïve iPSCs. In some embodiments, the iPSC comprises one or more genetic imprints, and wherein the one or more genetic imprints comprised in the iPSC are retained in the pluripotent stem cell derived hematopoietic cells differentiated therefrom.

In some embodiments of the method for directing differentiation of pluripotent stem cells into cells of a hematopoietic lineage, the differentiation of the pluripotent stem cells into cells of hematopoietic lineage is void of generation of embryoid bodies, and is in a monolayer culturing form.

In some embodiments of the above method, the obtained pluripotent stem cell-derived definitive hemogenic endothelium cells are CD34+. In some embodiments, the obtained definitive hemogenic endothelium cells are CD34+CD43−. In some embodiments, the definitive hemogenic endothelium cells are CD34+CD43−CXCR4−CD73−. In some embodiments, the definitive hemogenic endothelium cells are CD34+CXCR4−CD73−. In some embodiments, the definitive hemogenic endothelium cells are CD34+CD43−

CD93−. In some embodiments, the definitive hemogenic endothelium cells are CD34+CD93−.

In some embodiments of the above method, the method further comprises (i) contacting pluripotent stem cell-derived definitive hemogenic endothelium with a composition comprising a ROCK inhibitor; one or more growth factors and cytokines selected from the group consisting of VEGF, bFGF, SCF, Flt3L, TPO, and IL7; and optionally a BMP activator; to initiate the differentiation of the definitive hemogenic endothelium to pre-T cell progenitors; and optionally, (ii) contacting the pre-T cell progenitors with a composition comprising one or more growth factors and cytokines selected from the group consisting of SCF, Flt3L, and IL7, but free of one or more of VEGF, bFGF, TPO, BMP activators and ROCK inhibitors, to initiate the differentiation of the pre-T cell progenitors to T cell progenitors or T cells. In some embodiments of the method, the pluripotent stem cell-derived T cell progenitors are CD34+CD45+ CD7+. In some embodiments of the method, the pluripotent stem cell-derived T cell progenitors are CD45+CD7+.

In yet some embodiments of the above method for directing differentiation of pluripotent stem cells into cells of a hematopoietic lineage, the method further comprises: (i) contacting pluripotent stem cell-derived definitive hemogenic endothelium with a composition comprising a ROCK inhibitor; one or more growth factors and cytokines selected from the group consisting of VEGF, bFGF, SCF, Flt3L, TPO, IL3, IL7, and IL15; and optionally, a BMP activator, to initiate differentiation of the definitive hemogenic endothelium to pre-NK cell progenitor; and optionally, (ii) contacting pluripotent stem cells-derived pre-NK cell progenitors with a composition comprising one or more growth factors and cytokines selected from the group consisting of SCF, Flt3L, IL3, IL7, and IL15, wherein the medium is free of one or more of VEGF, bFGF, TPO, BMP activators and ROCK inhibitors, to initiate differentiation of the pre-NK cell progenitors to NK cell progenitors or NK cells. In some embodiments, the pluripotent stem cell-derived NK progenitors are CD3−CD45+CD56+CD7+. In some embodiments, the pluripotent stem cell-derived NK cells are CD3−CD45+ CD56+, and optionally further defined by NKp46+, CD57+ and CD16+.

Another aspect of the invention provides a method for generating pluripotent stem cell-derived T lineage cells, which comprises: (i) contacting pluripotent stem cells with a composition comprising a BMP activator, and optionally bFGF, to initiate differentiation and expansion of mesodermal cells from pluripotent stem cells; (ii) contacting the mesodermal cells with a composition comprising a BMP activator, bFGF, and a GSK3 inhibitor, but free of TGFβ receptor/ALK inhibitor, to initiate differentiation and expansion of the mesodermal cells having definitive HE potential from the mesodermal cells; (iii) contacting mesodermal cells having definitive HE potential with a composition comprising a ROCK inhibitor; one or more growth factors and cytokines selected from the group consisting of bFGF, VEGF, SCF, IGF, EPO, IL6, and IL11; and optionally, a Wnt pathway activator; wherein the composition is free of TGFβ receptor/ALK inhibitor, to initiate differentiation and expansion of definitive hemogenic endothelium from mesodermal cells having definitive HE potential; (iv) contacting definitive hemogenic endothelium with a composition comprising a ROCK inhibitor; one or more growth factors and cytokines selected from the group consisting of VEGF, bFGF, SCF, Flt3L, TPO, and IL7; and optionally a BMP activator; to initiate differentiation of the definitive hemogenic endothelium to pre-T cell progenitors; and (v) contacting the pre-T cell progenitors with a composition comprising one or more growth factors and cytokines selected from the group consisting of SCF, Flt3L, and IL7, wherein the composition is free of one or more of VEGF, bFGF, TPO, BMP activators and ROCK inhibitors; to initiate differentiation of the pre-T cell progenitors to T cell progenitors or T cells; and optionally, the seeded pluripotent stem cells, mesodermal cells, mesodermal cells having definitive HE potential, and/or definitive hemogenic endothelium may be subject to low oxygen tension between about 2% to about 10%. In some embodiments, group II of the above method further comprises: contacting iPSCs with a composition comprising a MEK inhibitor, a GSK3 inhibitor, and a ROCK inhibitor, but free of TGFβ receptor/ALK inhibitors, to seed and expand pluripotent stem cells; and/or wherein the pluripotent stem cells. In some embodiments, the pluripotent stem cells are iPSCs. In some embodiments, the iPSCs are naïve iPSC. In some embodiments of the method, the differentiation of the pluripotent stem cells into T cell lineages is void of generation of embryoid bodies, and is in a monolayer culturing format.

Yet another aspect of the invention provides a method for generating pluripotent stem cell-derived NK lineage cells, which comprises: (i) contacting pluripotent stem cells with a composition comprising a BMP activator, and optionally bFGF, to initiate differentiation and expansion of mesodermal cells from the pluripotent stem cells; (ii) contacting mesodermal cells with a composition comprising a BMP activator, bFGF, and a GSK3 inhibitor, and optionally free of TGFβ receptor/ALK inhibitor, to initiate differentiation and expansion of mesodermal cells having definitive HE potential from mesodermal cells; (iii) contacting mesodermal cells having definitive HE potential with a composition comprising one or more growth factors and cytokines selected from the group consisting of bFGF, VEGF, SCF, IGF, EPO, IL6, and IL11; a ROCK inhibitor; optionally a Wnt pathway activator; and optionally free of TGFβ receptor/ALK inhibitor, to initiate differentiation and expansion of pluripotent stem cell-derived definitive hemogenic endothelium from the pluripotent stem cell-derived mesodermal cells having definitive HE potential; (iv) contacting pluripotent stem cell-derived definitive hemogenic endothelium with a composition comprising a ROCK inhibitor; one or more growth factors and cytokines selected from the group consisting of VEGF, bFGF, SCF, Flt3L, TPO, IL3, IL7, and IL15, and optionally, a BMP activator, to initiate differentiation of the pluripotent stem cell-derived definitive hemogenic endothelium to pre-NK cell progenitors; and (v) contacting pluripotent stem cell-derived pre-NK cell progenitors with a composition comprising one or more growth factors and cytokines selected from the group consisting of SCF, Flt3L, IL3, IL7, and IL15, but free of one or more of VEGF, bFGF, TPO, BMP activators and ROCK inhibitors, to initiate differentiation of the pluripotent stem cell-derived pre-NK cell progenitors to pluripotent stem cell-derived NK cell progenitors or NK cells; and optionally, subjecting seeded pluripotent stem cells, pluripotent stem cell-derived-mesodermal cells, and/or definitive hemogenic endothelium under low oxygen tension between about 2% to about 10%. In some embodiments, the method for generating pluripotent stem cell-derived NK lineage cells of group II further comprises contacting iPSCs with a composition comprising a MEK inhibitor, a GSK3 inhibitor, and a ROCK inhibitor, but free of TGFβ receptor/ALK inhibitors, to seed and expand the iPSCs. In some embodiments, the iPSCs are naïve iPSCs. In some embodiments, the method for generating pluripotent stem cell-derived NK lineage cells is void of generation of embryoid bodies, and is in a monolayer culturing format.

Another aspect of the invention provides a method for generating pluripotent stem cell-derived definitive hemogenic endothelium, the method comprises: (i) contacting iPSCs with a composition comprising a BMP activator, and optionally bFGF, to initiate differentiation and expansion of pluripotent stem cell-derived mesodermal cells from pluripotent stem cells; (ii) contacting pluripotent stem cell-derived mesodermal cells with a composition comprising a BMP activator, bFGF, and a GSK3 inhibitor, and optionally free of TGFβ receptor/ALK inhibitor, to initiate differentiation and expansion of pluripotent stem cell-derived mesodermal cells having definitive HE potential from pluripotent stem cell-derived mesodermal cells; (iii) contacting pluripotent stem cell-derived mesodermal cells having definitive HE potential with a composition comprising one or more growth factors and cytokines selected from the group consisting of bFGF, VEGF, SCF, IGF, EPO, IL6, and IL11; a ROCK inhibitor; and optionally a Wnt pathway activator, and optionally free of TGFβ receptor/ALK inhibitor, to initiate differentiation and expansion of pluripotent stem cell-derived definitive hemogenic endothelium from the pluripotent stem cell-derived mesodermal cells having definitive HE potential; and optionally, subjecting seeded pluripotent stem cells, pluripotent stem cell-derived mesodermal cells, and/or definitive hemogenic endothelium under low oxygen tension between about 2% to about 10%. In some embodiments, the above method for generating pluripotent stem cell-derived definitive hemogenic endothelium, further comprises: contacting iPSCs with a composition comprising a MEK inhibitor, a GSK3 inhibitor, and a ROCK inhibitor, but free of TGFβ receptor/ALK inhibitors, to seed and expand the iPSCs; and/or wherein the iPSCs are naïve iPSCs. In some embodiments, the iPSC comprises one or more genetic imprints, and wherein the one or more genetic imprints comprised in the iPSC are retained in the pluripotent stem cell derived definitive hemogenic endothelium cells differentiated therefrom. In some embodiments, the above method of differentiating iPSCs into cells of a definitive hemogenic endothelium is void of generation of embryoid bodies, and is in monolayer culturing format.

Another aspect of the invention provides a method for generating pluripotent stem cell-derived multipotent progenitors of hematopoietic lineage, comprising: (i) contacting iPSCs with a composition comprising a BMP activator, and optionally bFGF, to initiate differentiation and expansion of pluripotent stem cell-derived mesodermal cells from iPSCs; (ii) contacting pluripotent stem cell-derived mesodermal cells with a composition comprising a BMP activator, bFGF, and a GSK3 inhibitor, but free of TGFβ receptor/ALK inhibitor, to initiate differentiation and expansion of the mesodermal cells having definitive HE potential from the mesodermal cells; (iii) contacting mesodermal cells having definitive HE potential with a composition comprising a ROCK inhibitor; one or more growth factors and cytokines selected from the group consisting of bFGF, VEGF, SCF, IGF, EPO, IL6, and IL11; and optionally, a Wnt pathway activator, wherein the composition is free of TGFβ receptor/ ALK inhibitor, to initiate differentiation and expansion of definitive hemogenic endothelium from mesodermal cells having definitive HE potential; (iv) contacting definitive hemogenic endothelium with a composition comprising a BMP activator, a ROCK inhibitor, one or more growth factors and cytokines selected from the group consisting of TPO, IL3, GMCSF, EPO, bFGF, VEGF, SCF, IL6, Flt3L and IL11, to initiate differentiation of definitive hemogenic endothelium to pre-HSC; and (v) contacting pre-HSC with a composition comprising a BMP activator, one or more growth factors and cytokines selected from the group consisting of TPO, IL3, GMCSF, EPO, bFGF, VEGF, SCF, IL6, and IL11, but free of ROCK inhibitor, to initiate differentiation of the pre-HSC to hematopoietic multipotent progenitors; and optionally, subjecting seeded pluripotent stem cells, mesodermal cells, and/or definitive hemogenic endothelium under low oxygen tension between about 2% to about 10%. In some embodiments, the above method for generating pluripotent stem cell-derived hematopoiesis multipotent progenitors further comprises contacting pluripotent stem cells with a composition comprising a MEK inhibitor, a GSK3 inhibitor, and a ROCK inhibitor, but free of TGFβ receptor/ALK inhibitors, to seed and expand the pluripotent stem cells. In some embodiments, the pluripotent stem cells are iPSCs. In some embodiments, the iPSCs are naïve iPSCs. In some embodiments, the iPSC comprises one or more genetic imprints, and wherein the one or more genetic imprints comprised in the iPSC are retained in the pluripotent stem cell derived hematopoietic multipotent progenitors cells differentiated therefrom. In some embodiments, the differentiation of the pluripotent stem cells into hematopoiesis multipotent progenitors using the above method is void of generation of embryoid bodies, and is in monolayer culturing format.

A further aspect of the invention provides a composition comprising: one or more cell populations generated from the culture platform disclosed herein: pluripotent stem cells-derived (i) CD34+ definitive hemogenic endothelium (iCD34), wherein the iCD34 cells have capacity to differentiate into multipotent progenitor cells, T cell progenitors, NK cell progenitors, T cells, NK cells, NKT cells and B cells, and wherein the iCD34 cells are CD34+CD43−; (ii) definitive hemogenic endothelium (iHE), wherein the iTHE cells are CD34+, and at least one of CD43−, CD93−, CXCR4−, CD73−, and CXCR4−CD73−; (iii) pluripotent stem cell-derived definitive HSCs, wherein the iHSC is CD34+CD45+; (iv) hematopoietic multipotent progenitor cells, wherein the iMPP cells are CD34+CD45+; (v) T cell progenitors, wherein the T cell progenitors are CD34+ CD45+CD7+ or CD34−CD45+CD7+; (vi) T cells, wherein the T cells are CD45+CD3+CD4+ or CD45+CD3+CD8+; (vii) NK cell progenitors, wherein the NK cell progenitors are CD45+CD56+CD7+; (viii) NK cells, wherein the NK cells are CD3−CD45+CD56+, and optionally further defined by NKp46+, CD57+, and CD16+; (ix) NKT cells, wherein the NKT cells are CD45+Vα24Jα18+CD3+; and (x) B cells, wherein the B cells are CD45+CD19+.

Still a further aspect of the invention provides one or more cell lines, or clonal cells generated using the methods disclosed herein: pluripotent stem cell-derived (i) CD34+ definitive hemogenic endothelium (iCD34), wherein the iCD34 cells have capacity to differentiate into multipotent progenitor cells, T cell progenitors, NK cell progenitors, T cells, NK cells, and NKT cells, and wherein the iCD34 cells are CD34+CD43−; (ii) definitive hemogenic endothelium (iHE), wherein the HE cell line or clonal cells are CD34+, and at least one of CD43−, CD93−, CXCR4−, CD73−, and CXCR4−CD73−; (iii) definitive HSCs, wherein the iHSCs is CD34+CD45+; (iv) hematopoietic multipotent progenitor cells (iMPP), wherein the iMPP cells are CD34+CD45+; (v) T cell progenitors, wherein the T cell progenitors are CD34+ CD45+CD7+ or CD34−CD45+CD7+; (vi) T cells, wherein the T cells are CD45+CD3+CD4+ or CD45+CD3+CD8+; (vii) NK cell progenitors, wherein the NK cell progenitors are CD45+CD56+CD7+; (viii) NK cells, wherein the NK cells are CD3−CD45+CD56+, and optionally further defined by NKp46+, CD57+, and CD16+; (ix) NKT cells, wherein the NKT cells are CD45+Vα24Jα18+CD3+; and (x) B cells, wherein the B cells are CD45+CD19+.

Another aspect of the present invention provides a method of promoting hematopoietic self-renewal, reconstitution or engraftment using one or more of cell populations, cell lines or clonal cells generated using methods as disclosed: pluripotent stem cell-derived (i) CD34+ definitive hemogenic endothelium (iCD34), wherein the iCD34 cells have capacity to differentiate into multipotent progenitor cells, T cell progenitors, NK cell progenitors, T cells NK cells and NKT cells, and wherein the iCD34 cells are CD34+CD43−; (ii) definitive hemogenic endothelium (iHE), wherein the iHE cell line or clonal cells are CD34+, and at least one of CD43−, CD93−, CXCR4−, CD73−, and CXCR4−CD73−; (iii) definitive HSCs, wherein the iHSCs are CD34+CD45+; (iv) hematopoietic multipotent progenitor cells, wherein the iMPP cells are CD34+CD45+; (v) T cell progenitors, wherein the T cell progenitors are CD34+CD45+CD7+ or CD34−CD45+CD7+; (vi) T cells, wherein the T cells are CD45+CD3+CD4+ or CD45+CD3+CD8+; (vii) NK cell progenitors, wherein the NK cell progenitors are CD45+CD56+CD7+; (viii) NK cells, wherein the NK cells are CD3−CD45+CD56+, and optionally further defined by NKp46+, CD57+, and CD16+; (ix) NKT cells, wherein the NKT cells are CD45+Vα24Jα18+CD3+; and (x) B cells, wherein the B cells are CD45+CD19+.

A further aspect of the present invention provides a method of generating hematopoietic lineage cells with enhanced therapeutic properties, and the method comprises: obtaining iPSCs comprising one or more genetic imprints; and directing differentiation of iPSCs to hematopoietic lineage cells. The step of directed differentiation further comprises: (i) contacting the pluripotent stem cells with a composition comprising a BMP pathway activator, and optionally bFGF, to obtain mesodermal cells; and (ii) contacting the mesodermal cells with a composition comprising a BMP pathway activator, bFGF, and a WNT pathway activator, to obtain mesodermal cells having definitive hemogenic endothelium (HE) potential, wherein the mesodermal cells having definitive hemogenic endothelium (HE) potential are capable of providing hematopoietic lineage cells. Preferably, the mesodermal cells and mesodermal cells having definitive HE potential are obtained in steps (i) and (ii) without the step of forming embryoid bodies, and the obtained hematopoietic lineage cells comprise definitive hemogenic endothelium cells, hematopoietic stem and progenitor cells (HSC), hematopoietic multipotent progenitor cell (MPP), pre-T cell progenitor cells, pre-NK cell progenitor cells, T cell progenitor cells, NK cell progenitor cells, T cells, NK cells, NKT cells, or B cells. Moreover, the hematopoietic lineage cells retain the genetic imprints comprised in the iPSCs for directed differentiation.

In some embodiments, the step of directed differentiation of the above method further comprises: (i) contacting the mesodermal cells having definitive HE potential with a composition comprising bFGF and a ROCK inhibitor to obtain definitive HE cells; (ii) contacting the definitive HE cells with a composition comprising a BMP activator, and optionally a ROCK inhibitor, and one or more growth factors and cytokines selected from the group consisting of TPO, IL3, GMCSF, EPO, bFGF, VEGF, SCF, IL6, Flt3L and IL11 to obtain hematopoietic multipotent progenitor cells (MPP); (iii) contacting the definitive HE cells with a composition comprising one or more growth factors and cytokines selected from the group consisting of SCF, Flt3L, and IL7; and optionally one or more of a BMP activator, a ROCK inhibitor, TPO, VEGF and bFGF to obtain pre-T cell progenitors, T cell progenitors, and/or T cells; or (iv) contacting the definitive HE cells with a composition comprising one or more growth factors and cytokines selected from the group consisting of SCF, Flt3L, TPO, IL7 and IL15, and optionally one or more of a BMP activator, a ROCK inhibitor, VEGF and bFGF to obtain pre-NK cell progenitors, NK cell progenitors, and/or NK cells.

To obtain iPSCs comprising one or more genetic imprints, one approach may be introducing one or more genetic imprints to iPSC by genetic editing during or after reprogramming a non-pluripotent cell to iPSC, wherein the genetic imprint comprises one or more genetically modified modalities, and the genetic imprint is introduced through genomic insertion, deletion or substitution in the genome of the iPSC. Another approach may be (i) introducing one or more genetic imprints to iPSC by obtaining a source specific immune cell that is donor-, disease-, or treatment response-specific, wherein the immune cell presents retainable therapeutic attributes; (ii) reprogramming the source specific immune cell to iPSC; and optionally (iii) introducing additional genetic imprints to iPSC of step (ii) by genetic editing during or after reprogramming the source specific immune cell to iPSC. As to the genetically modified modalities comprised in the source cells, iPSCs and or iPSC derived cells, they may comprise one or more of safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the iPSCs or derivative cells thereof.

In some embodiments, the genetically modified modalities comprise one or more of (i) deletion or reduced expression of B2M, TAP1, TAP2, Tapasin, NLRC5, PD1, LAG3, TIM3, RFXANK, CITTA, RFX5, or RFXAP; (ii) introduced or increased expression of HLA-E, HLA-G, HACD16, 41BBL, CD3, CD4, CD8, CD47, CD137, CD80, PDL1, $A_{2A}R$, CAR, TCR, or surface triggering receptors for bi- or multi-specific engagers. In some embodiments, the above genetically modified modalities are retained in one or more of pluripotent stem cell derived definitive HE cells, hematopoietic multipotent progenitors, T cell progenitors, NK cell progenitors, T cells, NK cells, NKT cells, and B cells. In some embodiments, the bi- or multi-specific engagers are specific to one or more lymphoid cell surface receptors, and are specific to one or more tumor-specific antigen on the surface of a tumor cell. In particular embodiments, the surface triggering receptor is universal for the hematopoietic lineage cells comprising T, NK, NKT, macrophage, and neutrophils. In certain embodiments, the universal surface triggering receptor comprises an anti-epitope and a co-stimulatory domain, wherein the anti-epitope is specific to the bi- or multi-specific engager. In some embodiments, the co-stimulatory domain comprise IL2. In some embodiments, the lymphoid cell surface receptor comprises one or more of surface expressing engineered modalities, CD3, CD16, CD64, and CD89; whereas the tumor-specific antigen comprises one or more of CD19, CD20, CD30, EGFR, HER2/ERBB2/neu, EPCAM, EphA2 and CEA. In some embodiments, the therapeutic attributes of the source specific immune cell comprise one or more of (i) antigen targeting receptor expression; (ii) HLA presentation or lack thereof; (iii) resistance to tumor microenvironment; (iv) induction of bystander immune cells and immune modulations; (iv) improved on-target specificity with reduced off-tumor effect; (v) resistance to treatment such as chemotherapy; and (vi) improved homing, persistence, and cytotoxicity.

Yet another aspect of the present invention provides hematopoietic lineage cells having enhanced therapeutic properties, which cells comprise the same genetic imprints comprised in pluripotent stem cells from which the hematopoietic lineage cells are derived. In some embodiments, the genetic imprints of the pluripotent stem cells comprise (i) one or more genetically modified modalities obtained through genomic insertion, deletion or substitution in the genome of the pluripotent cells during or after reprogramming a non-pluripotent cell to iPSC; or (ii) one or more retainable therapeutic attributes of a source specific immune cell that is donor-, disease-, or treatment response-specific, and wherein the pluripotent cells are reprogrammed from the source specific immune cell. In some embodiments, the genetically modified modalities comprise one or more of: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the iPSCs or derivative cells thereof.

In some embodiments, the genetically modified modalities comprise one or more of (i) deletion or reduced expression of B2M, TAP1, TAP2, Tapasin, NLRC5, PD1, LAG3, TIM3, RFXANK, CITTA, RFX5, or RFXAP; (ii) introduced or increased expression of HLA-E, HLA-G, HACD16, 41BBL, CD3, CD4, CD8, CD47, CD137, CD80, PDL1, A2AR, CAR, TCR, or surface triggering receptors for bi- or multi-specific engagers. In particular embodiments, the surface triggering receptor is universal for the hematopoietic lineage cells comprising T, NK, NKT, macrophage, and neutrophils. In certain embodiments, the universal surface triggering receptor comprises an anti-epitope and a co-stimulatory domain, wherein the anti-epitope is specific to the bi- or multi-specific engager. In some embodiments, the co-stimulatory domain comprise IL2. In still some embodiments, the hematopoietic lineage cells comprise the therapeutic attributes of the source specific immune cell relating to one or more of (i) antigen targeting receptor expression; (ii) HLA presentation or lack thereof; (iii) resistance to tumor microenvironment; (iv) induction of bystander immune cells and immune modulations; (iv) improved on-target specificity with reduced off-tumor effect; (v) resistance to treatment such as chemotherapy; and (vi) improved homing, persistence, and cytotoxicity.

In particular embodiments, a bi- or multi-specific engager is specific to the universal surface triggering receptor, and is specific to one or more tumor-specific antigen on the surface of a tumor cell. In some embodiments, the tumor-specific antigen comprises one or more of CD19, CD20, CD30, EGFR, HER2/ERBB2/neu, EPCAM, EphA2 and CEA. In particular embodiments, the therapeutic attributes of the source specific immune cell comprise one or more of (i) antigen targeting receptor expression; (ii) HLA presentation or lack thereof; (iii) resistance to tumor microenvironment; (iv) induction of bystander immune cells and immune modulations; (iv) improved on-target specificity with reduced off-tumor effect; (v) resistance to treatment such as chemotherapy; and (vi) improved homing, persistence, and cytotoxicity.

Particular embodiments comprise contacting the pluripotent stem cells with a composition comprising a MEK inhibitor, a GSK3 inhibitor, and a ROCK inhibitor, to seed and expand the cells prior to introducing one or more genetic imprints to iPSC.

In particular embodiments, the surface triggering receptor is universal for hematopoietic lineage cells comprising T, NK, NKT, macrophage, and neutrophils. In certain embodiments, a universal surface triggering receptor comprises an anti-epitope and a co-stimulatory domain, wherein the anti-epitope is specific to the bi- or multi-specific engager.

In some embodiments, a co-stimulatory domain comprises IL2.

In particular embodiments, a bi- or multi-specific engager is specific to one or more tumor-specific antigen on the surface of a tumor cell.

In some embodiments, the hematopoietic lineage cells comprise definitive hemogenic endothelium cells, hematopoietic stem and progenitor cells (HSC), hematopoietic multipotent progenitor cell (MPP), pre-T cell progenitor cells, pre-NK cell progenitor cells, T cell progenitor cells, NK cell progenitor cells, T cells, NK cells, NKT cells, B cells, macrophage, or neutrophils. In some embodiments, the T cells comprise T regulatory cells (Treg), central memory T cells (Tcm), stem cell memory (Tscm), and/or effector memory T cells (Tem). In particular embodiments, NK cells comprise adaptive NK cells.

In particular embodiments, hematopoietic lineage cells comprise one or more bi- or multi-specific engagers for surface receptor. In some embodiments, a bi- or multi-specific engager a) is hematopoietic lineage cell type specific, and wherein the engager is specific to a surface receptor comprising CD3, CD16, CD64, or CD89; orb) is hematopoietic lineage cell type independent, wherein the hematopoietic lineage cells comprise a universal surface triggering receptor, and wherein the engager is specific to the universal surface triggering receptor.

Particular aspects are drawn to methods of treating a subject in need of cell therapy comprising administering a therapeutically sufficient number of T cell progenitors derived from induced pluripotent stem cell (iPSC) differentiation. In some embodiments, the subject (i) is a candidate for bone marrow or stem cell transplantation, or the subject has received chemotherapy or irradiation therapy; (ii) has received bone marrow ablative or non-myeolablative chemotherapy or radiation therapy; (iii) has a hyperproliferative disorder or a cancer of hematopoietic system; (iv) has a solid tumor; or (v) has a virus infection or a disease associated with virus infection; wherein the administered T cell progenitors rejuvenate thymus and reconstitute T cells in vivo.

In some embodiments, the methods of treating a subject in need of cell therapy further comprise administering a pharmaceutical composition comprising a bi- or multi-specific engager, wherein the bi- or multi-specific engager a) is effector cell type specific, and wherein the engager is specific to a surface receptor comprising CD3, CD16, CD64, or CD89; or b) is effector cell type independent, and wherein the engager is specific to a universal surface triggering receptor comprised in the T-progenitor cells and T cells derived therefrom. In some embodiments, the genetic imprint from the source specific immune cells comprises one or more of (i) antigen targeting receptor expression; (ii) HLA presentation or lack thereof, (iii) resistance to tumor microenvironment; (iv) induction of bystander immune cells and immune modulations; (iv) improved on-target specificity with reduced off-tumor effect; (v) resistance to treatment such as chemotherapy; and (vi) improved homing, persistence, and cytotoxicity.

Also provided is a pharmaceutical composition comprising a pharmaceutically acceptable medium, and one or more of the hematopoietic lineage cells having enhanced therapeutic properties produced using a method described herein. These hematopoietic lineage cells having enhanced therapeutic properties include definitive hemogenic endothelium cells, hematopoietic stem and progenitor cells (HSC), hematopoietic multipotent progenitor cell (MPP), pre-T cell progenitor cells, pre-NK cell progenitor cells, T cell progenitor cells, NK cell progenitor cells, T cells, NK cells, NKT cells, or B cells. In some embodiments, the T cells comprise T regulatory cells (Treg), central memory T cells (Tcm), stem cell memory (Tscm), and/or effector memory T cells (Tem). In some embodiments, the NK cells comprise adaptive NK cells. Further provided is the therapeutic use of the above pharmaceutical composition by introducing the composition to a subject suitable for adoptive cell therapy, wherein the subject has an autoimmune disorder; a hematological malignancy; a solid tumor; cancer; or an infection associated with HIV, RSV, EBV, CMV, adenovirus, or BK polyomavirus.

Another aspect of the invention provides an antibody composition comprising one or more antibodies specific to at least one markers selected from CCR10, CD164, CD95, CD144, CD166, Lymphotoxin β Receptor, CD252, CD55, CD40, CD46, CD340, CD19, CD106, CD66a/c/e, CD49d, CD45RB, DLL4, CD107a, CD116, CD324, CD123, CD49f, CD200, CD71, CD172a, CD21, CD184, CD263, CD221, Notch 4, MSC, CD97, CD319, CD69, CD338, Podoplanin, CD111, CD304, CD326, CD257, CD100, CD32, CD253, CD79b, CD33, CD83, GARP, CD183, CD357, CD31, CD165, CD102, CD146, CD49c, CD13, CD58, Integrin α9β1, CD51, CD10, CD202b, CD141, CD49a, CD9, CD201, CD47, CD262, CD109, CD39, CD317, CD143, integrin β5, CD105, CD155, SSEA-4 and CD 93; wherein the markers are for identifying definitive hemogenic endothelium. In one embodiment, the antibody composition comprises an antibody specific to CD93; wherein the cells conjugated with the antibody specific to CD93 have one or more of CD34+, CD43−, CD73−, CXCR4−, and CD73−CXCR4− phenotype.

Yet another aspect of the present invention provides a method of identifying definitive hemogenic endothelium in pluripotent stem cell differentiation, which comprises (i) obtaining a cell population undergoing differentiation; (ii) introducing to the cell population an antibody specific to CD93; and (iii) identifying the cell population having CD93 expression level less than 1%. In some embodiments, the cell population undergoing differentiation comprises CD34+ or CD34+CD43− cells. In some embodiments, the method further comprises isolating CD34+ cells from the cell population undergoing differentiation; or isolating CD34+CD43− cells from the cell population undergoing differentiation.

Further provided is a method of generating pluripotent stem cell derived definitive hemogenic endothelium, which comprises culturing pluripotent stem cell derived mesodermal cells having definitive hemogenic endothelium (HE) potential in a medium comprising a Wnt pathway agonist to obtain definitive HE cells. Obtaining definitive HE in the presence of a Wnt pathway activator increases HE numbers and percentage in cell population; improves HE differentiation potency; and/or improves HE cellularity as compared to culturing without the Wnt pathway activator. In some embodiments, the medium further comprises a ROCK inhibitor, and one or more growth factors and cytokines selected from the group consisting of bFGF, VEGF, SCF, IGF, EPO, IL6, and IL11. In some embodiments, the pluripotent stem cell pluripotent stem cells are iPSCs. In some embodiments the iPSCs are naïve iPSCs. In some embodiments, the iPSC comprises one or more genetic imprints as described above, which are retained in the pluripotent stem cell-derived definitive HE.

Particular aspects of the present invention are directed to antigen-specific iPSC or derivative hematopoietic lineage cells produced by a method described herein. Certain aspects of the present invention are drawn to compositions comprising antigen-specific iPSC or derivative hematopoietic lineage cells produced by a method described herein. Some aspects of the present invention are drawn to pharmaceutical compositions comprising antigen-specific iPSC or derivative hematopoietic lineage cells produced by a method described herein and a pharmaceutically acceptable medium.

Also provided herein is a method of generating antigen-specific induced pluripotent stem cells (iPSC) and derivative hematopoietic lineage cells, which comprises: (i) isolating primary antigen specific T cells from a selected source that is donor-, disease-, or treatment response-specific; (ii) reprogramming the primary antigen-specific T cells to obtain pluripotent stem cells; and (iii) directing differentiation of the pluripotent stem cells to hematopoietic lineage cells. In some embodiments, the step of directed differentiation comprises (i) contacting the pluripotent stem cells with a composition comprising a BMP pathway activator, and optionally bFGF, to obtain mesodermal cells; and (ii) contacting the mesodermal cells with a composition comprising a BMP pathway activator, bFGF, and a WNT pathway activator, to obtain mesodermal cells having definitive hemogenic endothelium (HE) potential without forming embryoid bodies. In some embodiments, the isolated primary antigen specific T cells are enriched by: (i) co-culturing primary antigen specific T cells with tumor cells, non-transformed cells, dendritic cells, thymic epithelial cell, endothelial cells or artificial antigen presenting cells, plasma particles or peptides expressing antigen(s) of interest expressing antigen(s) of interest; or sorting the primary antigen specific T cells using T cell receptor-specific binding agents that are specific to antigen(s) of interest. In some embodiments, the primary antigen specific T cells or enriched primary antigen specific T cells may be modulated using transcription factors or small molecules to rejuvenate the cells.

Particular aspects of the present invention are directed to antigen-specific iPSC or derivative hematopoietic lineage cells produced by a method described herein. Certain aspects of the present invention are drawn to compositions comprising antigen-specific iPSC or derivative hematopoietic lineage cells produced by a method described herein. Some aspects of the present invention are drawn to pharmaceutical compositions comprising antigen-specific iPSC or derivative hematopoietic lineage cells produced by a method described herein and a pharmaceutically acceptable medium.

In some embodiments, the antigen-specific pluripotent stem cells obtained from the above method may be further genetically engineered during or after reprogramming to include genetic imprints comprising one or more genetically modified modalities through genomic insertion, deletion or substitution. In some embodiments, the genetically modified modalities comprise one or more of: safety switch proteins, targeting modalities, receptors, signaling molecules, transcription factors, pharmaceutically active proteins and peptides, drug target candidates; cell surface proteins conveying a secondary or tertiary antigen specificity; or proteins promoting engraftment, trafficking, homing, viability, self-renewal, persistence, immune response regulation and modulation, and/or survival of the iPSCs or derivative cells thereof. In some embodiments, the genetically modified modalities comprise one or more of (i) deletion or reduced expression of B2M, TAP1, TAP2, Tapasin, NLRC5, PD1, LAG3, TIM3, RFXANK, CIITA, RFX5, or RFXAP; (ii) introduced or increased expression of HLA-E, HLA-G, HACD16, 41BBL, CD3, CD4, CD8, CD47, CD137, CD80, PDL1, $A_{2A}R$, CAR, TCR, or surface triggering receptor for bi- or multi-specific engagers. In some embodiments, the bi- or multi-specific engager is hematopoietic lineage cell type specific, as such the engager is specific to a surface receptor selected from CD3, CD16, CD64, or CD89. In some embodiments, the surface triggering receptor is universal for the hematopoietic lineage cells comprising T, NK, NKT, macrophage, and neutrophils. In some embodiments, the bi- or multi-specific engager is hematopoietic lineage cell type independent, and is capable of coupling with hematopoietic lineage cells comprising a matching universal surface triggering receptor. In some embodiments, the universal surface triggering receptor comprises an anti-epitope and a co-stimulatory domain, wherein the anti-epitope is specific to the epitope comprised in the bi- or multi-specific engager. In some embodiments, the co-stimulatory domain of the universal surface triggering receptor comprises the whole or partial IL2 for conotical or non-conotical cellular activation and/or effector cell function enhancement. In some embodiments, the bi- or multi-specific universal engager is specific to one or more tumor-specific antigen on the surface of a tumor cell. In some embodiments, the tumor-specific antigen comprises one or more of CD19, CD20, CD30, EGFR, HER2/ERBB2/neu, EPCAM, EphA2 and CEA. In some embodiments, the bi- or multi-specific engager is specific to the universal surface triggering receptor, and is specific to one or more tumor-specific antigen on the surface of a tumor cell.

In some embodiments, the antigen specific iPSC derived hematopoietic lineage cells comprise definitive hemogenic endothelium (HE) cells, hematopoietic stem and progenitor cells (HSC), hematopoietic multipotent progenitor cell (MPP), pre-T cell progenitor cells, pre-NK cell progenitor cells, T cell progenitor cells, NK cell progenitor cells, T cells, NK cells, NKT cells, B cells, macrophages, and/or neutrophils.

An additional aspect of the present invention provides a method for determine clonality of induced pluripotent stem cells and derivative cells thereof. The general method comprises reprogramming a mature source T or B cell to obtain induced pluripotent stem cells (iPSCs); and detecting the presence, in the iPSCs or the hematopoietic lineage cells derived therefrom, of a specific V(D)J recombination that is same as the one comprised in the mature T or B cell for generating the iPSC. In some embodiments, the above method further comprises isolating iPSCs or hematopoietic lineage cells comprising the same V(D)J recombination as that of the mature source T or B cell. In some embodiments, the above method comprises, prior to reprogramming the source cells, obtaining a mature source T or B cell for reprogramming; and determining V(D)J recombination comprised in immunoglobulins (Ig) or T cell receptors (TCR) that is specific to the mature source T or B cell.

Yet still another aspect of the present invention provides a method of tracking adoptive cell in vivo in a cell therapy, which comprises obtaining a sample of blood, tissue, or tumor biopsy from a subject receiving adoptive cells for therapy, isolating effector cells in the sample; and determining the V(D)J recombination in the effector cells; wherein the adoptive cells are derived from pluripotent stem cells reprogrammed from a mature source T or B cell; wherein the mature source T or B cell comprises a specific V(D)J recombination; and wherein the presence of a same V(D)J recombination as that of the mature source T or B cell is indicative of adoptive cell homing, persistence and/or expansion.

Also provided is a pharmaceutical composition comprising a pharmaceutically acceptable medium, and one or more of the antigen-specific hematopoietic lineage cells generated using the above methods, including definitive hemogenic endothelium cells, hematopoietic stem and progenitor cells (HSC), hematopoietic multipotent progenitor cell (MPP), pre-T cell progenitor cells, pre-NK cell progenitor cells, T cell progenitor cells, NK cell progenitor cells, T cells, NK cells, NKT cells, or B cells. In some embodiments, the T cells comprise T regulatory cells (Treg), central memory T cells (Tcm), stem cell memory (Tscm), and/or effector memory T cells (Tem). In some embodiments, the NK cells comprise adaptive NK cells. Further provided is the therapeutic use of the above pharmaceutical composition by introducing the composition to a subject suitable for adoptive cell therapy, wherein the subject has an autoimmune disorder; a hematological malignancy; a solid tumor; cancer; or an infection associated with HIV, RSV, EBV, CMV, adenovirus, or BK polyomavirus.

In summary, the present invention provides methods and compositions enabling a direct differentiation of pluripotent stem cells in monolayer without generating embryoid bodies from pluripotent stem cells, thereby achieving differentiation and expansion of mesodermal cells, definitive HE, and definitive HSCs, from which other hematopoietic lineage cells can be obtained in a scalable, reliable manner with a very high level of efficiency.

BRIEF DESCRIPTION OF THE DRAWINGS

FIG. 2 shows a schematic diagram for a multi-staged culture process for the hematopoietic differentiation of induced pluripotent stem cells to T cell progenitors (ipro-T) and fully differentiated T (iT) cells. Note that culture can be converted to fully-defined with the substitution of Matrigel™ for Vitronectin.

FIG. 8A-D shows the ability of sorted Day 10 iCD34 cells to be cryopreserved and maintain pan-hematopoietic and lymphoid potential. A) Cryopreserved Day 10 iCD34 cells can survive and exhibit a similar phenotype to fresh iCD34+ cells when thawed. B) Viability of cryopreserved Day 10 sorted CD34+ cells immediately after thaw. C) Cyropreserved Day 10 sorted iCD34+ cells can survive and generate CD45+ hematopoietic cells during iMPP assay. D) Cryopreserved Day 10 sorted iCD34+ cells can survive and generate iT and iNK lymphoid progenitors.

FIG. 10A-C shows early CD34+CD7+ T cell progenitors and mature CD4+ and CD8+ T cell subsets derived from hiPSCs utilizing a CD45+CD56− gating strategy. A) Early T cell lineage markers mark the presence of ipro-T cells as defined by CD34+/CD7+. B) Mature T cell markers mark the presence of mature T cells as defined by CD4+ or CD8+ cells. C) 5 day T cell differentiation comparing the potential of CD34 positive cells from umbilical cord blood and iCD34 positive cells to give rise to ipro-T cells.

FIG. 11A-C shows early CD56+CD7+CD161+NK cell progenitors and mature CD56+CD16+CD8+NK cell subsets derived from hiPSCs utilizing a CD45+ gating strategy. A) Early NK lineage markers mark the presence of ipro-NK cells as defined by CD7 and CD56. B) Mature NK lineage markers mark the presence of mature NK cells as defined by CD57, CD16, CD94 and CD56. C) 5 day NK cell differentiation comparing the potential of CD34 positive cells from umbilical cord blood and iCD34 positive cells to give rise to ipro-NK cells.

FIG. 26 shows the anti-human antibodies included in the analysis for cell surface proteins expression on hiPSC-derived CD34+ cells.

FIG. 40A-B shows the off-the-shelf targeting strategy for engaging cancer and other disease target cells with the entire effector repertoire. A. Illustration of hematopoietic effector cells derived from iPSCs with respective lineage specific triggering molecule that can be coupled to engagers recognizing specific target cells. B. Illustration of engineering a universal engager (specific and lineage independent triggering molecule comprising specific anti-epitope engagement) which is ubiquitously expressed on all derived hematopoietic cells.

DETAILED DESCRIPTION OF THE INVENTION

Figure 1:
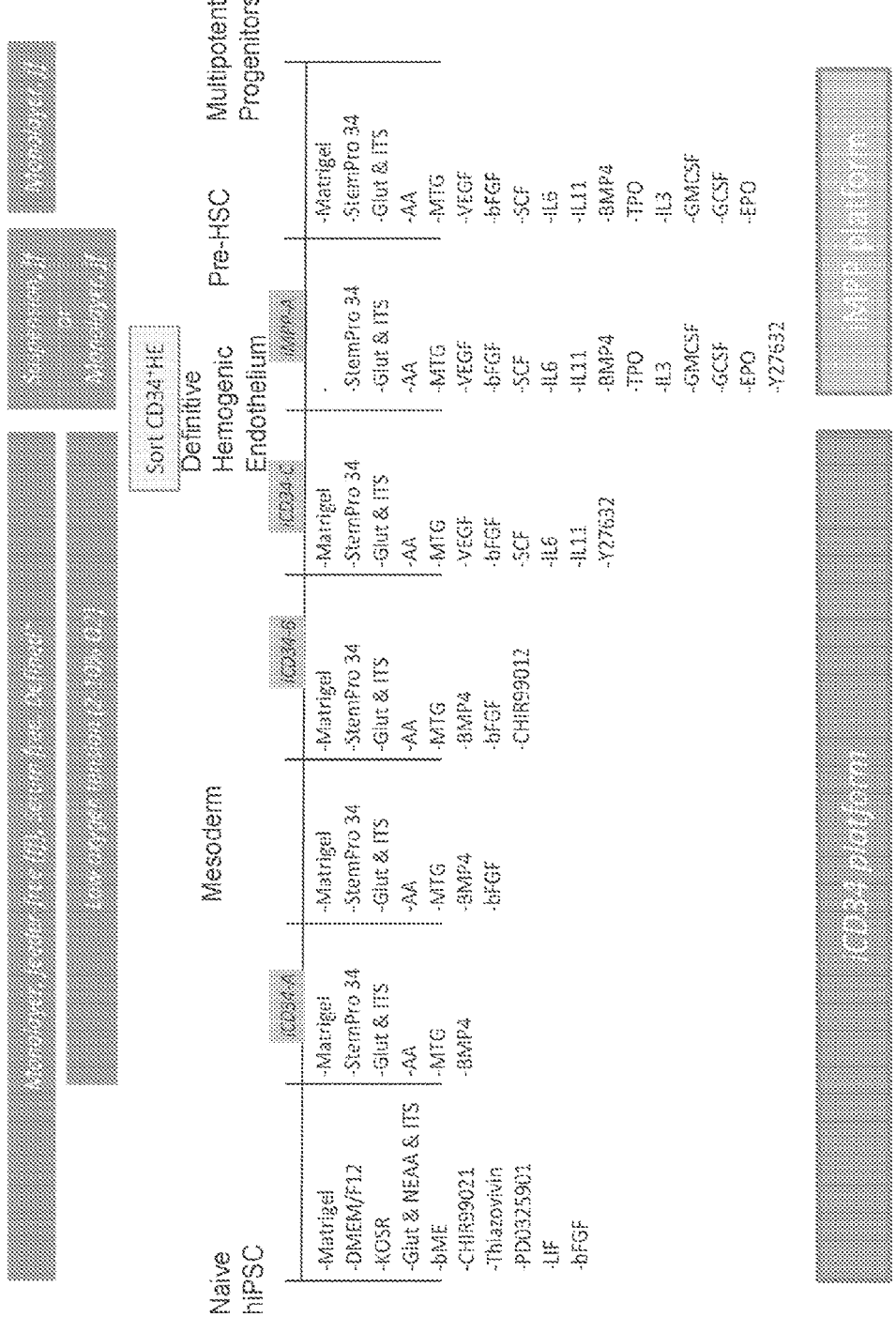
FIG. 1 shows a schematic diagram for a multi-staged culture process for the hematopoietic differentiation of induced pluripotent stem cells (iPSCs) to definitive hemogenic endothelium (iHE) and multipotent progenitors (iMPP). Note that culture can be converted to fully-defined with the substitution of Matrigel™ for Vitronectin.

The invention generally relates to methods and compositions for differentiating stem cells toward a definitive hematopoietic cell fate. More particularly, the invention provides a multi-stage differentiation platform wherein iPSC or iPSC-derived cells at various stages of development can be induced to assume a definitive hematopoietic phenotype, ranging from definitive hemogenic endothelium, to fully differentiated hematopoietic cells including, T cells, B cells, NKT cells, and NK cells. That is, the invention provides methods and compositions for making a cell more susceptible to assuming a definitive hematopoietic fate, for example, a CD34+ definitive hematopoietic stem cell. Alternatively, the method and compositions of the present invention generate definitive hemogenic endothelium (HE) from naïve iPSCs in a scalable manner by avoiding the formation of EBs or aggregates.

A. Definitions

Unless defined otherwise, all technical and scientific terms used herein have the same meaning as commonly understood by those of ordinary skill in the art to which the invention belongs. For the purposes of the present invention, the following terms are defined below. The articles "a," "an," and "the" are used herein to refer to one or to more than one (i.e. to at least one) of the grammatical object of the article. By way of example, "an element" means one element or more than one element.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% compared to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length 15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

As used herein, the term "substantially" or "essentially" refers to a quantity, level, value, number, frequency, percentage, dimension, size, amount, weight or length that is about 90%, 91%, 92%, 93%, 94%, 95%, 96%, 97%, 98%, or 99% or higher compared to a reference quantity, level, value, number, frequency, percentage, dimension, size, amount, weight or length. In one embodiment, the terms "essentially the same" or "substantially the same" refer a range of quantity, level, value, number, frequency, percentage, dimension, size, amount, weight or length that is about the same as a reference quantity, level, value, number, frequency, percentage, dimension, size, amount, weight or length.

As used herein, the terms "substantially free of" and "essentially free of" are used interchangeably, and when used to describe a composition, such as a cell population or culture media, refer to a composition that is free of a specified substance or its source thereof, such as, 95% free, 96% free, 97% free, 98% free, 99% free of the specified substance or its source thereof, or is undetectable as measured by conventional means. The term "free of" or "essentially free of" a certain ingredient or substance in a composition also means that no such ingredient or substance is (1) included in the composition at any concentration, or (2) included in the composition functionally inert, but at a low concentration. Similar meaning can be applied to the term "absence of," where referring to the absence of a particular substance or its source thereof of a composition.

As used herein, the term "appreciable" refers to a range of quantity, level, value, number, frequency, percentage, dimension, size, amount, weight or length or an event that is readily detectable by one or more standard methods. The terms "not-appreciable" and "not appreciable" and equivalents refer to a range of quantity, level, value, number, frequency, percentage, dimension, size, amount, weight or length or an event that is not readily detectable or undetectable by standard methods. In one embodiment, an event is not appreciable if it occurs less than 5%, 4%, 3%, 2%, 1%, 0.1%, 0.01%, 0.001% or less of the time.

Throughout this specification, unless the context requires otherwise, the words "comprise," "comprises" and "comprising" will be understood to imply the inclusion of a stated step or element or group of steps or elements but not the exclusion of any other step or element or group of steps or elements. In particular embodiments, the terms "include," "has," "contains," and "comprise" are used synonymously.

By "consisting of" is meant including, and limited to, whatever follows the phrase "consisting of" Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

The term "ex vivo" refers generally to activities that take place outside an organism, such as experimentation or measurements done in or on living tissue in an artificial environment outside the organism, preferably with minimum alteration of the natural conditions. In particular embodiments, "ex vivo" procedures involve living cells or tissues taken from an organism and cultured in a laboratory apparatus, usually under sterile conditions, and typically for a few hours or up to about 24 hours, but including up to 48 or 72 hours or longer, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The term "in vivo" refers generally to activities that take place inside an organism.

As used herein, the term "primitive streak" refers to the early embryonic structure that marks the start of gastrulation or the formation of the three germ layers; mesoderm, endoderm and ectoderm.

As used herein, the term "mesoderm" refers to one of the three germ layers that appears during early embryogenesis and which gives rise to various specialized cell types including blood cells of the circulatory system, muscles, the heart, the dermis, skeleton, and other supportive and connective tissues.

As used herein, the term "definitive hemogenic endothelium" (HE) or "pluripotent stem cell-derived definitive hemogenic endothelium" (iHE) refers to a subset of endothelial cells that give rise to hematopoietic stem and progenitor cells in a process called endothelial-to-hematopoietic transition. The development of hematopoietic cells in the embryo proceeds sequentially from lateral plate mesoderm through the hemangioblast to the definitive hemogenic endothelium and hematopoietic progenitors.

The term "hematopoietic stem cell," or "definitive hematopoietic stem cell" as used herein, refers to CD34+ stem cells capable of giving rise to both mature myeloid and lymphoid cell types including T cells, natural killer cells and B cells.

As used herein, the terms "reprogramming" or "dedifferentiation" or "increasing cell potency" or "increasing developmental potency" refers to a method of increasing the potency of a cell or dedifferentiating the cell to a less differentiated state. For example, a cell that has an increased cell potency has more developmental plasticity (i.e., can differentiate into more cell types) compared to the same cell in the non-reprogrammed state. In other words, a reprogrammed cell is one that is in a less differentiated state than the same cell in a non-reprogrammed state.

As used herein, the term "differentiation" is the process by which an unspecialized ("uncommitted") or less specialized cell acquires the features of a specialized cell such as, for example, a blood cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type.

As used herein, the term "differentiation marker gene," or "differentiation gene," refers to genes whose expression are indicative of cell differentiation occurring within a cell, such as a pluripotent cell. Differentiation marker genes include, but are not limited to, the following genes: FOXA2, FGF5, SOX17, XIST, NODAL, COL3A1, OTX2, DUSP6, EOMES, NR2F2, NR0B1, CXCR4, CYP2B6, GATA3, GATA4, ERBB4, GATA6, HOXC6, INHA, SMAD6, RORA, NIPBL, TNFSF11, CDH11, ZIC4, GAL, SOX3, PITX2, APOA2, CXCL5, CER1, FOXQ1, MLL5, DPP10, GSC, PCDH10, CTCFL, PCDH20, TSHZ1, MEGF10, MYC, DKK1, BMP2, LEFTY2, HES, CDX2, GNAS, EGR1, COL3A1, TCF4, HEPH, KDR, TOX, FOXA1, LCK, PCDH7, CD1D FOXG1, LEFTY1, TUJ1, T gene (Brachyury), ZIC1, GATA1, GATA2, HDAC4, HDAC5, HDAC7, HDAC9, NOTCH1, NOTCH2, NOTCH4, PAX5, RBPJ, RUNX1, STAT and STAT3.

As used herein, the term "differentiation marker gene profile," or "differentiation gene profile," "differentiation gene expression profile," "differentiation gene expression signature," "differentiation gene expression panel," "differentiation gene panel," or "differentiation gene signature" refers to the expression or levels of expression of a plurality of differentiation marker genes.

As used herein, the term "potency" refers to the sum of all developmental options accessible to the cell (i.e., the developmental potency). The continuum of cell potency includes, but is not limited to, totipotent cells, pluripotent cells, multipotent cells, oligopotent cells, unipotent cells, and terminally differentiated cells.

As used herein, the term "pluripotent" refers to the ability of a cell to form all lineages of the body or soma (i.e., the embryo proper). For example, embryonic stem cells are a type of pluripotent stem cells that are able to form cells from each of the three germs layers, the ectoderm, the mesoderm, and the endoderm. Pluripotency is a continuum of developmental potencies ranging from the incompletely or partially pluripotent cell (e.g., an epiblast stem cell or EpiSC), which is unable to give rise to a complete organism to the more primitive, more pluripotent cell, which is able to give rise to a complete organism (e.g., an embryonic stem cell).

As used herein, the term "induced pluripotent stem cells" or, iPSCs, means that the stem cells are produced from differentiated adult, neonatal or fetal cells that have been induced or changed, i.e., reprogrammed into cells capable of differentiating into tissues of all three germ or dermal layers: mesoderm, endoderm, and ectoderm. The iPSCs produced do not refer to cells as they are found in nature. iPSCs, as used herein, include genomic engineered iPSCs, or iPSCs reprogrammed from immune cells of preferential donor or patients, and thus unique genetic imprints are comprised in the iPSCs, and/or derived lymphoid effector cells.

As used herein, the term "genetic imprint" refers to genetic or epigenetic information that contributes to preferential therapeutic attributes in a source cell or an iPSC, and is retainable in the source cell derived iPSCs, and/or the iPSC-derived hematopoietic lineage cells. As used herein, "a source cell" is a non-pluripotent cell that may be used for generating iPSCs through reprogramming, and the source cell derived iPSCs may be further differentiated to specific cell types including any hematopoietic lineage cells. The source cell derived iPSCs, and differentiated cells therefrom are sometimes collectively called "derived cells" depending on the context. As used herein, the genetic imprint(s) conferring a preferential therapeutic attribute is incorporated into the iPSCs either through reprogramming a selected source cell that is donor-, disease-, or treatment response-specific, or through introducing genetically modified modalities to iPSC using genomic editing. In the aspect of a source cell obtained from a specifically selected donor, disease or treatment context, the genetic imprint contributing to preferential therapeutic attributes may include any context specific genetic or epigenetic modifications which manifest a retainable phenotype, i.e. a preferential therapeutic attribute, that is passed on to derivative cells of the selected source cell, irrespective of the underlying molecular events being identified or not. Donor-, disease-, or treatment response-specific source cells may comprise genetic imprints that are retainable in iPSCs and derived hematopoietic lineage cells, which genetic imprints include but are not limited to, prearranged monospecific TCR, for example, from a viral specific T cell or invariant natural killer T (iNKT) cell; trackable and desirable genetic polymorphisms, for example, homozygous for a point mutation that encodes for the high-affinity CD16 receptor in selected donors; and predetermined HLA requirements, i.e., selected HLA-matched donor cells exhibiting a haplotype with increased population. As used herein, preferential therapeutic attributes include improved engraftment, trafficking, homing, viability, self-renewal, persistence, immune response regulation and modulation, survival, and cytotoxicity of a derived cell. A preferential therapeutic attribute may also relate to antigen targeting receptor expression; HLA presentation or lack thereof; resistance to tumor microenvironment; induction of bystander immune cells and immune modulations; improved on-target specificity with reduced off-tumor effect; resistance to treatment such as chemotherapy.

The term "enhanced therapeutic property" as used herein, refers to a therapeutic property of a cell that is enhanced as compared to a typical immune cell of the same general cell type. For example, an NK cell with an "enhanced therapeutic property" will possess an enhanced, improved, and/or augmented therapeutic property as compared to a typical, unmodified, and/or naturally occurring NK cell. Therapeutic properties of an immune cell may include, but are not limited to, cell engraftment, trafficking, homing, viability, self-renewal, persistence, immune response regulation and modulation, survival, and cytotoxicity. Therapeutic properties of an immune cell are also manifested by antigen targeting receptor expression; HLA presentation or lack thereof; resistance to tumor microenvironment; induction of bystander immune cells and immune modulations; improved on-target specificity with reduced off-tumor effect; resistance to treatment such as chemotherapy.

As used herein, the term "engager" refers to a molecule, e.g. a fusion polypeptide, which is capable of forming a link between an immune cell, e.g. a T cell, a NK cell, a NKT cell, a B cell, a macrophage, a neutrophil, and a tumor cell; and activating the immune cell. Examples of engagers include, but are not limited to, bi-specific T cell engagers (BiTEs), bi-specific killer cell engagers (BiKEs), tri-specific killer cell engagers, or multi-specific killer cell engagers.

As used herein, the term "surface triggering receptor" refers to a receptor capable of triggering or initiating an immune response, e.g. a cytotoxic response. Surface triggering receptors may be engineered, and may be expressed on effector cells, e.g. a T cell, a NK cell, a NKT cell, a B cell, a macrophage, a neutrophil. In some embodiments, the surface triggering receptor facilitates bi- or multi-specific antibody engagement between the effector cells and specific target cell e.g. a tumor cell, independent of the effector cell's natural receptors and cell types. Using this approach, one may generate iPSCs comprising a universal surface triggering receptor, and then differentiate such iPSCs into populations of various effector cell types that express the universal surface triggering receptor. By "universal", it is meant that the surface triggering receptor can be expressed in, and activate, any effector cells irrespective of the cell type, and all effector cells expressing the universal receptor can be coupled or linked to the engagers having the same epitope recognizable by the surface triggering receptor, regardless of the engager's tumor binding specificities. In some embodiments, engagers having the same tumor targeting specificity are used to couple with the universal surface triggering receptor. In some embodiments, engagers having different tumor targeting specificity are used to couple with the universal surface triggering receptor. As such, one or multiple effector cell types can be engaged to kill one specific type of tumor cells in some case, and to kill two or more types of tumors in some other cases. A surface triggering receptor generally comprises a co-stimulatory domain for effector cell activation and an anti-epitope that is specific to the epitope of an engager. A bi-specific engager is specific to the anti-epitope of a surface triggering receptor on one end, and is specific to a tumor antigen on the other end.

As used herein, the term "safety switch protein" refers to an engineered protein designed to prevent potential toxicity or otherwise adverse effects of a cell therapy. In some instances, the safety switch protein expression is conditionally controlled to address safety concerns for transplanted engineered cells that have permanently incorporated the gene encoding the safety switch protein into its genome. This conditional regulation could be variable and might include control through a small molecule-mediated post-translational activation and tissue-specific and/or temporal transcriptional regulation. The safety switch could mediate induction of apoptosis, inhibition of protein synthesis, DNA replication, growth arrest, transcriptional and post-transcriptional genetic regulation and/or antibody-mediated depletion. In some instance, the safety switch protein is activated by an exogenous molecule, e.g. a prodrug, that when activated, triggers apoptosis and/or cell death of a therapeutic cell. Examples of safety switch proteins, include, but are not limited to suicide genes such as caspase 9, thymidine kinase, cytosine deaminase, B-cell CD20, modified EGFR, and any combination thereof. In this strategy, a prodrug that is administered in the event of an adverse event is activated by the suicide-gene product and kills the transduced cell.

As used herein, the term "pharmaceutically active proteins or peptides" refer to proteins or peptides that are capable of achieving a biological and/or pharmaceutical effect on an organism. A pharmaceutically active protein has healing curative or palliative properties against a disease and may be administered to ameliorate relieve, alleviate, reverse or lessen the severity of a disease. A pharmaceutically active protein also has prophylactic properties and is used to prevent the onset of a disease or to lessen the severity of such disease or pathological condition when it does emerge. Pharmaceutically active proteins include an entire protein or peptide or pharmaceutically active fragments thereof. It also includes pharmaceutically active analogs of the protein or peptide or analogs of fragments of the protein or peptide. The term pharmaceutically active protein also refers to a plurality of proteins or peptides that act cooperatively or synergistically to provide a therapeutic benefit. Examples of pharmaceutically active proteins or peptides include, but are not limited to, receptors, binding proteins, transcription and translation factors, tumor growth suppressing proteins, antibodies or fragments thereof, growth factors, and/or cytokines.

As used herein, the term "signaling molecule" refers to any molecule that modulates, participates in, inhibits, activates, reduces, or increases, the cellular signal transduction. Signal transduction refers to the transmission of a molecular signal in the form of chemical modification by recruitment of protein complexes along a pathway that ultimately triggers a biochemical event in the cell. Signal transduction pathways are well known in the art, and include, but are not limited to, G protein coupled receptor signaling, tyrosine kinase receptor signaling, integrin signaling, toll gate signaling, ligand-gated ion channel signaling, ERK/MAPK signaling pathway, Wnt signaling pathway, cAMP-dependent pathway, and IP3/DAG signaling pathway.

As used herein, the term "targeting modality" refers to a molecule, e.g., a polypeptide, that is genetically incorporated into a cell to promote antigen and/or epitope specificity that includes but not limited to i) antigen specificity as it related to a unique chimeric antigen receptor (CAR) or T cell receptor (TCR), ii) engager specificity as it related to monoclonal antibodies or bispecific engager, iii) targeting of transformed cell, iv) targeting of cancer stem cell, and v) other targeting strategies in the absence of a specific antigen or surface molecule.

As used herein, the term "pharmaceutically active proteins or peptides" refer to proteins or peptides that are capable of achieving a biological and/or pharmaceutical effect on an organism. Examples of pharmaceutically active proteins or peptides include, but are not limited to, antibodies or fragments thereof, growth factors, and/or cytokines.

As used herein, the term "signaling molecule" refers to any molecule that modulates, participates in, inhibits, activates, reduces, or increases, the cellular signal transduction. Signal transduction refers to the transmission of a molecular signal in the form of chemical modification by recruitment of protein complexes along a pathway that ultimately triggers a biochemical event in the cell. Signal transduction pathways are well known in the art, and include, but are not limited to, G protein coupled receptor signaling, tyrosine kinase receptor signaling, integrin signaling, toll gate signaling, ligand-gated ion channel signaling, ERK/MAPK signaling pathway, Wnt signaling pathway, cAMP-dependent pathway, and IP3/DAG signaling pathway.

As used herein, the term "specific" can be used to refer to the ability of a molecule, e.g., a receptor or an engager, to selectively bind to a target molecule, in constrast to non-specific or non-selective binding.

The term "adoptive cell therapy" as used herein refers to a cell-based immunotherapy that, as used herein, relates to the transfusion of autologous or allogenic lymphocytes, identified as T or B cells, genetically modified or not, that have been expanded ex vivo prior to said transfusion.

A "therapeutically sufficient amount", as used herein, includes within its meaning a non-toxic but sufficient and/or effective amount of the particular therapeutic and/or pharmaceutical composition to which it is referring to provide a desired therapeutic effect. The exact amount required will vary from subject to subject depending on factors such as the patient's general health, the patient's age and the stage and severity of the condition. In particular embodiments, a therapeutically sufficient amount is sufficient and/or effective to ameliorate, reduce, and/or improve at least one symptom associated with a disease or condition of the subject being treated.

As used herein, the term "embryonic stem cell" refers to naturally occurring pluripotent stem cells of the inner cell mass of the embryonic blastocyst. Embryonic stem cells are pluripotent and give rise during development to all derivatives of the three primary germ layers: ectoderm, endoderm and mesoderm. They do not contribute to the extra-embryonic membranes or the placenta, i.e., are not totipotent.

As used herein, the term "multipotent stem cell" refers to a cell that has the developmental potential to differentiate into cells of one or more germ layers (ectoderm, mesoderm and endoderm), but not all three. Thus, a multipotent cell can also be termed a "partially differentiated cell." Multipotent cells are well known in the art, and examples of multipotent cells include adult stem cells, such as for example, hematopoietic stem cells and neural stem cells. "Multipotent" indicates that a cell may form many types of cells in a given lineage, but not cells of other lineages. For example, a multipotent hematopoietic cell can form the many different types of blood cells (red, white, platelets, etc.), but it cannot form neurons. Accordingly, the term "multipotency" refers to a state of a cell with a degree of developmental potential that is less than totipotent and pluripotent.

Differentiation of pluripotent stem cells requires a change in the culture system, such as changing the stimuli agents in the culture medium or the physical state of the cells. The most conventional strategy utilizes the formation of embryoid bodies (EBs) as a common and critical intermediate to initiate the lineage-specific differentiation. EBs are three-dimensional clusters that have been shown to mimic embryo development as they give rise to numerous lineages within their three-dimensional area. Through the differentiation process, typically few hours to days, simple EBs (for example, aggregated pluripotent stem cells elicited to differentiate) continue maturation and develop into a cystic EB at which time, typically days to few weeks, they are further processed to continue differentiation. EB formation is initiated by bringing pluripotent stem cells into close proximity with one another in three-dimensional multilayered clusters of cells, typically this is achieved by one of several methods including allowing pluripotent cells to sediment in liquid droplets, sedimenting cells into "U" bottomed well-plates or by mechanical agitation. To promote EB development, the pluripotent stem cell aggregates require further differentiation cues, as aggregates maintained in pluripotent culture maintenance medium do not form proper EBs. As such, the pluripotent stem cell aggregates need to be transferred to differentiation medium that provides eliciting cues towards the lineage of choice. EB-based culture of pluripotent stem cells typically results in generation of differentiated cell populations (ectoderm, mesoderm and endoderm germ layers) with modest proliferation within the EB cell cluster. Although proven to facilitate cell differentiation, EBs, however, give rise to heterogeneous cells in variable differentiation state because of the inconsistent exposure of the cells in the three-dimensional structure to differentiation cues from the environment. In addition, EBs are laborious to create and maintain. Moreover, cell differentiation through EB is accompanied with modest cell expansion, which also contributes to low differentiation efficiency.

In comparison, "aggregate formation," as distinct from "EB formation," can be used to expand the populations of pluripotent stem cell derived cells. For example, during aggregate-based pluripotent stem cell expansion, culture media are selected to maintain proliferation and pluripotency. Cells proliferation generally increases the size of the aggregates forming larger aggregates, these aggregates can be routinely mechanically or enzymatically dissociated into smaller aggregates to maintain cell proliferation within the culture and increase numbers of cells. As distinct from EB culture, cells cultured within aggregates in maintenance culture maintain markers of pluripotency. The pluripotent stem cell aggregates require further differentiation cues to induce differentiation.

As used herein, "monolayer differentiation" is a term referring to a differentiation method distinct from differentiation through three-dimensional multilayered clusters of cells, i.e., "EB formation." Monolayer differentiation, among other advantages disclosed herein, avoids the need for EB formation for differentiation initiation. Because monolayer culturing does not mimic embryo development such as EB formation, differentiation towards specific lineages are deemed as minimal as compared to all three germ layer differentiation in EB.

Pluripotency can be determined, in part, by assessing pluripotency characteristics of the cells. Pluripotency characteristics include, but are not limited to: (i) pluripotent stem cell morphology; (ii) the potential for unlimited self-renewal; (iii) expression of pluripotent stem cell markers including, but not limited to SSEA1 (mouse only), SSEA3/4, SSEA5, TRA1-60/81, TRA1-85, TRA2-54, GC™-2, TG343, TG30, CD9, CD29, CD133/prominin, CD140a, CD56, CD73, CD90, CD105, OCT4, NANOG, SOX2, CD30 and/or CD50; (iv) ability to differentiate to all three somatic lineages (ectoderm, mesoderm and endoderm); (v) teratoma formation consisting of the three somatic lineages; and (vi) formation of embryoid bodies consisting of cells from the three somatic lineages.

Two types of pluripotency have previously been described: the "primed" or "metastable" state of pluripotency akin to the epiblast stem cells (EpiSC) of the late blastocyst, and the "Naïve" or "Ground" state of pluripotency akin to the inner cell mass of the early/preimplantation blastocyst. While both pluripotent states exhibit the characteristics as described above, the naïve or ground state further exhibits: (i) pre-inactivation or reactivation of the X-chromosome in female cells; (ii) improved clonality and survival during single-cell culturing; (iii) global reduction in DNA methylation; (iv) reduction of H3K27me3 repressive chromatin mark deposition on developmental regulatory gene promoters; and (v) reduced expression of differentiation markers relative to primed state pluripotent cells. Standard methodologies of cellular reprogramming in which exogenous pluripotency genes are introduced to a somatic cell, expressed, and then either silenced or removed from the resulting pluripotent cells are generally seen to have characteristics of the primed-state of pluripotency. Under standard pluripotent cell culture conditions such cells remain in the primed state unless the exogenous transgene expression is maintained, wherein characteristics of the ground-state are observed.

As used herein, the term "pluripotent stem cell morphology" refers to the classical morphological features of an embryonic stem cell. Normal embryonic stem cell morphology is characterized by being round and small in shape, with a high nucleus-to-cytoplasm ratio, the notable presence of nucleoli, and typical inter-cell spacing.

As used herein, "feeder cells" or "feeders" are terms describing cells of one type that are co-cultured with cells of a second type to provide an environment in which the cells of the second type can grow, as the feeder cells provide growth factors and nutrients for the support of the second cell type. The feeder cells are optionally from a different species as the cells they are supporting. For example, certain types of human cells, including stem cells, can be supported by primary cultures of mouse embryonic fibroblasts, or immortalized mouse embryonic fibroblasts. The feeder cells may typically be inactivated when being co-cultured with other cells by irradiation or treatment with an anti-mitotic agent such as mitomycin to prevent them from outgrowing the cells they are supporting. Feeder cells may include endothelial cells, stromal cells (for example, epithelial cells or fibroblasts), and leukemic cells. Without limiting the foregoing, one specific feeder cell type may be a human feeder, such as a human skin fibroblast. Another feeder cell type may be mouse embryonic fibroblasts (MEF). In general, various feeder cells can be used in part to maintain pluripotency, direct differentiation towards a certain lineage and promote maturation to a specialized cell types, such as an effector cell.

As used herein, a "feeder-free" (FF) environment refers to an environment such as a culture condition, cell culture or culture media which is essentially free of feeder or stromal cells, and/or which has not been pre-conditioned by the cultivation of feeder cells. "Pre-conditioned" medium refers to a medium harvested after feeder cells have been cultivated within the medium for a period of time, such as for at least one day. Pre-conditioned medium contains many mediator substances, including growth factors and cytokines secreted by the feeder cells cultivated in the medium.

As used herein, the term "subject" refers to any animal, preferably a human patient, livestock, or other domesticated animal.

A "pluripotency factor," or "reprogramming factor," refers to an agent capable of increasing the developmental potency of a cell, either alone or in combination with other agents. Pluripotency factors include, without limitation, polynucleotides, polypeptides, and small molecules capable of increasing the developmental potency of a cell. Exemplary pluripotency factors include, for example, transcription factors and small molecule reprogramming agents.

"Adhere" refers to cells attaching to a vessel, for example, a cell attaching to a sterile plastic (or coated plastic) cell culture dish or flask in the presence of an appropriate culture medium. Certain classes of cells are not sustained or do not grow in a culture unless they adhere to the cell culture vessel. Certain classes of cells ("non-adherent cells") are maintained and/or proliferate in culture without adhering.

"Culture" or "cell culture" refers to the maintenance, growth and/or differentiation of cells in an in vitro environment. "Cell culture media," "culture media" (singular "medium" in each case), "supplement" and "media supplement" refer to nutritive compositions that cultivate cell cultures.

"Cultivate," or "maintain," refers to the sustaining, propagating (growing) and/or differentiating of cells outside of tissue or the body, for example in a sterile plastic (or coated plastic) cell culture dish or flask. "Cultivation," or "maintaining," may utilize a culture medium as a source of nutrients, hormones and/or other factors helpful to propagate and/or sustain the cells.

As used herein, a "dissociated" cell refers to a cell that has been substantially separated or purified away from other cells or from a surface (e.g., a culture plate surface). For example, cells can be dissociated from an animal or tissue by mechanical or enzymatic methods. Alternatively, cells that aggregate in vitro can be dissociated from each other, such as by dissociation into a suspension of clusters, single cells or a mixture of single cells and clusters, enzymatically or mechanically. In yet another alternative embodiment, adherent cells are dissociated from a culture plate or other surface. Dissociation thus can involve breaking cell interactions with extracellular matrix (ECM) and substrates (e.g., culture surfaces), or breaking the ECM between cells.

As used herein, the terms "T lymphocyte" and "T cell" are used interchangeably and can be any T cell, such as a cultured T cell, e.g., a primary T cell, or a T cell from a cultured T cell line, e.g., Jurkat, SupT1, etc., or a T cell obtained from a mammal. The T cell can also be differentiated from a stem cell or progenitor cell. The T cell can be CD3+ cells. The T cell can be any type of T cell and can be of any developmental stage, including but not limited to, CD4+/CD8+ double positive T cells, CD4+ helper T cells (e.g., Th1 and Th2 cells), CD8+ T cells (e.g., cytotoxic T cells), peripheral blood mononuclear cells (PBMCs), peripheral blood leukocytes (PBLs), tumor infiltrating lymphocytes (TILs), memory T cells, naïve T cells, regulator T cells, gamma delta T cells (γδ T cells), and the like. Additional types of helper T cells include cells such as Th3 (Treg), Th17, Th9, or Tfh cells. Additional types of memory T cells include cells such as central memory T cells (Tcm cells), stem cell memory (Tscm cells), and effector memory T cells (Tem cells and TEMRA cells). The T cell can also refer to a genetically engineered T cell, such as a T cell modified to express a T cell receptor (TCR) or a chimeric antigen receptor (CAR).

As used herein, the term "naïve T cell" or Tn, refers to mature T cells that, unlike activated or memory T cells, have not encountered their cognate antigen within the periphery. Naïve T cells are commonly characterized by the surface expression of L-selectin (CD62L); the absence of the activation markers CD25, CD44 or CD69; and the absence of the memory CD45RO isoform. They also express functional IL-7 receptors, consisting of subunits IL-7 receptor-α, CD127, and common-γ chain, CD132. In the naïve state, T cells are thought to be quiescent and non-dividing, requiring the common-gamma chain cytokines IL-7 and IL-15 for homeostatic survival mechanisms.

As used herein, the term "central memory T cells" or Tcm, refers to a subgroup or subpopulation of T cells that have lower expression or pro-apoptotic signaling genes, for example, Bid, Bnip3 and Bad, and have higher expression of genes associated with trafficking to secondary lymphoid organs, which genes include CD62L, CXCR3, CCR7, in comparison to effector memory T cells, or Tcm.

As used herein, the term "stem memory T cells," or "stem cell memory T cells", or Tscm, refers to a subgroup or subpopulation of T cells that are capable of self-renewing and generating Tcm, Tem and Teff (effector T cells), and express CD27 and lymphoid homing molecules such as CCR7 and CD62L, which are properties important for mediating long-term immunity.

As used herein, the term "NK cell" or "Natural Killer cell" refer to a subset of peripheral blood lymphocytes defined by the expression of CD56 or CD16 and the absence of the T cell receptor (CD3). As provided herein, the NK cell can also be differentiated from a stem cell or progenitor cell. As used herein, the terms "adaptive NK cell" and "memory NK cell" are interchangeable and refer to a subset of NK cells that are phenotypically CD3- and CD56+, expressing NKG2C and CD57, and optionally, CD16, but lack expression of one or more of the following: PLZF, SYK, FceRγ, and EAT-2. In some embodiments, isolated subpopulations of CD56+NK cells comprise expression of CD16, NKG2C, CD57, NKG2D, NCR ligands, NKp30, NKp40, NKp46, activating and inhibitory KIRs, NKG2A and DNAM-1. CD56+ can be dim or bright expression.

As used herein, the term "NKT cells" or "natural killer T cells" refers to CD1d-restricted T cells, which express a T cell receptor (TCR). Unlike conventional T cells that detect peptide antigens presented by conventional major histocompatibility (MHC) molecules, NKT cells recognize lipid antigens presented by CD1d, a non-classical MHC molecule. Two types of NKT cells are currently recognized. Invariant or type I NKT cells express a very limited TCR repertoire—a canonical α-chain (Vα24-Jα18 in humans) associated with a limited spectrum of β chains (Vβ11 in humans). The second population of NKT cells, called non-classical or noninvariant type II NKT cells, display a more heterogeneous TCR αβ usage. Type I NKT cells are currently considered suitable for immunotherapy. Adaptive or invariant (type I) NKT cells can be identified with the expression of at least one or more of the following markers, TCR Vα24-Jα18, Vb11, CD11d, CD3, CD4, CD8, αGalCer, CD161 and CD56. As provided herein, the NKT cell can also be differentiated from a stem cell or progenitor cell.

As used herein, the terms "B lymphocyte" or "B cell" are used interchangeably and refer to a subset of lymphocytes defined by the expression of a B cell receptor comprised of immunoglobulin heavy and light chains (BCR, Ig), CD19 or CD20, in absence of the T cell receptor (CD3). As provided herein, the B cell can also be derived from a stem or progenitor cell via directed differentiation. The B cell comprises any subtype of B cell, and can be of any developmental stage, including but not limited to, pro-B cells, pre-B cells, naïve B cells, B-1 B cell, B-2 B cell, marginal zone B cells, follicular B cells, memory B cells, plasmablast cells, plasma cells, regulatory B cells.

B. Overview

The invention generally relates to a multistage process of differentiating a naïve pluripotent cell to non-pluripotent cells or a partially differentiated cells, including, mesodermal cells, definitive hemogenic endothelium, definitive hematopoietic stem or progenitor cells, CD34+ cells, multipotent progenitors (MPP) (capable of differentiating into myeloid, including neutrophil progenitors), T cell progenitors, NK cell progenitors; or fully differentiated terminal hematopoietic cells, such as, for example, T cells, B cells, NKT cells, or NK cells. The invention also relates to the compositions used in the disclosed methods; and cell populations, cell lines, or clonal cells generated using the disclosed methods.

In contrast to the methods used in the art, the present invention has avoided the formation of EB in iPSC differentiation. As provided, hematopoietic lineages cells derived from iPSC were obtained by seeding clonal iPSC cells in a TGFβ free culture medium to maintain their ground or naïve state of pluripotency, differentiating the clonal iPSCs in a monolayer format without EB formation, and utilizing a step-wise strategy to apply proper combination of small chemicals, growth factors and cytokines in the early and mid-stage of the differentiation. As such, the present invention enables direct transfer of expanded clonal iPSC to adherent culture in a form of monolayer for immediate differentiation without requiring formation of EB from iPSC.

The present invention thus provides culture platforms that enable differentiating stem cell to definitive hematopoiesis and functional hematopoietic lineage cells with high efficiency, without using TGFβ receptor/ALK inhibitors including SB431532. Furthermore, unlike previous studies, the present invention also provides a culture platform using feeder-free, serum-free conditions that support direct differentiation of iPSC in monolayer culture without the need for EB or aggregate intermediates from iPSC.

C. Culture Platforms

Existing methods for culturing pluripotent cells rely heavily on feeder cells or media pre-conditioned with feeder cells and containing fetal bovine serum; however, such environments may be unsuitable for producing cells for clinical and therapeutic use. For example, cells cultivated in such xeno-contaminated environments are generally considered unsuitable for human cell transplantation because the exposure to animal components may present a serious risk of immune rejection and transmitting unidentified pathogens to the treated patients, and could potentially reactivate animal retroviruses. Culture systems using animal-free culture media, such as the feeder-free environments contemplated herein, facilitate the manufacture of clinical-grade cell lines, particularly hESC, hiPSC, and pluripotent stem cell derived HSC, T, B, NKT, or NK cell lines.

In particular embodiments, the feeder-free environment is essentially free of human feeder cells and is not pre-conditioned by feeder cells, including without limitation, mouse embryonic fibroblasts, human fibroblasts, keratinocytes, and embryonic stem cells. The feeder-free cell culture medium is suitable for use in culturing pluripotent cells, reprogramming cells, single-cell culture, dissociation, and passaging of pluripotent cells, cell sorting of pluripotent cells, generation of ground state pluripotent cells, maintenance of ground state pluripotency, induction of pluripotent cell differentiation. In particular embodiments, the feeder-free environment is used to induce pluripotency, improve the efficiency of reprogramming, increase or maintain the potency of a cell, and/or induce differentiation. In certain embodiments, the feeder-free environment is additionally substantially free of cytokines and growth factors, including bFGF.

In some aspects of the invention, one or more of the stages of iPSC differentiation described above may be carried out under feeder-free conditions. Such feeder-free conditions may be in forms including, but not limited to, monolayer culture and suspension culture. In one embodiment of the invention, the differentiation of a pluripotent cell to a mesodermal cell is carried out under monolayer feeder-free conditions. In another embodiment of the invention, the differentiation of a mesodermal cell to a definitive hemogenic endothelial cell is carried out under monolayer feeder-free conditions. In yet another embodiment of the invention, the differentiation of a definitive hemogenic endothelial cell to a hematopoietic stem cell is carried out under monolayer feeder-free conditions. In one embodiment of the invention, the differentiation of a definitive hematopoietic stem cell to a multipotent progenitor, a T cell progenitor or a NK cell progenitor is carried out under suspension feeder-free conditions, or under monolayer feeder-free conditions followed by suspension feeder-free conditions. In another embodiment of the invention, the differentiation of a T cell progenitor to a fully differentiated T cell, or a NK cell progenitor to a fully differentiated NK cell, is carried out under suspension feeder-free conditions, or under monolayer feeder-free followed by suspension feeder-free conditions.

Any suitable vessel or cell culture container may be used as a support for cell cultures in the basal media and/or the cell culture supplements. In some embodiments, coating the surface of a culture vessel with adhesion-promoting matrics/substrata (for example, collagens, fibronectins, RGD-containing polypeptides, gelatins, and the like) however promotes attachment of the cells, and in particular embodiments may enhance the effect of the cell culture media and supplements disclosed herein. Suitable substrates for culturing and passaging cells are known in the art and include, without limitation, vitronectin, gelatin, laminin, fibronectin, collagen, elastin, osteopontin, thrombospondin, mixtures of naturally occurring cell line-produced matrices such as Matrigel™, and synthetic or man-made surfaces such as polyamine monolayers and carboxy-terminated monolayers. In some embodiments, providing feeder-free conditions comprise culturing the cells on a matrix-coated surface. In one embodiment, a culture platform contemplated herein comprises a matrix/substrate comprising Matrigel™ or vitronectin. In some embodiments of the cultures, Matrigel™ is used, and thus the culture is fully defined.

In some aspects of the invention, one or more of the stages of differentiation described above may be carried out under serum-free conditions. Examples of commercially available serum-free media suitable for cell attachment and/or induction include mTeSR™, TeSR™2 or StemSpan™ from Stem Cell Technologies (Vancouver, Canada), Primate ES/iPS cell medium from ReproCELL (Boston, Mass.), StemPro®-34 from Invitrogen (Carlsbad, Calif.), StemPro® hESC SFM from Invitrogen, and X-VIVO™ from Lonza (Basel, Switzerland).

In additional embodiments, one or more of the media of the culture platform is a feeder-free environment, and optionally is substantially free of cytokines and/or growth factors. In other embodiments, the cell culture media contains supplements such as serums, extracts, growth factors, hormones, cytokines and the like. Generally, the culture platform comprises one or more of stage specific feeder-free, serum-free media, each of which further comprises one or more of the followings: nutrients/extracts, growth factors, hormones, cytokines and medium additives. Suitable nutrients/extracts may include, for example, DMEM/F-12 (Dulbecco's Modified Eagle Medium/Nutrient Mixture F-12), which is a widely used basal medium for supporting the growth of many different mammalian cells; KOSR (knockout serum replacement); L-glut; NEAA (Non-Essential Amino Acids). Other medium additives may include, but not limited to, MTG, ITS, PME, anti-oxidants (for example, ascorbic acid). In some embodiments, a culture medium of the present invention comprises one or more of the following cytokines or growth factors: epidermal growth factor (EGF), acidic fibroblast growth factor (aFGF), basic fibroblast growth factor (bFGF), leukemia inhibitory factor (LIF), hepatocyte growth factor (HGF), insulin-like growth factor 1 (IGF-1), insulin-like growth factor 2 (IGF-2), keratinocyte growth factor (KGF), nerve growth factor (NGF), platelet-derived growth factor (PDGF), transforming growth factor beta (TGF-β), bone morphogenetic protein (BMP4), vascular endothelial cell growth factor (VEGF) transferrin, various interleukins (such as IL-1 through IL-18), various colony-stimulating factors (such as granulocyte/macrophage colony-stimulating factor (GM-CSF)), various interferons (such as IFN-γ) and other cytokines having effects upon stem cells such as stem cell factor (SCF) and erythropoietin (EPO). These cytokines may be obtained commercially, for example from R&D Systems (Minneapolis, Minn.), and may be either natural or recombinant. In some other embodiments, the culture medium of the present invention comprises one or more of bone morphogenetic protein (BMP4), insulin-like growth factor-1 (IGF-1), basic fibroblast growth factor (bFGF), vascular endothelial growth factor (VEGF), hematopoietic growth factor (for example, SCF, GMCSF, GCSF, EPO, IL3, TPO, EPO), Fms-Related Tyrosine Kinase 3 Ligand (Flt3L); and one or more cytokines from Leukemia inhibitory factor (LIF), IL3, IL6, IL7, IL11, IL15. In some embodiments, the growth factors/mitogens and cytokines are stage and/or cell type specific in concentrations that are determined empirically or as guided by the established cytokine art.

Generally, techniques for differentiating an induced pluripotent cell involve modulation of specific cellular pathways, either directly or indirectly, using polynucleotide-, polypeptide- and/or small molecule-based approaches. The developmental potency of a cell may be modulated, for example, by contacting a cell with one or more modulators.

"Contacting", as used herein, can involve culturing cells in the presence of one or more factors (such as, for example, small molecules, proteins, peptides, etc.). In some embodiments, a cell is contacted with one or more agents to induce cell differentiation. Such contact, may occur for example, by introducing the one or more agents to the cell during in vitro culture. Thus, contact may occur by introducing the one or more agents to the cell in a nutrient cell culture medium. The cell may be maintained in the culture medium comprising one or more agents for a period sufficient for the cell to achieve the differentiation phenotype that is desired. In some other embodiments, "contact" occurs when one or more factors are introduced into the cell via vectors. In some embodiments, the one or more vectors are introduced by a retrovirus, Sendai virus, an adenovirus, an episome, minicircle, vector system with expression cassette, or mRNA.

In other embodiments, one or more of stage specific feeder-free, serum-free media of the culture platform as disclosed herein further comprise one or more small molecules. In some embodiments, the culture platform comprises a cell culture medium comprising a GSK-3 inhibitor, a MEK inhibitor, a Rho Kinase (ROCK) inhibitor, and does not comprise, or is free of, a small molecule inhibitor of a TGFβ/activin signaling pathway including but not limited to TGFβ receptor or ALK5 inhibitors.

The culture platforms contemplated herein also offer numerous advantages by utilizing a homogenous population of industrial- or clinical-grade pluripotent cells having reduced spontaneous differentiation and/or having achieved ground state pluripotency. In one embodiment, the homogenous iPSC is maintained in a composition comprising a GSK-3 inhibitor, a MEK inhibitor, and a Rho Kinase (ROCK) inhibitor; and the composition is free of TGFβ receptor/ALK inhibitors. As used herein, the term "homogenous" refers to a population of cells wherein each cell is the same or substantially the same as the other cells in the population. In one embodiment, a cell is the same as other cells in the population if each cell expresses one or more of the same pluripotency markers as contemplated herein, e.g., SSEA4 and TRA1-81. In one embodiment, the population is homogenous if at least 90%, at least 95%, at least 96%, at least 97%, at least 98%, at least 99%, or more of the cells are the same or substantially the same as other cells in the population.

In various embodiments, the cell culture media of the culture platform for generating hematopoietic cell lineages through definitive hemogenic endothelium herein do not comprise, or is essentially free of, an inhibitor of TGFβ/activin signaling pathways, including TGFβ receptor (TGFβR) inhibitors and ALK5 inhibitors. In one embodiment, the culture platform comprises a seeding medium for maintaining a naïve hiPSC, which medium comprises a GSK-3 inhibitor, a MEK inhibitor, and a Rho Kinase (ROCK) inhibitor. Without wishing to be bound to any particular theory, the inventors discovered that while TGFβR/ALK5 inhibitors increase the efficiency of reprogramming, these inhibitors counteract the long-term maintenance, quality and homogeneity of a pluripotent cell population. That is, while the inhibition of TGFβ pathway signaling improved the efficiency of cellular reprogramming, relief from this inhibition contributes to subsequent maintenance of the pluripotent cell population in in vitro culture systems, particularly in systems using feeder-cell free and single cell, enzymatic passage where a homogeneous pluripotent population with reduced spontaneous differentiation, and remaining in the "ground" or "naïve" pluripotency state is preferred. As used herein, the term "long-term," as measured by, without being limited to, the number of passages, often means at least 10, 15, 20, 25, 30, 35, 40, 45, 50, or more passages. As defined, "passage" refers to the act of subdividing and plating cells into multiple cell culture surfaces or vessels when the cells have proliferated to a desired extent. In addition, culturing metastable pluripotent cells in media comprising a GSK3 inhibitor and a MEK inhibitor and optionally a ROCK inhibitor, but free of, TGFβR/ALK5 inhibitors, as disclosed herein, transition pluripotent cells to achieve reduced spontaneous differentiation, and/or to achieve ground state pluripotency.

Achieving the ground or naïve pluripotency of the iPSC is also important to obtain hematopoietic lineage cells by differentiating iPSC without forming EB intermediates. In addition, the efficiency of naïve iPSC differentiation into definitive HE is also greatly impacted by the use of monolayer culturing without forming EB and aggregates thereof. In some embodiments, the culture platform comprises a medium that comprises a ROCK inhibitor, and is free of, or essentially free of, TGFβR/ALK5 inhibitors. In some other embodiments, the culture platform comprises a medium comprising a GSK3 inhibitor, but free of TGFβR/ALK5 inhibitors, which medium promotes the generation of definitive HE and/or definitive HSC cells using the culture platforms provided herein.

1. TGFβ Receptor/ALK INHIBITORS

TGFβ receptor (e.g., ALK5) inhibitors can include antibodies to, dominant negative variants of, and antisense nucleic acids that suppress expression of, TGFβ receptors (e.g., ALK5). Exemplary TGFβ receptor/ALK inhibitors include, but are not limited to, SB431542 (see, e.g., Inman, et al., Molecular Pharmacology 62(1):65-74 (2002)); A-83-01, also known as 3-(6-Methyl-2-pyridinyl)-N-phenyl-4-(4-quinolinyl)-1H-pyrazole-1-carbothioamide (see, e.g., Tojo, et al., Cancer Science 96(11):791-800 (2005) and commercially available from, e.g., Tocris Bioscience); 2-(3-(6-Methylpyridin-2-yl)-1H-pyrazol-4-yl)-1,5-naphthyridine; Wnt3a/BIO (see, e.g., Dalton, et al., WO2008/094597, herein incorporated by reference); GW788388 (-{4-[3-(pyridin-2-yl)-1H-pyrazol-4-yl]pyridin-2-yl}-N-(tetrahydro-2H-pyran-4-yl)benzamide) (see, e.g., Gellibert, et al., Journal of Medicinal Chemistry 49(7):2210-2221 (2006)); SM16 (see, e.g., Suzuki, et al., Cancer Research 67(5):2351-2359 (2007)); IN-1130 (3-((5-(6-methylpyridin-2-yl)-4-(quinoxalin-6-yl)-1H-imidazol-2-yl)methyl)benzamide) (see, e.g., Kim, et al., Xenobiotica 38(3):325-339 (2008)); GW6604 (2-phenyl-4-(3-pyridin-2-yl-1H-pyrazol-4-yl)pyridine) (see, e.g., de Gouville, et al., Drug News Perspective 19(2):85-90 (2006)); SB-505124 (2-(5-benzo[1,3]dioxol-5-yl-2-tert-butyl-3H-imidazol-4-yl)-6-methylpyridine hydrochloride) (see, e.g., DaCosta, et al., Molecular Pharmacology 65(3): 744-752 (2004)); and pyrimidine derivatives (see, e.g., those listed in Stiefl, et al., WO2008/006583, herein incorporated by reference). Further, while "an ALK5 inhibitor" is not intended to encompass non-specific kinase inhibitors, an "ALK5 inhibitor" should be understood to encompass inhibitors that inhibit ALK4 and/or ALK7 in addition to ALK5, such as, for example, SB-431542 (see, e.g., Inman, et al., J, Mol. Pharmacol. 62(1): 65-74 (2002). Without intending to limit the scope of the invention, it is believed that ALK5 inhibitors affect the mesenchymal to epithelial conversion/transition (MET) process. TGFβ/activin pathway is a driver for epithelial to mesenchymal transition (EMT). Therefore, inhibiting the TGFβ/activin pathway can facilitate MET (i.e. reprogramming) process.

In view of the data showing the effect of inhibiting ALK5, it is believed that inhibition of the TGFβ/activin pathway will have similar effects of inhibiting ALK5. Thus, any inhibitor (e.g., upstream or downstream) of the TGFβ/activin pathway can be used in combination with, or instead of, ALK5 inhibitors as described in each paragraph herein. Exemplary TGFβ/activin pathway inhibitors include but are not limited to: TGFβ receptor inhibitors, inhibitors of SMAD 2/3 phosphorylation, inhibitors of the interaction of SMAD 2/3 and SMAD 4, and activators/agonists of SMAD 6 and SMAD 7. Furthermore, the categorizations described below are merely for organizational purposes and one of skill in the art would know that compounds can affect one or more points within a pathway, and thus compounds may function in more than one of the defined categories.

TGFβ receptor (TGFβR) inhibitors can include antibodies to, dominant negative variants of and siRNA or antisense nucleic acids that target TGFβ receptors. Specific examples of TGFβ receptor inhibitors include but are not limited to SU5416; 2-(5-benzo[1,3]dioxol-5-yl-2-tert-butyl-3H-imidazol-4-yl)-6-methylpyridine hydrochloride (SB-505124); lerdelimumb (CAT-152); metelimumab (CAT-192); GC-1008; ID11; AP-12009; AP-11014; LY550410; LY580276; LY364947; LY2109761; SB-505124; SB-431542; SD-208; SM16; NPC-30345; Ki26894; SB-203580; SD-093; Gleevec; 3,5,7,2',4'-pentahydroxyflavone (Morin); activin-M108A; P144; soluble TBR2-Fc; and antisense transfected tumor cells that target TGFβ receptors. (See, e.g., Wrzesinski, et al., Clinical Cancer Research 13(18):5262-5270 (2007); Kaminska, et al., Acta Biochimica Polonica 52(2): 329-337 (2005); and Chang, et al., Frontiers in Bioscience 12:4393-4401 (2007).)

Inhibitors of SMAD 2/3 phosphorylation can include antibodies to, dominant negative variants of and antisense nucleic acids that target SMAD2 or SMAD3. Specific examples of inhibitors include PD169316; SB203580; SB-431542; LY364947; A77-01; and 3,5,7,2',4'-pentahydroxyflavone (Morin). (See, e.g., Wrzesinski, supra; Kaminska, supra; Shimanuki, et al., Oncogene 26:3311-3320 (2007); and Kataoka, et al., EP1992360, incorporated herein by reference.)

Inhibitors of the interaction of SMAD 2/3 and SMAD4 can include antibodies to, dominant negative variants of and antisense nucleic acids that target SMAD2, SMAD3 and/or smad4. Specific examples of inhibitors of the interaction of SMAD 2/3 and SMAD4 include but are not limited to Trx-SARA, Trx-xFoxH1b and Trx-Lef1. (See, e.g., Cui, et al., Oncogene 24:3864-3874 (2005) and Zhao, et al., Molecular Biology of the Cell, 17:3819-3831 (2006).)

Activators/agonists of SMAD 6 and SMAD 7 include but are not limited to antibodies to, dominant negative variants of and antisense nucleic acids that target SMAD 6 or SMAD 7. Specific examples of inhibitors include but are not limited to Smad7—as PTO-oligonucleotides. (See, e.g., Miyazono, et al., U.S. Pat. No. 6,534,476, and Steinbrecher, et al., US2005119203, both incorporated herein by reference.

2. WNT Pathway Agonists

As used herein, the terms "Wnt signal-promoting agent," "Wnt pathway activator," "Wnt pathway activating agent," or "Wnt pathway agonist," refers to an agonist of the Wnt signaling pathway, including but not limited to an agonist of one or more of Wnt1, Wnt2, Wnt2b/13, Wnt3, Wnt3a, Wnt4, Wnt5a, Wnt5b, Wnt6, Wnt7a, Wnt7b, Wnt7c, Wnt8, Wnt8a, Wnt8b, Wnt8c, Wnt10a, Wnt10b, Wnt11, Wnt14, Wnt15, and Wnt16. Wnt pathway agonists further include, but are not limited to, one or more of the following polypeptides or a fragment thereof: a Dkk polypeptide, a crescent polypeptide, a cerberus polypeptide, an axin polypeptide, a Frzb polypeptide, a T-cell factor polypeptide, or a dominant negative disheveled polypeptide.

Non-limiting examples of Wnt pathway agonists further include one or more of the following: a nucleic acid comprising a nucleotide sequence that encodes a Wnt polypeptide, a polypeptide comprising an amino acid sequence of a Wnt polypeptide, a nucleic acid comprising a nucleotide sequence that encodes an activated Wnt receptor, a polypeptide comprising an amino acid sequence of an activated Wnt receptor, a small organic molecule that promotes Wnt/β-catenin signaling, a small organic molecule that inhibits the expression or activity of a Wnt antagonist, an antisense oligonucleotide that inhibits expression of a Wnt antagonist, a ribozyme that inhibits expression of a Wnt antagonist, an RNAi construct, siRNA, or shRNA that inhibits expression of a Wnt antagonist, an antibody that binds to and inhibits the activity of a Wnt antagonist, a nucleic acid comprising a nucleotide sequence that encodes a β-catenin polypeptide, a polypeptide comprising an amino acid sequence of a β-catenin polypeptide, a nucleic acid comprising a nucleotide sequence that encodes a Lef-1 polypeptide, and a polypeptide comprising an amino acid sequence of a Lef-1 polypeptide.

Wnt pathway agonists further include GSK3 inhibitors, such as, for example, a nucleic acid comprising a nucleotide sequence that encodes a dominant negative GSK-3, GSK3a, or GSK3 polypeptide, a polypeptide comprising an amino acid sequence of a dominant negative GSK-3, GSK3a, or GSK3 polypeptide, a small organic molecule that binds to and inhibits the expression or activity of GSK-3, GSK3a, or GSK3, an RNAi construct, siRNA, or shRNA that binds to and inhibits the expression and/or activity of GSK-3, GSK3a, or GSK3, an antisense oligonucleotide that binds to and inhibits the expression of GSK-3, GSK3a, or GSK3, an antibody that binds to and inhibits the expression and/or activity of GSK-3, GSK3a, or GSK3, a ribozyme that binds to and inhibits the expression of GSK-3, GSK3a, or GSK3, and any GSK-3-independent reagent that activates β-catenin target genes similar in effect to GSK-3 inhibition.

3. GSK3 Inhibitors

GSK3 inhibitors are specific exemplary Wnt pathway agonists suitable for use in compositions contemplated herein, and may include, but are not limited to, polynucleotides, polypeptides, and small molecules. GSK3 inhibitors contemplated herein may decrease GSK3a/β expression and/or GSK3a/β activity. Illustrative examples of GSK3 inhibitors contemplated herein include, but are not limited to, anti-GSK3 antibodies, dominant negative GSK3 variants, siRNA, shRNA, miRNA and antisense nucleic acids that target GSK3.

Other illustrative GSK3 inhibitors include, but are not limited to: Kenpaullone, 1-Azakenpaullone, CHIR99021, CHIR98014, AR-A014418, CT 99021, CT 20026, SB216763, AR-A014418, lithium, TDZD-8, BIO, BIO-Acetoxime, (5-Methyl-1H-pyrazol-3-yl)-(2-phenylquinazolin-4-yl)amine, Pyridocarbazole-cyclopenadienylruthenium complex, TDZD-8 4-Benzyl-2-methyl-1,2,4-thiadiazolidine-3,5-dione, 2-Thio(3-iodobenzyl)-5-(1-pyridyl)-[1,3,4]-oxadiazole, OTDZT, alpha-4-Dibromoacetophenone, AR-AO 144-18, 3-(1-(3-Hydroxypropyl)-1H-pyrrolo[2,3-b]pyridin-3-yl]-4-pyrazin-2-yl-pyrrole-2,5-dione, TWS119 pyrrolopyrimidine compound, L803 H-KEAPPAPPQSpP-NH2 or its myristoylated form, 2-Chloro-1-(4,5-dibromo-thiophen-2-yl)-ethanone, GF109203X, R0318220, TDZD-8, TIBPO, and OTDZT.

In particular illustrative embodiments, the GSK3 inhibitor is CHIR99021, BIO, or Kenpaullone.

In a preferred embodiment, the GSK3 inhibitor is CHIR99021.

In another embodiment, the GSK3 inhibitor is BRD0705.

4. ERK/MEK Inhibitors

ERK/MEK inhibitors suitable for use in compositions contemplated herein include, but are not limited to, polynucleotides, polypeptides, and small molecules. ERK/MEK inhibitors contemplated herein may decrease MEK or ERK expression and/or MEK or ERK activity. Illustrative examples of MEK/ERK inhibitors contemplated herein include, but are not limited to, anti-MEK or anti-ERK antibodies, dominant negative MEK or ERK variants, siRNA, shRNA, miRNA and antisense nucleic acids that target MEK or ERK.

Other illustrative ERK/MEK inhibitors include, but are not limited to, PD0325901, PD98059, U0126, SL327, ARRY-162, PD184161, PD184352, sunitinib, sorafenib, Vandetanib, pazopanib, Axitinib, GSKI 120212, ARRY-438162, RO5126766, XL518, AZD8330, RDEA1 19, AZD6244, FR180204 and PTK787.

Additional illustrative MEK/ERK inhibitors include those compounds disclosed in International Published Patent Applications WO 99/01426, WO 02/06213, WO 03/077914, WO 05/051301 and WO2007/044084.

Further illustrative examples of MEK/ERK inhibitors include the following compounds: 6-(4-Bromo-2-chloro-phenylamino)-7-fluoro-3-methyl-3H-benzoimidazole-5-carboxylic acid (2,3-dihydroxy-propoxy)-amide, 6-(4-Bromo-2-chloro-phenylamino)-7-fluoro-3-(tetrahydro-pyran-2-ylm-ethyl)-3H-benzoimidazole-5-carboxylic acid (2-hydroxy-ethoxy)-amide, 1-[6-(4-Bromo-2-chloro-phenylamino)-7-fluoro-3-methyl-3H-benzoimidazol-5-yl]-2-hydroxy-ethanone, 6-(4-Bromo-2-chloro-phenylamino)-7-fluoro-3-methyl-3H-benzoimidazole-5-carboxylic acid (2-hydroxy-1,1-dimethyl-ethoxy)-amide, 6-(4-Bromo-2-chloro-phenylamino)-7-fluoro-3-(tetrahydro-furan-2-ylm-ethyl)-3H-benzoimidazole-5-carboxylic acid (2-hydroxy-ethoxy)-amide, 6-(4-Bromo-2-fluoro-phenylamino)-7-fluoro-3-methyl-3H-benzoimidazole-5-carboxylic acid (2-hydroxy-ethoxy)-amide, 6-(2,4-Dichloro-phenylamino)-7-fluoro-3-methyl-3H-benzoimidazole-5-carboxylic acid (2-hydroxy-ethoxy)-amide, 6-(4-Bromo-2-chloro-phenylamino)-7-fluoro-3-methyl-3H-benzoimidazole-5-carboxylic acid (2-hydroxy-ethoxy)-amide, referred to hereinafter as MEK inhibitor 1, 2-[(2-fluoro-4-iodophenyl)amino]-N-(2-hydroxyethoxy)-1,5-dimethyl-6-oxo-1,6-dihydropyridine-3-carboxamide(referred to hereinafter as MEK inhibitor 2), 4-(4-bromo-2-fluorophenylamino)-N-(2-hydroxyethoxy)-1,5-dimethyl-6-oxo-1,6-dihydro-pyridazine-3-carboxamide, and a pharmaceutically acceptable salt thereof.

In a preferred embodiment, the MEK/ERK inhibitor is PD98059.

5. Rock Inhibitors

Rho associated kinases (ROCK) are serine/threonine kinases that serve downstream effectors of Rho kinases (of which three isoforms exist—RhoA, RhoB and RhoC). ROCK inhibitors suitable for use in compositions contemplated herein include, but are not limited to, polynucleotides, polypeptides, and small molecules. ROCK inhibitors contemplated herein may decrease ROCK expression and/or ROCK activity. Illustrative examples of ROCK inhibitors contemplated herein include, but are not limited to, anti- ROCK antibodies, dominant negative ROCK variants, siRNA, shRNA, miRNA and antisense nucleic acids that target ROCK.

Illustrative ROCK inhibitors contemplated herein include, but are not limited to: thiazovivin, Y27632, Fasudil, AR122-86, Y27632 H-1152, Y-30141, Wf-536, HA-1077, hydroxyl-HA-1077, GSK269962A, SB-772077-B, N-(4-Pyridyl)-N'-(2,4,6-trichlorophenyl)urea, 3-(4-Pyridyl)-1H-indole, and (R)-(+)-trans-N-(4-Pyridyl)-4-(1-aminoethyl)-cyclohexanecarboxamide, and ROCK inhibitors disclosed in U.S. Pat. No. 8,044,201, which is herein incorporated by reference in its entirety.

In one embodiment, the ROCK inhibitor is thiazovivin, Y27632, or pyrintegrin.

In a preferred embodiment, the ROCK inhibitor is thiazovivin.

The amount of the small molecules in the compositions and cell culture media contemplated herein can vary and may be optimized according to the specific culture conditions, including the specific molecules and combinations used, the type of cell being cultured in the media, and the specific application. In one embodiment, a small molecule is present in a composition at a concentration sufficient to induce pluripotency, improve the efficiency of reprogramming, increase or maintain the potency of a cell, or induce or maintain ground state pluripotency.

Another aspect of the invention concerns Notch activators for use with the invention. Notch encompasses all members of the Notch receptor family, including, but not limited to, Notch1. Notch activators, include, but are not limited to, agonists of Notch receptor. The Notch agonist will bind Notch receptor, and as well, initiate or mediate the signaling event associated with the Notch receptor, such as, for example, to cause the intracellular domain of Notch to be cleaved and translocated to the nucleus. Notch activators include, but are not limited to, Jag1, Jag2, DLL-1, DLL-3 and DLL-4. Notch activators include, but are not limited to, those disclosed in EP 2606884, U.S. Pat. Nos. 6,689,744, and 5,780,300, the disclosures of which are incorporated herein by reference. In some embodiments, one or more of the Notch ligand can be introduced as soluble peptide, or immobilized on a solid material. The solid material may include, but not limited to, polystyrene plates, or beads. The beads for Notch ligands immobilization may be agarose beads, magnetic beads, and latex beads. In one embodiment, the Notch ligand peptide is conjugated/immobilized to beads. In another embodiment, the Notch ligand peptide is conjugated/immobilized to the surface of a polystyrene plate. In some embodiments, the immobilization of the Notch ligand is non-covalent. In some embodiments, the Notch ligand peptide is presented by cells.

Yet another aspect of the invention concerns BMP pathway activators, which include those agents disclosed in the following publications, the disclosures of which are incorporated herein by reference: WO 2014011540, WO 2014062138, and WO 2005117994. BMP pathway activators for use with the invention include, but are not limited to, BMP-5, BMP-6, BMP-7, BMP-8, BMP-2, and BMP-4. In one non-limiting embodiment of the invention, the BMP pathway activator is BMP-4. BMPs are multifunctional cytokines which are members of the transforming growth factor-beta superfamily. Bone morphogenetic protein (BMP) receptors mediate BMP signaling through activating Smad. BBMP ligands bind to the BMP receptors BMPRI and BMPRII. After BMPRII phosphorylated, following activates BMPRI. Phosphorylated BMPRI subsequently phosphorylates receptor-activated Smad proteins (R-Smads), which associate with common mediator-Smad (co-Smad) and enter the nucleus, where they regulate gene expression. In one embodiment, the BMP pathway activator is BMP4.

The present invention provides compositions for obtaining hematopoietic lineage cells from iPSC either through definitive HSC differentiated from iPSCs or through definitive hemogenic endothelium differentiated from iPSCs, and each of the approaches is void of the EB formation from iPSC for desired cell differentiation.

6. hiPSC Differentiation Platforms
 I. iCD34 Platform

One aspect of the present invention provides a culture platform for obtaining definitive hemogenic endothelium using pluripotent stem cells. As used herein, definitive hemogenic endothelium is a hemogenic cell population directed towards definitive hematopoiesis with the capacity to give rise to all hematopoietic cells including, but not limited to, definitive HSCs, hematopoietic multipotent progenitors (MPP), T cell progenitors, NK cell progenitors, T cells, NK cells, NKT cells, and/or B cells.

In one embodiment, the culture platform for obtaining definitive hemogenic endothelium using pluripotent stem cells including iPSCs comprises a seeding medium comprising MEKi, GSKi, and ROCKi. In some embodiments, the seeding medium is free of, or essentially free of, TGFβ receptor/ALK inhibitors. In one embodiment, the combinations of the small molecules in the seeding culture media of the invention are shown in Table 9 as Fate Maintenance Medium (FMM). The components of the medium may be present in the medium in amounts within the concentration ranges shown in Table 1. In one embodiment, the iPSC used for obtaining definitive hemogenic endothelium was a cell line generated using the Fate Reprogramming Medium (FRM), and further maintained in FMM to establish and sustain the ground or naïve state of the iPSC cell line, which is suitable for stage specific differentiation as disclosed herein. The ground state or naïve iPSC so obtained is amenable to cryopreservation. In the present invention, an iPSC cell line or a clonal iPSC preserved may be seeded in FMM for the subsequence differentiation into definitive hemogenic endothelium.

TABLE 1

Seeding culture for Naïve iPSC to obtain CD34+ definitive hemogenic endothelium, multipotent progenitors, T cell progenitors and NK cell progenitors:

| Conventional hESC Medium (Conv.) | Fate Reprogramming Medium | Fate Maintenance Medium (FMM) |
|---|---|---|
| DMEM/F12 Knockout Serum | DMEM/F12 Knockout Serum N2 B27 | DMEM/F12 Knockout Serum |
| Glutamine Non-Essential Amino Acids β-mercaptoethanol bFGF (0.2-50 ng/mL) | Glutamine Non-Essential Amino Acids β-mercaptoethanol bFGF (2-500 ng/mL) | Glutamine (1x) Non-Essential Amino Acids β-mercaptoethanol bFGF (2-500 ng/mL) |
| | LIF (0.2-50 ng/mL) Thiazovivin (0.1-25 μM) PD0325901 (0.005-2 μM) CHIR99021 (0.02-5 μM) SB431542 (0.04-10 μM) | LIF (0.2-50 ng/mL) Thiazovivin (0.1-25 μM) PD0325901 (0.005-2 μM) CHIR99021 (0.02-5 μM) |
| In combination with MEF | Feeder-free, in combination with Matrigel ™ or Vitronectin | |

One aspect of the present invention provides a culture medium for mesoderm differentiation and expansion from pluripotent stem cells including iPSCs. In some embodiments, the iPSC is naïve iPSC. In one embodiment, the culture medium comprises a BMP activator, and optionally bFGF, and a CD34 base medium comprising small molecules in a combination as shown in Table 2. In some embodiments, the culture medium comprises an extracellular matrix protein. In other embodiments, the culture medium herein comprises small molecules, growth factors, and/or cytokines in concentration ranges as shown in Table 2. In some embodiments, the culture medium is fully defined with the substitution of Matrigel™ for Vitronectin.

TABLE 2

| iCD34-A culture medium for obtaining mesoderm from naïve iPSC | |
|---|---|
| iCD34 base medium | StemPro 34 |
| | Glutamine |
| | Non-Essential Amino Acids |
| | Ascorbic Acid (1-250 ng/ml) |
| | MTG (10-2500 µM) |
| BMP4 (0.05-15 ng/ml) | |
| Feeder-free, in combination with Matrigel ™ or Vitronectin | |

In one embodiment, the above culture medium for mesoderm differentiation and expansion from pluripotent stem cells further comprises bFGF between 0.2-50 ng.

One aspect of the present invention provides a culture medium for obtaining mesodermal cells with definitive hemogenic endothelium potential from pluripotent stem cells including iPSCs. In some embodiments, the iPSC is naïve iPSC. In one embodiment, the culture medium comprises a BMP activator, a Wnt pathway activator, and bFGF. In one embodiment, the Wnt pathway activator is a GSK3 inhibitor. In one embodiment, the culture medium comprising GSK3 inhibitor is only applied after mesodermal cell specification in order to achieve definitive HE potential. In one embodiment the culture medium comprising a BMP activator, a GSK3 inhibitor and bFGF, further comprises a CD34 base medium comprising small molecules in a combination as shown in Table 3. In one embodiment, the above culture medium is free of TGFβ receptor/ALK inhibitors. In some embodiments, the culture medium comprises an extracellular matrix protein. In other embodiments, the culture medium herein comprises small molecules, growth factors, and/or cytokines in concentration ranges as shown in Table 11. In some embodiments, the culture medium is fully defined with the substitution of Matrigel™ for Vitronectin.

TABLE 3

| iCD34-B culture medium for obtaining mesodermal cells with definitive hemogenic endothelium potential | |
|---|---|
| iCD34 base medium | StemPro 34 |
| | Glutamine |
| | Non-Essential Amino Acids |
| | Ascorbic Acid (1-250 ng/ml) |
| | MTG (10-2500 µM) |
| BMP4 (0.05-15 ng/ml) | |
| bFGF (0.2-50 ng/ml) | |
| CHIR99012 (0.04-10 µM) | |
| Feeder-free, in combination with Matrigel ™ or Vitronectin | |

One aspect of the present invention provides a culture medium for obtaining definitive hemogenic endothelium from mesodermal cells. In one embodiment, the culture medium comprises a ROCK inhibitor, and one or more growth factors and cytokines selected from the group consisting of VEGF, bFGF, SCF, IL6, and IL11. In one embodiment, the culture medium comprises VEGF, bFGF, SCF, IL6, IL11 and a ROCK inhibitor, and a CD34 base medium comprising small molecules in a combination as shown in Table 4. In one embodiment, the culture medium comprising a ROCK inhibitor, and one or more growth factors and cytokines selected from the group consisting of VEGF, bFGF, SCF, IL6, and IL11 further comprises one or more of a Wnt pathway activator, IGF, and EPO. In some embodiments, the culture medium for generating definitive HE from mesodermal cells comprises a ROCK inhibitor, a Wnt pathway activator, VEGF, bFGF, SCF, IL6, and IL11, and one or more of IGF and EPO. In some embodiments, the Wnt pathway activator is a GSK3 inhibitor. In some embodiments, the Wnt pathway activator is CHIR99021. In one embodiment the culture medium comprising VEGF, bFGF, SCF, IL6, IL11 and a ROCK inhibitor is free of one or more of a Wnt pathway activator, TGFβ receptor/ALK inhibitor, IGF1, and EPO. In other embodiments, the culture medium herein comprises small molecules, growth factors, and/or cytokines in concentration ranges as shown in Table 4.

TABLE 4

| iCD34-C culture medium for obtaining definitive hemogenic endothelium from mesoderm | |
|---|---|
| iCD34 base medium | StemPro 34 |
| | Glutamine |
| | Non-Essential Amino Acids |
| | Ascorbic Acid (1-250 ng/ml) |
| | MTG (10-2500 µM) |
| VEGF (0.2-50 ng/ml) | |
| bFGF (0.1-25 ng/ml) | |
| SCF (1-250 ng/ml) | |
| IL6 (0.2-50 ng/ml) | |
| IL11 (0.2-50 ng/ml) | |
| Y27632 (0.2-50 µM) | |
| Feeder-free, in combination with Matrigel ™ or Vitronectin | |

One aspect of the present invention provides a culture platform for obtaining multipotent progenitor (MPP) cells from definitive hemogenic endothelium. The MPP can be further differentiated into myeloid, including neutrophil progenitors. In one embodiment, the culture platform comprises (i) a culture medium comprising a BMP activator, a ROCK inhibitor, and one or more growth factors and cytokines selected from the group consisting of TPO, IL3, GMCSF, EPO, bFGF, VEGF, SCF, IL6, Flt3L and IL11, wherein the culture medium is suitable for differentiating definitive hemogenic endothelium into a pre-HSC (Table 5). In another embodiment the culture platform comprising the culture medium for differentiating definitive hemogenic endothelium into a pre-HSC, further comprises (ii) a culture medium comprising a BMP activator, TPO, IL3, GMCSF, EPO, bFGF, VEGF, SCF, IL6, and IL11, wherein the culture medium is free of ROCK inhibitor and is suitable to differentiate the pre-HSC into multipotent progenitors. In some embodiments, the ROCK inhibitor is thiazovivin or Y27632. In some embodiments the ROCK inhibitor is Y27632. In some embodiments, the BMP activator is BMP4. In other embodiments, the culture medium herein comprises small molecules, growth factors, and/or cytokines in concentration ranges as shown in Table 5.

TABLE 5 iMPP-A culture medium for obtaining multipotent progenitors from definitive HE

| iCD34 base medium | StemPro 34 |
|---|---|
| | Glutamine |
| | Non-Essential Amino Acids |
| | Ascorbic Acid (1-250 ng/ml) |
| | MTG (10-2500 µM) |
| VEGF (0.2-50 ng/ml) | |
| bFGF (0.2-25 ng/ml) | |
| SCF (1-250 ng/ml) | |
| Flt3L (0.5-150 ng/ml) | |
| IL6 (0.2-50 ng/ml) | |
| IL11 (0.2-50 ng/ml) | |
| Y27632 (0.2-50 µM)* not included when differentiating the pre-HSC into multipotent progenitors | |
| BMP4 (0.5-150 ng/ml) | |
| TPO (0.5-150 ng/ml) | |
| IL3 (0.5-150 ng/ml) | |
| GMCSF (0.1-25 ng/ml) | |
| EPO (0.02-5 ng/ml) | |
| Feeder-free, in combination with Matrigel™ or Vitronectin | |

II. iNK/iT PLATFORMS

One aspect of the present invention provides a culture platform for generating T cell progenitors or T-cells from definitive hemogenic endothelium. In one embodiment, the culture platform comprises (i) a medium comprising a ROCK inhibitor; one or more growth factors and cytokines selected from the group consisting of VEGF, bFGF, SCF, Flt3L, TPO, and IL7; and optionally, a BMP activator; wherein the medium is suitable for differentiating definitive hemogenic endothelium into pre-T cell progenitor (pre-iproT); and/or (ii) a medium comprising one or more growth factors and cytokines selected from the group consisting of SCF, Flt3L, and IL7, wherein the medium is free of one or more of VEGF, bFGF, TPO, BMP activators and ROCK inhibitors, and is suitable for differentiating the pre-T cell progenitors to T cell progenitors or T cells (Table 6). In some embodiments, the medium differentiating definitive HE into pre-iproT comprises a ROCK inhibitor, SCF, Flt3L, TPO, and IL7; and is without a BMP activator. In some embodiments, the medium differentiating pre-iproT to T cell progenitors or T cells comprises SCF, Flt3L, and IL7. In some embodiments, the ROCK inhibitor is thiazovivin or Y27632. In some embodiments the ROCK inhibitor is Y27632. In some embodiments, the BMP activator is BMP4. In other embodiments, the culture medium herein comprises small molecules, growth factors, and/or cytokines in concentration ranges as shown in Table 6.

TABLE 6 iTC-A2 culture medium for obtaining pre-T cell progenitors from definitive HE

| iCD34 base medium | StemPro 34 |
|---|---|
| | Glutamine |
| | Non-Essential Amino Acids |
| | Ascorbic Acid (1-250 ng/ml) |
| | MTG (10-2500 µM) |
| Flt3L (0.2-50 ng/ml) | |
| IL7 (0.2-50 ng/ml) | |
| SCF (1-250 ng/ml) | |
| TPO (0.2-50 ng/ml) | |
| *: Not included in iTC-B2 for obtaining pre-T progenitors to T cell progenitors or T cells | BMP4(0.5-150 ng/ml)* |
| | VEGF (0.2-50 ng/ml)* |
| | bFGF (0.1-25 ng/ml)* |
| | Y27632 (0.2-50 µM)* |
| Feeder-free, Suspension or monolayer | |

One aspect of the present invention provides a culture platform for generating NK cell progenitors or NK cells from definitive hemogenic endothelium. In one embodiment, the culture platform comprises (i) a medium comprising a ROCK inhibitor; one or more growth factors and cytokines selected from the group consisting of VEGF, bFGF, SCF, Flt3L, TPO, IL3, IL7, and IL15; and optionally, a BMP activator, wherein the medium is suitable for differentiating definitive hemogenic endothelium into pre-NK cell progenitor (pre-iproNK); and (ii) a medium comprising one or more growth factors and cytokines selected from the group consisting of SCF, Flt3L, IL3, IL7, and IL15, wherein the medium is free of one or more of VEGF, bFGF, TPO, BMP activators and ROCK inhibitors and is suitable for differentiating the pre-NK cell progenitors to NK cell progenitors or NK cells. In some embodiments, the medium differentiating definitive HE into pre-iproNK comprises a ROCK inhibitor, SCF, Flt3L, TPO, IL3, IL7 and IL5; and is without a BMP activator. In some embodiments, the medium differentiating pre-iproNK to NK progenitors or NK cells comprises SCF, Flt3L, and IL15. In some embodiments, the ROCK inhibitor is thiazovivin or Y27632. In some embodiments the ROCK inhibitor is Y27632. In some embodiments, the BMP activator is BMP4. In other embodiments, the culture medium herein comprises small molecules, growth factors, and/or cytokines in concentration ranges as shown in Table 7.

TABLE 7 iNK-A2 culture medium for obtaining pre-NK cell progenitors from definitive HE

| iCD34 base medium | StemPro 34 |
|---|---|
| | Glutamine |
| | Non-Essential Amino Acids |
| | Ascorbic Acid (1-250 ng/ml) |
| | MTG(10-2500 µM) |
| SCF (1-250 ng/ml) | |
| Flt3L (0.2-50 ng/ml) | |
| TPO (0.1-25 ng/ml) | |
| IL7 (0.2-50 ng/ml) | |
| IL15 (0.4-100 ng/ml) | |
| IL3 (0.1-25 ng/ml) | |
| *: Not included in iNK-B2 for obtaining pre-NK progenitors to NK progenitors or NK cells | VEGF (0.2-50 ng/ml)* |
| | bFGF (0.1-25 ng/ml)* |
| | BMP4 (0.5-150 ng/ml)* |
| | Y27632 (0.2-50 µM)* |
| Feeder-free, Suspension, monolayer | |

Another aspect of the present invention provides a culture platform for obtaining a T cell progenitor or T cell, which comprises one or more of (i) a medium that comprises one or more growth factors and cytokines selected from the group consisting of SCF, Ft3L, and IL7, and is free, or essentially free, of one or more of VEGF, bFGF, BMP activators and ROCK inhibitors, which medium is suitable for differentiating the pre-T cell progenitor to T cell progenitor or T cell; (ii) a medium that comprises a ROCK inhibitor; one or more growth factors and cytokines selected from the group consisting of VEGF, bFGF, SCF, Flt3L, TPO, and IL7; and optionally, a BMP activator, which is suitable for differentiating definitive hemogenic endothelium into pre-T cell progenitor; (iii) a culture medium that comprises a ROCK inhibitor; one or more growth factors and cytokines selected from the group consisting of bFGF, VEG, SCF, IGF, EPO, IL6, and IL11; and optionally a Wnt pathway activator, and is suitable for definitive hemogenic endothelium differentiation and expansion from mesodermal cells; (iv) a culture medium that comprises a BMP activator, bFGF, and a GSK3 inhibitor, and is suitable for obtaining definitive hemogenic endothelium potential in mesodermal cells; (v) a culture medium that comprises a BMP activator, and optionally bFGF, and is suitable for generating and expanding mesodermal cells from iPSC; and (vi) a culture medium that comprises MEKi, GSKi, and ROCKi, is free, or essentially free, of TGFβ receptor/ALK inhibitors, and is suitable for seeding and expanding naïve iPSC. In some embodiments, all above media are free, or essentially free, of TGFβ receptor/ALK inhibitors. In some embodiments, the GSK3 inhibitor is CHIR99012 or BIO. In some embodiments, the GSK3 inhibitor is CHIR99012. In some embodiments, the ROCK inhibitor is thiazovivin or Y27632. In some embodiments the ROCK inhibitor is Y27632. In some embodiments, the BMP activator is BMP4.

In one embodiment, the culture platform for generating a T cell progenitor or T cell comprises (i) a medium that comprises SCF, Flt3L, and IL7, is free, or essentially free, of one or more of VEGF, bFGF, BMP activators and ROCK inhibitors, and is suitable for differentiating the pre-T cell progenitor to T cell progenitors or T cells. In another embodiment, the culture platform for generating a T cell progenitor or T cell comprising medium (i), further comprises (ii) a medium that comprises a ROCK inhibitor; one or more growth factors and cytokines selected from the group consisting of VEGF, bFGF, SCF, Flt3L, TPO, and IL7; and optionally a BMP activator; which is suitable for differentiating definitive hemogenic endothelium into pre-T cell progenitor. In another embodiment, the culture platform for generating a T cell progenitor or T cell comprising medium (i) and (ii), further comprises (iii) a culture medium that comprises a ROCK inhibitor; one or more growth factors and cytokines selected from the group consisting of bFGF, VEGF, SCF, IGF, EPO, IL6, and IL11; optionally, a Wnt pathway activator, wherein the composition is suitable for definitive hemogenic endothelium differentiation and expansion from mesodermal cells. In still another embodiment, the culture platform for generating a T cell progenitor or T cell comprising medium (i), (ii) and (iii), further comprises (iv), a culture medium that comprises a BMP activator, bFGF, and a GSK3 inhibitor, and is suitable for obtaining definitive hemogenic endothelium potential in mesodermal cells. In yet another embodiment, the culture platform for generating a T cell progenitor or T cell comprising medium (i), (ii), (iii) and (iv) further comprises (v), a culture medium that comprises a BMP activator, and optionally bFGF, and is suitable for generating and expanding mesodermal cells from iPSC. In another embodiment, the culture platform for generating a T cell progenitor or T cell comprising medium (i), (ii), (iii), (iv) and (v) further comprises (vi), a culture medium that comprises MEKi, GSKi, and ROCKi, is free, or essentially free, of TGFβ receptor/ALK inhibitors, and is suitable for seeding and expanding naïve iPSC. In some embodiments, all above media are free, or essentially free, of TGFβ receptor/ALK inhibitors. In some embodiments, the GSK3 inhibitor is CHIR99012 or BIO. In some embodiments, the GSK3 inhibitor is CHIR99012. In some embodiments, the ROCK inhibitor is thiazovivin or Y27632. In some embodiments the ROCK inhibitor is Y27632. In some embodiments, the BMP activator is BMP4. In some embodiments, Notch factors are used in the culture platform for generating a T cell progenitor or T cell. In some embodiments, Notch factors including Jag1, Jag2, DLL-1, DLL-3 and DLL-4 can be introduced as soluble peptide, peptide conjugated to beads, peptide conjugated to the surface, or peptide presented by cells.

Another aspect of the present invention provides a culture platform for obtaining a NK cell progenitor or NK cell comprising one or more of (i) a medium comprising one or more growth factors and cytokines selected from the group consisting of SCF, Flt3L, IL3, IL7, and IL15, wherein the medium is free, or essentially free, of one or more of VEGF, bFGF, BMP activators and ROCK inhibitors and is suitable for differentiating the pre-NK cell progenitors to NK cell progenitors or NK cells; (ii) a medium comprising a ROCK inhibitor; one or more growth factors and cytokines selected from the group consisting of VEGF, bFGF, SCF, Flt3L, TPO, IL3, IL7, and IL15; and optionally, a BMP activator, wherein the medium is suitable for differentiating definitive hemogenic endothelium into pre-NK cell progenitor; (iii) a culture medium that comprises a ROCK inhibitor; one or more growth factors and cytokines selected from the group consisting of bFGF, VEGF, SCF, IGF, EPO, IL6, and IL11; and optionally, a Wnt pathway activator; wherein the composition is suitable for definitive hemogenic endothelium differentiation and expansion from mesodermal cells to; (iv) a culture medium that comprises a BMP activator, bFGF, and a GSK3 inhibitor, and is suitable for obtaining definitive hemogenic endothelium potential in mesodermal cells; (v) a culture medium that comprises a BMP activator, and optionally bFGF, and is suitable for generating and expanding mesodermal cells from iPSCs; (vi) a culture medium that comprises MEKi, GSKi, and ROCKi, is free, or essentially free, of TGFβ receptor/ALK inhibitors, and is suitable for seeding and expanding naïve iPSC. In some embodiments, all above media are free, or essentially free, of TGFβ receptor/ALK inhibitors. In some embodiments, the GSK3 inhibitor is CHIR99012 or BIO. In some embodiments, the GSK3 inhibitor is CHIR99012. In some embodiments, the ROCK inhibitor is thiazovivin or Y27632. In some embodiments the ROCK inhibitor is Y27632. In some embodiments, the BMP activator is BMP4. In some embodiments, NK maturation is conducted using one or more of artificial antigens to stimulate NK growth, development, and maturation, introduced in the forms of bead conjugation, plasma membrane particles and/or antigen presenting cells.

In one embodiment, the culture platform for generating a NK cell progenitor or NK cell comprises (i) a medium comprising one or more growth factors and cytokines selected from the group consisting of SCF, Flt3L, IL3, IL7, and IL15, wherein the medium is free, or essentially free, of one or more of VEGF, bFGF, BMP activators and ROCK inhibitors and is suitable for differentiating the pre-NK cell progenitors to NK cell progenitors or NK cells. In some embodiments, NK maturation is conducted using one or more of artificial antigens to stimulate NK growth, development, and maturation, introduced in the forms of bead conjugation, plasma membrane particles and/or antigen presenting cells. In another embodiment, the culture platform for generating a NK cell progenitor or NK cell comprising medium (i), further comprises (ii) a medium comprising a ROCK inhibitor, one or more growth factors and cytokines selected from the group consisting of VEGF, bFGF, SCF, Flt3L, TPO, IL3, IL7, and IL15; and optionally, a BMP activator, wherein the medium is suitable for differentiating definitive hemogenic endothelium into pre-NK cell progenitor. In another embodiment, the culture platform for generating a NK cell progenitor or NK cell comprising medium (i) and (ii), further comprises (iii), a culture medium that comprises a ROCK inhibitor; one or more growth factors and cytokines selected from the group consisting of bFGF, VEGF, SCF, IGF, EPO, IL6, and IL11; and optionally a Wnt pathway activator; and the composition is suitable for definitive hemogenic endothelium differentiation and expansion from mesodermal cells. In still another embodiment, the culture platform for generating a NK cell progenitor or NK cell comprising medium (i), (ii) and (iii), further comprises (iv), a culture medium that comprises a BMP activator, bFGF, and a GSK3 inhibitor, and is suitable for obtaining definitive hemogenic endothelium potential in mesodermal cells. In yet another embodiment, the culture platform for generating a NK cell progenitor or NK cell comprising medium (i), (ii), (iii) and (iv), further comprises (v), a culture medium that comprises a BMP activator, and optionally bFGF, and is suitable for generating and expanding mesodermal cells from iPSCs. In another embodiment, the culture platform for generating a NK cell progenitor or NK cell comprising medium (i), (ii), (iii), (iv) and (v) further comprises (vi), a culture medium that comprises MEKi, GSKi, and ROCKi, is free, or essentially free, of TGFβ receptor/ALK inhibitors, and is suitable for seeding and expanding naïve iPSC. In some embodiments, all above media are free, or essentially free, of TGFβ receptor/ALK inhibitors. In some embodiments, the GSK3 inhibitor is CHIR99012 or BIO. In some embodiments, the GSK3 inhibitor is CHIR99012. In some embodiments, the ROCK inhibitor is thiazovivin or Y27632. In some embodiments the ROCK inhibitor is Y27632. In some embodiments, the BMP activator is BMP4.

One aspect of the present invention provides a culture platform for generating definitive hemogenic endothelium, which comprises one or more of (i) a culture medium for definitive hemogenic endothelium differentiation and expansion from mesoderm cells, comprising a ROCK inhibitor; one or more growth factors and cytokines selected from the group consisting of bFGF, VEGF, SCF, IGF, EPO, IL6, and IL11; and optionally, a Wnt pathway activator; (ii) a culture medium for obtaining definitive hemogenic potential in mesodermal cells, comprising a BMP activator, bFGF, and a GSK3 inhibitor; (iii) a culture medium for differentiating and expanding mesodermal cells from naïve iPSC, comprising a BMP activator, and optionally bFGF; and (iv) a naïve iPSC seeding and expansion culture comprising MEKi, GSKi, and ROCKi, and the seeding culture is free of TGFβ receptor/ALK inhibitors. In some embodiments, the definitive hemogenic endothelium are CD34+. In some embodiments, all above media are free, or essentially free, of TGFβ receptor/ALK inhibitors. In some embodiments, the GSK3 inhibitor is CHIR99012 or BIO. In some embodiments, the GSK3 inhibitor is CHIR99012. In some embodiments, the ROCK inhibitor is thiazovivin or Y27632. In some embodiments the ROCK inhibitor is Y27632. In some embodiments, the BMP activator is BMP4.

In one embodiment, the culture platform for obtaining a definitive hemogenic endothelium comprises (i) a culture medium comprising a ROCK inhibitor; one or more growth factors and cytokines selected from the group consisting of bFGF, VEGF, SCF, IGF, EPO, IL6, and IL11; and optionally, a Wnt pathway activator; wherein the culture medium is suitable for differentiating and expanding definitive hemogenic endothelium from mesodermal cells. In one embodiment, the culture platform comprising the culture media (i), further comprises (ii), a culture medium comprising a BMP activator, bFGF, and a GSK3 inhibitor, wherein the culture medium (ii) is suitable for obtaining definitive hemogenic potential in mesodermal cells. In another embodiment, the culture platform comprising the culture media (i), and (ii), further comprises (iii), a culture medium comprising a BMP activator, and optionally bFGF, wherein the culture medium (iii) is suitable for differentiating and expanding mesodermal cells from naïve iPSCs. In yet another embodiment, the culture platform comprising the culture media (i), (ii) and (iii), further comprises (iv), a culture medium comprising MEKi, GSKi, and ROCKi, and the culture medium (v) is free, or essentially free, of TGFβ receptor/ALK inhibitors, wherein the culture medium (v) is suitable for seeding and expanding naïve iPSC. In some embodiments, all above media are free, or essentially free, of TGFβ receptor/ALK inhibitors. In some embodiments, the GSK3 inhibitor is CHIR99012 or BIO. In some embodiments, the GSK3 inhibitor is CHIR99012. In some embodiments, the ROCK inhibitor is thiazovivin or Y27632. In some embodiments the ROCK inhibitor is Y27632. In some embodiments, the BMP activator is BMP4.

One aspect of the present invention provides a culture platform for generating CD34+ definitive hemogenic endothelium, which comprises one or more of (i) a culture medium for differentiating and expanding definitive hemogenic endothelium from mesodermal cells, comprising a ROCK inhibitor; one or more growth factors and cytokines selected from the group consisting of bFGF, VEGF, SCF, IGF, EPO, IL6, and IL11; and optionally, a Wnt pathway activator, wherein the definitive hemogenic endothelium comprises CD34+ definitive hemogenic endothelium; (ii) a culture medium for obtaining definitive hemogenic potential in mesodermal cells, comprising a BMP activator, bFGF, and a GSK3 inhibitor; (iii) a culture medium for differentiating and expanding mesodermal cells from naïve iPSC, comprising a BMP activator, and optionally bFGF; and (iv) a naïve iPSC seeding or expanding culture comprising MEKi, GSKi, and ROCKi, and the seeding culture is free, or essentially free, of TGFβ receptor/ALK inhibitors. In some embodiments, all above media are free, or essentially free, of TGFβ receptor/ALK inhibitors. In some embodiments, the GSK3 inhibitor is CHIR99012 or BIO. In some embodiments, the GSK3 inhibitor is CHIR99012. In some embodiments, the ROCK inhibitor is thiazovivin or Y27632. In some embodiments the ROCK inhibitor is Y27632. In some embodiments, the BMP activator is BMP4.

One aspect of the present invention provides a culture platform for generating mesodermal cells, which comprises one or more of (i) a culture medium for differentiating and expanding mesodermal cells from naïve iPSC, comprising a BMP activator, and optionally bFGF; and (ii) a naïve iPSC seeding or expanding culture comprising MEKi, GSKi, and ROCKi, and the seeding culture is free, or essentially free, of TGFβ receptor/ALK inhibitors. In some embodiments, all above media are free, or essentially free, of TGFβ receptor/ALK inhibitors. In some embodiments, the GSK3 inhibitor is CHIR99012 or BIO. In some embodiments, the GSK3 inhibitor is CHIR99012. In some embodiments, the ROCK inhibitor is thiazovivin or Y27632. In some embodiments the ROCK inhibitor is Y27632. In some embodiments, the BMP activator is BMP4. In some embodiments, the culture platform for generating mesodermal cells may further comprise (iii) a culture medium comprising a BMP activator, bFGF, and a GSK3 inhibitor, wherein the culture medium is for obtaining definitive hemogenic potential in mesodermal cells. In some embodiments, the culture medium comprising a BMP activator, bFGF, and a GSK3 inhibitor is free of TGFβ receptor/ALK inhibitors.

C. Method of Obtaining Definitive Hemogenic Endothelium, Multipotent Progenitors, T Cell or NK Cell Progenitors, T Cells and/or NK Cells The present invention provides a method of generating pluripotent stem cell-derived definitive hematopoietic cells using a multi-staged culture platform comprising one or more culture media. The method is suitable for feeder-free conditions. The method is also suitable for monolayer culturing, and thus without requiring EB formation or aggregate intermediates in order for pluripotent stem cell differentiation as compared to the methods known in the art. The method, as provided, generates, and at the same time, expands pluripotent stem cell-derived definitive hemogenic endothelium (iHE), CD34+HE (iCD34), which are capable of being further differentiated into multipotent progenitor cells (iMPP), natural killer cell progenitors (ipro-NK), T cell progenitors (ipro-T), mature NK cells (iNK) and T cells (iT). Additional aspect of the invention also provides a method of generating myeloid cells differentiated from pluripotent stem cell-derived CD34+, HE, HSC, and/or MPP.

In one embodiment, the invention provides a method for differentiating and expanding cells of the hematopoietic lineage from pluripotent cells in monolayer culturing, which comprises contacting the pluripotent cells with a BMP pathway activator, and optionally, bFGF, wherein pluripotent stem cell-derived mesodermal cells are obtained and expanded without forming embryoid bodies from pluripotent stem cells, which are then subjected to contact with a BMP pathway activator, bFGF, and a WNT pathway activator to obtain expanded pluripotent stem cell-derived mesodermal cells having definitive hemogenic endothelium (HE) potential without forming embryoid bodies from pluripotent stem cells. By subsequent contact with bFGF, and optionally, a ROCK inhibitor, and/or a WNT pathway activator, the mesodermal cells having definitive HE potential are differentiated to definitive HE cells, which are also expanded during differentiation.

The provided methods for obtaining cells of the hematopoietic lineage are superior to EB-mediated pluripotent stem cell differentiation, because EB formation does not lead to cell expansion, does not allow monolayer culturing, and is laborious and low efficiency. Additionally, the present invention disclosed that monolayer culturing using the methods provided herein leads to functional hematopoietic lineage cells that enable in vivo long-term hematopoietic self-renewal, reconstitution and engraftment.

As detailed below, the invention provides a method of obtaining hematopoietic lineage cells from pluripotent cells through obtaining definitive hemogenic endothelium. Particularly, the invention provides a method of directing hematopoietic lineage cell differentiation from pluripotent cells without forming EBs for differentiation.

I. iCD34 Platform

1. Deriving and Expanding Definitive iHE

One aspect of the invention provides a method of using an optimized multistage process to generate definitive hemogenic endothelium (iHE). Generally, the method begins with a first stage wherein pluripotent stem cells are seeded and expanded. The pluripotent stem cells are then differentiated to mesodermal cells, which expand in this stage. The expanded mesodermal population is then differentiated to a mesodermal population with definitive hemogenic endothelium potential, which is then differentiated and expanded into definitive hemogenic endothelium. In some embodiments, the pluripotent stem cells are iPSCs. In some embodiments, the iPSCs are naïve iPSCs. The invention further provides a method of generating and expanding definitive hemogenic endothelium (iHE) that comprises differentiating and expanding pluripotent stem cell-derived mesodermal cells, and obtaining mesodermal cells having definitive iTHE potential, which are then differentiated into iHE. Alternatively, the invention provides a method of generating and expanding definitive hemogenic endothelium comprises differentiating pluripotent stem cell-derived mesodermal cells having definitive HE potential to definitive iHE. The methods disclosed herein utilize the optimized monolayer iCD34 culture platform without EB formation, and is free, or essentially free, of TGFβ receptor/ALK inhibitors.

In one embodiment of the method of producing definitive hemogenic endothelium (iHE) from pluripotent stem cells, the method comprises (1) differentiating and expanding a mesodermal population from the pluripotent stem cells by contacting the cells with a medium comprising a BMP activator, and optionally bFGF; (2) differentiating and expanding the mesodermal population to obtain definitive HE potential in the mesodermal cells by contacting the cells with a medium comprising a BMP activator, a Wnt pathway activator and bFGF; (3) differentiating and expanding the mesodermal cells with definitive HE potential to definitive HE cells by contacting the cells with a medium comprising a ROCK inhibitor; one or more of the growth factors and cytokines selected from the group consisting of VEGF, bFGF, SCF, IL6, and IL11; and optionally a Wnt pathway activator. In some embodiments, the pluripotent stem cells are iPSCs. In some embodiments, the iPSCs are naïve iPSCs. In some embodiments, the iHE cells obtained from the above method express CD34. In some embodiments, the above method further comprises sorting the obtained iTHE cells using CD34, CD43, CD73, CXCR4, and/or CD93. In some embodiments, the sorting uses CD34 positive. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In some other embodiments, the sorting uses CD34 positive, CD43 negative, CD93-. In some other embodiments, the sorting uses CD34 positive, CD93 negative. In some embodiments, the media in the above method are free, or essentially free, of TGFβ receptor inhibitor. In some embodiments, the BMP activator of the method is BMP4. In some embodiments, the Wnt pathway activator is a GSK3 inhibitor. In some embodiments, contacting cell with a culture medium comprising GSK3 inhibitor is only after mesodermal cell specification in order to achieve definitive HE potential. In some embodiments, the method above further comprises subjecting the seeded iPSC, and/or mesodermal cells under a low oxygen tension between about 2% and about 10%. In some embodiments, the method above further comprises seeding the pluripotent stem cells by contacting the pluripotent cells with a medium comprising a MEKi, a GSKi, and a ROCKi, wherein the pluripotent stem cells expand.

In one embodiment of the method of generating definitive hemogenic endothelium (iHE) from seeded pluripotent stem cells, the method comprises (1) differentiating and expanding mesodermal cells from pluripotent stem cells by contacting the pluripotent stem cells with a medium comprising a BMP activator, and optionally bFGF; (2) obtaining mesodermal cells having definitive iHE potential by contacting the mesodermal cells with a medium comprising a BMP activator, a Wnt pathway activator and bFGF; (3) differentiating and expanding definitive HE cells from the mesodermal cells with iHE potential by contacting the mesodermal cells with a medium comprising a ROCK inhibitor; one or more of the growth factors and cytokines selected from the group consisting of VEGF, bFGF, SCF, IL6, and IL11; and optionally a Wnt pathway activator. In some embodiments, the pluripotent stem cells are iPSCs. In some embodiments, the iPSCs are naïve iPSCs. In some embodiments, the iHE cells obtained from the above method express CD34. In some embodiments, the above method further comprises sorting the obtained iTHE cells using CD34, CD43, CD73, CXCR4, and/or CD93. In some embodiments, the above method further comprises sorting using CD34 positive. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In some embodiments, the sorting uses CD34 positive, CD43 negative, and CD93 negative. In some embodiments, the sorting uses CD34 positive, and CD93 negative. In some embodiments, the media in the above method are free, or essentially free, of TGFβ receptor inhibitor. In some embodiments, the BMP activator of the method is BMP4. In some embodiments, the Wnt pathway activator is a GSK3 inhibitor. In some embodiments, the method above further comprises subjecting the seeded iPSC, and/or mesodermal cells under a low oxygen tension between about 2% and about 10%.

In one embodiment of the method of generating definitive hemogenic endothelium (iHE) from pluripotent stem cell-derived mesodermal cells, the method comprises (1) obtaining mesodermal cells having definitive HE potential by contacting the mesodermal cells with a medium comprising a BMP activator, a Wnt pathway activator and bFGF; (2) differentiating and expanding definitive HE cells from the mesodermal cells having definitive HE potential by contacting the mesodermal cells with a medium comprising a ROCK inhibitor; one or more of the growth factors and cytokines selected from the group consisting of VEGF, bFGF, SCF, IL6, and IL11; and optionally a Wnt pathway activator. In some embodiments, the iHE cells obtained from the above method express CD34. In some embodiments, the pluripotent stem cells are iPSCs. In some embodiments, the iPSCs are naïve iPSCs. In some embodiments, the above method further comprises sorting the obtained iHE cells using CD34, CD43, CD73, CXCR4, and/or CD93. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In some embodiments, the sorting uses CD34 positive, CD43 negative, and CD93 negative. In some embodiments, the sorting uses CD34 positive, and CD93 negative. In some embodiments, the media in the above method are free, or essentially free, of TGFβ receptor inhibitor. In some embodiments, the BMP activator of the method is BMP4. In some embodiments, the Wnt pathway activator is a GSK3 inhibitor. In some embodiments, the method above further comprises subjecting the mesodermal cells under a low oxygen tension between about 2% and about 10%.

In one embodiment of the method of obtaining definitive hemogenic endothelium (iHE) potential in pluripotent stem cell-derived mesodermal cells, the method comprises contacting the mesodermal cells with a medium comprising a ROCK inhibitor; one or more of the growth factors and cytokines selected from the group consisting of VEGF, bFGF, SCF, IL6, and IL11; and optionally a Wnt pathway activator, wherein the mesodermal cells expand. In some embodiments, the pluripotent stem cells are iPSCs. In some embodiments, the iPSCs are naïve iPSCs. In some embodiments, the iHE cells obtained from the above method express CD34. In some embodiments, the above method further comprises sorting the obtained iHE cells using CD34, CD43, CD73, CXCR4, and/or CD93. In some embodiments, the media in the above method are free, or essentially free, of TGFβ receptor inhibitor. In some embodiments, the Wnt pathway activator is a GSK3 inhibitor. In some embodiments, the method above further comprises subjecting the mesodermal cells under a low oxygen tension between about 2% and about 10%.

2. Deriving and Expanding Pluripotent Stem Cell-Derived Mesodermal Cells with Definitive Hemogenic Endothelium Potential One aspect of the invention provides a method of using an optimized multistage process to generate pluripotent stem cell-derived mesodermal cells. Generally, the method begins with seeding a pluripotent stem cell. The seeded pluripotent stem cell is then developed into mesoderm, which is further differentiated to a mesodermal cell with definitive hemogenic endothelium potential. Alternatively, the invention provides a method of generating pluripotent stem cell-derived mesodermal cells that comprises differentiating seeded pluripotent stem cell to mesoderm, and then differentiating mesoderm to mesodermal cells with definitive hemogenic potential. The invention further provides a method of generating pluripotent stem cell-derived mesodermal cells having definitive HE potential, and the method comprises differentiating a pluripotent stem cell-derived mesoderm to mesodermal cells with definitive hemogenic endothelium potential. In some embodiments, the pluripotent stem cells are iPSCs. In some embodiments, the iPSCs are naïve iPSCs. The methods disclosed herein utilize the optimized iCD34 culture platform, which is free, or essentially free, of TGFβ receptor/ALK inhibitors.

In one embodiment of the method of obtaining definitive hemogenic endothelium potential in mesodermal cells derived from pluripotent stem cells, the method comprises (1) differentiating and expanding mesodermal cells from pluripotent stem cells by contacting the pluripotent stem cells with a medium comprising a BMP activator, and optionally bFGF; and (2) obtaining definitive hemogenic endothelium potential in the mesodermal cells by contacting the cells with a medium comprising a BMP activator, a Wnt pathway activator and bFGF. In some embodiments, the pluripotent stem cells are iPSCs. In some embodiments, the iPSCs are naïve iPSCs. In some embodiments, the media in the above method are free, or essentially free, of TGFβ receptor inhibitor. In some embodiments, the BMP activator of the method is BMP4. In some embodiments, the Wnt pathway activator is a GSK3 inhibitor. In some embodiments, the method above further comprises subjecting the pluripotent stem cells under a low oxygen tension between about 2% and about 10%. In some embodiments, the above method further comprises seeding pluripotent stem cells by contacting the cells with a medium comprising a MEKi, a GSKi, and a ROCKi.

In one embodiment of the method of generating pluripotent stem cell-derived mesodermal cells having definitive hemogenic endothelium potential from pluripotent stem cell-derived mesoderm, the method comprises differentiating the mesoderm to mesodermal cells with definitive hemogenic endothelium potential by contacting the cells with a medium comprising a BMP activator, a Wnt pathway activator and bFGF. In some embodiments, the pluripotent stem cells are iPSCs. In some embodiments, the iPSCs are naïve iPSCs. In some embodiments, the media in the above method are free, or essentially free, of TGFβ receptor inhibitor. In some embodiments, the BMP activator of the method is BMP4. In some embodiments, the Wnt pathway activator is a GSK3 inhibitor. In some embodiments, the method above further comprises subjecting the mesodermal cells under a low oxygen tension between about 2% and about 10%.

3. Deriving and Expanding Mesoderm from Pluripotent Stem Cell

One aspect of the invention provides a method of using an optimized multistage process to generate pluripotent stem cell-derived mesoderm. Generally, the method begins with a first stage wherein a pluripotent stem cell is seeded, and the seeded cell is then differentiated into mesoderm in the second stage. In some embodiments, the pluripotent stem cells are iPSCs. In some embodiments, the iPSCs are naïve iPSCs. The methods disclosed herein utilize the optimized iCD34 culture platform, which is free, or essentially free, of TGFβ receptor/ALK inhibitors.

In one embodiment of the method of producing pluripotent stem cell-derived mesoderm from a pluripotent cell, the method comprises differentiating and expanding mesoderm cells from the seeded pluripotent stem cell by contacting the cell with a medium comprising a BMP activator, and optionally bFGF. In some embodiments, the pluripotent stem cells are iPSCs. In some embodiments, the iPSCs are naïve iPSCs. In some embodiments, the media in the above method are free, or essentially free, of TGFβ receptor inhibitor. In some embodiments, the BMP activator of the method is BMP4. In some embodiments, the method above further comprises subjecting the seeded iPSC under a low oxygen tension between about 2% and about 10%. In some embodiments, the above method further comprises seeding and expanding the iPSCs by contacting the pluripotent cells with a medium comprising a MEKi, a GSKi, and a ROCKi.

4. Deriving Hematopoietic Multipotent Progenitors (iMPP)

One aspect of the invention provides a method of using an optimized multistage process to generate pluripotent stem cell-derived multipotent progenitors (iMPP). Generally, the method begins with seeding a pluripotent stem cell. The seeded cell is expanded and differentiated into mesodermal cells. The mesoderm is expanded and differentiated to a mesodermal cell with definitive hemogenic endothelium potential, which is subsequently differentiated to definitive hemogenic endothelium. The definitive HE cells are expanded and differentiated to pre-HSC, and then multipotent progenitors that are capable of differentiating into myeloid cells, including neutrophil progenitors. Alternatively, the invention provides a method of generating pluripotent stem cell-derived multipotent progenitors (iMPP) that comprises differentiating seeded pluripotent cells to mesoderm, differentiating mesoderm to mesodermal cells with definitive hemogenic endothelium potential, then the mesodermal cells are differentiated to definitive iHE, which are then differentiated into iMPP. The invention further provides a method of generating pluripotent stem cell-derived iMPP that comprises differentiating pluripotent stem cell-derived mesoderm to mesodermal cells with definitive hemogenic endothelium potential, then the mesodermal cells are differentiated to definitive iHE, which are then differentiated into iMPP. Alternatively, the invention provides a method of generating pluripotent stem cell-derived iMPP that comprises differentiating pluripotent stem cell-derived mesodermal cells to definitive iHE, which are then differentiated into iMPP. Further, the invention provides a method of generating pluripotent stem cell-derived iMPP that comprises differentiating pluripotent stem cell-derived iTHE into iMPP. In some embodiments, the pluripotent stem cells are iPSCs. In some embodiments, the iPSCs are naïve iPSCs. The methods disclosed herein utilize the optimized monolayer iCD34 culture platform without EB formation, which is free, or essentially free, of TGFβ receptor/ALK inhibitors.

In one embodiment of the method of producing hematopoiesis multipotent progenitors (iMPP) from pluripotent stem cells, the method comprises (1) differentiating and expanding mesodermal cells from pluripotent stem cells by contacting the pluripotent cells with a medium comprising a BMP activator, and optionally bFGF; (2) obtaining definitive hemogenic endothelium potential in mesodermal cells by contacting the mesodermal cells with a medium comprising a BMP activator, a Wnt pathway activator and bFGF; (3) differentiating and expanding definitive HE cells from the mesodermal cells having definitive hemogenic endothelium potential by contacting the cells with a medium comprising a ROCK inhibitor, one or more of the growth factors and cytokines selected from the group consisting of VEGF, bFGF, SCF, IL6, and IL11; and optionally a Wnt pathway activator; and (4) differentiating the definitive HE cells to iMPP by contacting the HE cells with a medium comprising a BMP activator, one or more of the growth factors and cytokines selected from the group consisting of TPO, IL3, GMCSF, EPO, bFGF, VEGF, SCF, IL6, Flt3L and IL11, and optionally, a ROCK inhibitor. In some embodiments, the above method further comprises seeding and expanding the pluripotent stem cells by contacting the cells with a medium comprising a MEKi, a GSKi, and a ROCKi. In some embodiments, the method above further comprises differentiating the definitive HE cells to pre-HSC by contacting the HE cells with a medium comprising a BMP activator, a ROCK inhibitor, and one or more of the growth factors and cytokines selected from the group consisting of TPO, IL3, GMCSF, EPO, bFGF, VEGF, SCF, IL6, Flt3L and IL11. In other embodiments, the method comprising differentiating the definitive HE cells to pre-HSC, further comprises differentiating the pre-HSC to iMPP by contacting the pre-HSC cells with a medium comprising a BMP activator, and one or more of the growth factors and cytokines selected from the group consisting of TPO, IL3, GMCSF, EPO, bFGF, VEGF, SCF, IL6, and IL11, and the medium is free, or essentially free, of ROCK inhibitors. In some embodiments, the pluripotent stem cells are iPSCs. In some embodiments, the iPSCs are naïve iPSCs. In some embodiments, the media in the above method are free, or essentially free, of TGFβ receptor inhibitor. In some embodiments, the method above further comprises subjecting the seeded pluripotent stem cells, mesoderm, and/or mesodermal cells with definitive hemogenic endothelium potential under a low oxygen tension between about 2% and about 10%. In some embodiments, the iHE cells obtained from the above method express CD34. In some embodiments, the above method further comprises sorting the obtained iHE cells using CD34, CD43, CD73, CXCR4, and/or CD93. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In some embodiments, the sorting uses CD34 positive, CD43 negative, and CD93 negative. In some embodiments, the sorting uses CD34 positive, and CD93 negative. In some embodiments, the BMP activator of the method is BMP4. In some embodiments, the Wnt pathway activator is a GSK3 inhibitor. In some embodiments, the ROCK inhibitor is Y27632 or thiazovivin.

In one embodiment of the method of generating pluripotent stem cell-derived multipotent progenitors (iMPP) from pluripotent stem cell-derived mesoderm, the method comprises (1) obtaining definitive hemogenic endothelium potential in pluripotent stem cell-derived mesodermal cells by contacting the mesodermal cells with a medium comprising a BMP activator, a Wnt pathway activator and bFGF; (2) differentiating and expanding definitive HE cells from the mesodermal cells with definitive hemogenic endothelium potential by contacting the cells with a medium comprising a ROCK inhibitor; one or more of the growth factors and cytokines selected from the group consisting of VEGF, bFGF, SCF, IL6, and IL11; and optionally a Wnt pathway activator; (3) differentiating the definitive HE cells to iMPP by contacting the HE cells with a medium comprising a BMP activator, one or more of the growth factors and cytokines selected from the group consisting of TPO, IL3, GMCSF, EPO, bFGF, VEGF, SCF, IL6, Flt3L, and IL11, and optionally, a ROCK inhibitor. In some embodiments, the pluripotent stem cells are iPSCs. In some embodiments, the iPSCs are naïve iPSCs. In some embodiments, the method above further comprises differentiating the definitive HE cells to pre-HSC by contacting the HE cells with a medium comprising a BMP activator, a ROCK inhibitor, and one or more of the growth factors and cytokines selected from the group consisting of TPO, IL3, GMCSF, EPO, bFGF, VEGF, SCF, IL6, Flt3L, and IL11. In other embodiments, the method comprising differentiating the definitive HE cells to pre-HSC, further comprises differentiating the pre-HSC to iMPP by contacting the pre-HSC cells with a medium comprising a BMP activator, and one or more of the growth factors and cytokines selected from the group consisting of TPO, IL3, GMCSF, EPO, bFGF, VEGF, SCF, IL6, and IL11, and the medium is free, or essentially free, of ROCK inhibitors. In some embodiments, the media in the above method are free, or essentially free, of TGFβ receptor inhibitor. In some embodiments, the method above further comprises subjecting the mesoderm, and/or mesodermal cells with definitive hemogenic endothelium potential under a low oxygen tension between about 2% and about 10%.

In one embodiment of the method of generating pluripotent stem cell-derived multipotent progenitors (iMPP) from pluripotent stem cell-derived mesodermal cells with definitive hemogenic endothelium potential, the method comprises (1) differentiating and expanding definitive HE cells from the pluripotent stem cell-derived mesodermal cells with definitive hemogenic endothelium potential by contacting the cells with a medium comprising one or more of the growth factors and cytokines selected from the group consisting of VEGF, bFGF, SCF, IL6, and IL11, a ROCK inhibitor, and optionally a Wnt pathway activator; and (2) differentiating the definitive HE cells to iMPP by contacting the HE cells with a medium comprising a BMP activator, and one or more of the growth factors and cytokines selected from the group consisting of TPO, IL3, GMCSF, EPO, bFGF, VEGF, SCF, IL6, Flt3L, and IL11, and optionally, a ROCK inhibitor. In some embodiments, the pluripotent stem cells are iPSCs. In some embodiments, the iPSCs are naïve iPSCs. In some embodiments, the method above further comprises differentiating the definitive HE cells to pre-HSC by contacting the HE cells with a medium comprising a BMP activator, a ROCK inhibitor, and one or more of the growth factors and cytokines selected from the group consisting of TPO, IL3, GMCSF, EPO, bFGF, VEGF, SCF, IL6, Flt3L, and IL11. In other embodiments, the method comprising differentiating the definitive HE cells to pre-HSC further comprises differentiating the pre-HSC to iMPP by contacting the pre-HSC cells with a medium comprising a BMP activator, and one or more of the growth factors and cytokines selected from the group consisting of TPO, IL3, GMCSF, EPO, bFGF, VEGF, SCF, IL6, and IL11, and the medium is free, or essentially free, of ROCK inhibitors. In some embodiments, the media in the above method are free, or essentially free, of TGFβ receptor inhibitor. In some embodiments, the method above further comprises subjecting mesodermal cells with definitive hemogenic endothelium potential under a low oxygen tension between about 2% and about 10%.

In one embodiment of the method of generating pluripotent stem cell-derived multipotent progenitors (iMPP) from pluripotent stem cell-derived definitive HE cells, the method comprises differentiating the definitive HE cells to iMPP by contacting the HE cells with a medium comprising a BMP activator, one or more of the growth factors and cytokines selected from the group consisting of TPO, IL3, GMCSF, EPO, bFGF, VEGF, SCF, IL6, Flt3L, and IL11, and optionally, a ROCK inhibitor. In some embodiments, the pluripotent stem cells are iPSCs. In some embodiments, the iPSCs are naïve iPSCs. In some embodiments, the method above further comprises differentiating the definitive HE cells to pre-HSC by contacting the HE cells with a medium comprising a BMP activator, a ROCK inhibitor, and one or more of the growth factors and cytokines selected from the group consisting of TPO, IL3, GMCSF, EPO, bFGF, VEGF, SCF, IL6, Flt3L, and IL11. In other embodiments, the method comprising differentiating the definitive HE cells to pre-HSC further comprises differentiating the pre-HSC to iMPP by contacting the pre-HSC cells with a medium comprising a BMP activator, and one or more of the growth factors and cytokines selected from the group consisting of TPO, IL3, GMCSF, EPO, bFGF, VEGF, SCF, IL6, and IL11, and the medium is free, or essentially free, of ROCK inhibitors. In some embodiments, the media in the above method are free, or essentially free, of TGFβ receptor inhibitor. In some embodiments, the method above further comprises subjecting mesodermal cells with definitive hemogenic endothelium potential under a low oxygen tension between about 2% and about 10%.

5. Obtaining Pluripotent Stem Cell-Derived T Cell Progenitors (Ipro-T) or T Cells iCD34 Platform and iT Platform One aspect of the invention provides a method of using an optimized multistage process to generate pluripotent stem cell-derived T cell progenitors (ipro-T) or pluripotent stem cell-derived T cells. Generally, the method begins with pluripotent stem cells, from which mesodermal cells are differentiated and expanded. In some embodiments, the pluripotent stem cells are iPSCs. In some embodiments, the iPSCs are naïve iPSCs. The mesoderm is then differentiated to a mesodermal cell with definitive hemogenic endothelium potential. The mesodermal cells with definitive hemogenic endothelium potential are subsequently differentiated to definitive hemogenic endothelium, which are at the same time expanded in the medium. The definitive HE cells are then differentiated to pre-iproT, and then to T cell progenitors (pro-T), which can be continuously differentiated into T cells in the same medium. Alternatively, the invention provides a method of generating pluripotent stem cell-derived T cell progenitors (ipro-T) or T cells that comprises differentiating seeded pluripotent stem cells to mesoderm, differentiating mesoderm to mesodermal cells with definitive hemogenic endothelium potential, then the mesodermal cells with definitive hemogenic endothelium potential are differentiated to iHE, which are then differentiated into T cell progenitors or T cells. The invention further provides a method of generating pluripotent stem cell-derived T cell progenitors (ipro-T) or T cells that comprises differentiating pluripotent stem cell-derived mesoderm to mesodermal cells with definitive hemogenic endothelium potential, which then are differentiated to iHE, which are then differentiated into ipro-T or T cells. Alternatively, the invention provides a method of generating pluripotent stem cell-derived T cell progenitors or T cells, which comprises differentiating pluripotent stem cell-derived mesodermal cells with definitive hemogenic endothelium potential to iHE, which are then differentiated into ipro-T or T cells. Further, the invention provides a method of generating pluripotent stem cell-derived T cell progenitors (ipro-T) or T cells that comprises differentiating pluripotent stem cell-derived iHE into ipro-T or T cells. In some embodiments, the pluripotent stem cells are iPSCs. In some embodiments, the iPSCs are naïve iPSCs. The methods disclosed herein utilize the optimized iCD34 culture platform, which is free, or essentially free, of TGFβ receptor/ALK inhibitors. In some embodiments, the Notch factors including, but not limited to, Jag1, Jag2, DLL-1, DLL-3 and DLL-4 can be introduced as soluble peptide, peptide conjugated to beads, peptide conjugated to the surface, or peptide presented by cells.

In one embodiment of the method of generating pluripotent stem cell-derived T cell progenitors (ipro-T) or T cells (iT) from pluripotent stem cell, the method comprises (1) differentiating the seeded pluripotent stem cells to mesoderm by contacting the cells with a medium comprising a BMP activator, and optionally bFGF; (2) differentiating the mesoderm to mesodermal cells with definitive hemogenic endothelium potential by contacting the cells with a medium comprising a BMP activator, a Wnt pathway activator and bFGF; (3) differentiating the mesodermal cells with definitive hemogenic endothelium potential to definitive HE cells by contacting the cells with a medium comprising a ROCK inhibitor; one or more of the growth factors and cytokines selected from the group consisting of VEGF, bFGF, SCF, IL6, and IL1; and optionally a Wnt pathway activator, and (4) differentiating the definitive HE cells to ipro-T or iT by contacting the HE cells with a medium comprising one or more of the growth factors and cytokines selected from the group consisting SCF, Flt3L, and IL7, and optionally, one or more factors selected from the group consisting of VEGF, bFGF, a BMP activator, and a ROCK inhibitor. In some embodiments, the above method further comprises seeding and expanding pluripotent stem cells by contacting the cells with a medium comprising a MEKi, a GSKi, and a ROCKi. In some embodiments, the pluripotent stem cells are iPSCs. In some embodiments, the iPSCs are naïve iPSCs. In some embodiments, the method above further comprises differentiating the definitive HE cells to pre-iproT by contacting the HE cells with a medium comprising, a ROCK inhibitor; one or more of the growth factors and cytokines selected from the group consisting of SCF, Flt3L, TPO, IL7, VEGF, and bFGF; and optionally a BMP activator. In other embodiments, the method comprising differentiating the definitive HE cells to pre-iproT, further comprises differentiating the pre-iproT to ipro-T or iT by contacting the pre-iproT cells with a medium comprising one or more of the growth factors and cytokines selected from the group consisting of SCF, Flt3L, and IL7, and the medium is free, or essentially free, of one or more of VEGF, bFGF, a BMP activator, and a ROCK inhibitor. In some embodiments, the above method comprising pluripotent stem cell-derived pro-T with one or more Notch factors. In some embodiments, the Notch factor is Jag1, Jag2, DLL-1, DLL-3, or DLL-4. In some embodiments, DLL-1 and -4 can be introduced as soluble peptide, peptide conjugated to beads, peptide conjugated to the surface, or peptide presented by cells. In some embodiments, the method above further comprises subjecting the seeded pluripotent stem cell, mesoderm, and/or mesodermal cells with definitive hemogenic endothelium potential under a low oxygen tension between about 2% and about 10%. In some embodiments, the iHE cells obtained from the above method express CD34. In some embodiments, the above method further comprises sorting the obtained iHE cells using CD34, CD43, CD73, CXCR4, and/or CD93. In some embodiments, the BMP activator of the method is BMP4. In some embodiments, the Wnt pathway activator is a GSK3 inhibitor. In some embodiments, the ROCK inhibitor is Y27632 or thiazovivin. In some embodiments, the media in the above method are free, or essentially free, of TGFβ receptor inhibitor.

In one embodiment of the method of generating pluripotent stem cell-derived T cell progenitors (ipro-T) or T cells from pluripotent stem cell-derived mesoderm, the method comprises (1) differentiating the mesoderm to mesodermal cells with definitive hemogenic endothelium potential by contacting the cells with a medium comprising a BMP activator, a Wnt pathway activator and bFGF; (2) differentiating the mesodermal cells with definitive hemogenic endothelium potential to definitive HE cells by contacting the cells with a medium comprising a ROCK inhibitor; one or more of the growth factors and cytokines selected from the group consisting of VEGF, bFGF, SCF, IL6, and IL11; and optionally a Wnt pathway activator, and (3) differentiating the definitive HE cells to ipro-T or iT by contacting the HE cells with a medium comprising one or more of the growth factors and cytokines selected from the group consisting SCF, Flt3L, and IL7, and optionally, one or more factors selected from the group consisting of VEGF, bFGF, a BMP activator, and a ROCK inhibitor. In some embodiments, the pluripotent stem cells are iPSCs. In some embodiments, the iPSCs are naïve iPSCs. In some embodiments, the method above further comprises differentiating the definitive HE cells to pre-iproT by contacting the HE cells with a medium comprising a ROCK inhibitor; one or more of the growth factors and cytokines selected from the group consisting of SCF, Flt3L, TPO, IL7, VEGF, and bFGF; and optionally, a BMP activator. In other embodiments, the method comprising differentiating the definitive HE cells to pre-iproT, further comprises differentiating the pre-iproT to ipro-T or iT by contacting the pre-iproT cells with a medium comprising one or more of the growth factors and cytokines selected from the group consisting of SCF, Flt3L, and IL7, and the medium is free, or essentially free, of one or more of VEGF, bFGF, a BMP activator, and a ROCK inhibitor. In some embodiments, the above method comprising pluripotent stem cell-derived pro-T with one or more Notch factors. In some embodiments, the Notch factor is Jag1, Jag2, DLL-1, DLL-3 or DLL-4. In some embodiments, DLL-1 and -4 can be introduced as soluble peptide, peptide conjugated to beads, peptide conjugated to the surface, or peptide presented by cells. In some embodiments, the method above further comprises subjecting the mesoderm, and/or mesodermal cells with definitive hemogenic endothelium potential under a low oxygen tension between about 2% and about 10%. In some embodiments, the iHE cells obtained from the above method express CD34. In some embodiments, the above method further comprises sorting the obtained iHE cells using CD34, CD43, CD73, CXCR4, and/or CD93. In some embodiments, the BMP activator of the method is BMP4. In some embodiments, the Wnt pathway activator is a GSK3 inhibitor. In some embodiments, the ROCK inhibitor is Y27632 or thiazovivin. In some embodiments, the media in the above method are free, or essentially free, of TGFβ receptor inhibitor.

In one embodiment of the method of generating pluripotent stem cell-derived T cell progenitors (ipro-T) or T cells (iT) from pluripotent stem cell-derived mesodermal cells with definitive hemogenic endothelium potential, the method comprises (1) differentiating the mesodermal cells with definitive hemogenic endothelium potential to definitive HE cells by contacting the cells with a medium comprising a ROCK inhibitor; one or more of the growth factors and cytokines selected from the group consisting of VEGF, bFGF, SCF, IL6, and IL11; and optionally a Wnt pathway activator; and (2) differentiating the definitive HE cells to ipro-T or iT by contacting the HE cells with a medium comprising one or more of the growth factors and cytokines selected from the group consisting SCF, Flt3L, and IL7, and optionally, one or more factors selected from the group consisting of VEGF, bFGF, a BMP activator, and a ROCK inhibitor. In some embodiments, the pluripotent stem cells are iPSCs. In some embodiments, the iPSCs are naïve iPSCs. In some embodiments, the method above further comprises differentiating the definitive HE cells to pre-iproT by contacting the HE cells with a medium comprising a ROCK inhibitor; one or more of the growth factors and cytokines selected from the group consisting of SCF, Flt3L, TPO, IL7, VEGF, and bFGF; and optionally a BMP activator. In other embodiments, the method comprising differentiating the definitive HE cells to pre-iproT further comprises differentiating the pre-iproT to ipro-T or iT by contacting the pre-iproT cells with a medium comprising one or more of the growth factors and cytokines selected from the group consisting of SCF, Flt3L, and IL7, and the medium is free, or essentially free, of one or more of VEGF, bFGF, a BMP activator, and a ROCK inhibitor. In some embodiments, the above method comprising pluripotent stem cell-derived pro-T with one or more Notch factors. In some embodiments, the Notch factor is Jag1, Jag2, DLL-1, DLL-3 or DLL-4. In some embodiments, DLL-1 and -4 can be introduced as soluble peptide, peptide conjugated to beads, peptide conjugated to the surface, or peptide presented by cells. In some embodiments, the method above further comprises subjecting the mesodermal cells with definitive hemogenic endothelium potential under a low oxygen tension between about 2% and about 10%. In some embodiments, the iHE cells obtained from the above method express CD34. In some embodiments, the above method further comprises sorting the obtained iHE cells using CD34, CD43, CD73, CXCR4, and/or CD93. In some embodiments, the BMP activator of the method is BMP4. In some embodiments, the Wnt pathway activator is a GSK3 inhibitor. In some embodiments, the ROCK inhibitor is Y27632 or thiazovivin. In some embodiments, the media in the above method are free, or essentially free, of TGFβ receptor inhibitor.

In one embodiment of the method of generating pluripotent stem cell-derived T cell progenitors (ipro-T) or T cells (iT) from pluripotent stem cell-derived HE cells, the method comprises differentiating the definitive HE cells to ipro-T or T by contacting the definitive HE cells with a medium comprising one or more of the growth factors and cytokines selected from the group consisting SCF, Flt3L, and IL7, and optionally, one or more factors selected from the group consisting of VEGF, bFGF, a BMP activator, and a ROCK inhibitor. In some embodiments, the pluripotent stem cells are iPSCs. In some embodiments, the iPSCs are naïve iPSCs. In some embodiments, the method above further comprises differentiating the definitive HE cells to pre-iproT by contacting the HE cells with a medium comprising a ROCK inhibitor; one or more of the growth factors and cytokines selected from the group consisting of SCF, Flt3L, TPO, IL7, VEGF, and bFGF; and optionally a BMP activator. In other embodiments, the method comprising differentiating the definitive HE cells to pre-iproT further comprises differentiating the pre-iproT to ipro-T or iT by contacting the pre-iproT cells with a medium comprising one or more of the growth factors and cytokines selected from the group consisting of SCF, Flt3L, and IL7, and the medium is free, or essentially free, of one or more of VEGF, bFGF, a BMP activator, and a ROCK inhibitor. In some embodiments, the above method comprising pluripotent stem cell-derived pro-T with one or more Notch factors. In some embodiments, the Notch factor is Jag1, Jag2, DLL-1, DLL-3 or DLL-4. In some embodiments, DLL-1 and -4 can be introduced as soluble peptide, peptide conjugated to beads, peptide conjugated to the surface, or peptide presented by cells. In some embodiments, the method above further comprises subjecting the pluripotent stem cell-derived HE cells under a low oxygen tension between about 2% and about 10%. In some embodiments, the iHE cells obtained from the above method express CD34. In some embodiments, the above method further comprises sorting the obtained iHE cells using CD34, CD43, CD73, CXCR4, and/or CD93. In some embodiments, the BMP activator of the method is BMP4. In some embodiments, the Wnt pathway activator is a GSK3 inhibitor. In some embodiments, the ROCK inhibitor is Y27632 or thiazovivin. In some embodiments, the media in the above method are free, or essentially free, of TGFβ receptor inhibitor.

6. Obtaining Pluripotent Stem Cell-Derived NK Cell Progenitors (Ipro-NK) or NK Cells iCD34 Platform and iNK Platform One aspect of the invention provides a method of using an optimized multistage process to generate pluripotent stem cell-derived NK cell progenitors (ipro-NK) or NK cells (iNK). Generally, the method begins with pluripotent stem cells, which in some embodiments are seeded. The pluripotent stem cells are developed into mesoderm cells which are expanded and subsequently differentiated to mesodermal cells with definitive hemogenic endothelium potential. Definitive hemogenic endothelium are then differentiated and expanded from the mesodermal cells with definitive hemogenic endothelium potential. The HE cells are capable of being differentiated to pre-iproNK, and then to NK cell progenitors (pro-NK), which can be continuously differentiate into NK cells in the same medium. Alternatively, the invention provides a method of generating pluripotent stem cell-derived NK cell progenitors (ipro-NK) or NK cells that comprises differentiating seeded pluripotent stem cells to mesoderm, differentiating mesoderm to mesodermal cells with definitive hemogenic endothelium potential, then the mesodermal cells with definitive hemogenic endothelium potential are differentiated to iHE, which are then differentiated into NK cell progenitors. The invention further provides a method of generating pluripotent stem cell-derived NK cell progenitors (ipro-NK) or NK cells that comprises differentiating pluripotent stem cell-derived mesoderm to mesodermal cells with definitive hemogenic endothelium potential, then the mesodermal cells with definitive hemogenic endothelium potential are differentiated to iHE, which are then differentiated into ipro-NK or iNK. Alternatively, the invention provides a method of generating pluripotent stem cell-derived NK cell progenitors or iNK comprises differentiating pluripotent stem cell-derived mesodermal cells with definitive hemogenic endothelium potential to iHE, which are then differentiated into ipro-NK or iNK. Further, the invention provides a method of generating pluripotent stem cell-derived NK cell progenitors (ipro-NK) or NK cells comprises differentiating pluripotent stem cell-derived iHE into ipro-NK or iNK. In some embodiments, the pluripotent stem cells are iPSCs. In some embodiments, the iPSCs are naïve iPSCs. In some embodiments, the culture platform for obtaining a NK cell progenitor comprises deriving NK cells by contacting pro-NK cells with one or more of artificial antigens to stimulate NK growth, development and maturation, wherein the artificial antigens are introduced in the forms of bead conjugation, plasma membrane particles and/or antigen presenting cells. The methods disclosed herein utilize the optimized iCD34 culture platform, which is free, or essentially free, of TGFβ receptor/ALK inhibitors.

In one embodiment of the method of generating pluripotent stem cell-derived NK cell progenitors (ipro-NK) or NK cells (iNK) from seeded iPSC, the method comprises (1) differentiating and expanding mesodermal cells from pluripotent stem cells by contacting the cells with a medium comprising a BMP activator, and optionally bFGF; (2) obtaining definitive hemogenic endothelium potential in the mesodermal cells by contacting the mesodermal cells with a medium comprising a BMP activator, a Wnt pathway activator and bFGF; (3) differentiating and expanding definitive HE cells from the mesodermal cells with definitive hemogenic endothelium potential by contacting the cells with a medium comprising a ROCK inhibitor; one or more of the growth factors and cytokines selected from the group consisting of VEGF, bFGF, SCF, IL6, and IL11; and optionally a Wnt pathway activator; and (4) differentiating the definitive HE cells to ipro-NK or iNK by contacting the HE cells with a medium comprising one or more of the growth factors and cytokines selected from the group consisting SCF, Flt3L, IL3, IL7, and IL15, and optionally, one or more factors selected from the group consisting of VEGF, bFGF, a BMP activator, and a ROCK inhibitor. In some embodiments, the pluripotent stem cells are iPSCs. In some embodiments, the iPSCs are naïve iPSCs. In some embodiments, the method above further comprises differentiating the definitive HE cells to pre-iproNK by contacting the HE cells with a medium comprising a BMP activator, a ROCK inhibitor, and one or more of the growth factors and cytokines selected from the group consisting of SCF, Flt3L, TPO, IL3, IL7, IL15, VEGF, and bFGF. In other embodiments, the method comprising differentiating the definitive HE cells to pre-iproNK, further comprises differentiating the pre-iproNK to pro-iNK or iNK by contacting the pre-iproNK cells with a medium comprising one or more of the growth factors and cytokines selected from the group consisting of SCF, Flt3L, IL3, IL7, and IL15, and the medium is free, or essentially free, of one or more of VEGF, bFGF, a BMP activator, and a ROCK inhibitor. In some embodiments, the culture platform for obtaining a NK cell progenitor comprises deriving NK cells by contacting pro-NK cells with one or more of artificial antigens to stimulate NK growth, development and maturation, wherein the artificial antigens are introduced in the forms of bead conjugation, plasma membrane particles and/or antigen presenting cells. In one embodiment, the above method further comprises seeding and expanding naïve pluripotent cells by contacting the pluripotent cells with a medium comprising a MEKi, a GSKi, and a ROCKi. In some embodiments, the method above further comprises subjecting the seeded iPSC, mesoderm, and/or mesodermal cells with definitive hemogenic endothelium potential under a low oxygen tension between about 2% and about 10%. In some embodiments, the iHE cells obtained from the above method express CD34. In some embodiments, the above method further comprises sorting the obtained iHE cells using CD34, CD43, CD73, CXCR4, and/or CD93. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In some embodiments, the sorting uses CD34 positive, CD43 negative, and CD93 negative. In some embodiments, the sorting uses CD34 positive, and CD93 negative. In some embodiments, the BMP activator of the method is BMP4. In some embodiments, the Wnt pathway activator is a GSK3 inhibitor. In some embodiments, the ROCK inhibitor is Y27632 or thiazovivin. In some embodiments, the media in the above method are free, or essentially free, of TGFβ receptor inhibitor.

In one embodiment of the method of generating pluripotent stem cell-derived NK cell progenitors (ipro-NK) or NK cells (iNK) from pluripotent stem cell-derived mesoderm, the method comprises (1) differentiating the mesoderm by contacting the mesoderm with a medium comprising a BMP activator, a Wnt pathway activator and bFGF to obtain mesodermal cells having definitive hemogenic endothelium potential; (2) differentiating the mesodermal cells with definitive hemogenic endothelium potential by contacting the cells with a medium comprising a ROCK inhibitor; one or more of the growth factors and cytokines selected from the group consisting of VEGF, bFGF, SCF, IL6, and IL11; and optionally a Wnt pathway activator, to obtain definitive HE cells; and (3) differentiating the definitive HE cells by contacting the HE cells with a medium comprising one or more of the growth factors and cytokines selected from the group consisting SCF, Flt3L, IL3, IL7, and IL15, and optionally, one or more factors selected from the group consisting of VEGF, bFGF, a BMP activator, and a ROCK inhibitor to obtain ipro-NK or iNK. In some embodiments, the pluripotent stem cells are iPSCs. In some embodiments, the iPSCs are naïve iPSCs. In some embodiments, the method above further comprises differentiating the definitive HE cells to pre-iproNK by contacting the HE cells with a medium comprising a BMP activator, a ROCK inhibitor, and one or more of the growth factors and cytokines selected from the group consisting of SCF, Flt3L, TPO, IL3, IL7, IL15, VEGF, and bFGF. In other embodiments, the method comprising differentiating the definitive HE cells to pre-iproNK, further comprises differentiating the pre-iproNK to ipro-NK or iNK by contacting the pre-iproNK cells with a medium comprising one or more of the growth factors and cytokines selected from the group consisting of SCF, Flt3L, IL3, IL7, and IL15, and the medium is free, or essentially free, of one or more of VEGF, bFGF, a BMP activator, and a ROCK inhibitor. In some embodiments, the culture platform for obtaining a NK cell progenitor comprises deriving NK cells by contacting pro-NK cells with one or more of artificial antigens to stimulate NK growth, development and maturation, wherein the artificial antigens are introduced in the forms of bead conjugation, plasma membrane particles and/or antigen presenting cells. In some embodiments, the method above further comprises subjecting the mesoderm, and/or mesodermal cells with definitive hemogenic endothelium potential under a low oxygen tension between about 2% and about 10%. In some embodiments, the iHE cells obtained from the above method express CD34. In some embodiments, the above method further comprises sorting the obtained iTHE cells using CD34, CD43, CD73, CXCR4 and/or CD93. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In some embodiments, the sorting uses CD34 positive, CD43 negative, and CD93 negative. In some embodiments, the sorting uses CD34 positive, and CD93 negative. In some embodiments, the BMP activator of the method is BMP4. In some embodiments, the Wnt pathway activator is a GSK3 inhibitor. In some embodiments, the ROCK inhibitor is Y27632 or thiazovivin. In some embodiments, the media in the above method are free, or essentially free, of TGFβ receptor inhibitor.

In one embodiment of the method of generating pluripotent stem cell-derived NK cell progenitors (ipro-NK) or NK cells (iNK) from pluripotent stem cell-derived mesodermal cells with definitive hemogenic endothelium potential, the method comprises: (1) differentiating and expanding definitive HE cells by contacting the mesodermal cells with definitive hemogenic endothelium potential with a medium comprising a ROCK inhibitor; one or more of the growth factors and cytokines selected from the group consisting of VEGF, bFGF, SCF, IL6, and IL11; and optionally a Wnt pathway activator; and (2) differentiating the definitive HE cells to ipro-NK or iNK by contacting the HE cells with a medium comprising one or more of the growth factors and cytokines selected from the group consisting SCF, Flt3L, IL3, IL7, and IL15, and optionally, one or more factors selected from the group consisting of VEGF, bFGF, a BMP activator, and a ROCK inhibitor. In some embodiments, the pluripotent stem cells are iPSCs. In some embodiments, the iPSCs are naïve iPSCs. In some embodiments, the method above further comprises differentiating the definitive HE cells to pre-iproNK by contacting the HE cells with a medium comprising a BMP activator, a ROCK inhibitor, and one or more of the growth factors and cytokines selected from the group consisting of SCF, Flt3L, TPO, IL3, IL7, IL15, VEGF, and bFGF. In other embodiments, the method comprising differentiating the definitive HE cells to pre-iproNK, further comprises differentiating the pre-iproNK to ipro-NK or iNK by contacting the pre-iproNK cells with a medium comprising one or more of the growth factors and cytokines selected from the group consisting of SCF, Flt3L, IL3, IL7, and IL15, and the medium is free, or essentially free, of one or more of VEGF, bFGF, a BMP activator, and a ROCK inhibitor. In some embodiments, the culture platform for obtaining a NK cell progenitor comprises deriving NK cells by contacting pro-NK cells with one or more of artificial antigens to stimulate NK growth, development and maturation, wherein the artificial antigens are introduced in the forms of bead conjugation, plasma membrane particles and/or antigen presenting cells. In some embodiments, the method above further comprises subjecting the seeded pluripotent stem cells, mesoderm, and/or mesodermal cells with definitive hemogenic endothelium potential under a low oxygen tension between about 2% and about 10%. In some embodiments, the iHE cells obtained from the above method express CD34. In some embodiments, the above method further comprises sorting the obtained iHE cells using CD34, CD43, CD73, CXCR4, and/or CD93. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In some embodiments, the sorting uses CD34 positive, CD43 negative, and CD93 negative. In some embodiments, the sorting uses CD34 positive, and CD93 negative. In some embodiments, the BMP activator of the method is BMP4. In some embodiments, the Wnt pathway activator is a GSK3 inhibitor. In some embodiments, the ROCK inhibitor is Y27632 or thiazovivin. In some embodiments, the media in the above method are free, or essentially free, of TGFβ receptor inhibitor.

In one embodiment of the method of generating pluripotent stem cell-derived NK cell progenitors (ipro-NK) or NK cells (iNK) from pluripotent stem cell-derived HE cells, the method comprises differentiating the definitive HE cells to ipro-NK or iNK by contacting the definitive HE cells with a medium comprising one or more of the growth factors and cytokines selected from the group consisting SCF, Flt3L, IL3, IL7, and IL15, and optionally, one or more factors selected from the group consisting of VEGF, bFGF, a BMP activator, and a ROCK inhibitor. In some embodiments, the pluripotent stem cells are iPSCs. In some embodiments, the iPSCs are naïve iPSCs. In some embodiments, the method above further comprises differentiating the definitive HE cells to pre-iproNK by contacting the HE cells with a medium comprising a BMP activator, a ROCK inhibitor, and one or more of the growth factors and cytokines selected from the group consisting of SCF, Flt3L, TPO, IL3, IL7, IL15, VEGF, and bFGF. In other embodiments, the method comprising differentiating the definitive HE cells to pre-iproNK, further comprises differentiating the pre-iproNK to ipro-NK or iNK by contacting the pre-iproNK cells with a medium comprising one or more of the growth factors and cytokines selected from the group consisting of SCF, Flt3L, IL3, IL7, and IL15, and the medium is free, or essentially free, of one or more of VEGF, bFGF, a BMP activator, and a ROCK inhibitor. In some embodiments, the culture platform for obtaining a NK cell progenitor comprises deriving NK cells by contacting ipro-NK cells with one or more of artificial antigens to stimulate NK growth, development and maturation, wherein the artificial antigens are introduced in the forms of bead conjugation, plasma membrane particles and/or antigen presenting cells. In some embodiments, the method above further comprises subjecting the seeded pluripotent stem cell, mesoderm, and/or mesodermal cells with definitive hemogenic endothelium potential under a low oxygen tension between about 2% and about 10%. In some embodiments, the iHE cells obtained from the above method express CD34. In some embodiments, the above method further comprises sorting the obtained iTHE cells using CD34, CD43, CD73, CXCR4, and/or CD93. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In some other embodiments, the sorting uses CD34 positive, CD43 negative, and CD93 negative. In some other embodiments, the sorting uses CD34 positive, and CD93 negative. In some embodiments, the BMP activator of the method is BMP4. In some embodiments, the Wnt pathway activator is a GSK3 inhibitor. In some embodiments, the ROCK inhibitor is Y27632 or thiazovivin. In some embodiments, the media in the above method are free, or essentially free, of TGFβ receptor inhibitor.

In light of the above, one of the advantages offered by the culture platforms contemplated herein is the enhanced viability and survival of culturing, passaging, and dissociating single pluripotent cells without EB formation for pluripotent stem cell differentiation. In some embodiments, the pluripotent stem cells are iPSCs. In some embodiments, the iPSCs are naïve iPSCs. In some embodiments, the iPSCs are genomically engineered. In some embodiments, the iPSCs are reprogrammed from immune cells of specific donor or patient. Disassociation of cells into single cells, such as into a single cell suspension, can be accomplished by enzymatic or mechanical means. Any enzymatic agent known in the art to allow dissociation of cells into single cells may be used in the methods of the invention. In one embodiment, the dissociation agent is selected from Trypsin/EDTA, TrypLE-Select, Collagenase IV and Dispase. A chelator, such as EDTA, Accutase, or AccuMax, may also be used, alone or in combination with an enzymatic agent, in dissociating cells in accordance with the methods contemplated herein. The dissociation agent may be dissolved in calcium and magnesium free PBS to facilitate dissociation to single cells. To enhance the survival of the cells during and after dissociation, in some embodiments, a survival promoting substance is added, for example, one or more growth factors, inhibitors of cellular pathways involved in cell death and apoptosis, or conditioned media. In one embodiment, the survival promoting substance is a ROCK inhibitor, including but not limited to thiazovivin.

In some embodiments, the iPSC for differentiation comprises genetic imprints. In some embodiments, the genetic imprints of the pluripotent stem cells comprise (i) one or more genetically modified modalities obtained through genomic insertion, deletion or substitution in the genome of the pluripotent cells during or after reprogramming a non-pluripotent cell to iPSC; or (ii) one or more retainable therapeutic attributes of a source specific immune cell that is donor-, disease-, or treatment response-specific, and wherein the pluripotent cells are reprogrammed from the source specific immune cell, wherein the iPSC retain the source therapeutic attributes, which are also comprised in the iPSC derived hematopoietic lineage cells. In some embodiments, the genetically modified modalities comprise one or more of safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the iPSCs or derivative cells thereof. In some other embodiments, the genetically modified modalities comprise one or more of (i) deletion or reduced expression of B2M, TAP1, TAP2, Tapasin, NLRC5, PD1, LAG3, TIM3, RFXANK, CITTA, RFX5, or RFXAP; (ii) introduced or increased expression of HLA-E, HLA-G, HACD16, 41BBL, CD3, CD4, CD8, CD47, CD137, CD80, PDL1, A2AR, CAR, TCR, or surface triggering receptor for bi- or multi-specific engagers. In some embodiments, the surface triggering receptor is universal, i.e., compatible with any effector cell type, and the effector cells expressing the universal surface triggering receptor can couple with the same bi- or multi-specific engager irrespective of its cell type. In some embodiments, the universal surface triggering receptor comprises an anti-epitope and a co-stimulatory domain, wherein the anti-epitope is specific to the epitope of the bi- or multi-specific engager. In some embodiments, the co-stimulatory domain of the universal surface triggering receptor comprises IL2 for canonical or non-cononical cellular activation and effector cell function enhancement. In still some other embodiments, the hematopoietic lineage cells comprise the therapeutic attributes of the source specific immune cell relating to one or more of (i) antigen targeting receptor expression; (ii) HLA presentation or lack thereof; (iii) resistance to tumor microenvironment; (iv) induction of bystander immune cells and immune modulations; (iv) improved on-target specificity with reduced off-tumor effect; (v) resistance to treatment such as chemotherapy; and (vi) improved homing, persistence, and cytotoxicity.

In some embodiments, the engager is cell type specific, i.e., the engager binds to and/or activates a particular immune cell type. In particular embodiments, the engager is cell type independent, i.e., the engager binds to and/or activates multiple immune cells, e.g., T cells, NK cells, NKT cells, B cells, macrophages, or neutrophils.

In some embodiments, the iPSC and its derivative hematopoietic cells comprise one or more of B2M null, HLA-E/G, PDL1, $A_{2A}R$, CD47, LAG3 null, TIM3 null, TAP1 null, TAP2 null, Tapasin null, NLRC5 null, PD1 null, RFKANK null, CITTA null, RFX5 null and RFXAP null. These cells with modified HLA class I and/or II have increased resistance to immune detection, and therefore present improved in vivo persistence. Moreover, such cells can avoid the need for HLA matching in adoptive cell therapy and thus provide a source of universal, off-the-shelf therapeutic regimen.

In some embodiments, the iPSC and its derivative hematopoietic cells comprise one or more of HACD16, 41BBL, CD3, CD4, CD8, CAR, TCR, CD137 or CD80. Such cells have improved immune effector ability.

In some embodiments, the iPSC and its derivative hematopoietic cells comprise a surface triggering receptor for coupling with bi- or multi-specific engagers. Such cells have improved tumor targeting specificity.

In some embodiments, the iPSC and its derivative hematopoietic cells are antigen specific.

Techniques in cell culture and media collection are outlined in Hu et al., Curr. Opin. Biotechnol. 8:148, 1997; K. Kitano, Biotechnology 17:73, 1991; Curr. Opin. Biotechnol. 2:375, 1991; Birch et al., Bioprocess Technol. 19:251, 1990; "Teratocarcinomas and embryonic stem cells: A practical approach" (E. J. Robertson, ed., IRL Press Ltd. 1987); "Guide to Techniques in Mouse Development" (P. M. Wasserman et al. eds., Academic Press 1993); "Embryonic Stem Cell Differentiation in vitro" (M. V. Wiles, Meth. Enzymol. 225:900, 1993); "Properties and uses of Embryonic Stem Cells: Prospects for Application to Human Biology and Gene Therapy" (P. D. Rathjen et al., al., 1993). Differentiation of stem cells is reviewed in Robertson, Meth. Cell Biol. 75:173, 1997; and Pedersen, Reprod. Fertil. Dev. 10:31, 1998.

In the present invention, strategies for enriching a population of cells with specific characterizations are provided at various stages of the methods. In one embodiment, the method of enriching pluripotent stem cells from a cell population comprises making a single cell suspension by dissociating the cells in the population and resuspending the cells. The dissociated cells may be resuspended in any suitable solution or media for maintaining cells or performing cell sorting. In particular embodiments, the pluripotent single cell suspension contains a GSK3 inhibitor, a MEK inhibitor, and a Rock inhibitor and lacks a TFGβ inhibitor. In certain embodiments, the GSK3 inhibitor is CHIR99021, the MEK inhibitor is PD0325901, and/or the Rock inhibitor is thiazovivin.

In a particular embodiment, a population of cells is sorted to positively select pluripotent cells, and/or the population is depleted of non-reprogrammed or non-pluripotent cells, thereby obtaining a population of cells enriched for pluripotent cells. In one embodiment, a single cell suspension is prepared, and then the single cells are prepared for sorting, such as by staining for markers of pluripotency using, e.g., appropriate antibodies. Cells may be sorted by any suitable method of sorting cells, such as by magnetic bead or flow cytometry (FACS) sorting.

Cells may be sorted based on one or more markers of pluripotency, or markers indicating cell differentiation, including without limitation, expression of SSEA3/4, TRA1-60/81, TRA1-85, TRA2-54, GCTM-2, TG343, TG30, CD9, CD29, CD133/prominin, CD140a, CD56, CD73, CD105, OCT4, NANOG, SOX2, KLF4, SSEA1 (Mouse), CD30, SSEA5, CD90 and/or CD50. In various embodiments, cells are sorted based on at least two, at least three, or at least four markers of pluripotency or differentiation. In certain embodiments, cells are sorted based on expression of SSEA4, and in certain particular embodiments based on expression of SSEA4 in combination with TRA1-81 and/or TRA1-60. In certain embodiments, cells are sorted based on SSEA4, TRA1-81, or TRA-60, and/or CD30 expression. In one embodiment, cells are sorted based on SSEA4, TRA1-81 and CD30. In another embodiment, cells are sorted based on SSEA4, TRA1-60 and CD30. In certain embodiments, cells sorting using one or more surface markers of differentiation includes, but not limited to, CD13, CD26, CD34, CD45, CD31, CD46 and CD7, and pluripotent markers such as SSEA4, TRA1-81 and/or CD30.

In some embodiments, a population of cells undergoing reprogramming or a population of pluripotent cells is depleted of differentiated cells. In one embodiment, a population of pluripotent cells or cells induced to reprogram can be depleted of cells having one or more cells surface markers of differentiated cells. Illustrative examples of cell surface markers of differentiating cells include but are not limited to, CD13, CD26, CD34, CD45, CD31, CD46, and CD7. In particular embodiments, CD13 is used as a surface marker of differentiating cells.

In other embodiments, a population of cells is induced to differentiate into a desired lineage and is depleted of pluripotent cells to obtain an enriched population of differentiating or differentiated cells. In some embodiments, the population of differentiated cells comprises a population of cells, such as ESCs or iPSCs that has been induced to differentiate into a specific lineage. In some embodiments, a population of cells may be depleted of pluripotent cells using the negative cell sorting techniques described above ("panning"), such as sorting cells in the population according to magnetic beads or FACs based on markers of pluripotency. In some embodiments, a population of cells comprising differentiated cells is sorted by FACs using pluripotency markers, and a fraction is obtained that is depleted of cells expressing pluripotency markers. In other embodiments, a population of cells is sorted by FACs based on markers of differentiation, such as lineage-specific markers including, but not limited to, CD13, CD26, CD34, CD45, CD31, CD46, and CD7, to obtain a fraction depleted of markers of pluripotency. In some particular embodiments of the invention, CD13 is used as a surface marker of differentiating cells.

D. Cell Populations and Cell Lines Generated from the Methods and Platforms Provided Herein In some embodiments, the cells cultured after reprogramming are induced to differentiate for at least 1, 2, 3, 4, 5, 6, 7, 8, 9, 10, 11, 12, 15, 18, 20, 22, 24, 26, 28, 30, 32, 35, 40, 42, or 45 days, or any number of days in between. In some embodiments, the cells cultured after reprogramming are induced for about 1 to 42 days, 2 to 40 days, 2 to 35 days, 2 to 20 days, 2 to 10 days, 4 to 30 days, about 4 to 24 days, about 6 to 22 days, or about 8 to about 12 days. In some embodiments, the cells are pluripotent stem cells including iPSCs. In some embodiments, the iPSCs are naïve iPSCs. In one embodiment, enrichment provides a method for obtaining clonal pluripotent stem cell-derived differentiating cell colonies in a relatively short time, thereby improving the efficiency of generating pluripotent stem cell-derived differentiated cells at various stages. In one embodiment, enrichment provides a method for deriving CD34 expressing HE cells, CD34 expressing HSC cells, T or NK cell progenitors and T or NK cells, thereby improving the efficiency of generating each of the cell populations. Enrichment may comprise sorting a population of cells, to identify and obtain cells expressing specific characteristic marker(s) indicative of differentiation stage/cell types. In some embodiments, the sorting uses CD34, CD43, CD73, CXCR4, and/or CD93. In some embodiments, the sorting uses CD34 positive. In some embodiments, the sorting uses CD34 positive, and CD43 negative. In some embodiments, the sorting uses CD34 positive, CD43 negative, and CD73 negative. In some other embodiments, the sorting uses CD34 positive, CD43 negative, CD73 negative, and CXCR4 negative. In some other embodiments, the sorting uses CD34 positive, CD43 negative, and CD93 negative. In some other embodiments, the sorting uses CD34 positive, and CD93 negative. An additional enrichment methodology comprises the depletion of cells expressing markers representing undesired cell types to obtain an enriched population of desired cell types.

As such, one aspect of the invention provides a composition comprising one or more cell populations, cell lines, or clonal cells of (i) pluripotent stem cell-derived CD34+HE cells (iCD34), wherein the iCD34 cells have capacity to differentiate into multipotent progenitor cells, and wherein the iCD34 cells are CD34+CD43−; (ii) pluripotent stem cell-derived definitive hemogenic endothelium (iHE), wherein the iHE cell line or clonal cells are CD34+, and at least one of CD93−, CXCR4−, CD73−, and CXCR4−CD73−; (iii) pluripotent stem cell-derived multipotent progenitor cells (iMPP), wherein the iMPP cells are CD34+CD45+; (v) pluripotent stem cell-derived T cell progenitors (ipro-T), wherein the T cell progenitors are CD34+CD45+CD7+; (iv) pluripotent stem cell-derived T cells (iT), wherein the T cells are CD45+CD4+CD3+ or CD45+CD8+CD3+; (vi) pluripotent stem cell-derived NK cell progenitors (ipro-NK), wherein the NK cell progenitors are CD45+CD56+CD7+CD3−; and (vii) pluripotent stem cell-derived NK cells (iNK), wherein the NK cells are CD45+CD56+NKp46+. In some embodiments, the above compositions, cell populations, cell lines or clonal cells are amenable to cryopreservation. In some embodiments, the compositions, cell populations, cell lines or clonal cells are amenable to ambient storage conditions for more than 12 hrs, 24 hrs, 36 hrs, 48 hrs, but not longer than 3 days, 4 days, 5 days, 6 days, or a week.

Another aspect of the invention provides a mixture comprising one or more of pluripotent stem cell derived (i) CD34+IE cells (iCD34), and one or more culture medium selected from iMPP-A, iTC-A2, iTC-B2, iNK-A2, and iNK-B2; (ii) definitive hemogenic endothelium (iHE), and one or more culture medium selected from iMPP-A, iTC-A2, iTC-B2, iNK-A2, and iNK-B2; (iii) definitive HSCs, and one or more culture medium selected from iMPP-A, iTC-A2, iTC-B2, iNK-A2, and iNK-B2; (iv) multipotent progenitor cells (iMPP), and iMPP-A; (v) T cell progenitors (ipro-T), and one or more culture medium selected from iTC-A2, and iTC-B2; (vi) T cells (iTC), and iTC-B2; (vii) NK cell progenitors (ipro-NK), and one or more culture medium selected from iNK-A2, and iNK-B2; and/or (viii) NK cells (iNK), and iNK-B2; wherein
   a. iCD34-C comprises a ROCK inhibitor, one or more growth factors and cytokines selected from the group consisting of bFGF, VEGF, SCF, IL6, IL11, IGF, and EPO, and optionally, a Wnt pathway activator; and is free of TGFβ receptor/ALK inhibitor;
   b. iMPP-A comprises a BMP activator, a ROCK inhibitor, and one or more growth factors and cytokines selected from the group consisting of TPO, IL3, GMCSF, EPO, bFGF, VEGF, SCF, IL6, Flt3L and L11;
   c. iTC-A2 comprises a ROCK inhibitor; one or more growth factors and cytokines selected from the group consisting of SCF, Ft3L, TPO, and IL7; and optionally, a BMP activator;
   d. iTC-B2 comprises one or more growth factors and cytokines selected from the group consisting of SCF, Flt3L, and IL7; wherein the composition is free of one or more of VEGF, bFGF, BMP activators, and ROCK inhibitors;
   e. iNK-A2 comprises a ROCK inhibitor, and one or more growth factors and cytokines selected from the group consisting of SCF, Flt3L, TPO, IL3, IL7, and IL15; and optionally, a BMP activator, and
   f. iNK-B2 comprises one or more growth factors and cytokines selected from the group consisting of SCF, Flt3L, IL7 and IL15.

E. Therapeutic Use of iPSC Derived Immune Cells

The present invention provides a composition comprising an isolated population or subpopulation of immune cells that have been derived from iPSC using the methods and compositions as disclosed, wherein the immune cells are suitable for cell based adoptive therapies. In one embodiment, the isolated population or subpopulation of immune cell comprises iPSC derived HSC cells. In one embodiment, the isolated population or subpopulation of immune cell comprises iPSC derived T cells. In one embodiment, the isolated population or subpopulation of immune cell comprises iPSC derived NK cells. In some embodiments, the iPSC derived immune cells are further modulated ex vivo for improved therapeutic potential. In one embodiment, an isolated population or subpopulation of immune cells that have been derived from iPSC comprises an increased number or ratio of naïve T cells, stem cell memory T cells, and/or central memory T cells. In one embodiment, the isolated population or subpopulation of immune cell that has been derived from iPSC comprises an increased number or ratio of type I NKT cells. In another embodiment, the isolated population or subpopulation of immune cell that has been derived from iPSC comprises an increased number or ratio of adaptive NK cells. In some embodiments, the isolated population or subpopulation of HSC cells, T cells, or NK cells derived from iPSC are allogenic. In some other embodiments, the isolated population or subpopulation of HSC cells, T cells, or NK cells derived from iPSC are autogenic.

In some embodiments, the iPSC for differentiation comprises genetic imprints conveying desirable therapeutic attributes in effector cells, which genetic imprints are retained and functional in the differentiated hematopoietic cells derived from said iPSC.

In some embodiments, the genetic imprints of the pluripotent stem cells comprise (i) one or more genetically modified modalities obtained through genomic insertion, deletion or substitution in the genome of the pluripotent cells during or after reprogramming a non-pluripotent cell to iPSC; or (ii) one or more retainable therapeutic attributes of a source specific immune cell that is donor-, disease-, or treatment response-specific, and wherein the pluripotent cells are reprogrammed from the source specific immune cell, wherein the iPSC retain the source therapeutic attributes, which are also comprised in the iPSC derived hematopoietic lineage cells.

In some embodiments, the genetically modified modalities comprise one or more of: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the iPSCs or derivative cells thereof. In some other embodiments, the genetically modified modalities comprise one or more of (i) deletion or reduced expression of B2M, TAP1, TAP2, Tapasin, NLRC5, PD1, LAG3, TIM3, RFXANK, CITTA, RFX5, or RFXAP; (ii) introduced or increased expression of HLA-E, HLA-G, HACD16, 41BBL, CD3, CD4, CD8, CD47, CD137, CD80, PDL1, A2AR, CAR, TCR, or surface triggering receptors for coupling with bi- or multi-specific engagers.

In still some other embodiments, the hematopoietic lineage cells comprise the therapeutic attributes of the source specific immune cell relating to one or more of (i) antigen targeting receptor expression; (ii) HLA presentation or lack thereof; (iii) resistance to tumor microenvironment; (iv) induction of bystander immune cells and immune modulations; (iv) improved on-target specificity with reduced off-tumor effect; (v) resistance to treatment such as chemotherapy; and (vi) improved homing, persistence, and cytotoxicity.

In some embodiments, the iPSC and its derivative hematopoietic cells comprise one or more of B2M null, HLA-E/G, PDL1, $A_{24}R$, CD47, LAG3 null, TIM3 null, TAP1 null, TAP2 null, Tapasin null, NLRC5 null, PD1 null, RFKANK null, CITTA null, RFX5 null and RFXAP null. These cells with modified HLA class I and/or II have increased resistance to immune detection, and therefore present improved in vivo persistence. Moreover, such cells can avoid the need for HLA matching in adoptive cell therapy and thus provide a source of universal, off-the-shelf therapeutic regimen.

In some embodiments, the iPSC and its derivative hematopoietic cells comprise one or more of HACD16, 41BBL, CD3, CD4, CD8, CAR, TCR, CD137 or CD80. Such cells have improved immune effector ability.

In some embodiments, the iPSC and its derivative hematopoietic cells are antigen specific.

A variety of diseases may be ameliorated by introducing the immune cells of the invention to a subject suitable for adoptive cell therapy. Examples of diseases including various autoimmune disorders, including but not limited to, alopecia areata, autoimmune hemolytic anemia, autoimmune hepatitis, dermatomyositis, diabetes (type 1), some forms of juvenile idiopathic arthritis, glomerulonephritis, Graves' disease, Guillain-Barre syndrome, idiopathic thrombocytopenic purpura, myasthenia gravis, some forms of myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus, erythematosus, some forms of thyroiditis, some forms of uveitis, vitiligo, granulomatosis with polyangiitis (Wegener's); hematological malignancies, including but not limited to, acute and chronic leukemias, lymphomas, multiple myeloma and myelodysplastic syndromes; solid tumors, including but not limited to, tumor of the brain, prostate, breast, lung, colon, uterus, skin, liver, bone, pancreas, ovary, testes, bladder, kidney, head, neck, stomach, cervix, rectum, larynx, or esophagus; and infections, including but not limited to, HIV- (human immunodeficiency virus), RSV- (Respiratory Syncytial Virus), EBV- (Epstein-Barr virus), CMV- (cytomegalovirus), adenovirus- and BK polyomavirus-associated disorders.

Particular embodiments of the present invention are directed to methods of treating a subject in need thereof by administering to the subject a composition comprising any of the cells described herein. In particular embodiments, the terms "treating," "treatment," and the like are used herein to generally mean obtaining a desired pharmacologic and/or physiologic effect. The effect may be prophylactic in terms of completely or partially preventing a disease and/or may be therapeutic in terms of a partial or complete cure for a disease and/or adverse effect attributable to the disease. "Treatment" as used herein covers any treatment of a disease in a mammal, and includes: preventing the disease from occurring in a subject which may be predisposed to the disease but has not yet been diagnosed as having it; inhibiting the disease, i.e., arresting its development; or relieving the disease, i.e., causing regression of the disease. The therapeutic agent or composition may be administered before, during or after the onset of disease or injury. The treatment of ongoing disease, where the treatment stabilizes or reduces the undesirable clinical symptoms of the patient, is of particular interest.

In particular embodiments, the subject has a disease, condition, and/or an injury that can be treated, ameliorated, and/or improved by a cell therapy. Some embodiments contemplate that a subject in need of cell therapy is a subject with an injury, disease, or condition, whereby a cell therapy, e.g., a therapy in which a cellular material is administered to the subject, can treat, ameliorate, improve, and/or reduce the severity of at least one symptom associated with the injury, disease, or condition. Certain embodiments contemplate that a subject in need of cell therapy, includes, but is not limited to, a candidate for bone marrow or stem cell transplantation, a subject who has received chemotherapy or irradiation therapy, a subject who has or is at risk of having a hyperproliferative disorder or a cancer, e.g. a hyperproliferative disorder or a cancer of hematopoietic system, a subject having or at risk of developing a tumor, e.g., a solid tumor, a subject who has or is at risk of having a viral infection or a disease associated with a viral infection.

According, the present invention further provides pharmaceutical compositions comprising the pluripotent cell derived hematopoietic lineage cells made by the methods and composition disclosed herein, wherein the pharmaceutical compositions further comprise a pharmaceutically acceptable medium. In one embodiment, the pharmaceutical composition comprises the pluripotent cell derived T cells made by the methods and composition disclosed herein. In one embodiment, the pharmaceutical composition comprises the pluripotent cell derived NK cells made by the methods and composition disclosed herein. In one embodiment, the pharmaceutical composition comprises the pluripotent cell derived CD34 HE cells made by the methods and composition disclosed herein. In one embodiment, the pharmaceutical composition comprises the pluripotent cell derived HSCs made by the methods and composition disclosed herein.

Additionally, the present invention provides therapeutic use of the above pharmaceutical compositions by introducing the composition to a subject suitable for adoptive cell therapy, wherein the subject has an autoimmune disorder; a hematological malignancy; a solid tumor; or an infection associated with HIV, RSV, EBV, CMV, adenovirus, or BK polyomavirus.

The isolated pluripotent stem cell derived hematopoietic lineage cells can have at least 50%, 60%, 70%, 80%, 90%, 95%, 98%, or 99% T cells, NK cells, NKT cells, CD34+HE cells or HSCs. In some embodiments, the isolated pluripotent stem cell derived hematopoietic lineage cells has about 95% to about 100% T cells, NK cells, NKT cells, CD34+HE cells or HSCs. In some embodiments, the present invention provides pharmaceutical compositions having purified T cells, NK cells, NKT cells, CD34+HE cells or HSCs, such as a composition having an isolated population of about 95% T cells, NK cells, NKT cells, CD34+HE cells or HSCs to treat a subject in need of the cell therapy.

In some embodiments, the pharmaceutical composition includes an isolated population of pluripotent stem cell derived hematopoietic lineage cells, wherein population has less than about 0.1%, 0.5%, 1%, 2%, 5%, 10%, 15%, 20%, 25%, or 30% iPSC derived T cells, NK cells, NKT cells, CD34+HE cells or HSCs. The isolated population of derived hematopoietic lineage cells in some embodiments can have more than about 0.1%, 0.5%, 1%, 2%, 5%, 10%, 15%, 20%, 25%, or 30% T cells, NK cells, NKT cells, CD34+HE cells or HSCs. In other embodiments, the isolated population of derived hematopoietic lineage cells can have about 0.1% to about 1%, about 1% to about 3%, about 3% to about 5%, about 10%-about 15%, about 15%-20%, about 20%-25%, about 25%-30%, about 30%-35%, about 35%-40%, about 40%-45%, about 45%-50%, about 60%-70%, about 70%-80%, about 80%-90%, about 90%-95%, or about 95% to about 100% T cells, NK cells, NKT cells, CD34+HE cells or HSCs.

In particular embodiments, the derived hematopoietic lineage cells can have about 0.1%, about 1%, about 3%, about 5%, about 10%, about 15%, about 20%, about 25%, about 30%, about 35%, about 40%, about 45%, about 50%, about 60%, about 70%, about 80%, about 90%, about 95%, about 98%, about 99%, or about 100% T cells, NK cells, NKT cells, CD34+HE cells or HSCs.

As a person of ordinary skill in the art would understand, both autologous and allogeneic immune cells can be used in cell therapies. Autologous cell therapies can have reduced infection, low probability for GvHD, and rapid immune reconstitution. Allogeneic cell therapies can have an immune mediated graft-versus-malignancy (GVM) effect, and low rate of relapse. Based on the specific conditions of the patients or subject in need of the cell therapy, a person of ordinary skill in the art would be able to determine which specific type of therapy to administer.

In particular embodiments, the derived hematopoietic lineage cells of the pharmaceutical composition of the invention are allogeneic to a subject. In particular embodiments, the derived hematopoietic lineage cells of the pharmaceutical formulation of the invention are autologous to a subject. For autologous transplantation, the isolated population of derived hematopoietic lineage cells are either complete or partial HLA-match with the patient. In another embodiment, the derived hematopoietic lineage cells are not HLA-matched to the subject.

In some embodiments, the number of derived hematopoietic lineage cells in the pharmaceutical composition is at least $0.1 \times 10^5$ cells, at least $0.5 \times 10^5$ cells, at least $1 \times 10^5$ cells, at least $5 \times 10^5$ cells, at least $10 \times 10^5$ cells, at least $0.5 \times 10^6$ cells, at least $0.75 \times 10^6$ cells, at least $1 \times 10^6$ cells, at least 1.25×10⁶ cells, at least 1.5×10⁶ cells, at least 1.75×10⁶ cells, at least 2×10⁶ cells, at least 2.5×10⁶ cells, at least 3×10⁶ cells, at least 4×10⁶ cells, at least 5×10⁶ cells, at least 10×10⁶ cells, at least 15×10⁶ cells, at least 20×10⁶ cells, at least 25×10⁶ cells, or at least 30×10⁶ cells.

In some embodiments, the number of derived hematopoietic lineage cells in the pharmaceutical composition is about 0.1×10⁵ cells to about 10×10⁵ cells; about 0.5×10⁶ cells to about 5×10⁶ cells; about 1×10⁶ cells to about 3×10⁶ cells; about 1.5×10⁶ cells to about 2.5×10⁶ cells; or about 2×10⁶ cells to about 2.5×10⁶ cells.

In some embodiments, the number of derived hematopoietic lineage cells in the pharmaceutical composition is about 1×10⁶ cells to about 3×10⁶ cells; about 1.0×10⁶ cells to about 5×10⁶ cells; about 1.0×10⁶ cells to about 10×10⁶ cells, about 10×10⁶ cells to about 20×10⁶ cells, about 10×10⁶ cells to about 30×10⁶ cells, or about 20×10⁶ cells to about 30×10⁶ cells.

In some other embodiments, the number of derived hematopoietic lineage cells in the pharmaceutical composition is about 1×10⁶ cells to about 30×10⁶ cells; about 1.0×10⁶ cells to about 20×10⁶ cells; about 1.0×10⁶ cells to about 10×10⁶ cells, about 2.0×10⁶ cells to about 30×10⁶ cells, about 2.0×10⁶ cells to about 20×10⁶ cells, or about 2.0×10⁶ cells to about 10×10⁶ cells.

In yet other embodiments, the number of derived hematopoietic lineage cells in the pharmaceutical composition is about 1×10⁶ cells, about 2×10⁶ cells, about 5×10⁶ cells, about 7×10⁶ cells, about 10×10⁶ cells, about 15×10⁶ cells, about 17×10⁶ cells, about 20×10⁶ cells about 25×10⁶ cells, or about 30×10⁶ cells.

In one embodiment, the number of derived hematopoietic lineage cells in the pharmaceutical composition is the number of immune cells in a partial or single cord of blood, or is at least $0.1 \times 10^5$ cells/kg of bodyweight, at least $0.5 \times 10^5$ cells/kg of bodyweight, at least $1 \times 10^5$ cells/kg of bodyweight, at least $5 \times 10^5$ cells/kg of bodyweight, at least $10 \times 10^5$ cells/kg of bodyweight, at least $0.5 \times 10^6$ cells/kg of bodyweight, at least $0.75 \times 10^6$ cells/kg of bodyweight, at least $1 \times 10^6$ cells/kg of bodyweight, at least $1.25 \times 10^6$ cells/kg of bodyweight, at least $1.5 \times 10^6$ cells/kg of bodyweight, at least $1.75 \times 10^6$ cells/kg of bodyweight, at least $2 \times 10^6$ cells/kg of bodyweight, at least $2.5 \times 10^6$ cells/kg of bodyweight, at least $3 \times 10^6$ cells/kg of bodyweight, at least $4 \times 10^6$ cells/kg of bodyweight, at least $5 \times 10^6$ cells/kg of bodyweight, at least $10 \times 10^6$ cells/kg of bodyweight, at least $15 \times 10^6$ cells/kg of bodyweight, at least $20 \times 10^6$ cells/kg of bodyweight, at least $25 \times 10^6$ cells/kg of bodyweight, or at least $30 \times 10^6$ cells/kg of bodyweight.

The derived hematopoietic lineage cells provided by the invention can be administration to a subject without being expanded ex vivo or in vitro prior to administration. In particular embodiments, an isolated population of derived hematopoietic lineage cells is modulated and treated ex vivo using one or more agent to obtain immune cells with improved therapeutic potential. The modulated population of derived hematopoietic lineage cells can be washed to remove the treatment agent(s), and the improved population is administered to a patient without further expansion of the population in vitro.

In other embodiments, the invention provides an isolated population of derived hematopoietic lineage cells that are expanded prior to modulating the isolated population or subpopulation of T lymphocytes with one or more agents. The isolated population of derived hematopoietic lineage cells can be recombinantly produced to express TCR, CAR or other proteins.

For genetically engineered derived hematopoietic lineage cells that express recombinant TCR or CAR, whether prior to or after genetic modification of the cells, the cells can be activated and expanded using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

In certain embodiments, the primary stimulatory signal and the co-stimulatory signal for the derived hematopoietic lineage cells can be provided by different protocols. For example, the agents providing each signal can be in solution or coupled to a surface. When coupled to a surface, the agents can be coupled to the same surface (i.e., in "cis" formation) or to separate surfaces (i.e., in "trans" formation). Alternatively, one agent can be coupled to a surface and the other agent in solution. In one embodiment, the agent providing the co-stimulatory signal can be bound to a cell surface and the agent providing the primary activation signal is in solution or coupled to a surface. In certain embodiments, both agents can be in solution. In another embodiment, the agents can be in soluble form, and then cross-linked to a surface, such as a cell expressing Fc receptors or an antibody or other binding agent which will bind to the agents such as disclosed in U.S. Patent Application Publication Nos. 20040101519 and 20060034810 for artificial antigen presenting cells (aAPCs) that are contemplated for use in activating and expanding T lymphocytes in the present invention.

The compositions comprising a population of derived hematopoietic lineage cells of the invention can be sterile, and can be suitable and ready for administration (i.e., can be administered without any further processing) to human patients. In some embodiments, the therapeutic composition is ready for infusion into a patient. A cell based composition that is ready for administration means that the composition does not require any further treatment or manipulations prior to transplant or administration to a subject.

The sterile, therapeutically acceptable compositions suitable for administration to a patient can include one or more pharmaceutically acceptable carriers (additives) and/or diluents (e.g., pharmaceutically acceptable medium, for example, cell culture medium), or other pharmaceutically acceptable components. Pharmaceutically acceptable carriers and/or diluents are determined in part by the particular composition being administered, as well as by the particular method used to administer the therapeutic composition. Accordingly, there is a wide variety of suitable formulations of therapeutic compositions of the present invention (see, e.g., Remington's Pharmaceutical Sciences, 17$^{th}$ ed. 1985, the disclosure of which is hereby incorporated by reference in its entirety).

In particular embodiments, therapeutic cell compositions having an isolated population of derived hematopoietic lineage cells also have a pharmaceutically acceptable cell culture medium. A therapeutic composition comprising a population of derived hematopoietic lineage cells as disclosed herein can be administered separately by enteral or parenteral administration methods or in combination with other suitable compounds to effect the desired treatment goals.

The pharmaceutically acceptable carrier and/or diluent must be of sufficiently high purity and of sufficiently low toxicity to render it suitable for administration to the human subject being treated. It further should maintain or increase the stability of the therapeutic composition. The pharmaceutically acceptable carrier can be liquid or solid and is selected, with the planned manner of administration in mind, to provide for the desired bulk, consistency, etc., when combined with other components of the therapeutic composition of the invention. For example, the pharmaceutically acceptable carrier can be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulfate, etc.). Other suitable pharmaceutically acceptable carriers for the compositions of the present invention include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like.

Such carrier solutions also can contain buffers, diluents and other suitable additives. A buffer refers to a solution or liquid whose chemical makeup neutralizes acids or bases without a significant change in PH. Examples of buffers envisioned by the invention include, but are not limited to, Dulbecco's phosphate buffered saline (PBS), Ringer's solution, 5% dextrose in water (D5W), normal/physiologic saline (0.9% NaCl).

These pharmaceutically acceptable carriers and/or diluents can be present in amounts sufficient to maintain a PH of the therapeutic composition of between about 3 and about 10. As such, the buffering agent can be as much as about 5% on a weight to weight basis of the total composition. Electrolytes such as, but not limited to, sodium chloride and potassium chloride can also be included in the therapeutic composition. In one aspect, the PH of the therapeutic composition is in the range from about 4 to about 10. Alternatively, the PH of the therapeutic composition is in the range from about 5 to about 9, from about 6 to about 9, or from about 6.5 to about 8. In another embodiment, the therapeutic composition includes a buffer having a PH in one of said PH ranges. In another embodiment, the therapeutic composition has a PH of about 7. Alternatively, the therapeutic composition has a PH in a range from about 6.8 to about 7.4. In still another embodiment, the therapeutic composition has a PH of about 7.4.

The sterile composition of the invention can be a sterile solution or suspension in a nontoxic pharmaceutically acceptable medium. Suspension can refer to non-adherent conditions in which cells are not attached to a solid support. For example, cells maintained in suspension can be stirred and are not adhered to a support, such as a culture dish.

A suspension is a dispersion (mixture) in which a finely-divided species is combined with another species, with the former being so finely divided and mixed that it doesn't rapidly settle out. A suspension can be prepared using a vehicle such as a liquid medium, including a solution. In some embodiments, the therapeutic composition of the invention is a suspension, where the stem and/or progenitor cells are dispersed within an acceptable liquid medium or solution, e.g., saline or serum-free medium, and are not attached to a solid support. In everyday life, the most common suspensions are those of solids in liquid water. Among the acceptable diluents, e.g., vehicles and solvents, that can be employed are water, Ringer's solution, isotonic sodium chloride (saline) solution, and serum-free cell culture medium. In some embodiments, hypertonic solutions are employed in making suspensions. In addition, sterile, fixed oils are conventionally employed as a solvent or suspending medium. For parenteral application, particularly suitable vehicles consist of solutions, preferably oily or aqueous solutions, as well as suspensions, emulsions, or implants. Aqueous suspensions can contain substances which increase the viscosity of the suspension and include, for example, sodium carboxymethyl cellulose, sorbitol and/or dextran. In some embodiments, the infusion solution is isotonic to subject tissues. In some embodiments, the infusion solution is hypertonic to subject tissues.

The pharmaceutically acceptable carrier, diluents, and other components comprising the administration-ready pharmaceutical composition of the invention are derived from U.S. Pharmaceutical grade reagents that will permit the therapeutic composition to be used in clinical regimens. Typically, these finished reagents, including any medium, solution, or other pharmaceutically acceptable carriers and/or diluents, are sterilized in a manner conventional in the art, such as filter sterilized, and are tested for various undesired contaminants, such as *mycoplasma*, endotoxin, or virus contamination, prior to use. The pharmaceutically acceptable carrier in one embodiment is substantially free of natural proteins of human or animal origin, and suitable for storing the population of cells of the pharmaceutical composition, including hematopoietic stem and progenitor cells. The pharmaceutical composition is intended to be administered into a human patient, and thus is substantially free of cell culture components such as bovine serum albumin, horse serum, and fetal bovine serum.

The invention also provides, in part, the use of a pharmaceutically acceptable cell culture medium in particular compositions and/or cultures of the present invention. Such compositions are suitable for administration to human subjects. Generally speaking, any medium that supports the maintenance, growth, and/or health of the derived hematopoietic lineage cells of the invention are suitable for use as a pharmaceutical cell culture medium. In particular embodiments, the pharmaceutically acceptable cell culture medium is a serum free, and/or feeder free medium.

The pharmaceutical composition can have serum-free medium suitable for storing the modulated isolated population of derived hematopoietic lineage cells. In various embodiments, the serum-free medium is animal-free, and can optionally be protein-free. Optionally, the medium can contain biopharmaceutically acceptable recombinant proteins. Animal-free medium refers to medium wherein the components are derived from non-animal sources. Recombinant proteins replace native animal proteins in animal-free medium and the nutrients are obtained from synthetic, plant or microbial sources. Protein-free medium, in contrast, is defined as substantially free of protein.

One having ordinary skill in the art would appreciate that the above examples of media are illustrative and in no way limit the formulation of media suitable for use in the present invention and that there are many suitable media known and available to those in the art.

The pharmaceutical composition is substantially free of mycoplasm, endotoxin, and microbial contamination. In particular embodiments, the therapeutic composition contains less than about 10, 5, 4, 3, 2, 1, 0.1, or 0.05 µg/ml bovine serum albumin.

With respect to mycoplasma and microbial contamination, "substantially free" as used herein means a negative reading for the generally accepted tests known to those skilled in the art. For example, mycoplasma contamination is determined by subculturing a sample of the therapeutic composition in broth medium and distributed over agar plates on day 1, 3, 7, and 14 at 37° C. with appropriate positive and negative controls. The sample appearance is compared microscopically, at 100×, to that of the positive and negative control. Additionally, inoculation of an indicator cell culture is incubated for 3 and 5 days and examined at 600× for the presence of mycoplasmas by epifluorescence microscopy using a DNA-binding fluorochrome. The sample is considered satisfactory if the agar and/or the broth media procedure and the indicator cell culture procedure show no evidence of mycoplasma contamination.

An organic solvent or a suitable organic solvent relates generally to carbon containing liquids or gases that dissolve a solid, liquid, or gaseous solute, resulting in a solution. A suitable organic solvent is one that is appropriate for ex vivo administration to, or incubation with, mammalian cells, and can also be appropriate for in vivo administration to a subject, such as by having minimal toxicity or other inhibitory effects under ex vivo conditions (e.g., cell culture) or in vivo at a selected concentration for the time of incubation or administration. A suitable organic solvent should also be appropriate for storage stability and handling of the agents described herein.

Examples of suitable organic solvents include, but are not limited to, dimethyl sulfoxide (DMSO), N,N-dimethylformamide (DMF), dimethoxyethane (DME), and dimethylacetamide, including mixtures or combinations thereof. In certain embodiments, a composition or organic solvent is substantially free of methyl acetate, meaning that there should be no more than trace amounts of methyl acetate in the composition or solvent, and preferably undetectable amounts (e.g., as measured by high pressure liquid chromatography (HPLC), gas chromatography (GC), etc.).

A vessel or composition that is endotoxin free means that the vessel or composition contains at most trace amounts (i.e., amounts having no adverse physiological effects to a subject) of endotoxin, or undetectable amounts of endotoxin. Cells being "substantially free of endotoxin" means that there is less endotoxin per dose of cells than is allowed by the FDA for a biologic, which is a total endotoxin of 5 EU/kg body weight per day, which for an average 70 kg person is 350 EU per total dose of cells.

In one embodiment, the endotoxin free vessel and/or compositions is at least 95%, at least 96%, at least 97%, at least 98%, at least 99%, or 100% endotoxin free. Endotoxins are toxins associated with certain bacteria, typically gram-negative bacteria, although endotoxins can be found in gram-positive bacteria, such as *Listeria monocytogenes*. The most prevalent endotoxins are lipopolysaccharides (LPS) or lipooligosaccharides (LOS) found in the outer membrane of various Gram-negative bacteria, and which represent a central pathogenic feature in the ability of these bacteria to cause disease. Small amounts of endotoxin in humans can produce fever, a lowering of the blood pressure, and activation of inflammation and coagulation, among other adverse physiological effects. Therefore, it is often desirable to remove most or all traces of endotoxin from drug product containers, because even small amounts can cause adverse effects in humans. Endotoxins can be removed from vessels using methods known in the art, for example, vessels can be cleaned in HEPA filtered washing equipment with endotoxin-free water, depyrogenated at 250° C., and clean-packaged in HEPA filtered workstations located inside a class 100/10 clean room (e.g., a class 100 clean room, contains no more than 100 particles bigger than half a micron in a cubic foot of air).

EXAMPLES

The following examples are offered by way of illustration and not by way of limitation.

Example 1-hiPSC Generation and Maintenance

Somatic cells including fibroblast and blood cells were induced to reprogram towards a pluripotent state using various factor combinations including, but not limited to, OCT4/SOX2/LargeT, OCT4/SOX2 or OCT4/SOX2/NANOG/LargeT in the presence of reprogramming medium containing ROCK, MEK, GSK3 pathway and TGFβ receptor inhibitors (Valamehr et al. Sci Rep. 2012; 2: 213). Fourteen days after induction, reprogramming populations were switched to maintenance medium containing ROCK, GSK3, and MEK pathway inhibitors, basic fibroblast growth factor (bFGF), and leukemia inhibitory factor (LIF) (Valamehr et al. Stem Cell Reports 2014, 2(3): 366-381). Cells were kept indefinitely in the maintenance medium.

Approximately three weeks after induction, the reprogramming populations were sorted into individual wells of a 96-well plate. Selected clones were characterized and fully reprogrammed clones representative of naïve hiPSCs were selected for differentiation studies (Valamehr et al. Stem Cell Reports 2014, 2(3): 366-381). To determine the percent undifferentiated cells during maintenance and post differentiation, flow cytometry analysis was conducted for co-surface expression of SSEA4, TRA181 and CD30.

Genomically engineered iPSCs can also be generated during or after reprogramming somatic cells, using methods, for example, disclosed in the U.S. Application Serial Nos. 62/251,032 and 62/337,258, which are incorporated by reference in their entirety.

Further, hiPSC reprogramed from selected somatic cells, including cells of the immune system such as T cells, of preferential donor or patients may be obtained for having unique attributes that contribute to treating various diseases including cancer, and/or for being capable of differentiating into lymphoid effector cells that have the same unique attributes.

Example 2—Hematopoietic Differentiation Using iCD34 Culture Platform and Identification of HE Population Having Engraftment Potential The iCD34 platform is an optimized system for hematopoietic lineage cells differentiation. To initiate differentiation towards the hematopoietic lineage, hiPSCs were seeded as a monolayer on Day (D) 0 in the maintenance medium and allowed to adhere and expand for about 24 hours. At this point, the maintenance medium was removed and replaced with base medium without maintenance factors at D1. Hematopoietic differentiation was initiated at around D2 by switching the culture medium to iCD34-A (see FIG. 1). As illustrated in FIG. 1, the culture medium was supplemented with the growth factor bFGF at D3 and switched to iCD34-B medium subsequently for differentiation. The monolayers were maintained until around D5-D6 at which point they were dissociated into single cells and seeded as a low density monolayer in iCD34-C medium until differentiation around D10. Low oxygen tension (2-10% $O_2$) was maintained from the onset of hematopoietic differentiation around D2 up until around D10 of differentiation.

Figure 4A:
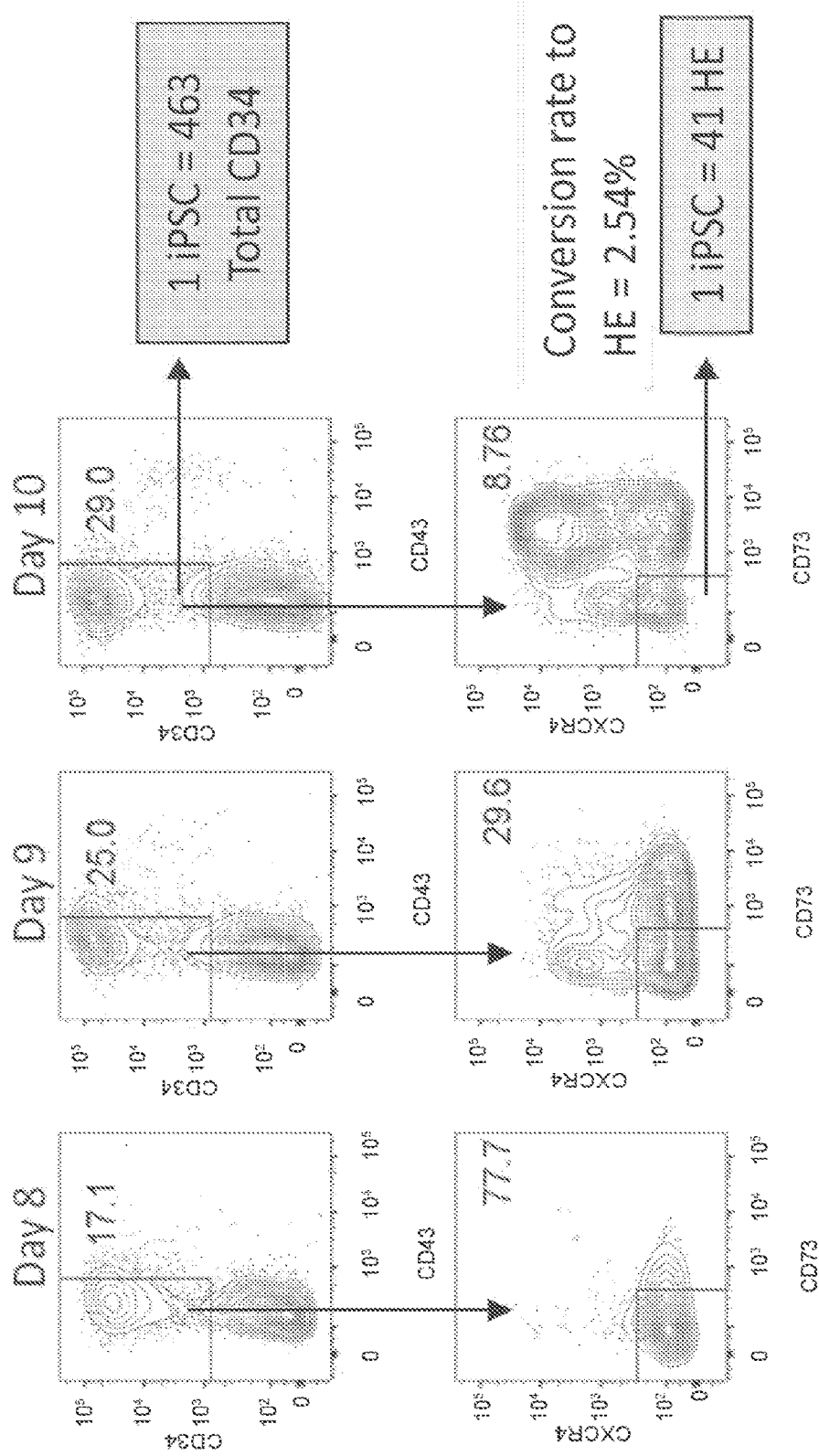
FIG. 4A-C shows flow cytometric profiles depicting the emergence of iHE over a 10 day time course and the output of iCD34 and iHE cells per iPSC differentiation. Calculations are based on snapshot of representative cultures and not optimized cultures.
Figure 4B:
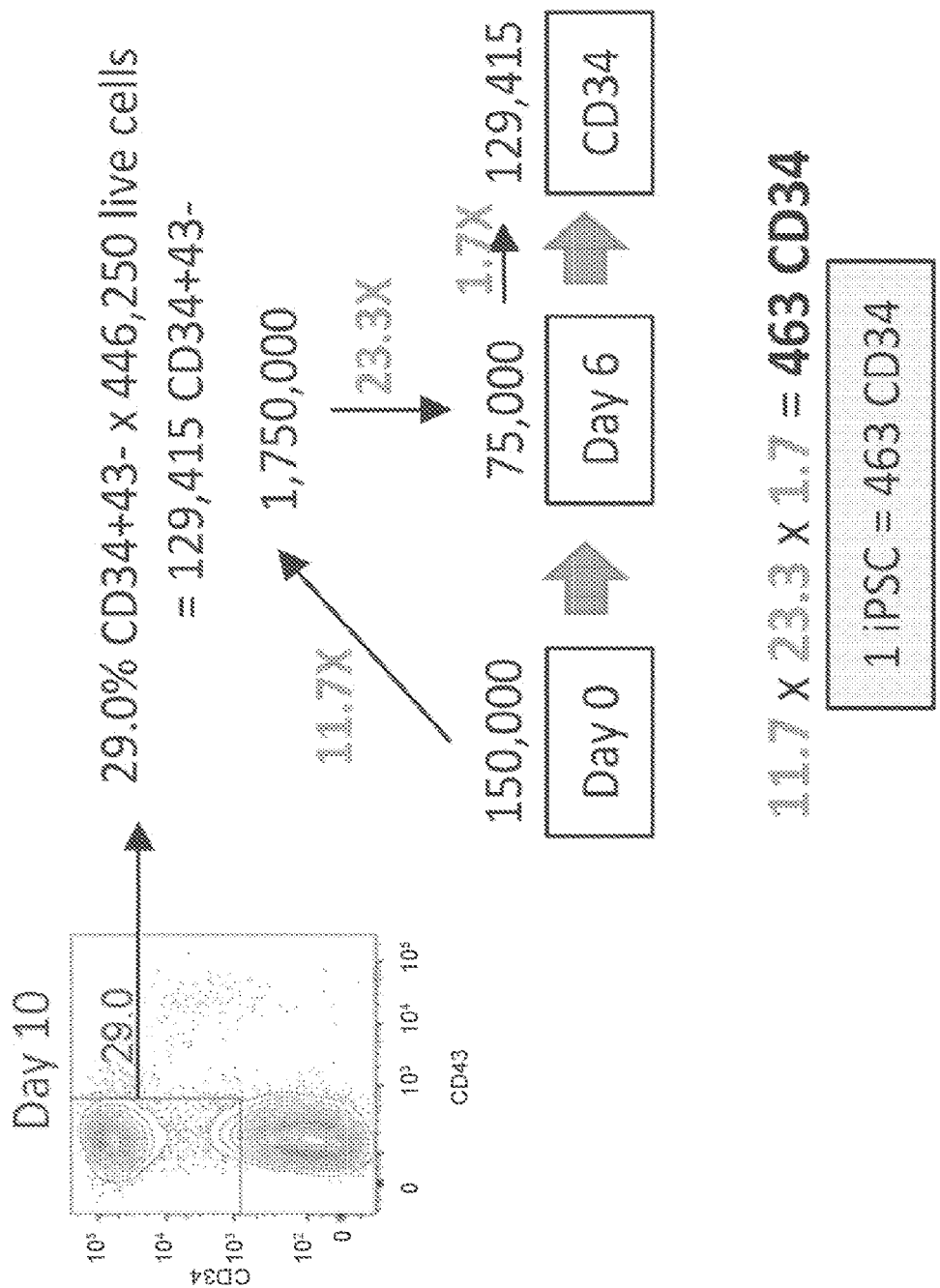

During the culture process, the directed differentiation towards the hematopoietic lineage was monitored by the dissociation of the monolayers into single cells and analysis for the surface marker expression of CD34, and optionally, CD43, CD45, CXCR4, CD73 and/or CD93 (FIG. 4A). At around D8 of differentiation, the appearance of a cell population representing HE was observed by the cell surface expression signature CD34+. CD43−CXCR4−CD73− was also observed in the CD34+ cells. The CD34+ population was maintained until around D10 (FIG. 4A). At D10, which time point can be shortened to about D9 or extended until about D12, the cells were dissociated into single cells and the CD34+HE population was sorted by FACS using a BD FACS Aria for further analysis and functional assessment. FIG. 4A represents an exemplary hematopoietic output capacity: for every input of a single iPSC, 463 total CD34+ cells and 41 CD34+CD43−CXCR4−CD73− cells were generated, demonstrating a conversion rate to definitive HE cells of at least 2.5% (FIG. 4A).

Figure 22:
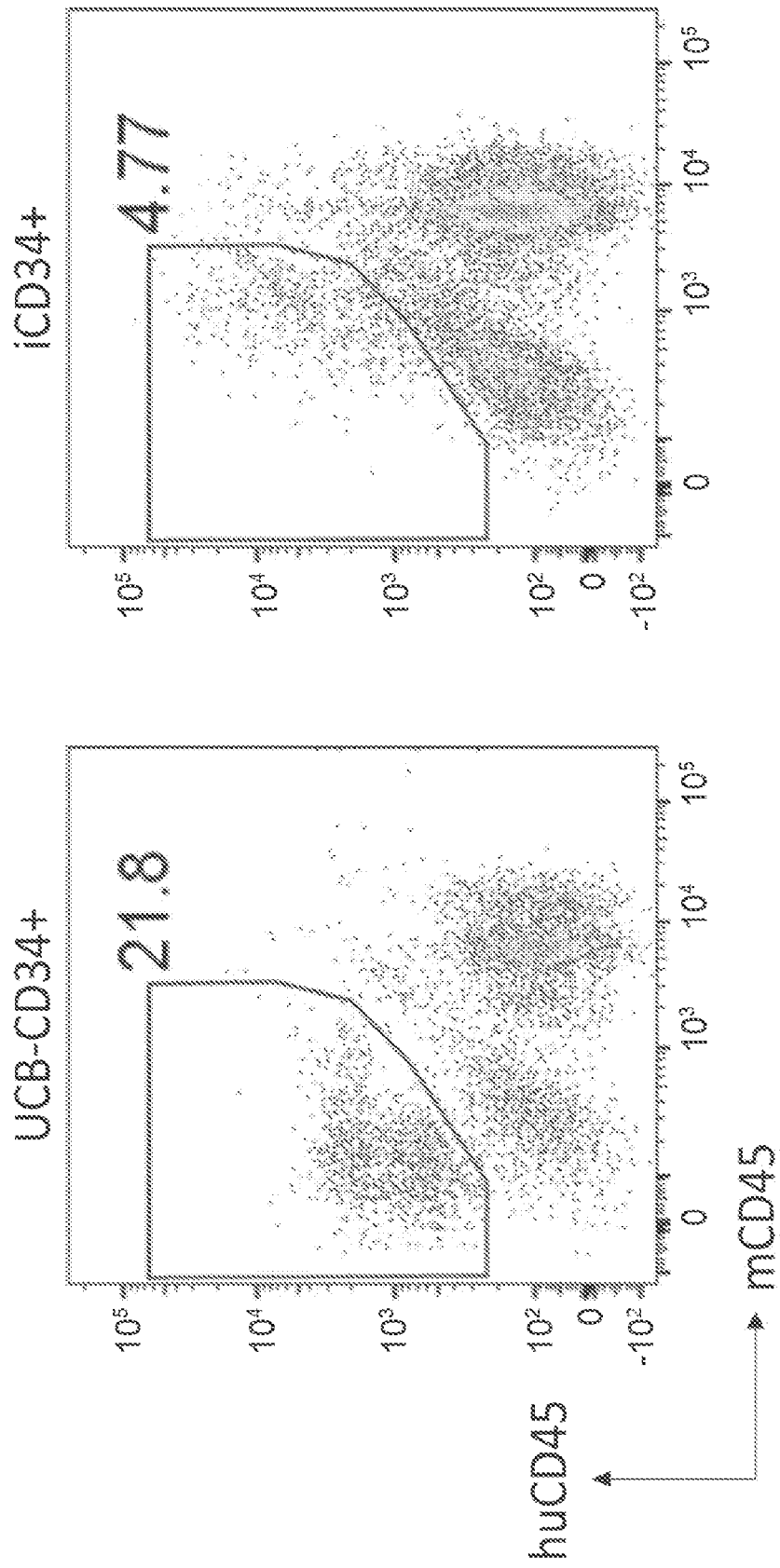
FIG. 22 shows engraftment of hiPSC-derived iCD34+ cells.

To demonstrate the engraftment potential of hiPSC-derived iHE, Day 10 CD34+ cells were sorted and cultured in the iMPP assay for 7 days as described above. After a total of 17 days in culture (10 days of iCD34 plus 7 days of iMPP) approximately 400,000 cells were injected into NSG via retro-orbital injection. 200,000 umbilical cord blood CD34+ cells were injected into separate mice as a control. FIG. 22 demonstrates 5 week reconstitution of engrafted CD34 positive cells as seen by the presence of cells expressing the human CD45 marker in the peripheral blood of the mouse.

Figure 4C:
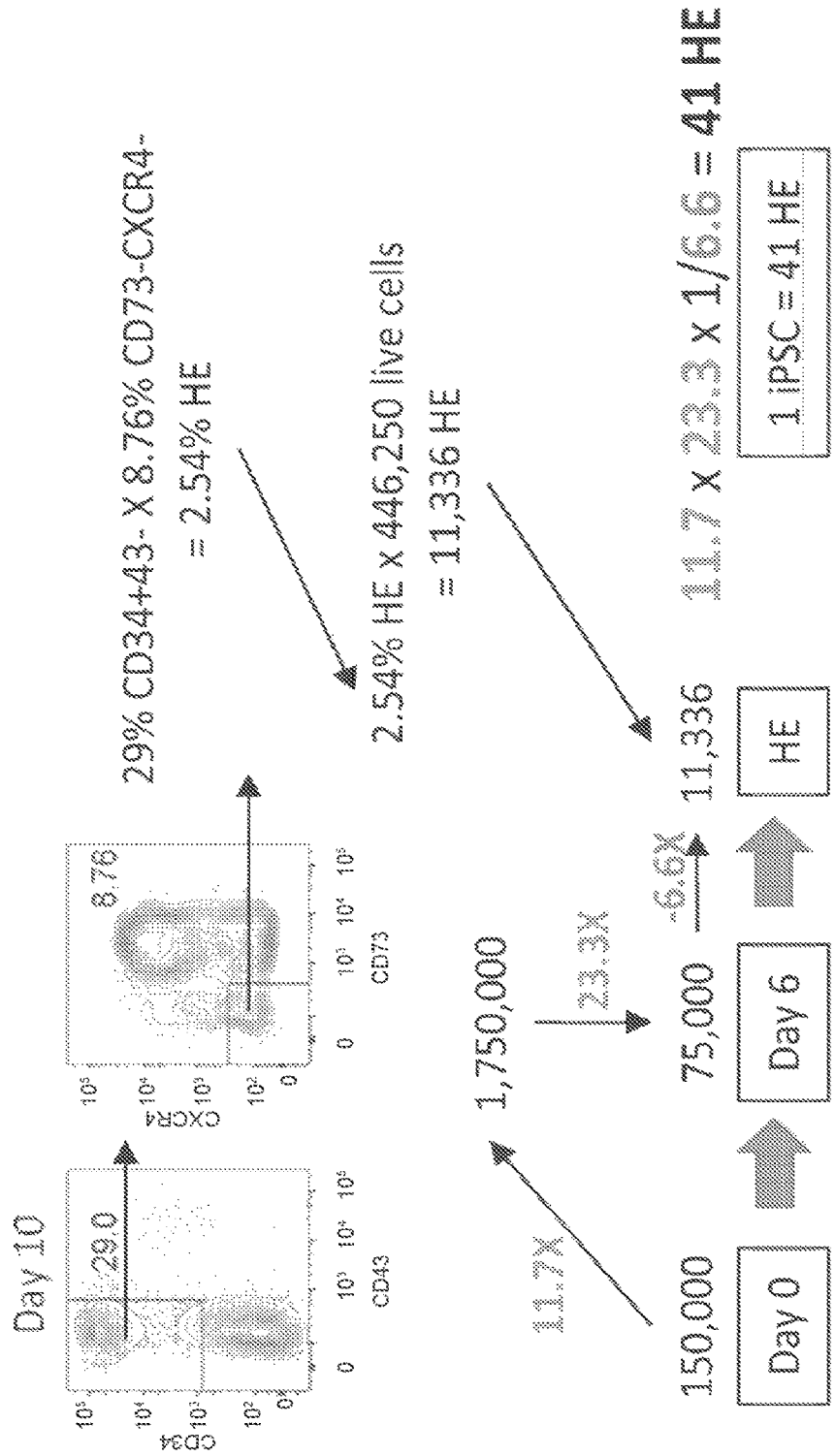
Figure 5A:
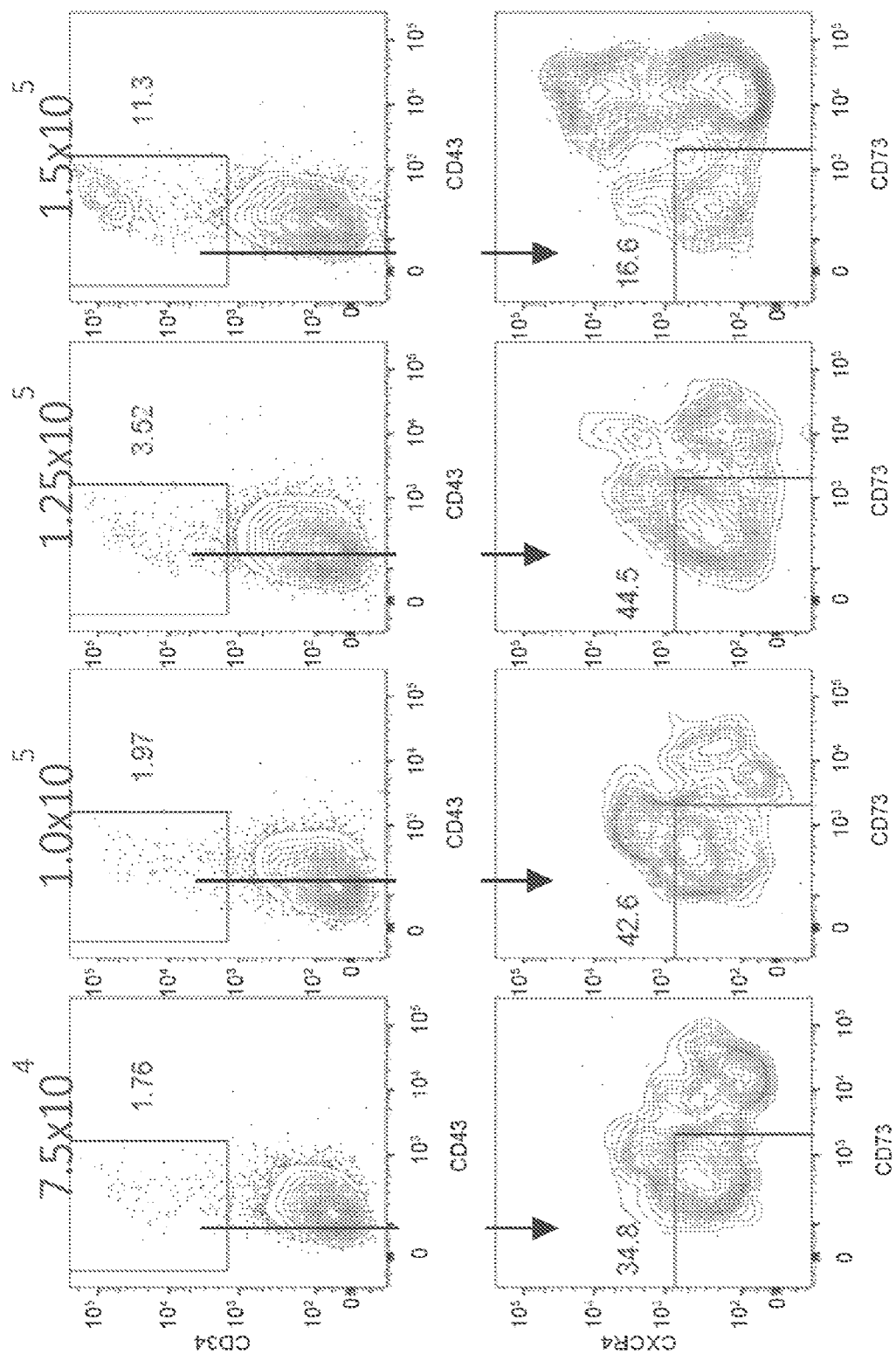
FIG. 5A-D shows modifications to the protocol, including plating density and growth factor titrations, to improve the output of HE at Day 10. A) Plating density at Day 0 influences HE population at Day 10. B) Concentration of BMP4 from Day 2-Day 6 influences HE population at Day 10. C) Concentration of CHIR at Day 3.75 influences HE population at Day 10. D) Plating density at Day 6 influences HE population at Day 10.

Example 3—Optimization of HE Generation by Small Molecule, Cytokine and Plating Density Modulation To optimize the efficient generation of HE from hiPSCs after around 10 days of differentiation several parameters were examined. The optimal plating density of the monolayers at D0 of differentiation was assessed by plating increasing numbers of hiPSCs from $7.5 \times 10^4$/well to $1.5 \times 10^5$/well on Matrigel™-coated 6 well culture dishes and then analyzing the generation of the CD34+HE population at about D10. FIG. 5A demonstrates that increasing the cellular plating density increases the total percentage of CD34+ cells but decreases the CXCR4−CD73− HE subpopulation. Despite this decrease, the highest conversion rate of hiPSCs to HE after 10 days of monolayer differentiation was at the highest plating density tested at $1.5 \times 10^5$/well (FIG. 4C).

Figure 5B:
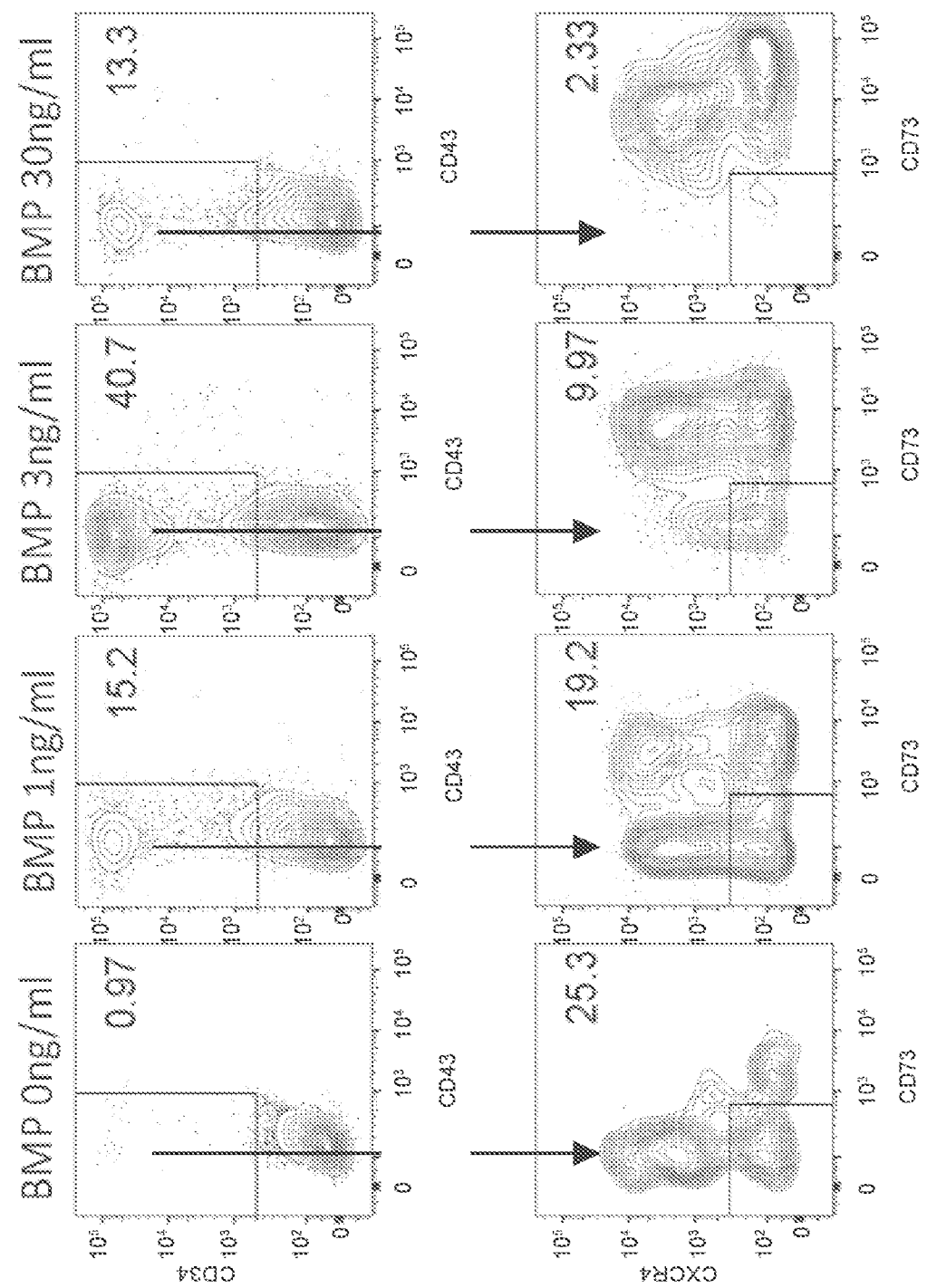

The effect of the concentration of BMP4 modulation during the initial stages of hematopoietic differentiation on the generation of HE was assessed by treating the cultures with increasing concentrations of BMP4 ranging from 0 ng/ml to 30 ng/ml from about D2 to about D6 of differentiation. The generation of HE at D10 was assessed by the detection of the CD34+HE population. FIG. 5B demonstrates that increasing concentrations of BMP4 from D2 to D6 increases the HE population at D10 below a threshold BMP4 concentration indicating an optimal concentration of about 3 ng/mL.

Figure 5C:
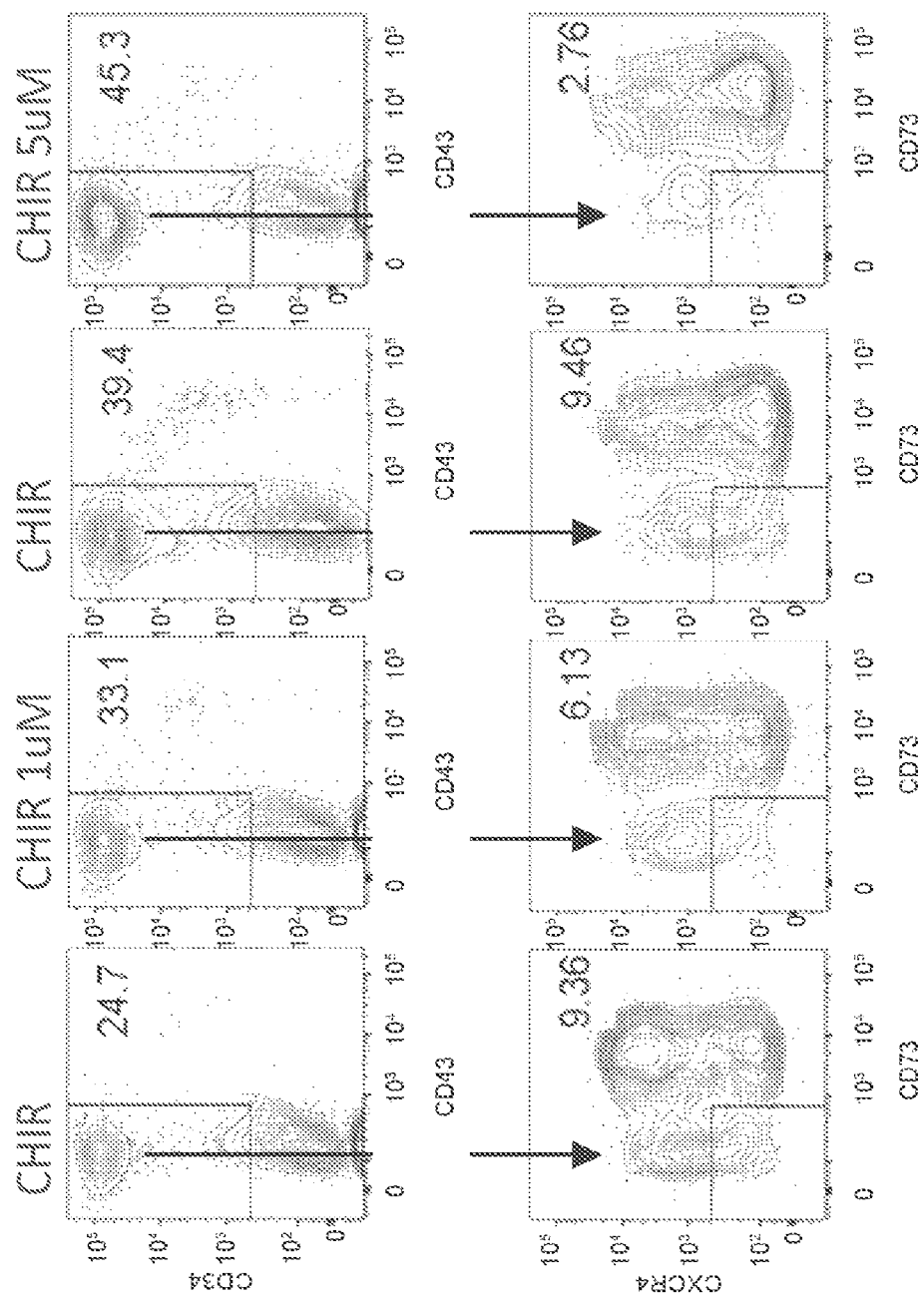

The Wnt pathway activator CHIR99021 is responsible for the induction of the definitive hematopoietic program from hiPSCs. The effect of the modulation of CHIR during the induction phase of the hematopoietic differentiation protocol was assessed by treating the cultures with increasing concentrations of CHIR from about D3.75 to about D6. FIG. 5C demonstrates that while increasing the concentration of CHIR99021 increases the total percentage of CD34+ cells it decreases the percentage of the HE subpopulation with the optimal concentration of CHIR99021 being approximately 1 uM.

Figure 5D:
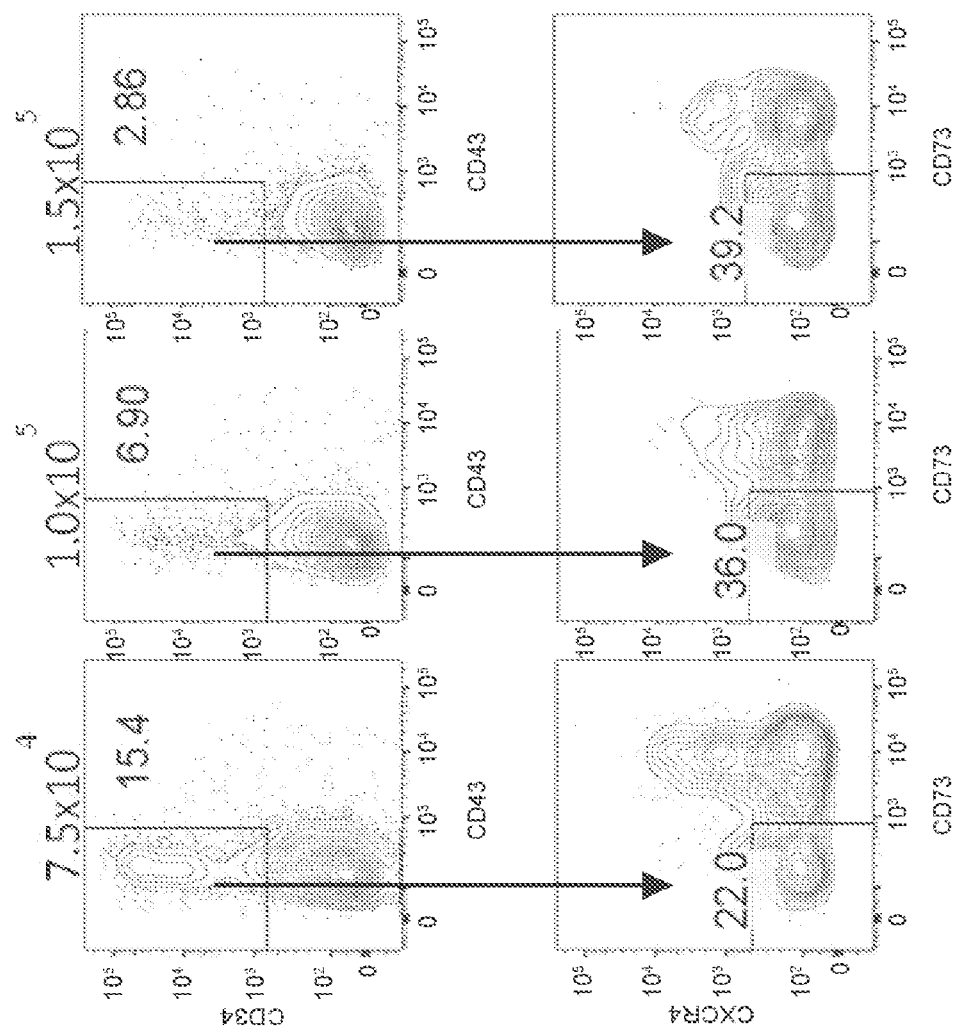

At D6 of the directed differentiation protocol the monolayer cultures dissociated to single cells and were replated as a monolayer for further differentiation to HE. The plating density at D6 was shown to influence the generation of HE as demonstrated in FIG. 5D in which decreasing cellular concentrations from $1.5 \times 10^5$ to $7.4 \times 10^4$ increases the percentage of the HE population.

Figure 6A:
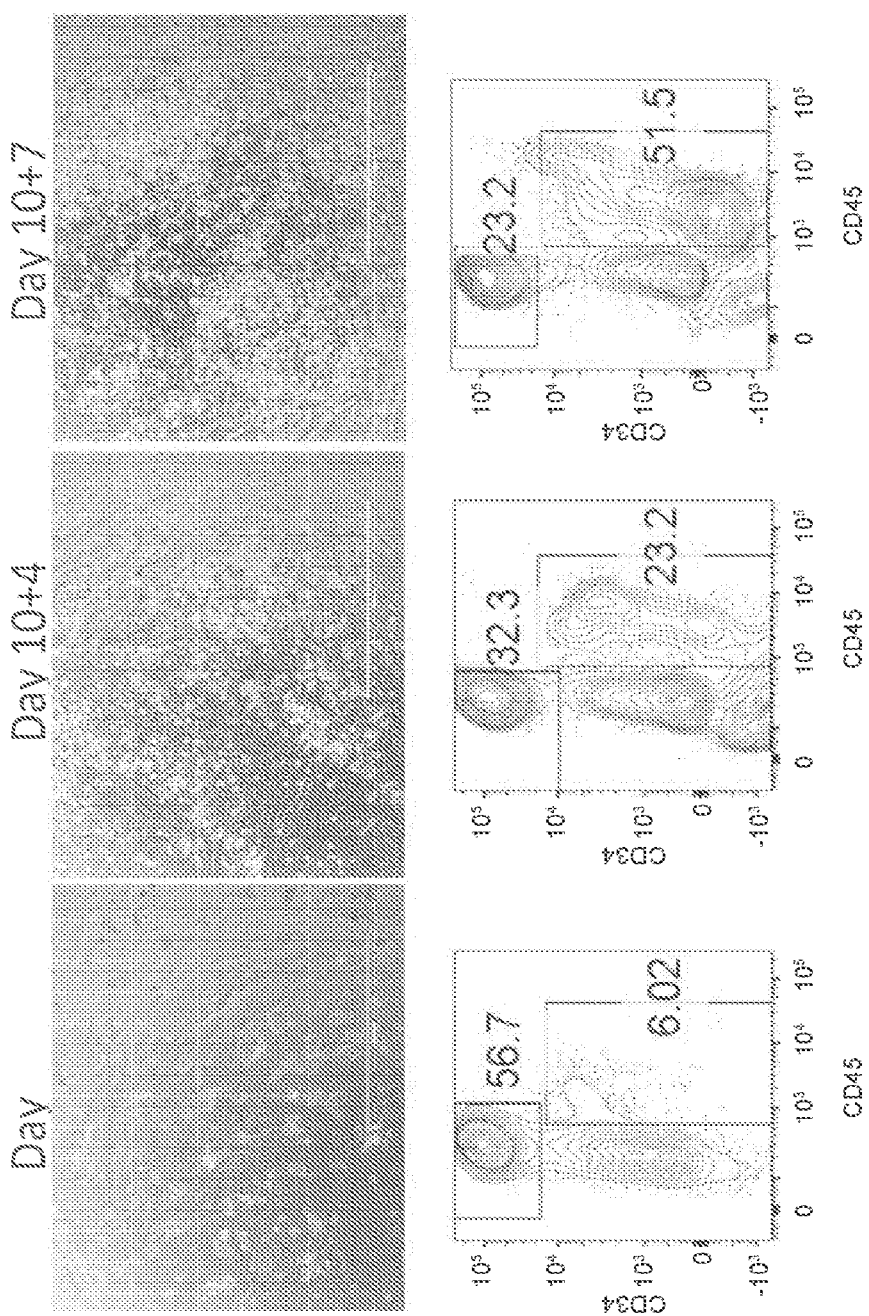
FIG. 6A-B shows the Day 10 HE represents definitive hematopoiesis that is multipotent and dependent upon the Notch signaling pathway. A) Morphological changes over the 7 day MPP assay with flow cytometric profiles of emerging CD45 hematopoietic cells. B) iPSC-derived CD34+ cells generate Notch-dependent definitive CD45+ cells during the iMPP assay.

Example 4—Determination of Hematopoietic Potential of HE by Notch-Dependent Hematopoiesis and MPP Differentiation To demonstrate the hematopoietic potential of the hiPSC-derived definitive population HE, cells were sorted using FACS and assessed for their ability to undergo the endothelial to hematopoietic transition to generate CD45+ hematopoietic progenitors as described in the multipotent progenitor assay (iMPP) in FIG. 1. Approximately 30,000 CD34+HE cells were plated as a monolayer in iMPP-A media and further cultured for 6-8 days. FIG. 6A illustrates the phenotypic alterations in the monolayer cultures with the emergence of round hematopoietic cells and flow cytometric staining identifies the presence of CD45+ over the 6-8 day culture period.

Figure 6B:
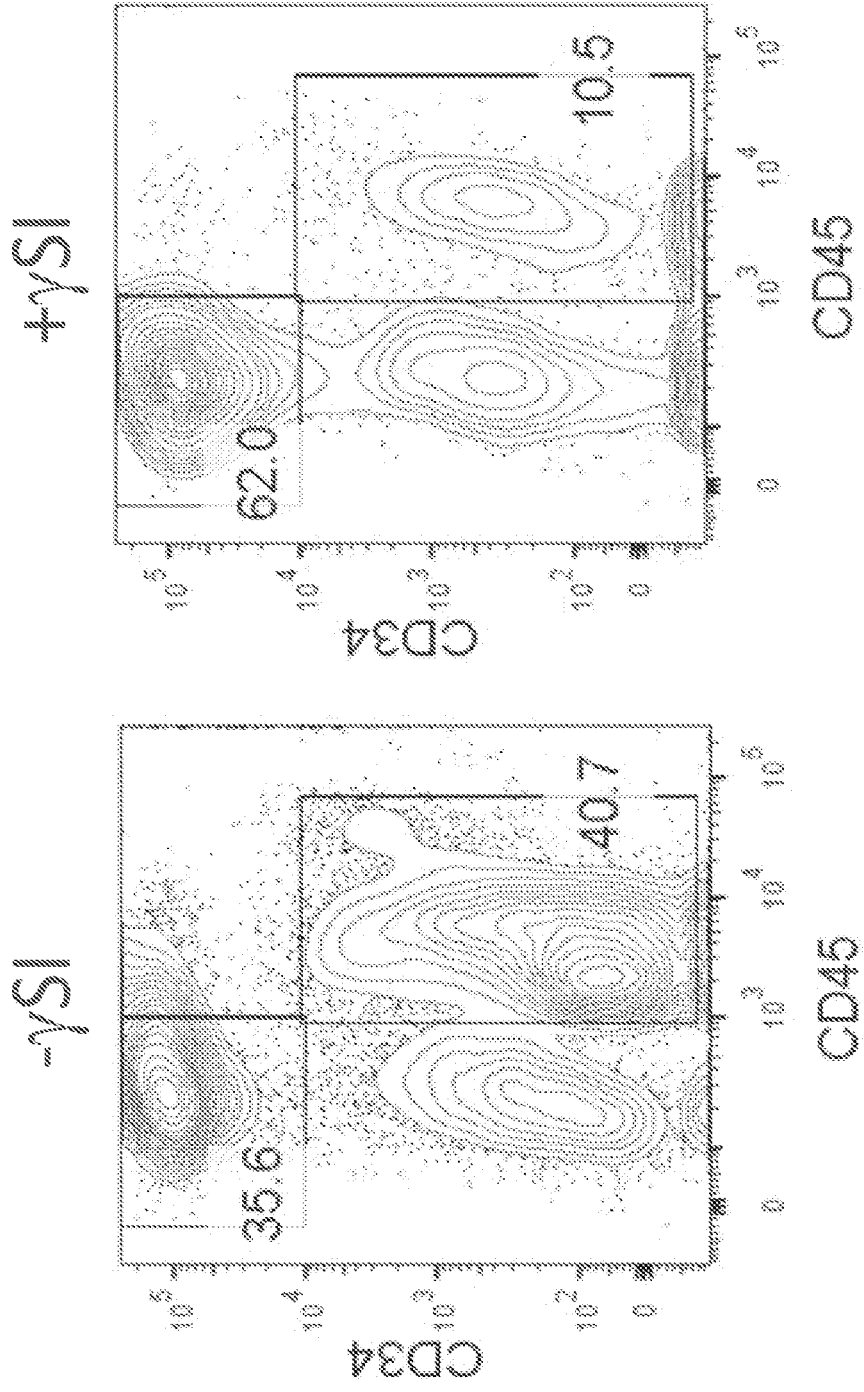

To assess whether the HE population generated at D10 of the directed differentiation protocol represents definitive HE, CD34+HE sorted cells were treated with the Notch pathway inhibitor gamma secretase inhibitor (γSI) for the duration of the 7-9 day iMPP assay. Fresh γSI was added to the iMPP-A culture media every 2 days. After about 8 days the monolayers cultures were assessed by flow cytometry for the emergence of CD45+ hematopoietic cells. In comparison to vehicle control, significantly less CD45+ cells were seen in the γSI-treated cultures demonstrating a dependence upon the Notch signaling pathway and thus the presence of definitive HE (FIG. 6B).

Figure 7A:
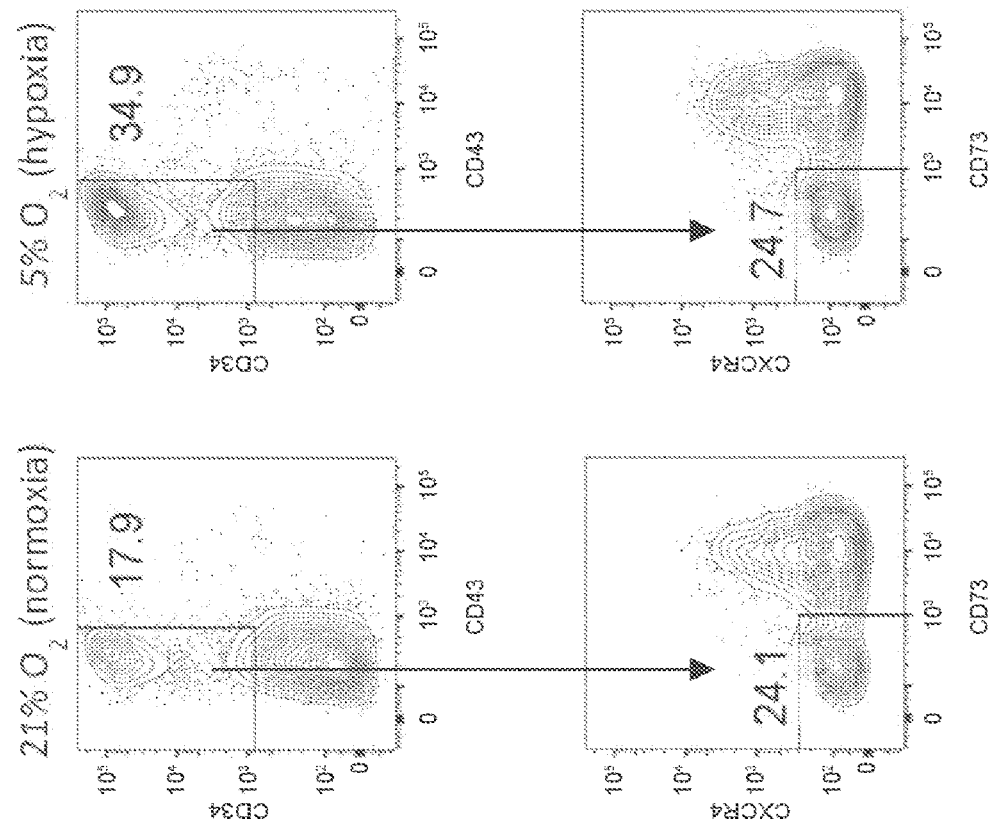
FIG. 7A-B shows the effect of differentiation under hypoxic conditions on the generation of iHE and iMPP hematopoietic progenitors. A) Monolayer differentiation in hypoxia increases both percentage of iCD34 positive cells and iHE cells at Day 10. B) Day 10 iCD34+HE cells generated under hypoxic conditions can be further differentiated in the iMPP assay.
Figure 7B:
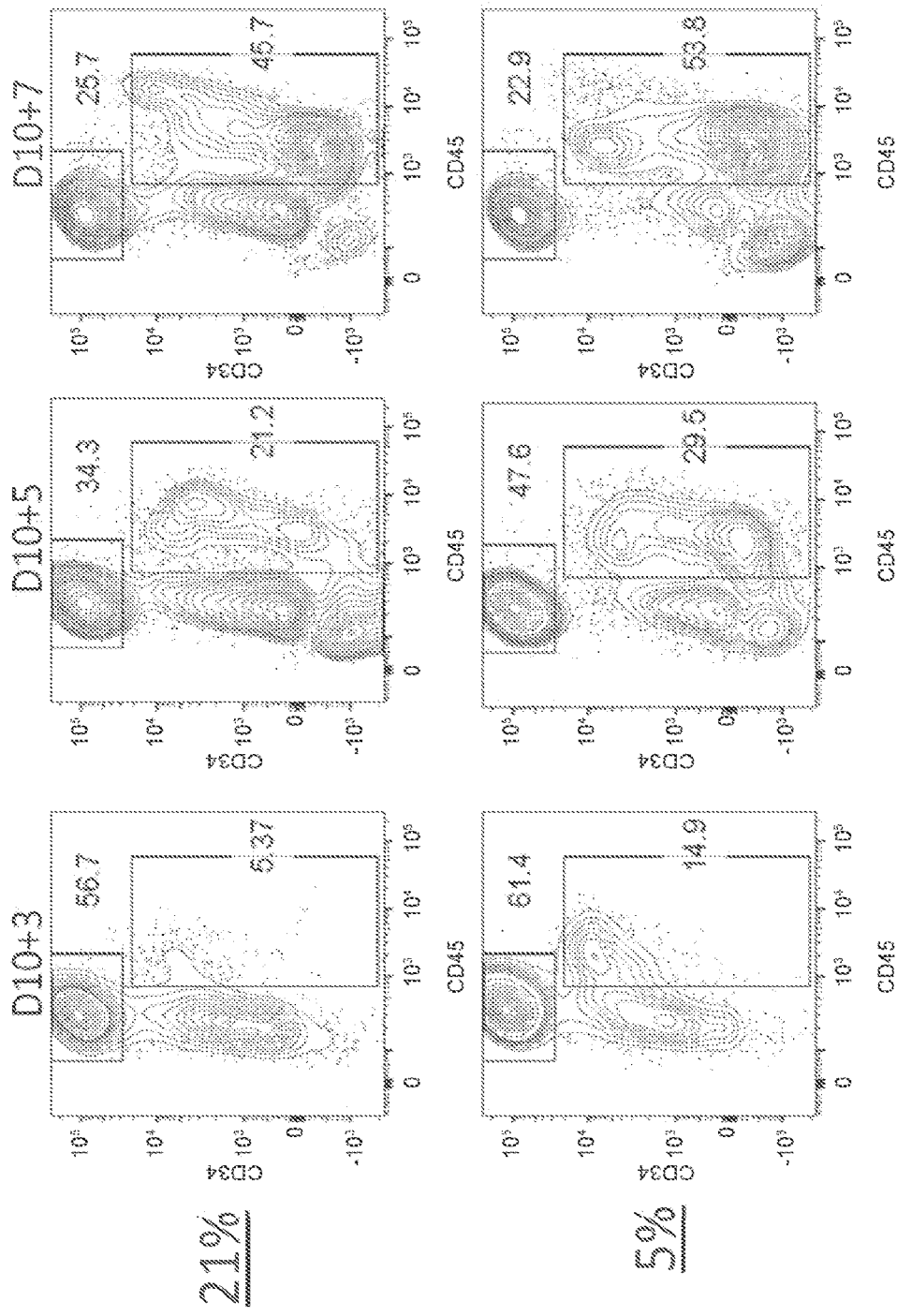

Example 5—Optimization of HE and iMPP Generation Through Manipulation of Oxygen Conditions To assess whether the oxygen environment affects the generation of definitive HE and iMPP hematopoietic progenitors, hiPSCs were differentiated as described in FIG. 1 under either normoxic (21% $O_2$) or hypoxic (5% $O_2$) conditions. At around D10 of differentiation the monolayers were counted and assessed by flow cytometry for the presence of the CD34+HE population. As seen in FIG. 7A differentiation under hypoxic conditions resulted in an increase in the amount of CD34+HE generated. To confirm that the HE generated under hypoxic conditions retained the potential to generate CD45+ hematopoietic progenitors, CD34+ cells were isolated by FACS from normoxic and hypoxic differentiation conditions and assessed by the iMPP assay. HE generated under both conditions have equivalent iMPP potential indicating that hematopoietic differentiation under hypoxic conditions increases the output of definitive HE (FIG. 7B)

Example 6—Cryopreservation of Day 8 Differentiation Cultures and HE

Figure 8A:
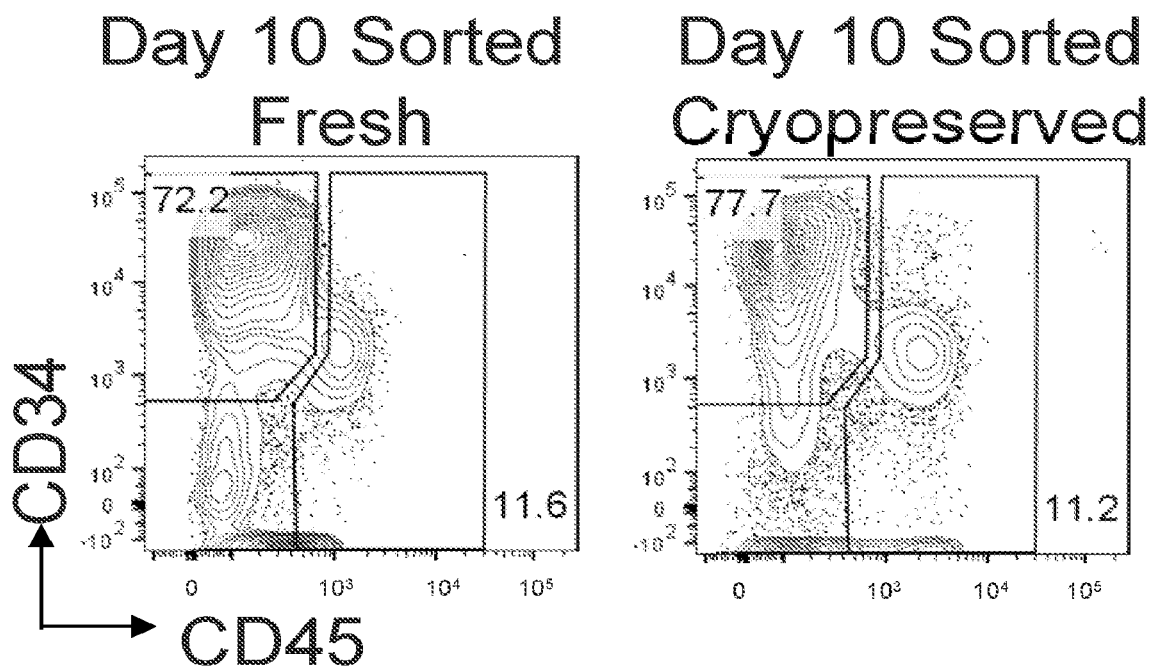

At around D10 of the direct differentiation protocol, entire cultures were dissociated to assess their ability to maintain hematopoietic potential following cryopreservation in day 8 medium supplemented with 10% DMSO. Thawed cells were resuspended and subsequently cultured in iMPP-A media as described in FIG. 1 for 7 days prior to flow analysis. As seen in FIG. 8A, cryopreserved D10 cells survived the freeze/thaw process and had comparable hematopoietic potential to unfrozen controls as seen by the presence of CD45+ cells.

Figure 8B:
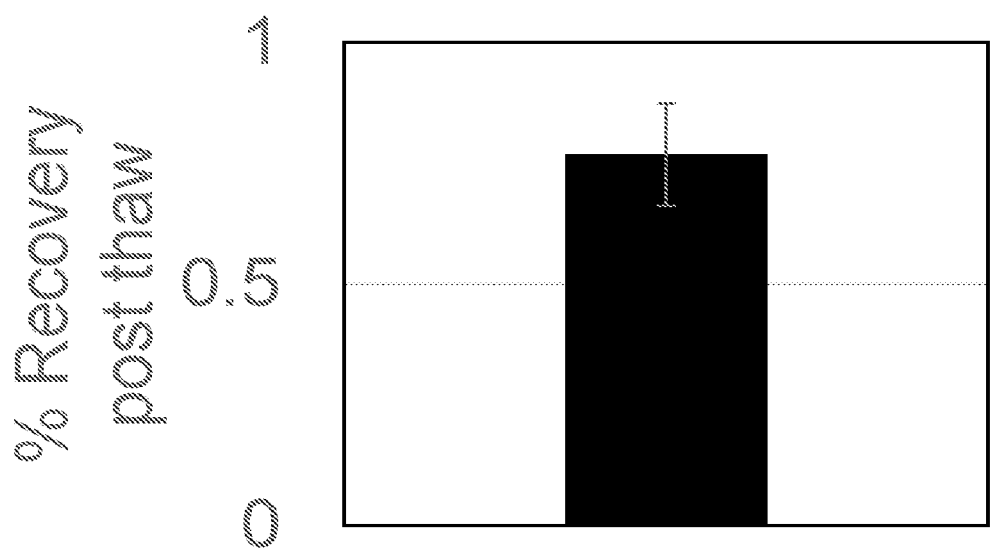

Sorted CD34+ cells were assessed for their ability to maintain hematopoietic potential following cryopreservation. D10 iCD34 generated under hypoxic conditions was isolated and plated directly into the iMPP assay as described in FIG. 1 or cryopreserved in iMPP-A media for 7 days and then thawed and plated in the iMPP assay. As seen in FIG. 8, the Cryopreserved Day 10iCD34 cells can survive and exhibit a similar phenotype to fresh iCD34+ cells when thawed (FIG. 8A). The viability of cryopreserved Day 10 sorted CD34+ cells immediately after thaw is above 70% (FIG. 8B). It is also shown that the cyropreserved Day 10 sorted iCD34+ cells can survive and generate CD45+ hematopoietic cells during iMPP assay (FIG. 8C), and are capable of generating iT and iNK lymphoid progenitors (FIG. 8D). This cryopreservation process is applicable to intermediate cells between Day 6-12, or other downstream cells during the guided differentiation, which cells include iHSC, iMPP, pre-iproT, pre-iproNK, ipro-T, ipro-NK, T cells, NK cells, NKT cells and B cells.

Example 7—Recovery of Day 8 Differentiation Cultures after Overnight Shipment

Figure 9A:
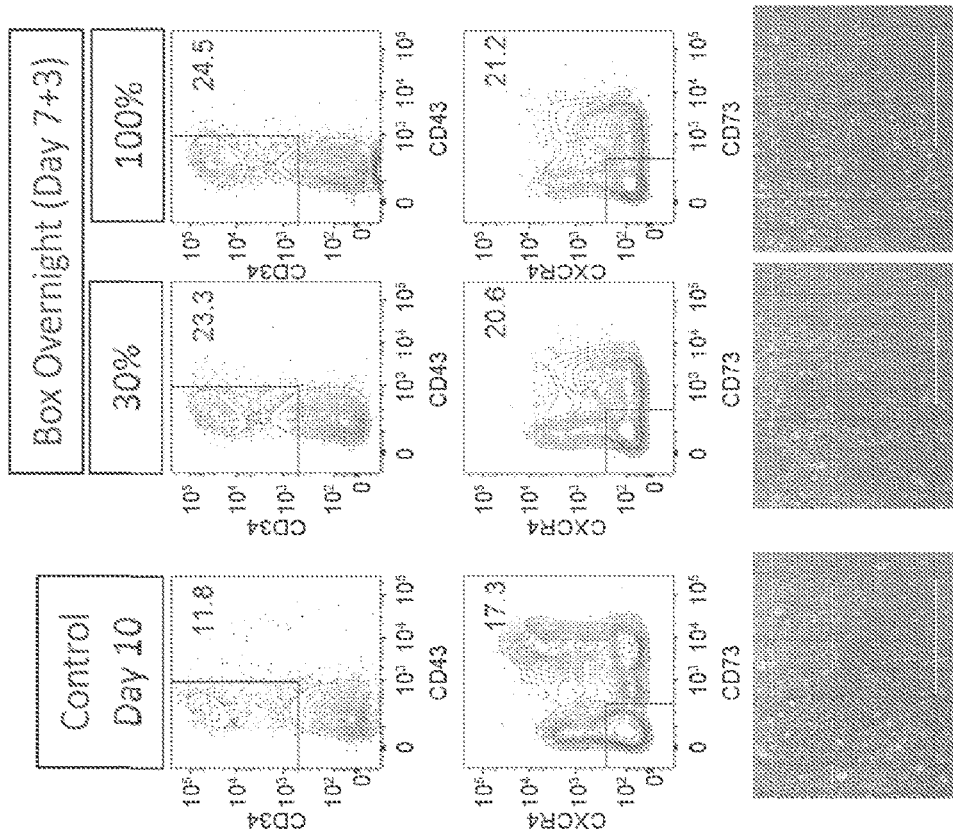
FIG. 9A-B shows that Day 10 differentiation cultures can be shipped overnight in ambient temperature without loss of HE potential. A) Cultures at day 7 were either maintained in the incubator (Control) or processed for overnight shipment followed by reintroduction into an incubator for the following two additional days. The cultures, both at day 10 were then analyzed for the presence of iCD34 and iHE cells. In the overnight shipped cultures, the T-flasks either contained 30% culture medium with 70% base or 100% culture medium. B) Calculations for number of cells.
Figure 9B:
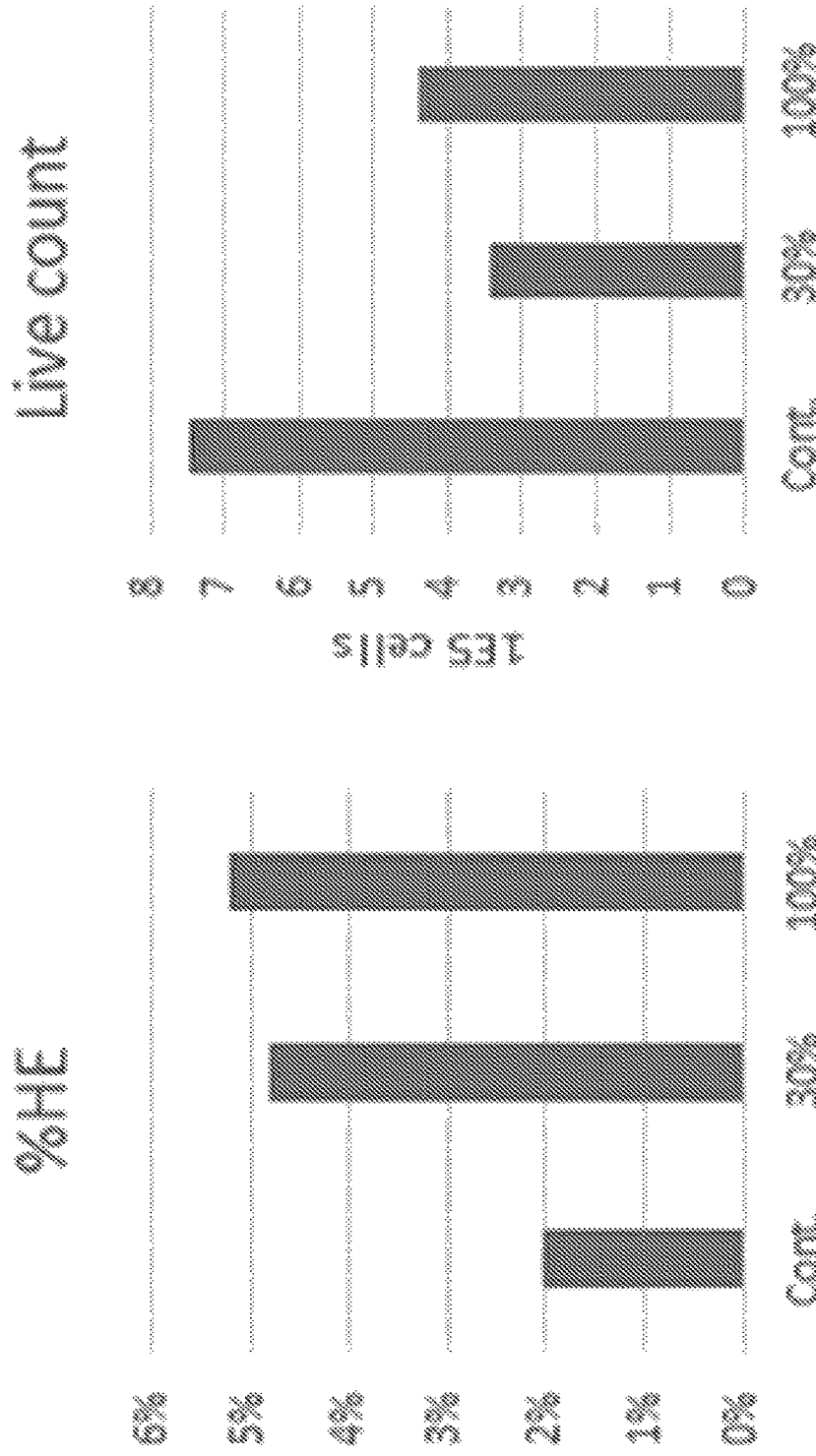

Day 6 differentiation cultures from 6 well plates were passaged into T25 cultures flasks at a seeding density of 200,000 cells/flask and then filled up completely with medium at Day 8 and kept in a Styrofoam box overnight to assess the feasibility of shipping fresh cells directly without the need for cryopreservation. Cold packs initially kept in a 37° C. water bath were also added to the Styrofoam box in order to preserve a 37° C. temperature for as long as possible. Two medium compositions were tested alongside a control flask kept in a 37° C. incubator: a flask with 30% concentration of the cytokines and morphogens utilized in the Day 8 step and a flask with 100% concentration. On Day 9, the flasks were removed from the box, medium replaced with 10 mL of Day 8 medium, along with new caps placed on the flasks and allowed to recover before processing for flow analysis on Day 10 for the presence of the CD34+HE population. As seen in FIG. 9 the overall output of HE was comparable between all conditions demonstrating the feasibility of fresh overnight shipment of Day 8 cultures as an effective means for delivering HE cells. This fresh shipping and handling process does not impact the differentiation capacity of other intermediate cells obtained during the guided differentiation, which cells include iHSC, iMPP, pre-iproT, pre-iproNK, ipro-T, and ipro-NK. The fresh shipping is also applicable to iPSC derived T cells, NK cells, NKT cells or B cells.

Figure 10C:
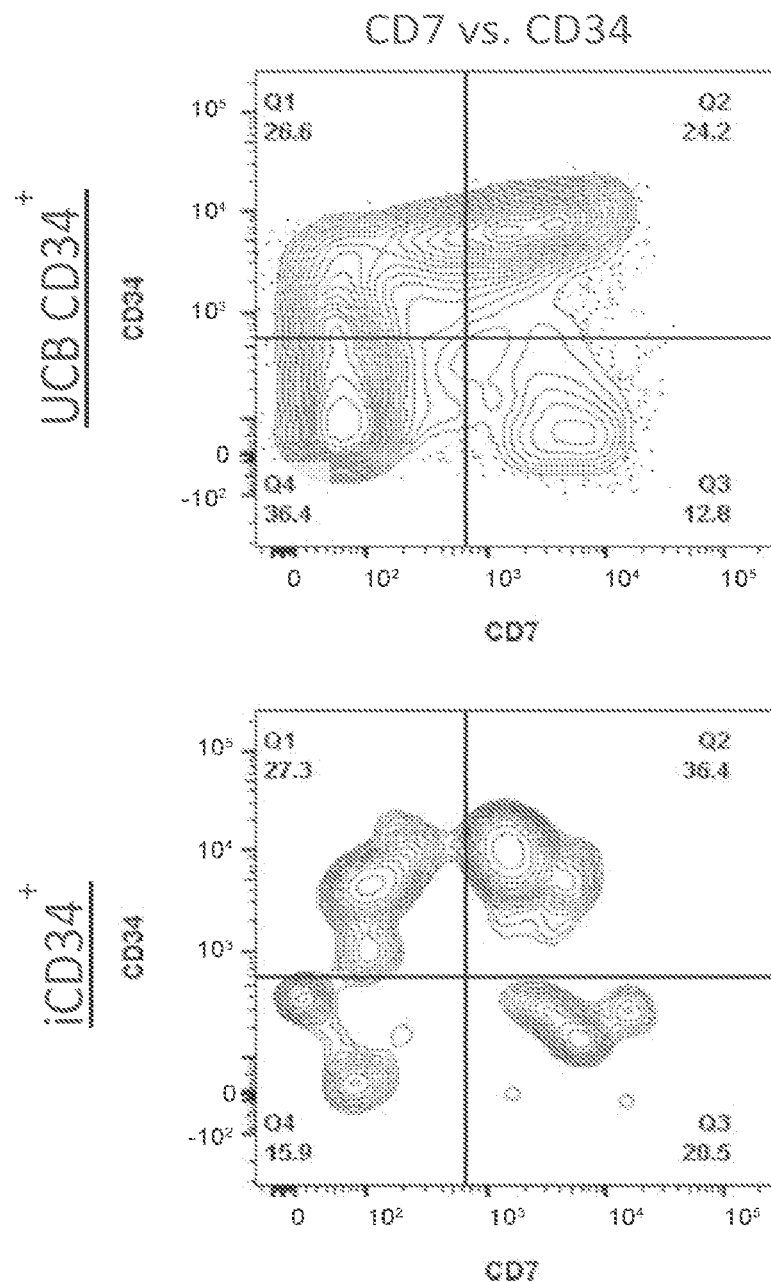
Figure 15:
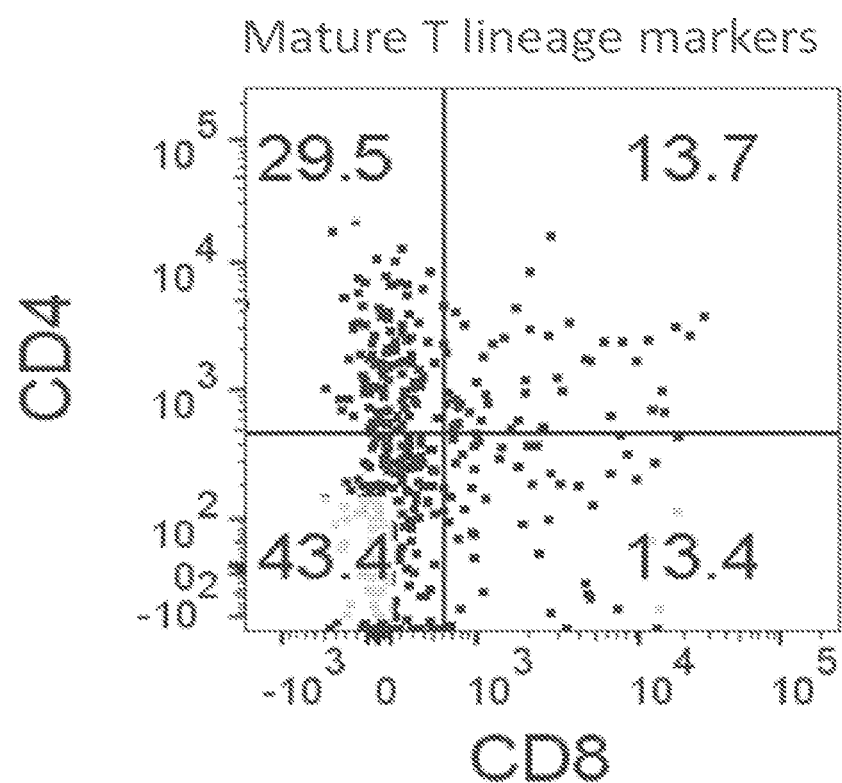
FIG. 15 shows mature CD4+ and CD8+ T cell subsets derived from hiPSCs 30 days post HE isolation using a CD45+CD56− gating strategy.

Example 8—Continuation of Differentiation of HE Towards Mature T and NK Lymphoid Lineages Using DLL4-Expressing Stromal Cells Sorted CD34+HE cells were further differentiated towards the T and NK lymphoid lineages. Specific to T cells, upon sorting, the HE cells were transferred to low attachment tissue culture plates in iTC-A2 serum-free differentiation media comprising a ROCK inhibitor, SCF, Flt3L, TPO, and IL7 (FIG. 2). After 5 days, the cells were transferred to adherent cultures containing DLL4-expressing stromal cells in iTC-B2 differentiation media containing SCF, Flt3L and IL7 to complete T cell differentiation. After approximately 10 days of culturing (post HE isolation) the cell culture was assessed for the generation of T cell progenitors by the co-expression of the cell surface markers CD34 and CD7. After further differentiation for approximately 15-20 days these CD34+CD7+ T cell progenitors gave rise to distinct populations of mature T cells as seen by the expression of CD4 and CD8. FIG. 10 depicts the in vitro differentiation capability of the Day 10 HE population to give rise to early T cell progenitors (FIG. 10A) and mature T cell (FIG. 10B) subsets by analysis of a CD45+CD56− population generated in the co-cultures. FIG. 15 depicts the in vitro differentiation capability of the Day 10 HE population to give rise to mature T cell subsets by analysis of a CD45+CD56− population generated in the co-cultures after approximately 30 days of culture (post HE isolation).

Figure 3:
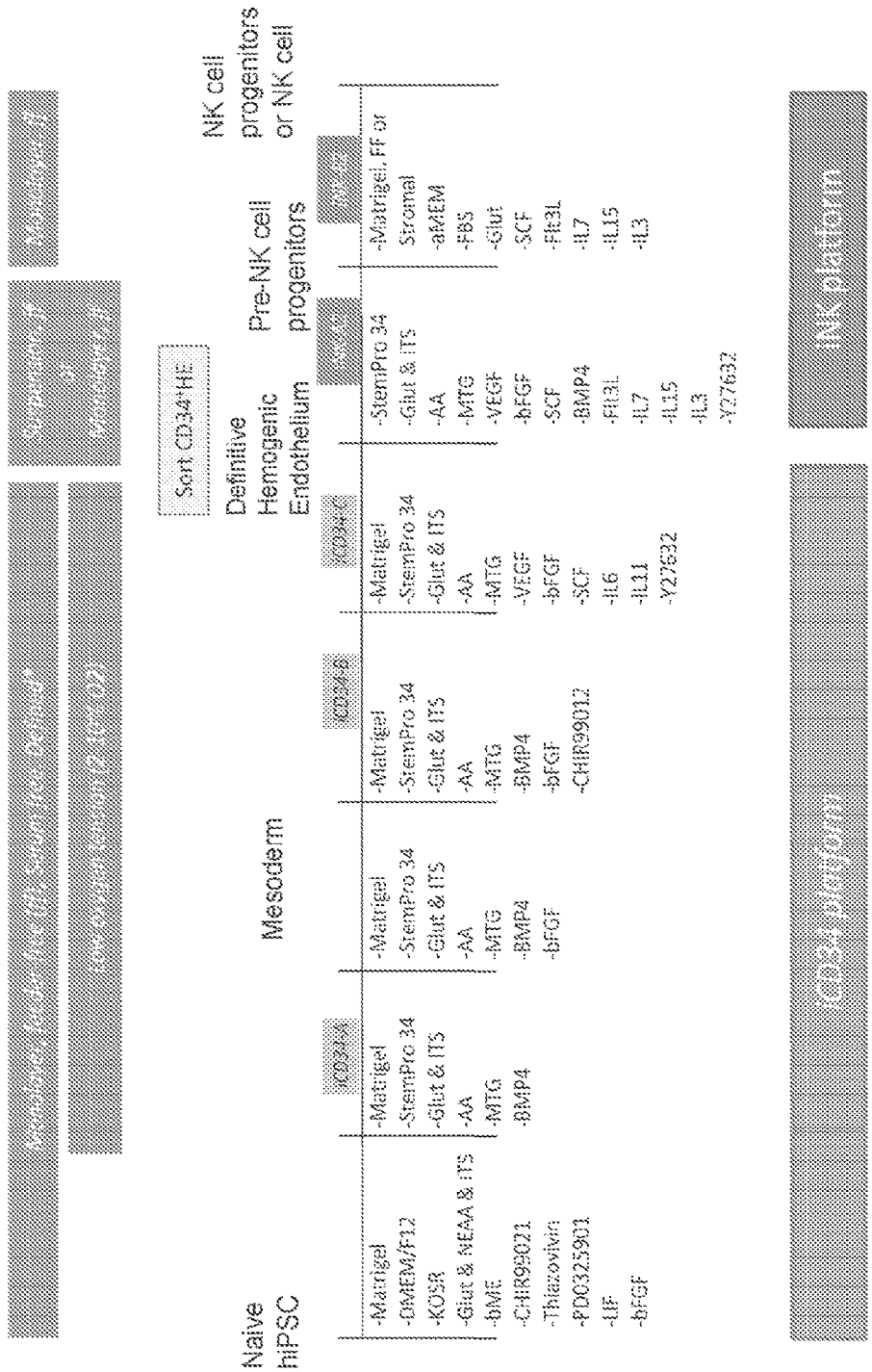
FIG. 3 shows a schematic diagram for a multi-staged culture process for the hematopoietic differentiation of induced pluripotent stem cells to NK cell progenitors (ipro-NK) and fully differentiated NK (iNK) cells. Note that culture can be converted to fully-defined with the substitution of Matrigel™ for Vitronectin.
Figure 11B:
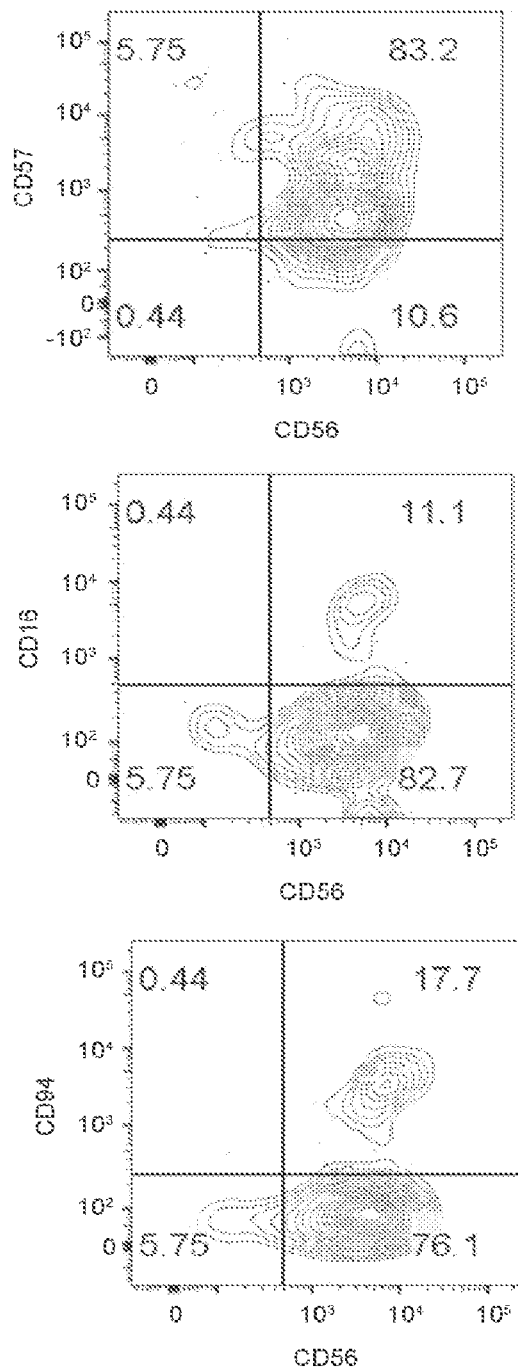
Figure 11C:
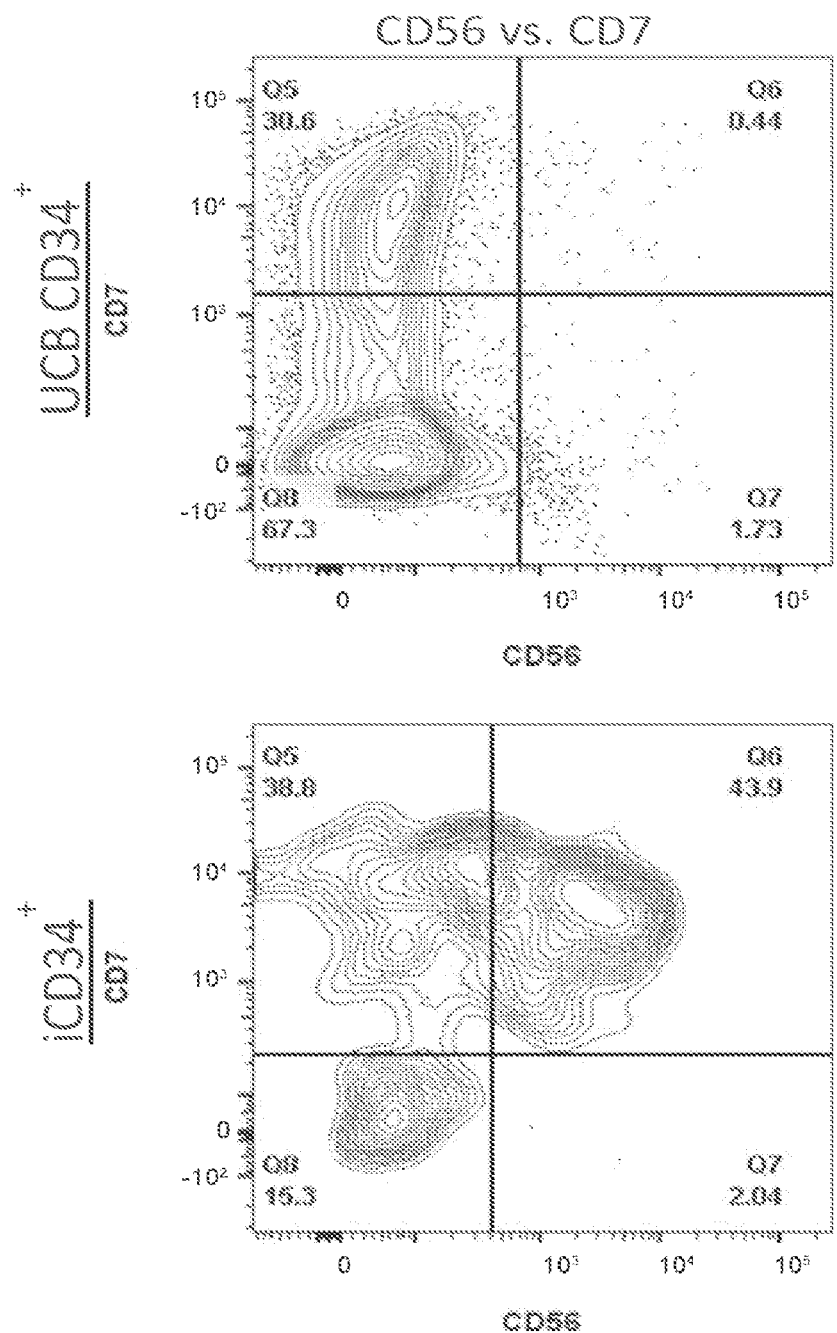

Specific to NK cells, upon sorting, the HE cells were cultured on low attachment tissue culture plates in iNK-A2 serum-free differentiation media containing SCF, TPO, Flt3L, IL3, IL15, and IL7 (FIG. 3). After 5 days, the cells were transferred to adherent cultures containing DLL4-expressing stromal cells in iNK-B2 differentiation media containing SCF, IL3, IL15, Flt3L and IL7 to complete NK cell differentiation. After approximately 10-15 days of culturing (post HE isolation) the cell culture was assessed for the generation of NK cell progenitors followed by mature NK subsets following an additional 10-15 days of culturing. CD56 and CD161 (NKR-P1A) are the first cell surface markers to be expressed during early NK cell development followed by the expression of CD16, KIR, CD8 and NKG2D (CD314) on later mature NK cell subsets. FIG. 11 depicts the in vitro differentiation capability of the Day 10 HE population to give rise to early NK cell progenitors and mature NK cell subsets by analysis of a CD45+ population generated in the co-cultures.

Figure 16:
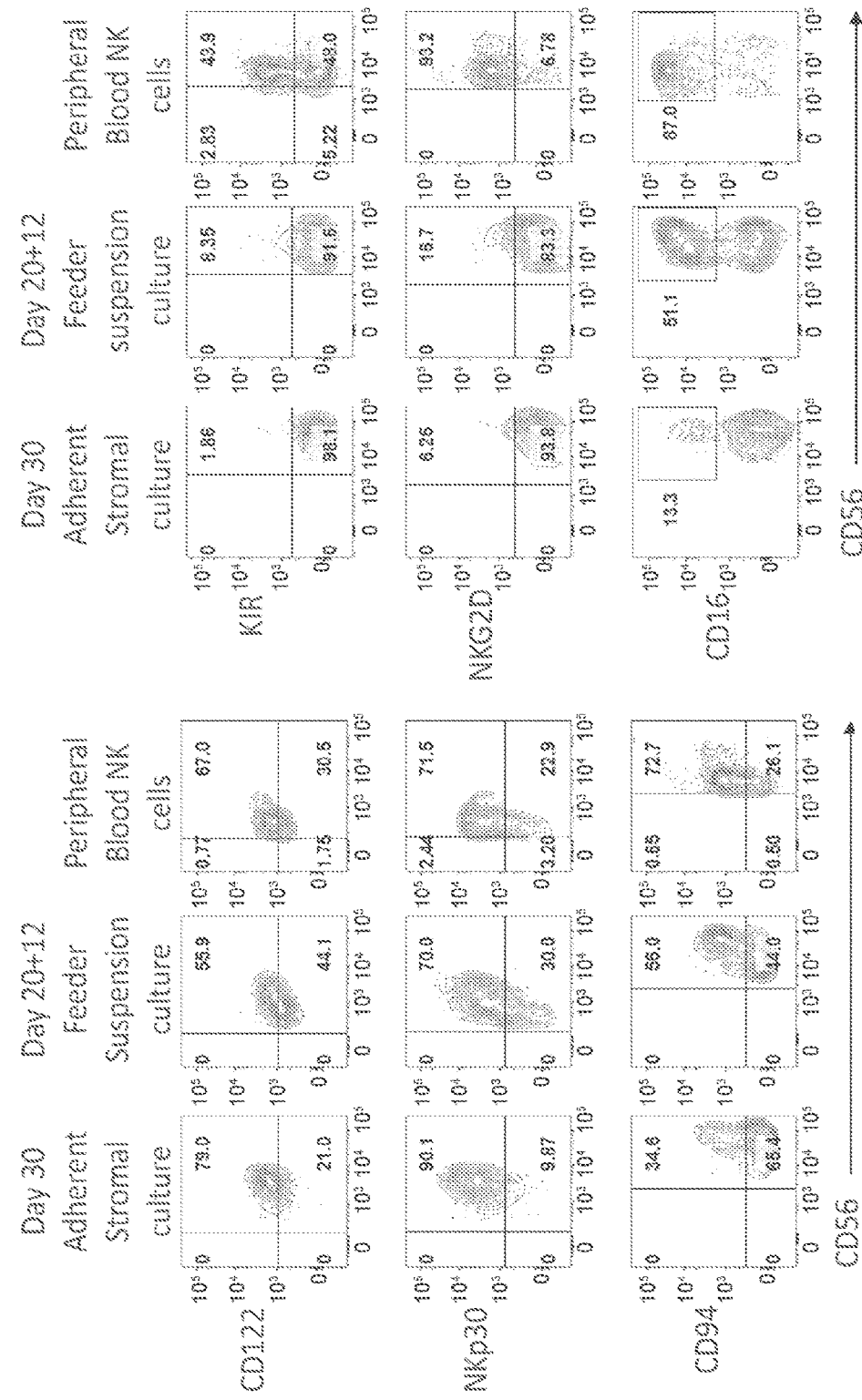
FIG. 16 shows feeder-based suspension culture supports the maturation of iCD34-derived NK cells.

An alternative method to enhance the maturation of NK cell progenitors is co-culture with feeder cells in a suspension culture. Day 20 iNK cells were transferred from DLL4-stromal cell culture to feeder-based suspension cultures in iNK-B2 media containing SCF, IL15, Flt3L and IL7 for an additional 12 days in culture. FIG. 16 depicts the in vitro differentiation capability of the Day 10 HE population to give rise to mature NK cell subsets using feeder suspension culture by analysis of a CD45+ population generated in the stromal and feeder-based co-cultures compared to peripheral blood-derived NK cells. hiPSC-derived CD34+ cells were differentiated towards the NK cell lineage for 20 days and then placed in suspension culture for further maturation. Mature NK lineage markers identify the presence of mature NK cells as defined by CD56, CD122, NKp30, CD94, CD16, NKG2D and KIR.

Figure 12A:
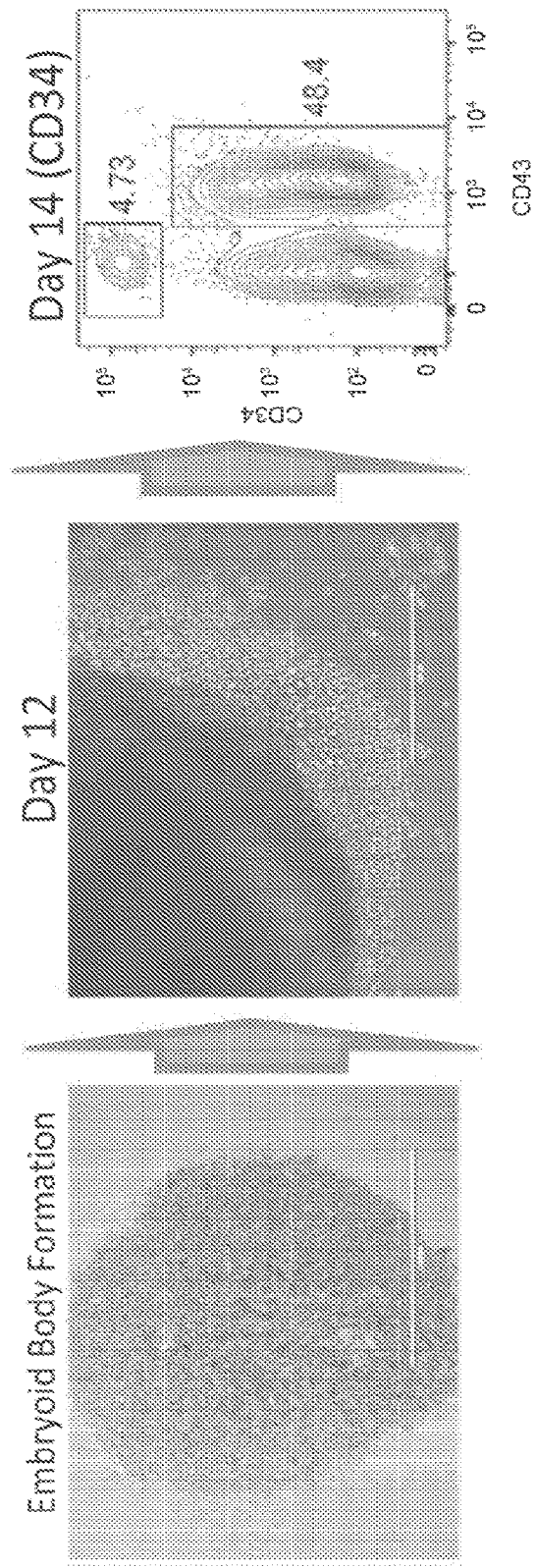
FIG. 12A-C shows monolayer hiPSC hematopoietic differentiation platform allows for a scalable expansion strategy that is not seen during EB formation. A. hiPSCs were aggregated to form Embryoid bodies and differentiated for 14 days prior to analysis for CD34 and 43 expression. B. hiPSCs were seeded as monolayer and differentiated for 8 days prior to analysis for CD34, CD43, CXCR4 and CD73. C. CD34 positive cells were counted and plotted over time for both monolayer and EB mediated hematopoietic differentiation.
Figure 12B:
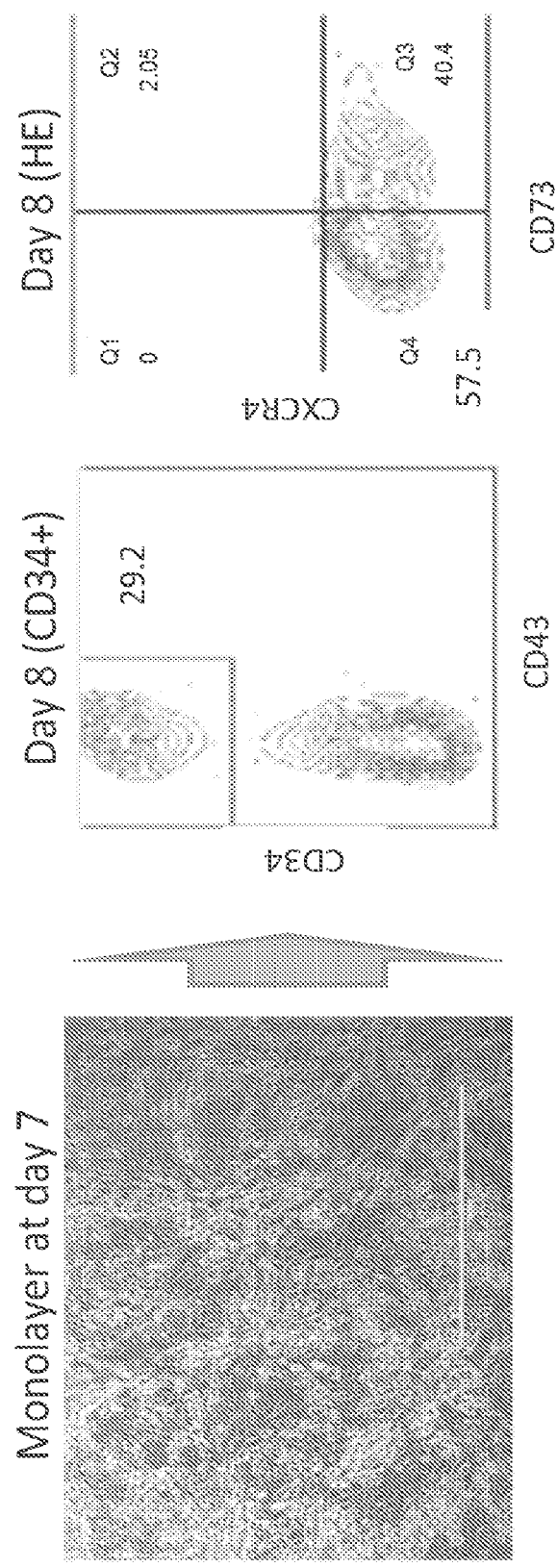
Figure 12C:
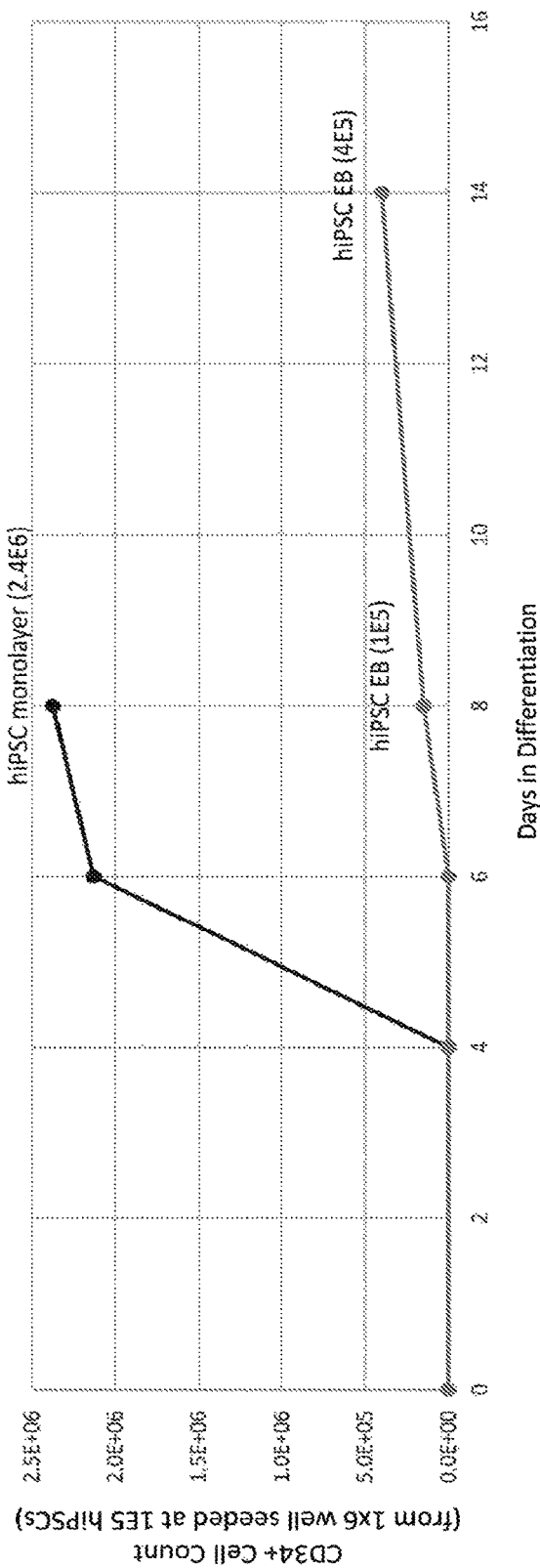
Figure 13:
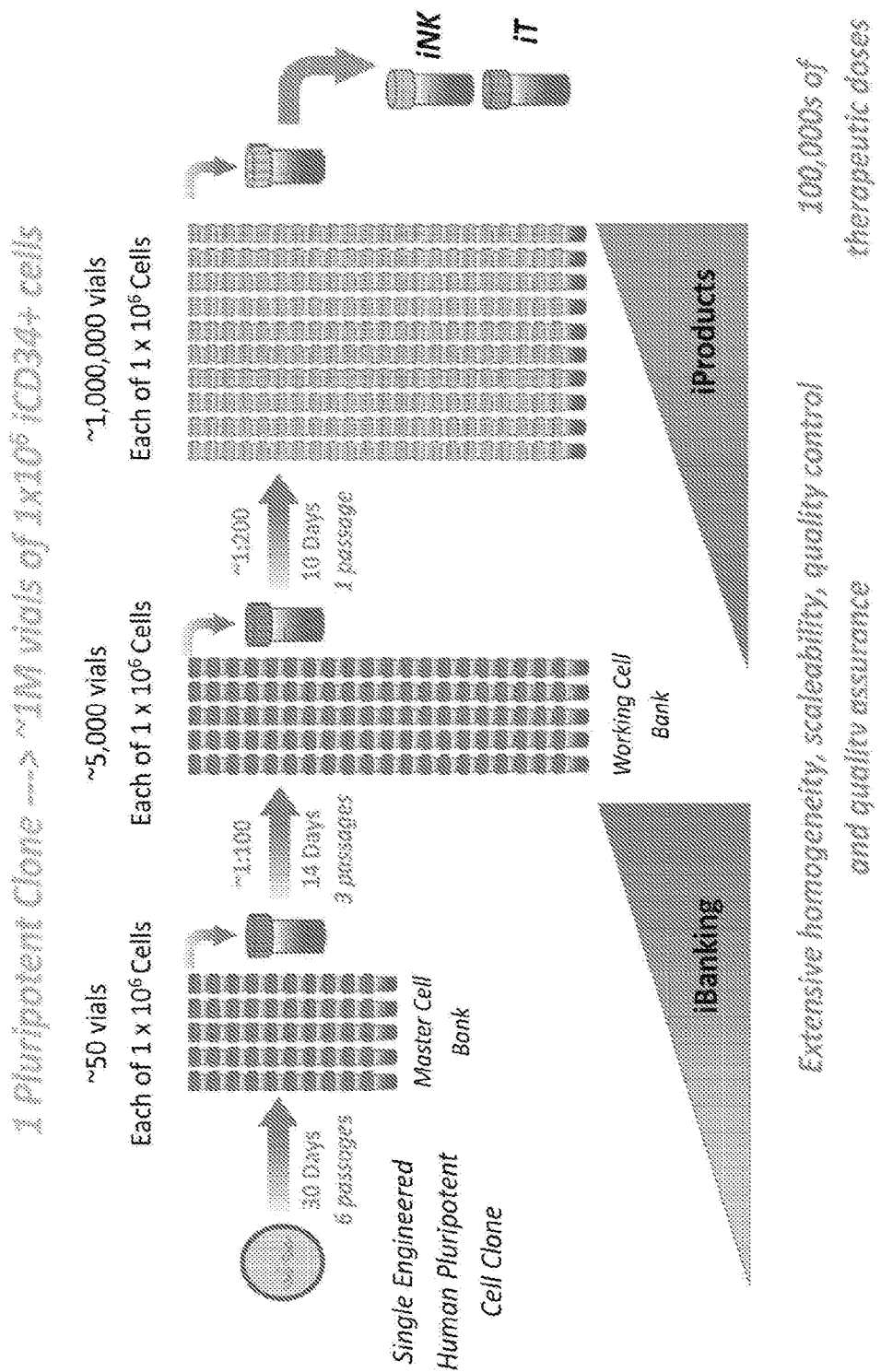
FIG. 13 shows a schematic diagram for the scalable expansion strategy of the monolayer hiPSC hematopoietic differentiation platform for the production of off-the-shelf iNK and iT cells. Calculations are based on a snapshot of representative cultures and not optimized cultures.

Example 9—Monolayer hiPSC Hematopoietic Differentiation Platform Allows for a Highly Scalable Expansion Strategy hiPSCs seeded as monolayer and differentiated towards hematopoietic cells in defined, serum-free and feeder-free culture as described in FIGS. 1-3 were compared to hiPSCs set up in aggregates to form embryoid bodies for initiating hematopoietic differentiation (Kennedy et al., Cell Reports 2012:1722-1735). Both culture sets used 100,000 hiPSCs as the initial starting number. During the hematopoietic differentiation process, cell counts and phenotype assessment were conducted routinely to demonstrate the expansion potential of each system. As shown by FIG. 12, by Day 6 of differentiation, a significant number of CD34 positive cells were detected in the monolayer culture—over 2 million CD34+ cells, versus in the EB format where no CD34 positive cells were detected. On Day 8 of differentiation, the monolayer format had generated approximately 2.4 million cells while in the EB format only approximately 100,000 CD34 positive cells were detected, despite roughly the same number of iPSCs as the starting material, representing a difference of approximately 24-fold. In addition, as the time of assessment, while the monolayer format produced only CD34+CD43− cells, suggestive of definitive hematopoiesis, the EB format produced majority CD34+CD43+ cells suggestive of primitive hematopoiesis (Kennedy et al., 2012). FIG. 13 further illustrates the scalable expansion of the monolayer hiPSC hematopoietic differentiation platform as disclosed herein for the production of off-the-shelf iNK and iT cells. The pluripotent cell clonal expansion platform provided herein further ensures off-the-shelf scalability, for example, from a single pluripotent cell clone to about one million vials of therapeutic doses, each having no less than 106NK or T cells that are therapeutically functional. The clonal expansion as disclosed further provides extensive homogeneity and therefore ensures product consistency, quality control and quality assurance. In some embodiments, the single pluripotent cell clone contains desired genetic imprint(s), which is either obtained through genetic engineering during or after reprogramming, or retained from donor-specific source cells from which the pluripotent cell is originally derived.

Figure 14:
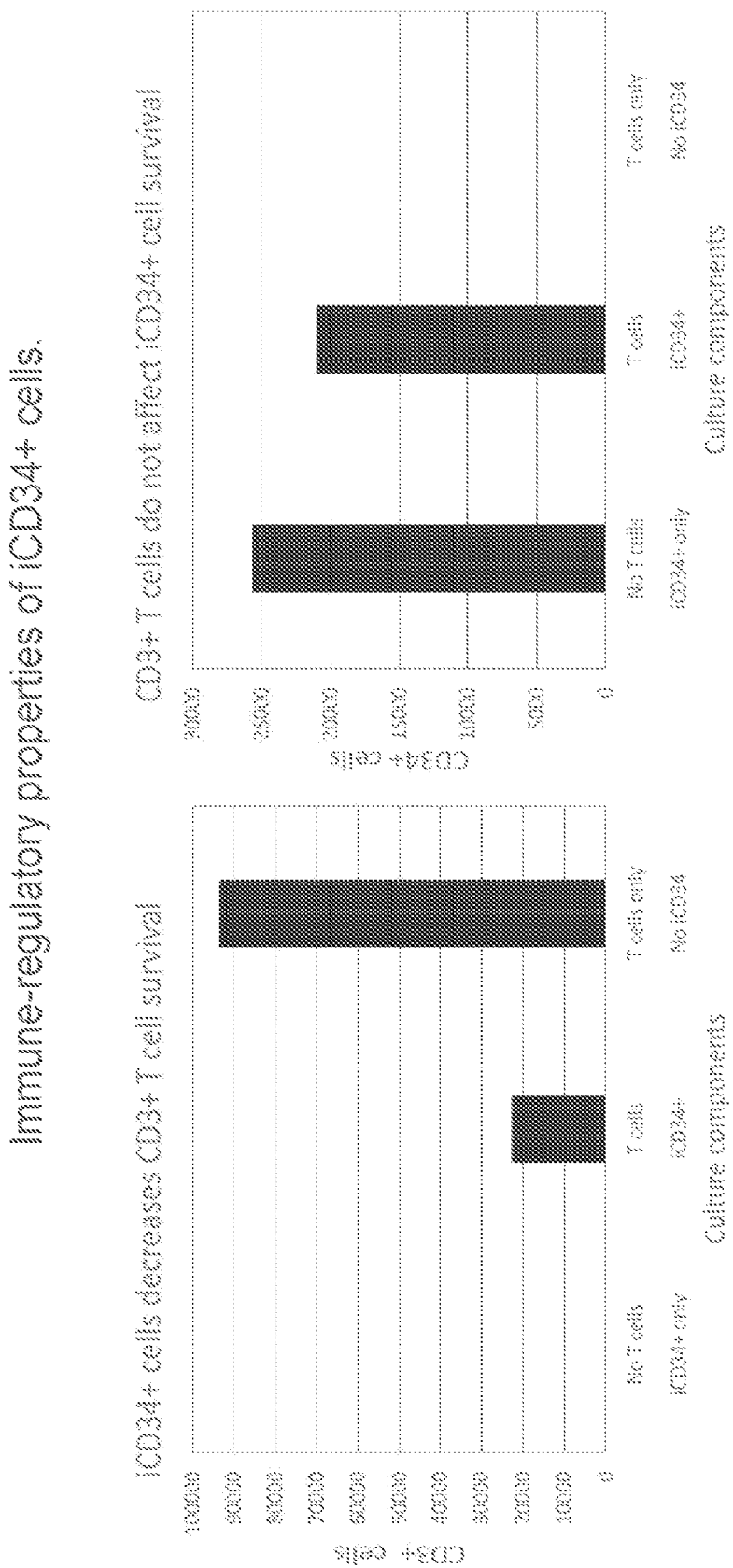
FIG. 14 shows hiPSC-derived CD34 positive cells have immune-regulatory properties by the suppression of CD3+ T cell survival.

Example 10—Immune-Regulatory Properties of iCD34+ Cells in Suppressing the Expansion of Activated T Cells To determine the immune-regulatory capacity of the hiPSC-derived CD34 positive cells (iCD34; CD34+CD43−), day 10 CD34 sorted cells were co-cultured with activated peripheral blood-derived CD3-expressing T cells in iMPP-A media at a 1:1 ratio. After 5 days incubation at 37° C., the co-cultures were mixed with counting beads and assayed via flow cytometry to determine the absolute number of T cells in each sample. FIG. 14 depicts the immune-regulatory potential of the hiPSC-derived CD34+ cells as seen by comparing the co-culture to the culture containing CD3+ T cells alone. The CD3+ T cells co-cultured with hiPSC-derived CD34+ cells had decreased cellular survival while the total number of CD34+ cells in the culture was unaffected (FIG. 14).

Figure 17:
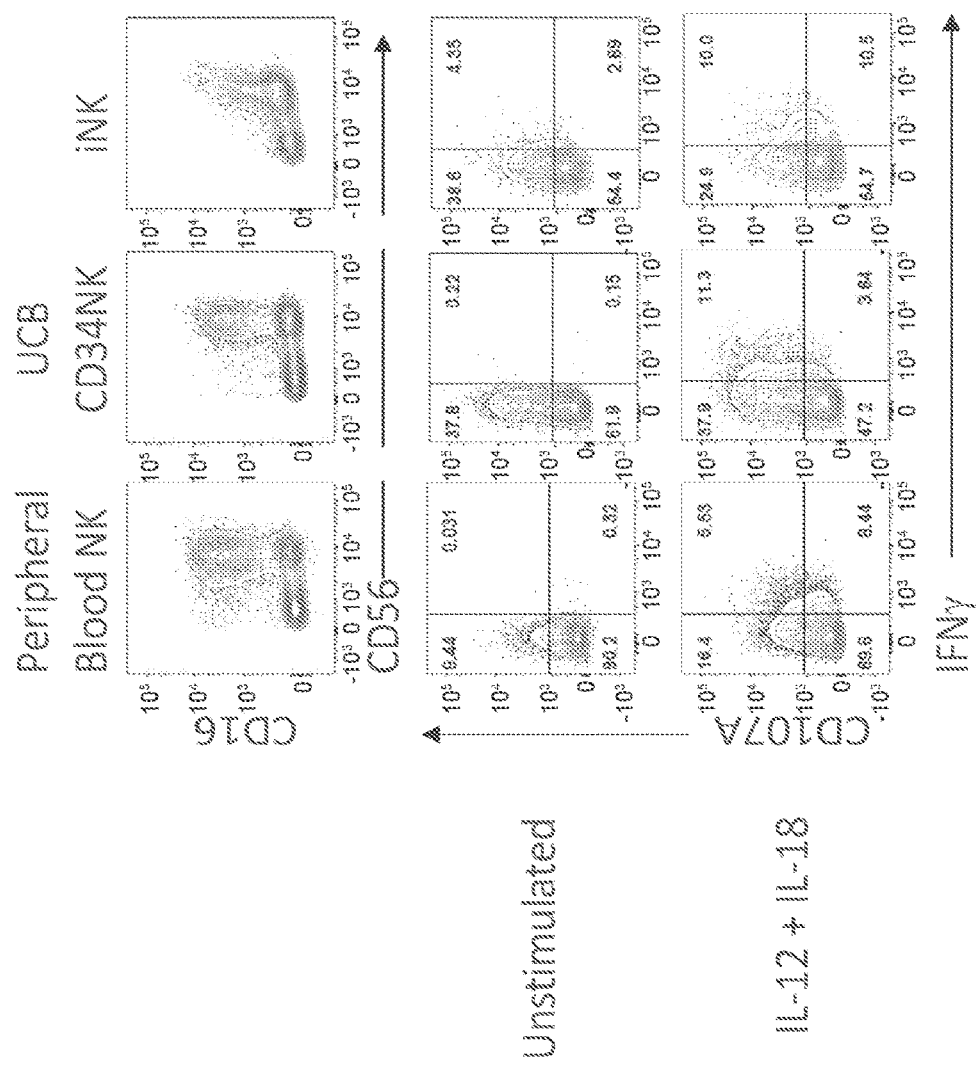
FIG. 17 shows iCD34-derived iNK can respond to cytokine stimulation to secrete pro-inflammatory cytokines in a similar manner to peripheral blood NK cells.

Example 11—Determination of iNK Cell Function by Cytokine-Induced Activation as Seen by Cytokine Release and Degranulation To demonstrate the functionality of the hiPSC-derived mature iNK cells, Day 20 (after HE isolation) iNK cells were transferred to feeder-based suspension cultures for an additional 10 days in iNK-B2 media containing SCF, IL15, IL7 and Flt3L. After 10 days of additional culture, iNK cells were stimulated with IL12 and IL18 to induce iNK cell activation. iCD34-derived iNK responded to cytokine stimulation and secreted pro-inflammatory cytokines in a similar manner to peripheral blood NK cells. FIG. 17 depicts the activation of iNK cells as seen by the expression of CD107A (a cell surface marker representative of degranulation) and the intracellular staining for interferon gamma based on a CD45+CD56+ gating strategy as compared to umbilical cord blood-derived NK cells generated using the same stromal and feeder suspension co-cultures and peripheral blood-derived NK cells.

Example 12—Establishment of Feeder-Free Differentiation Cultures for Generating T and NK Cells The above T and NK lymphoid differentiation platform was further optimized for the generation of umbilical cord blood-derived and hiPSC-derived iT and iNK progenitors using a feeder-free differentiation platform, including free of stromal cells.

Figure 18:
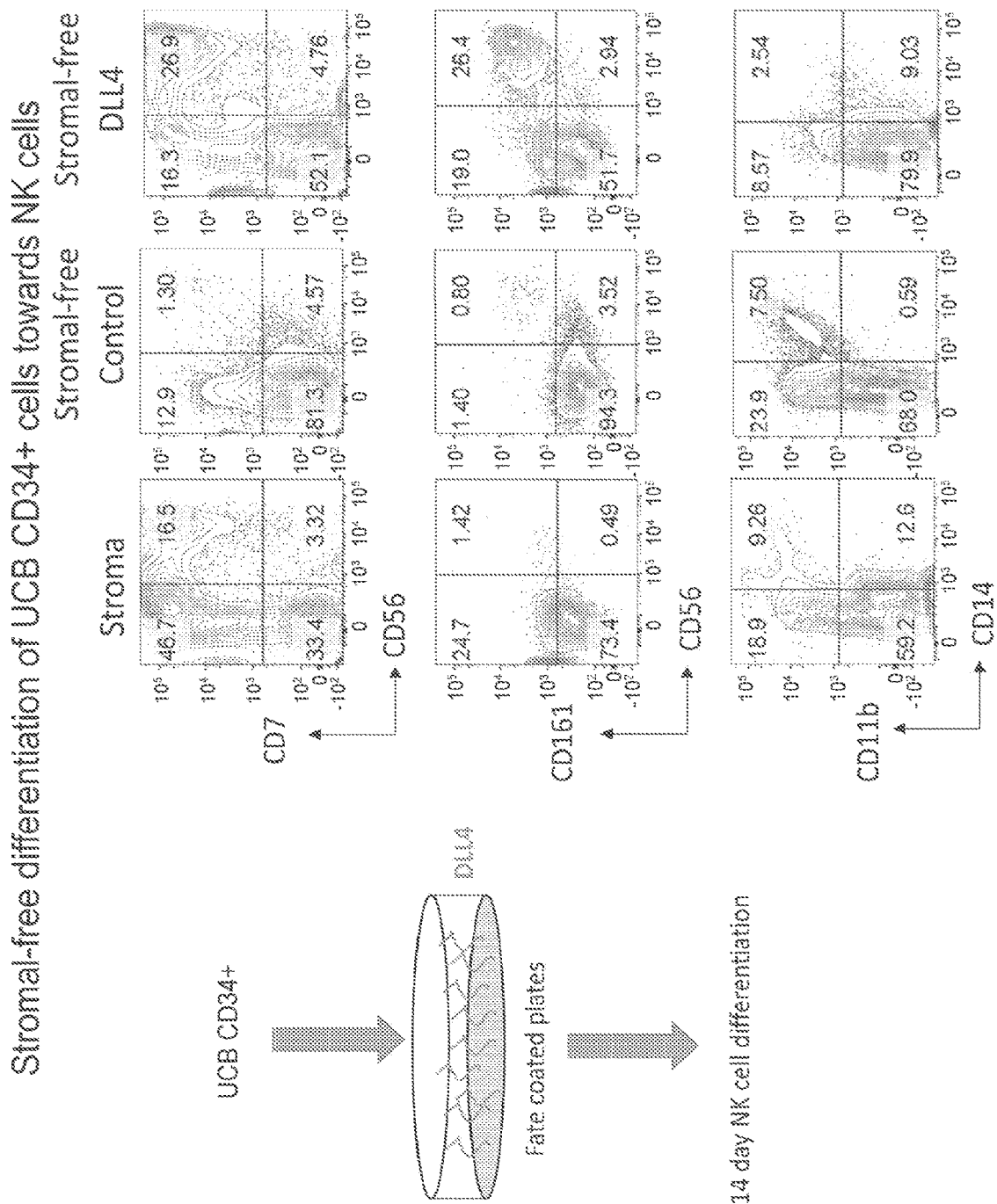
FIG. 18 shows the stromal-free differentiation of pro-NK cells derived from umbilical cord blood CD34 positive cells is more rapid than conventional stromal-based differentiation platform using a CD45+ gating strategy.

Specific to NK cells, enriched umbilical cord blood CD34+ cells were plated in iNK-A2 serum-free differentiation media containing SCF, Flt3L, TPO, IL3, IL15 and IL7 in culture plates containing DLL4 protein or control protein. After 5 days the iNK-B2 medium was maintained to complete NK cell differentiation. After approximately 10-15 days of culture, the culture was assessed for the generation of NK cell progenitors and the absence of myeloid cells. CD56, CD7 and CD161 are the first cell surface markers to be expressed during NK cell development. CD11b and CD14 are cell surface markers expressed on myeloid cell subsets. FIG. 18 depicts stromal-free differentiation of umbilical cord blood CD34+ cells towards NK cells. It was shown that the plate-bound DLL4 supports a more rapid and efficient differentiation of CD56+CD7+CD161+NK cell progenitors compared to stromal-based cultures and stromal-free control cultures, and that the umbilical cord blood CD34+ cells have the in vitro differentiation capacity to give rise to early NK cell progenitors (pro-NK) in a DLL4-expressing stromal-free differentiation platform in a similar manner (in terms of phenotype) to stromal-based differentiation platform using a CD45+ gating strategy. Early NK lineage markers identify the presence of ipro-NK cells as defined by CD56, CD7 and CD161 and the absence of myeloid markers CD11b and CD14.

Figure 19:
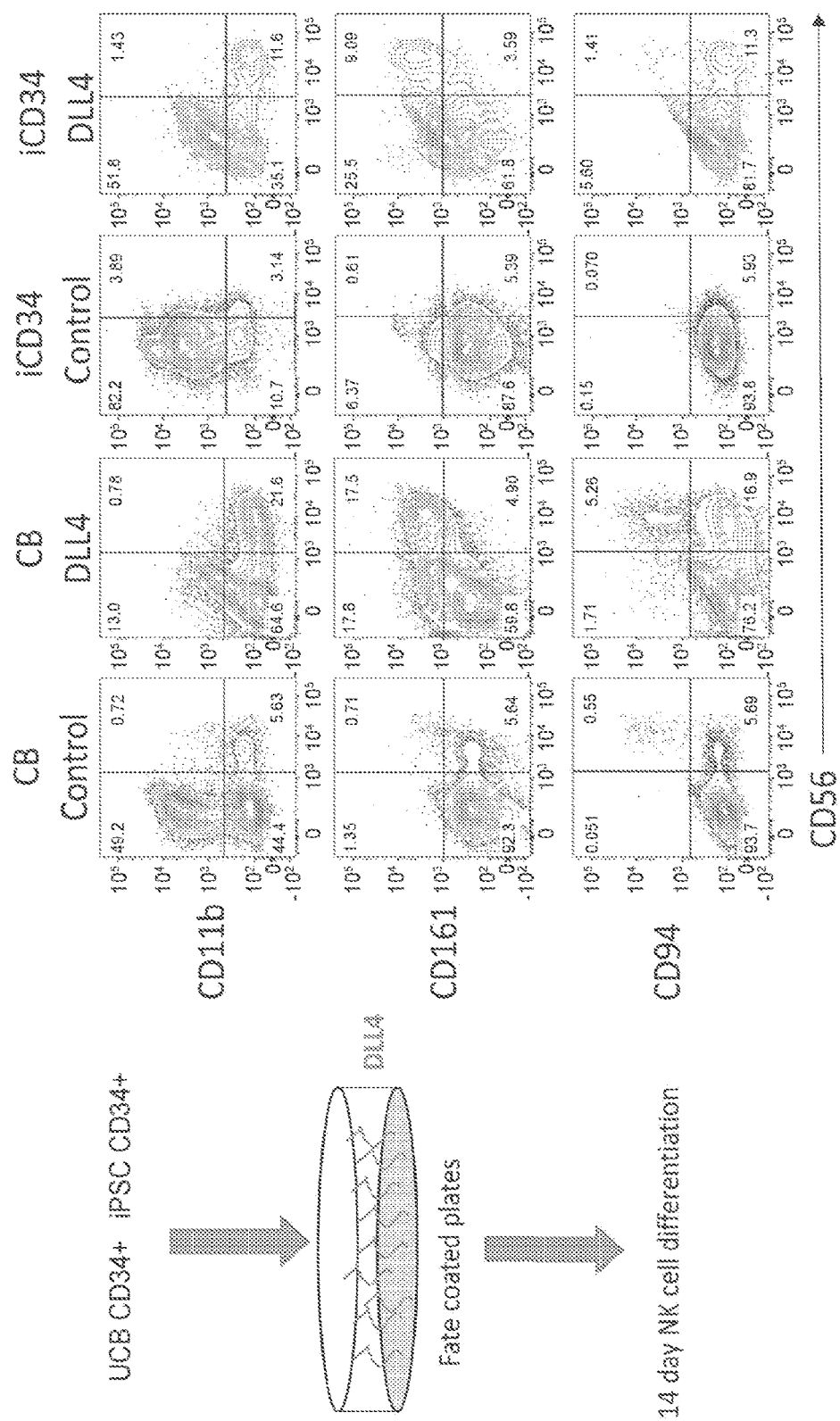
FIG. 19 stromal-free differentiation of iPSC-derived iCD34+ cells towards NK cells. Plate bound DLL4 supports the differentiation of CD56+CD7+CD161+NK cell progenitors but not CD11b+ myeloid cells.

To demonstrate the capacity of hiPSC-derived HE cells in giving rise to iNK cell progenitors in the stromal-free differentiation platform, Day 10 CD34+ iHE sorted cells were cultured in iNK-A2 media in cultures containing DLL4 protein or control protein. Then the hiPSC-derived CD34+ cells were differentiated towards the NK cell lineage for 20 days and then placed in suspension culture for further maturation. FIG. 19 illustrates the capability of hiPSC-derived iHE to give rise to iNK cell progenitors as seen by the expression of CD56, CD161 and CD94 using a CD45+ gating strategy. Plate bound DLL4 supports the differentiation of CD56+CD7+CD161+NK cell progenitors but not CD11b+ myeloid cells. After 5 days iNK-B2 media was maintained to complete NK cell differentiation. Markers for identifying the presence of mature NK cells include CD56, CD122, NKp30, CD94, CD16, NKG2D and KIR.

Figure 20:
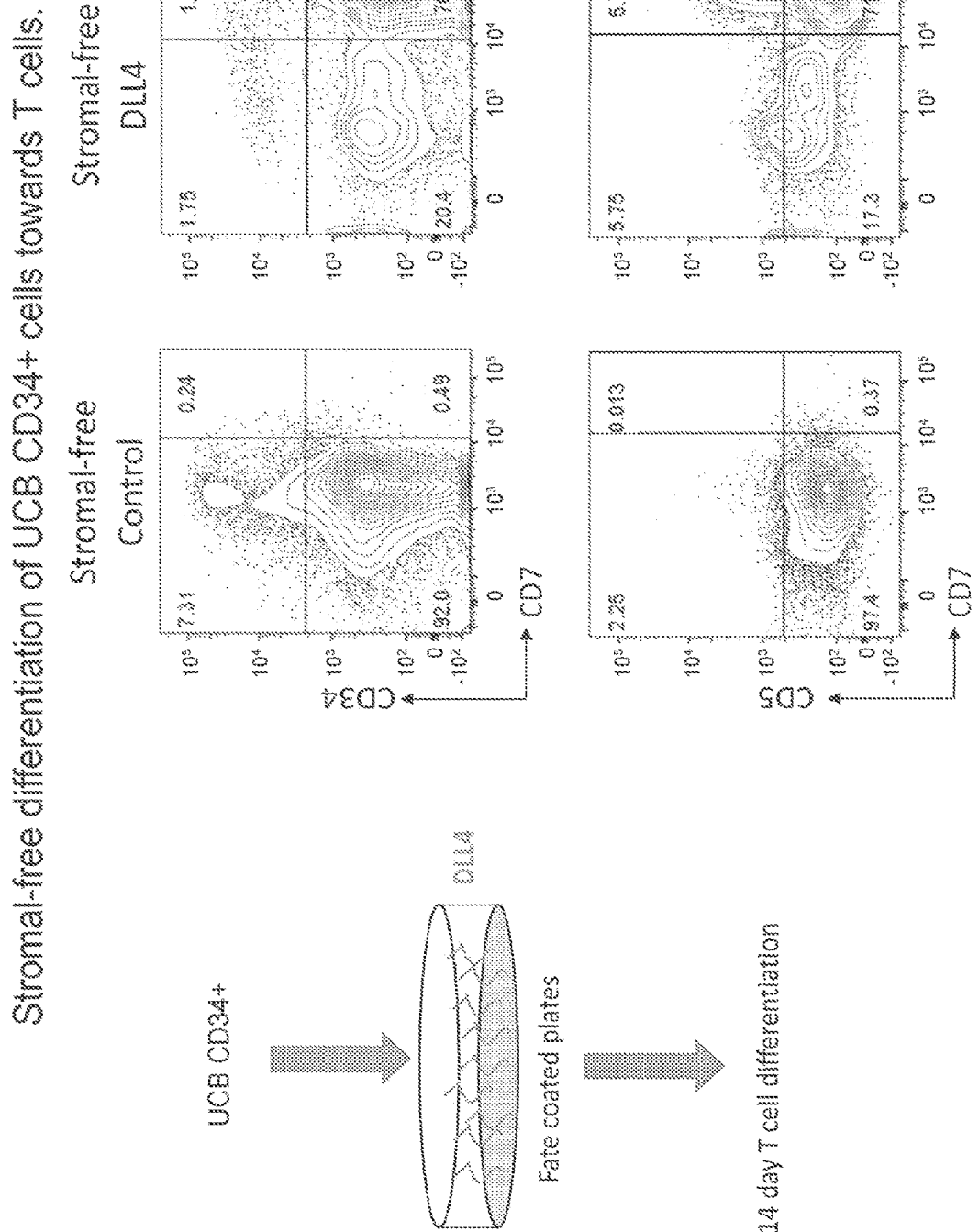
FIG. 20 shows stromal-free differentiation of UCB CD34+ cells towards T cells.

Specific to T cells, enriched CD34+ cells from umbilical cord blood were plated in iT-A2 media in cultures containing DLL4 protein or control protein. After 5 days iT-B2 media was maintained for the generation of T cell progenitors (proT). After approximately 10-15 days of culture the cultures were assessed for the generation of T cell progenitors by the co-expression of the cell surface markers CD34 and CD7. FIG. 20 depicts the ability of CD34+ umbilical cord blood cells to give rise to T cell progenitors in a DLL4-expressing stromal-free differentiation platform using a CD45+ gating strategy. The stromal-free differentiation platform of proT cells derived from umbilical cord blood CD34 positive cells was shown to be more rapid than stromal-based differentiation platform using a CD45+CD56-gating strategy. Early T lineage markers identify the presence of proT cells as defined by CD34, CD5 and CD7.

Figure 21:
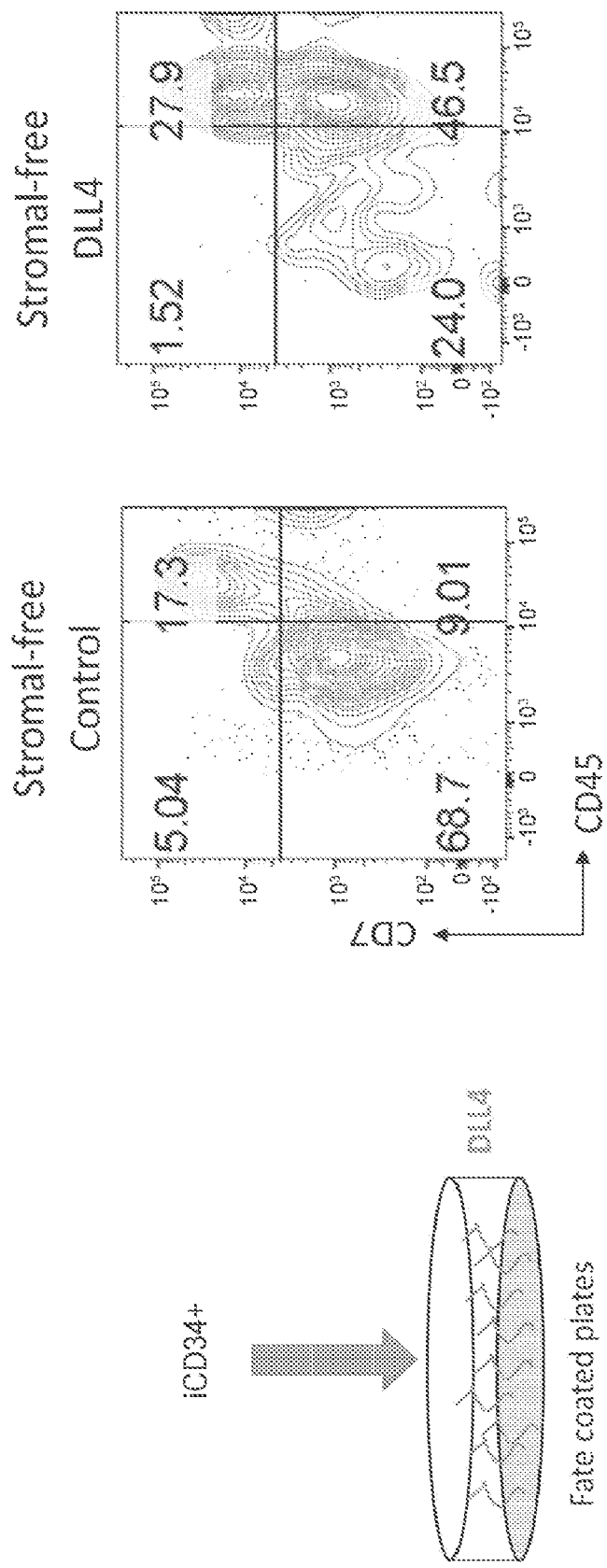
FIG. 21 shows stromal-free differentiation of iPSC-derived iCD34+ cells towards T cells.

To demonstrate the capacity of hiPSC-derived HE cells to give rise to iT cells in the stromal-free platform, Day 10 CD34+ iHE sorted cells were cultured in iT-A2 media in cultures containing DLL4 protein or control protein. FIG. 21 illustrates the capacity of hiPSC-derived iHE to give rise to iT progenitors as seen by the expression of CD45 and CD7.

Figure 23A:
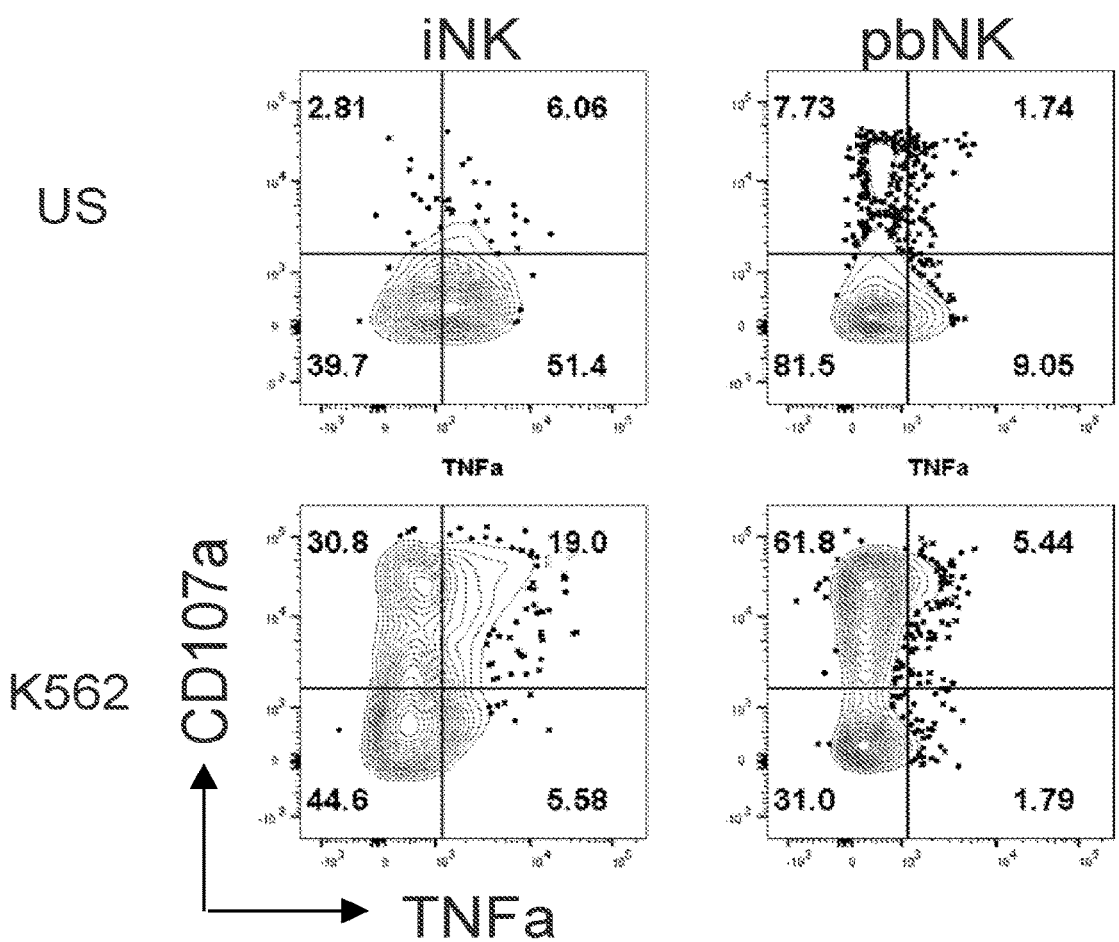
FIG. 23A-B shows iPSC-derived NK cells respond to cellular stimulation to secrete pro-inflammatory cytokines and have cytotoxic function comparable to peripheral blood and cord blood NK cells. A. iPSC-derived (iNK) or peripheral blood derived (pbNK) NK cells were either unstimulated (US) or stimulated at a 1:1 ratio with feeder cells for 4 hours, and then were collected and stained for CD45, CD56, and TNF-alpha and analyzed by flow cytometry. B. Cytotoxic function iNK or cord blood derived (CBNK) cells at an effector:target ration of 1:1, 3:1 and 10:1 for was assessed every 2 hours for 90 hours.
Figure 23B:
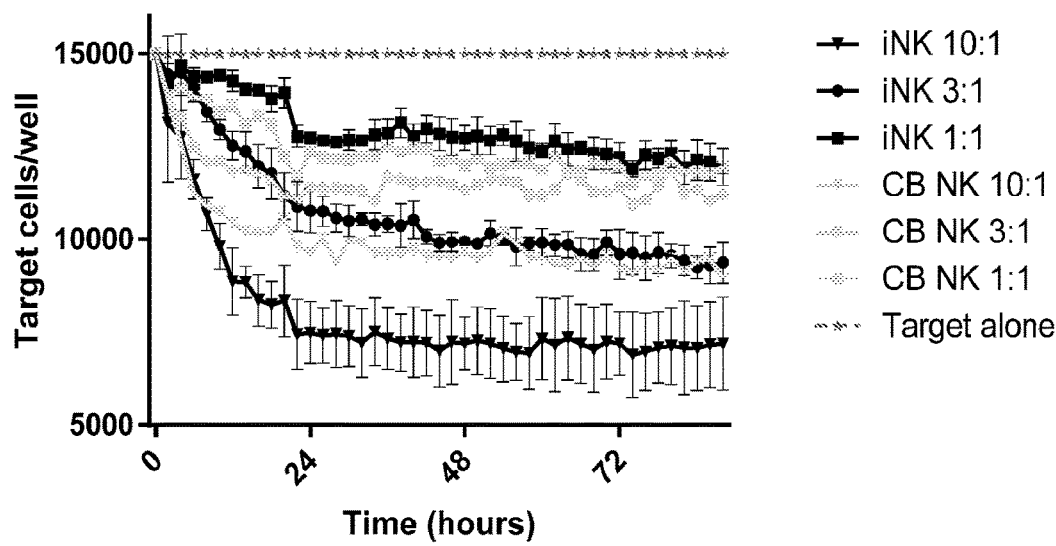

Example 13—iPSC-Derived iNK Respond to Cellular Stimulation to Secrete Pro-Inflammatory Cytokines and have Cytotoxic Function Comparable to Peripheral Blood and Cord Blood NK Cells iPSC-derived (iNK) or peripheral blood derived (pbNK) NK cells were either unstimulated (US) or stimulated at a 1:1 ratio with feeder cells for 4 hours. Golgistop (BD Biosciences) and Alexa-Fluor 647 conjugated anti-CD107a antibody (Biolegend) were included during the co-culture period. After four hours, cells were collected and stained for CD45, CD56, and TNF-alpha and analyzed by flow cytometry (FIG. 23A). To assess cytotoxic function iNK or cord blood derived (CBNK) cells were co-cultured with CFSE-labeled target cells at an effector:target ration of 1:1, 3:1 and 10:1 for 90 hours. Quantification of target cells was analyzed every 2 hours with the Incucyte ZOOM cell analysis system (FIG. 23B). It was shown that NK cells derived from iPSC (iNK) using the platform provided herein respond to cellular stimulation to secrete pro-inflammatory cytokines including, but not limited to, TNFα, and have cytotoxic function comparable to peripheral blood and cord blood NK cells.

Example 14—iPSC Derived T Cell Progenitors Rejuvenise Thymus and Reconstitute T Cells In Vivo The hiPSC-derived ipro-T cells are shown to be able to home to, colonize, and differentiate in the thymus of immunocompromised NSG recipient mice as functional T cell progenitors. Day 10 (post CD34+HE isolations) CD34+CD7+ ipro-T cells are isolated by FACS and injected intrahepatically into neonatal (Day 2-5 after birth) NSG mice. 8 weeks post injection the mice are analyzed for thymic engraftment by the expression of human CD45+CD4−CD8− double negative (DN), CD45+CD4+CD8+ double positive (DP), CD45+CD4+CD8− or CD45+CD4-CD8+ single positive (SP) T cell subsets by flow cytometry. Additionally, single positive T cells are assessed for the expression of TCR, CD3, CD27 and CCR7 to assess their state of naivety and maturity. The functionality of the mature single positive T cells are assessed by monitoring proliferative capacity and upregulation of CD25 activation marker expression following anti-CD3/CD28 stimulation.

There is a critical interplay between thymocytes and thymic epithelial cells (TECs) that can result in the generation and improvement of the thymic environment leading to thymic rejuvenation. Day 10 CD34+CD7+ hiPSC-derived ipro-T cells are assessed for their effect on thymic function. As above, FACS sorted ipro-T cells are injected intrahepatically into neonatal NSG recipient mice. 8-10 weeks post injections immunohistological analysis are performed on the thymus of control (non-injected) or ipro-T-injected mice by staining with anti-Cytokeratin 5 (K5) and anti-Cytokeratin 8 (K8) to identify the formation of the thymic cortex, medulla and a defined corticomedullary border. In the absence of ipro-T cells, a disorganized structure of epithelial cells presents is expected. Additionally, the expression of critical TEC-derived chemokines, CC19, CCL21 and CCL25, required for the recruitment of lymphoid progenitors to the thymus, are assessed. Lastly the expression of RANK ligand (RANKL; Receptor Activator of Nuclear factor Kappa-ligand) on the ipro-T cells and RANK on the TECs, an interaction that influences TEC maturation, is indicative of an increase in thymic rejuvenation.

Example 15—iPSC Derived iT Cells Respond to Cellular Stimulation and Present VDJ Recombination as Matured T Cell To demonstrate the functionality of the hiPSC-derived iT cells, Day 35 (after CD34+HE isolation) iT cells are treated with Cell Tracker Violet to monitor cellular proliferation, and then stimulated with anti-CD3/CD28 beads for 7 days to induce iT cell activation and proliferation. iCD34-derived iT cells respond to CD3/CD28 stimulation in a similar manner to cord blood-derived and peripheral blood T cells. The activation of iT cells is shown by the expression of CD25 and CD62L (surface markers indicative of activation) and intracellular staining for interferon gamma based on a CD45+CD3+ gating strategy. The activation of iT results in proliferation as seen by the depletion of cell tracker violet during cell division.

To further characterize the extent of hiPSC-derived iT cell development, the Day 35 iT cells are analyzed for recombination of the T cell receptor locus. Genomic DNA from CD3+ sorted Day 35 iT cells was analyzed for the presence of TCR Db2-Jb2 rearrangements, indicative of rearrangement of the endogenous T cell receptor locus. The multiple PCR products indicative of polyclonal Db2-Jb2 rearrangements are similar to what was observed in T cells derived from cord blood CD34+ HSCs.

Example 16—Cell Surface Antibody Screening for Novel Markers of Definitive Hemogenic Endothelium Cell markers serve as a monogram to help identify and classify cells. The majority of the markers are molecules or antigens within the plasma membrane of cells. Many surface markers are classified by their clusters of differentiation (CD) which are recognized by specific antibodies. Generally, specific combinations of markers are unique to different cell types.

During in vitro differentiation of pluripotent stem cells through mesoderm originated endothelium, the heterogeneous endothelial cells acquire arterial, venous, and hemogenic fates, and form respective subtype endothelial cells which are phenotypically and functionally specialized. These cell subtypes are formed in close space and time, and are currently distinguished mainly through gene expression profiling for lack of cell markers. Hematopoietic cells arise from a unique population of endothelial cells known as hemogenic endothelium (HE) through an endothelial-hematopoietic transition (EHT). EHT represents a continuous process in which cells with endothelial characteristics gradually acquire hematopoietic morphology and phenotype. Identifying markers specific to HE cell subtypes would greatly improve the efficiency of isolating early cell populations with desired quality and purity for subsequent hematopoietic cell differentiation. Therefore, additional potentially unique markers to discriminate all these different cellular lineages are desired.

To identify additional markers for the enrichment of CD34+ and HE cells with the capacity to give rise to hematopoietic cells, hiPSCs were seeded as a monolayer and differentiated towards hematopoietic cells using the methods and compositions using the platform, compositions and methods disclosed herein.

Figure 25:
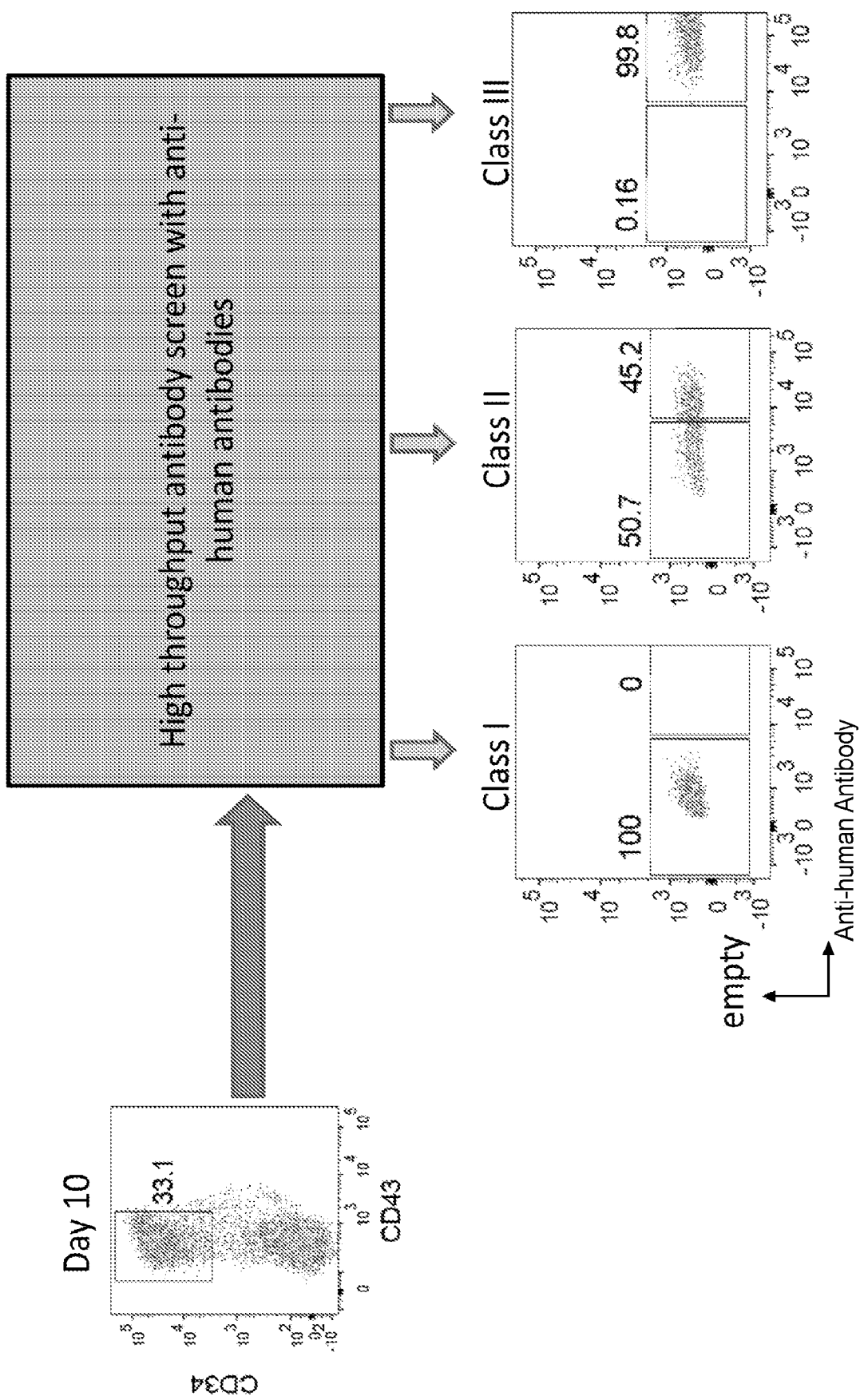
FIG. 25 shows a cell surface antibody screen of hiPSC-derived CD34+ cells using a CD34+CD43− gating strategy, and workflow of hiPSC-derived CD34+ antibody screen depicting representative outcomes of three separate classifications. Class I markers include cell surface proteins with <1% expression on hiPSC-derived CD34+ cells. Class II markers include cell surface proteins with 1%-99% expression on CD34+ cells. Class III markers include cell surface proteins with >99% expression on CD34+ cells.

Specific to CD34+ cells, at Day 10 of hiPSC differentiation, CD34+CD43− cells were stained with anti-human antibodies and analyzed by flow cytometry (FIG. 25). The anti-human antibodies included in the analysis are listed in FIG. 26. As shown in FIG. 25, class I markers include cell surface proteins with <1% expression on hiPSC-derived CD34+ cells. Class II markers include cell surface proteins with 1%-99% expression on CD34+ cells. Class III markers include cell surface proteins with >99% expression on CD34+ cells. The expression level of the markers in the iCD34+ population are demonstrated in FIG. 26. Class II markers identify cell surface proteins that may be expressed on iCD34+ cells with hematopoietic potential.

In this analysis, a marker is considered to be positive if it exhibits at least 1% expression in the chosen population. A marker is considered to be negative if it exhibits less than 1% expression on the chosen population. The expression level of a positive marker can also be quantified or categorized based on the mean florescence intensity (MFI) of the staining. This is depicted as a value on a log scale. As used herein, a marker that is considered as high or bright would have an MFI of about $10^4$-$10^5$. A marker that is considered intermediate or mid would have an MFI of about $10^2$-$10^4$. A marker that is considered low or dim would have an MFI of about $10$-$10^2$.

Figure 27:
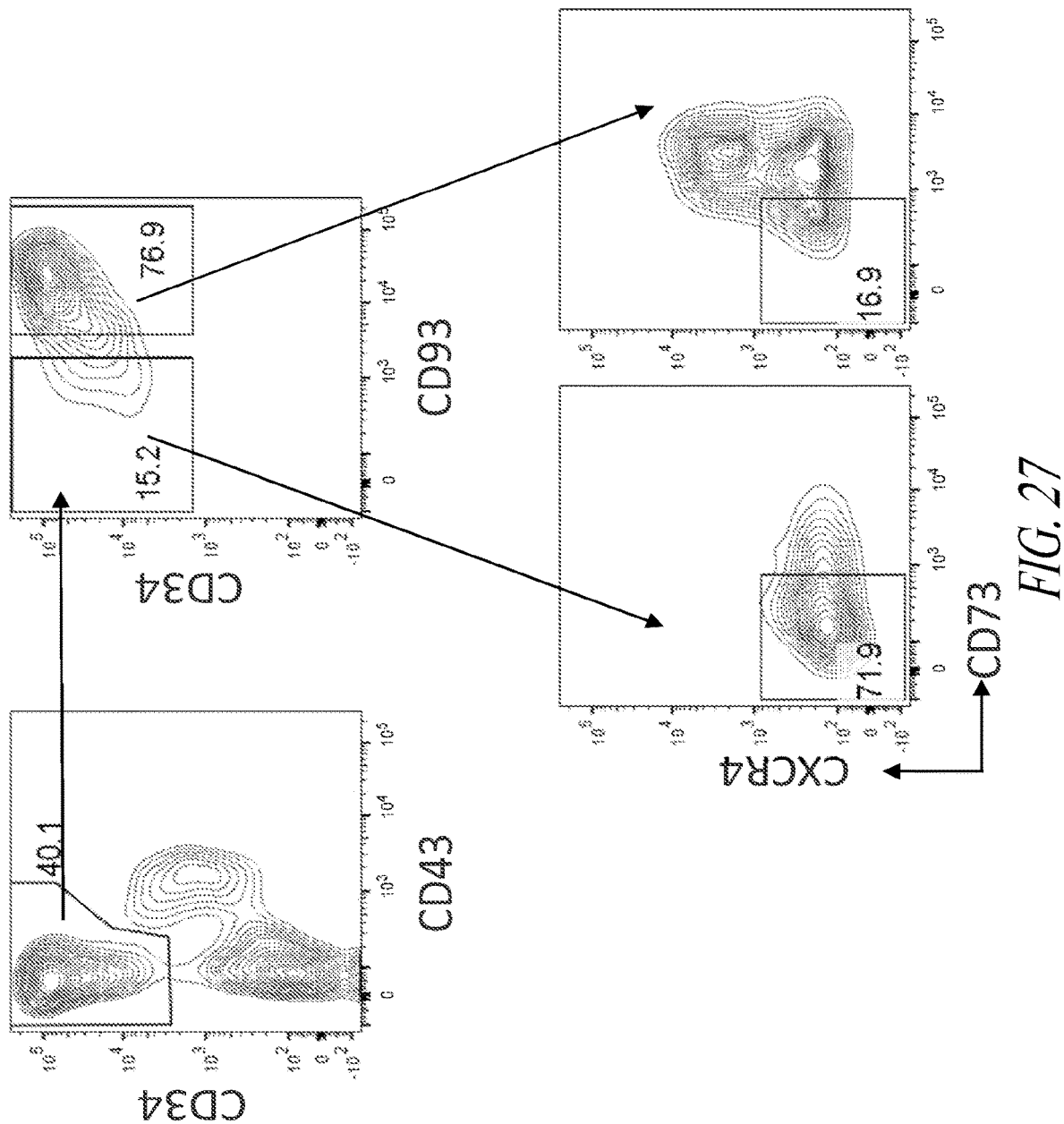
FIG. 27 shows the expression of the CD93 marker within the CD34+ population; and the expression of CXCR4 and CD73 in CD34+CD93− and CD34+CD93+ fractions of CD34+ cells.

Among the marker candidates in Class 11, the expression of the CD93 marker within the CD34+CD43− population is shown in FIG. 27. The CD34+CD93− and CD34+CD93+ populations were isolated and subsequently analyzed for the expression of CXCR4 and CD73. It was determined that the CD34+CD93− population contains the majority of CXCR4−CD73− population, which represents definitive IE cell population of interest. The expression of the murine homolog of CD93, rather than the lack thereof, however, has been previously identified to be a potential marker of early lymphohematopoietic progenitors (Yamane T et al, PNAS, 2009; 106(22):8953-8958).

Figure 28A:
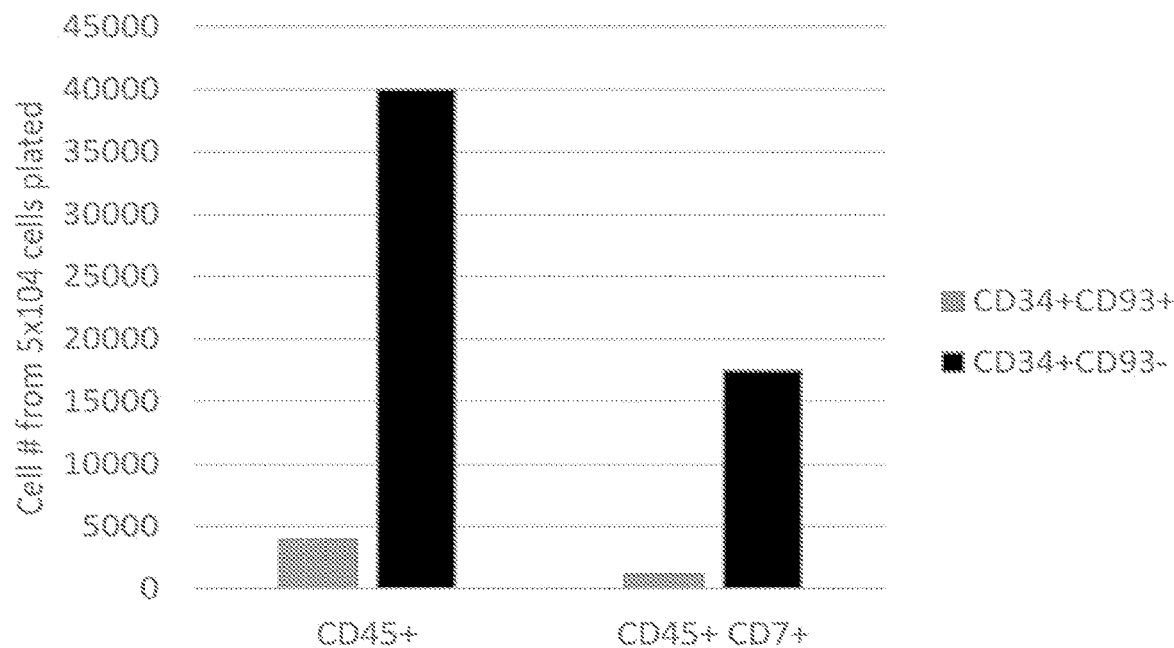
FIG. 28A-B shows that the definitive hematopoietic potential of the CD34+ population resides in the CD93− fraction. A. After 10 days of iNK cell differentiation from the CD34+CD93− population, the absolute number of CD45+ hematopoietic cells and CD45+CD7+ lymphoid progenitors was assessed. B. After an additional 10 days of iNK differentiation the cultures were assessed for the presence of iNK cells by the expression of the CD56 and NKp30 markers.
Figure 28B:
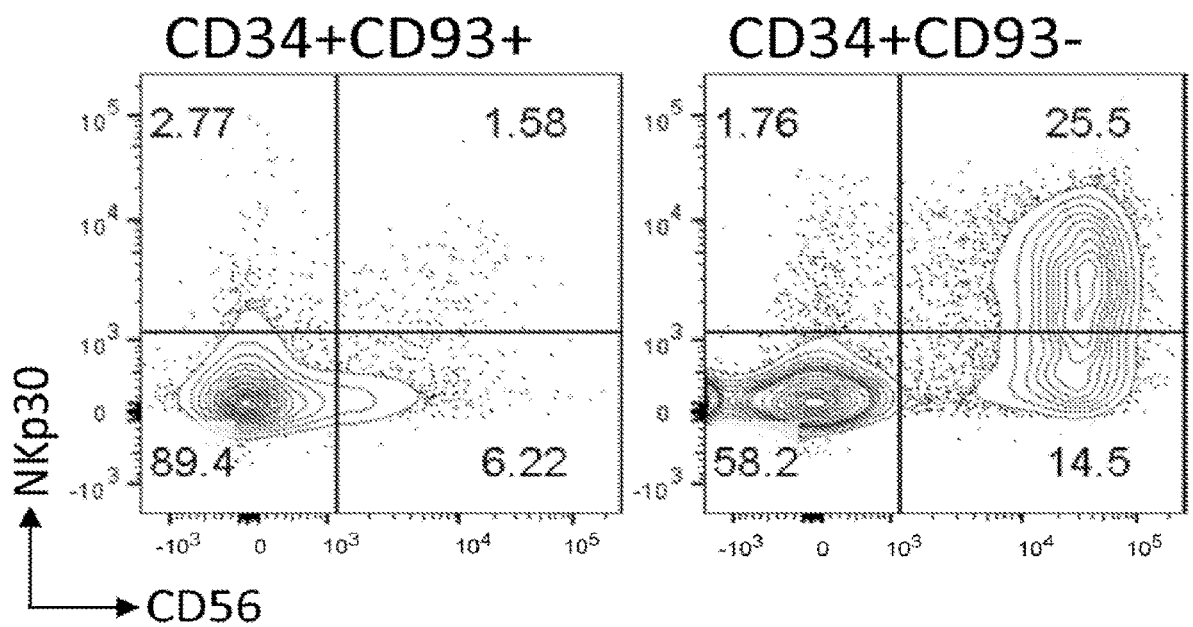

To further determine the definitive hematopoietic potential represented by CD93 expression or the lack thereof, the day 10 CD34+CD43−CD93− and CD34+CD43−CD93+ fractions were isolated by FACS and plated in iNK differentiation cultures, iNK-A2 and iNK-B2, as disclosed herein. After 10 days of differentiation the absolute number of CD45+ hematopoietic cells and CD45+CD7+ lymphoid progenitors were assessed (FIG. 28A). After an additional 10 days of iNK differentiation, the cultures were assessed for the presence of iNK cells by the expression of the CD56 and NKp30 markers. It was shown that the definitive hematopoietic potential of the CD34+ population is enriched in the CD93− fraction (FIG. 28B). As such, CD34+CD93− cells represent the definitive HE population in an early stage of iPSC directed differentiation towards hematopoietic cells; and the expression of CD93 can be used as a surrogate marker for CD73, or CD73/CXCR4 to identify the HE subpopulation.

Based on the percentage of CD34+CD93− cell fraction present in the CD34+ population at day 10 of iPSC differentiation, we estimated the percentage of definitive HE in the CD34+ population at day 10 or earlier would be around 30% or less. As such, markers, either positive or negative, having about 1% to about 30% of expression in the screening herein using day 10 CD34+ population would be also useful for identifying the definitive HE subpopulation (FIG. 26). As such, positive markers for identifying definitive HE in CD34+ population include: CCR10, CD164, CD95, CD144, CD166, Lymphotoxin β Receptor, CD252, CD55, CD40, CD46, CD340, CD119, CD106, CD66a/c/e, CD49d, CD45RB, DLL4, CD107a, CD116, CD324, CD123, CD49f, CD200, CD71, CD172a, CD21, CD184, CD263, CD221, Notch 4, MSC, CD97, CD319, CD69, CD338, Podoplanin, CD111, CD304, CD326, CD257, CD100, CD32, CD253, CD79b, CD33, CD83, GARP, CD183, and CD357. Alternatively, additional negative markers, similar to CD93, for identifying definitive HE in CD34+ population include: CD31, CD165, CD102, CD146, CD49c, CD13, CD58, Integrin α9β1, CD51, CD10, CD202b, CD141, CD49a, CD9, CD201, CD47, CD262, CD109, CD39, CD317, CD143, integrin β5, CD105, CD155, and SSEA-4.

Example 17—Modulation of WNT Signaling Improves the Output and Potency of iPSC Derived iCD34 (Definitive HE)

Figures 29A, 29B:
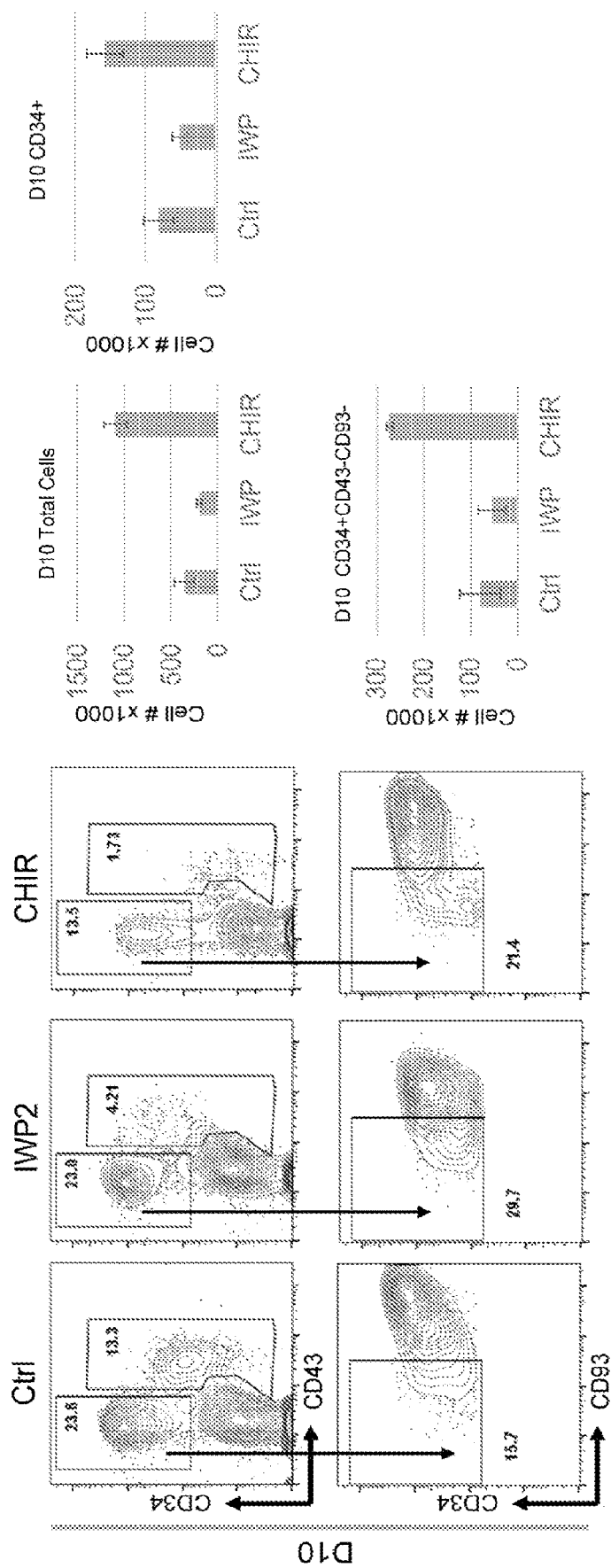
FIG. 29A-B shows modulation of WNT signaling improves the output of iCD34 cells. A. Day 6 cell cultures were differentiated in the presence of the GSK3 inhibitor CHIR99021, a Wnt agonist, or IWP2, a WNT inhibitor. B. CHIR99021 increased the number and the percentage of phenotypic CD34+CD43−CD93− HE.

To optimize the efficient generation of definitive HE from hiPSCs after 10 days of directed differentiation, the effect of modulation of the WNT signaling pathway was examined. At day 6 of differentiation, cell cultures were differentiated in the presence of the GSK3 inhibitor CHIR99021, a Wnt agonist, or IWP2, a WNT inhibitor (FIG. 29A). The generation of CD34+CD43−CD93− HE was analyzed at Day 10. FIG. 29B demonstrates that inhibiting the WNT pathway with IWP2 did not affect the percentage of phenotypic HE at Day 10 as seen by flow cytometry, it, however, did result in an overall decrease in HE cell numbers (FIG. 29B). Conversely, while the activation of the WNT pathway with CHIR99021 resulted in a slight decrease in the percentage of CD34+CD43− cells, it increased the number and the percentage of phenotypic CD34+CD43−CD93− HE around 2-3 fold, as well as improved HE cellularity, i.e., increased total HE cell number and increased HE proliferation as a result.

Figure 30A:
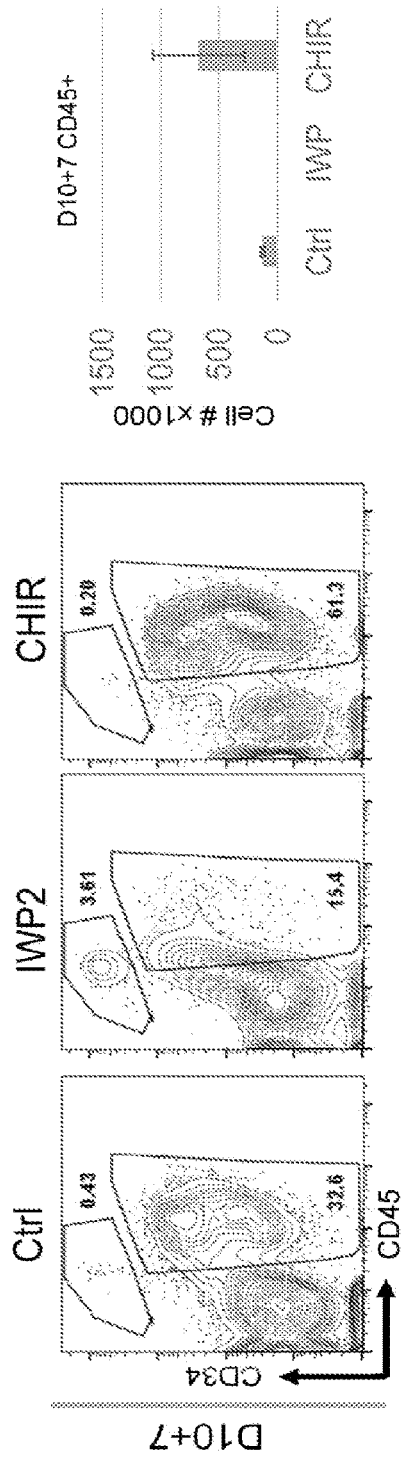
FIG. 30A-B shows modulation of WNT signaling improves pan hematopoietic and lymphoid output from iCD34 cells. A. CHIR99021 increased the production of CD45+ cells from the modulated HE. B. CHIR99021 increased the production of NK progenitor cells from the modulated HE.
Figure 30B:
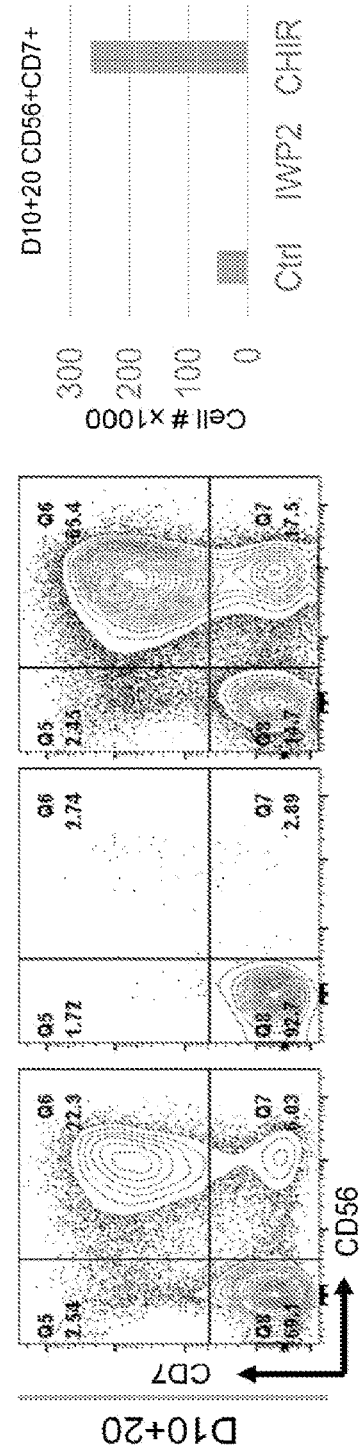

To determine the potency of the WNT modulated HE, the pan-hematopoietic and lymphoid potential of the untreated, IWP2- and CHIR99021-treated HE was each assessed. Day 10 CD34+CD43− cells were isolated by FACS and plated in MPP differentiation and iNK differentiation cultures as provided herein. FIG. 30A demonstrates that after 7 days of MPP differentiation, the CHIR99021 modulated HE exhibited increased hematopoietic potency as indicated by the increased presence of CD45+ cells of about 5-6 fold. FIG. 30B demonstrates that after 20 days of iNK differentiation, the CHIR99021 treated HE exhibited increased lymphoid capacity as shown by the increased presence of CD56+CD7+NK progenitor cells of about 5-6 fold.

Example 18—iPSC with Genetic Modification or Donor Attributes for Generating Hematopoietic Cells with Enhanced Properties for Immune Therapies Unique attributes that are preferential in treating various diseases may come from selected-donor derived cells, including cells of the immune system such as T cells. Donor attributes include genetic imprints that can be passed through differentiated progenies and may include but are not limited to, prearranged monospecific TCR, for example, from a viral specific T cell or invariant natural killer T (iNKT) cell; trackable and desirable genetic polymorphisms, for example, homozygous for a point mutation that encodes for the high-affinity CD16 receptor in selected donors; and predetermined HLA requirements, i.e., selected HLA-matched donor cells exhibiting a haplotype with increased population coverage. Additionally, during cellular therapy, genetically modified cells with new or enhanced therapeutic properties are desirable for improved disease outcome. It was not clear, however, whether any of the donor attributes or genetically engineered modalities existing at the level of iPSC or sourcing cells thereof can be retained and remain functional in differentiated cells derived from iPSCs due to any number of reasons ranging from gene silencing, mRNA degradation, genetic mutations, improper protein trafficking and cleavage, reduced differentiation potential, and suppressed cell growth in a heterogeneic population. It is demonstrated herein a method of generating iPSC-derived effector cells comprising genetic imprints retained by iPSCs originated either from source specific somatic cells, or from genetic editing through directed differentiation using the present differentiation platform and compositions as disclosed. These differentiated cells are shown to have retained the genetic imprints present in iPSCs or their original sourced parental population, and are more rejuvenated with enhanced capacity for proliferation and survival. Furthermore, when existing in the form of induced pluripotent stem cells, the preferential sourcing cells having the desired attributes can be maintained indefinitely in a pure/clonal population that is expandable and can readily be differentiated to a selected effector cell type including T, NK, NKT, CD34, T progenitor, and NK progenitor cell with reproducibility and improved efficacy.

Also illustrated herein, some desired attributes, for example, in vivo cell persistence, of an effector cell derived from the differentiation platform provided by the invention can also be obtained through small molecule modulation which permits the said cell to be used in allogeneic transplant without being recognized or destroyed by the patient's immune cell.

Associated with the differentiation methods provided herein, the known and unique imprinted feature(s) of a preferential cell source (donor-, patient-, disease-, or condition-specific) can also serve as a marker of clonality or clonal detection of reprogrammed iPSCs and intermediate cells at various stages of differentiation, as well as being tracked in vitro or in vivo using the selected imprinted marker. These markers comprise one of more of DNA rearrangements such as VDJ recombination, and/or transgene insertion sites.

Figure 31:
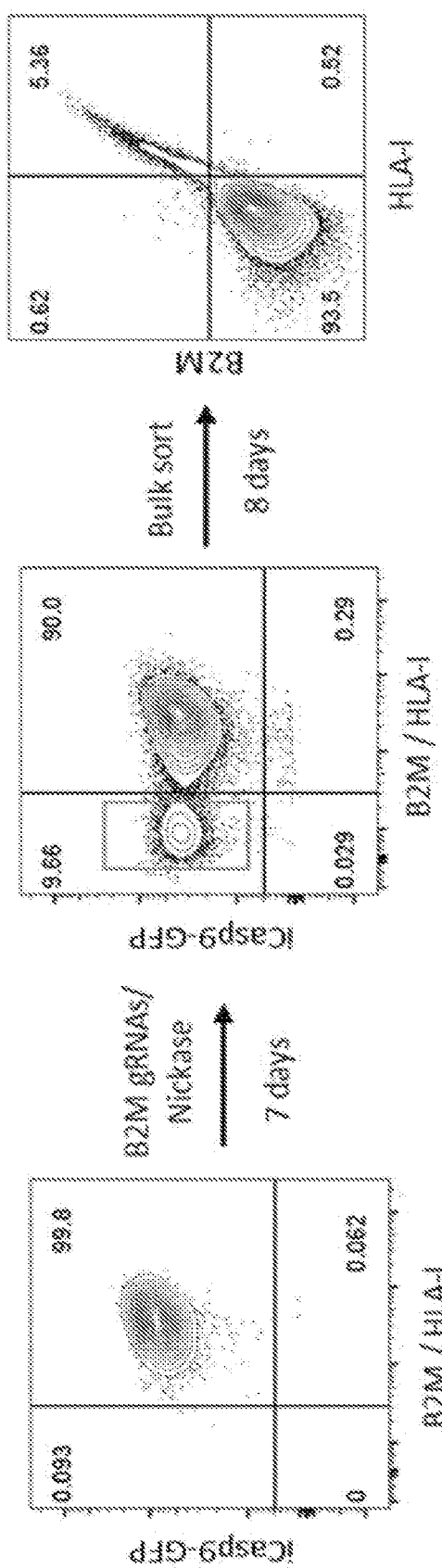
FIG. 31 shows that the deletion of B2-microglobulin (B2M) in iPSC resulted in the lack of expression of HLA class I genes.

1. HLA Class I Null iPSCs Differentiate into iCD34 HE and can be Further Differentiated into Pan-Hematopoietic and Lymphoid Progenitors To improve the immune-resistance and persistence of iPSC-derived effector lymphocytes, the effect of HLA class I deletion was examined. The deletion of B2-microglobulin (B2M) in iPSC resulted in the lack of expression of HLA class I (HLA-A, B, and C) as seen in FIG. 31. We have previously shown that the B2M−/− iPSC line is able to avoid T cell mediated killing while not inducing NK cell recognition, indicating a universally donor/recipient compatible hiPSC clonal line with improved persistence both in vitro and in vivo (data not shown).

Figure 32A:
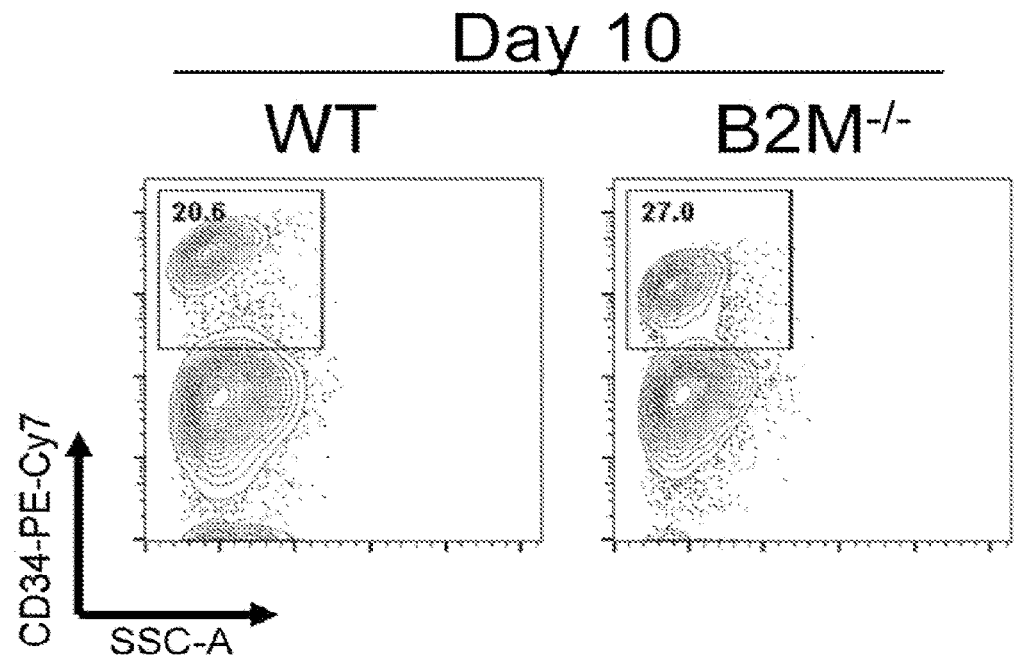
FIG. 32A-D shows HLA class I null iPSCs differentiate into iCD34 HE and can be further differentiated into pan-hematopoietic and lymphoid progenitors. A. B2M−/− iPSC and wildtype iPSC were differentiated for 10 days to generate HE. B. The B2M−/− iPSCs can differentiate into CD34+HE at a similar frequency as wildtype controls. C. B2M−/− HE can generate CD45+ pan-hematopoietic progenitors with similar efficiency as wildtype HE. D. B2M−/− iPSC-derived HE cells can generate iNK progenitors cells with similar efficiency as wildtype HE.
Figure 32B:
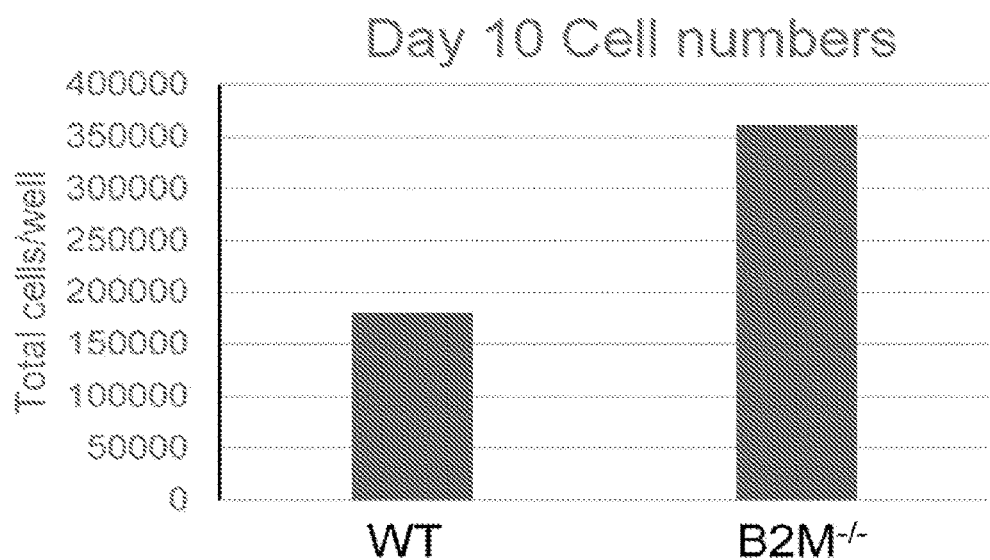
Figure 33:
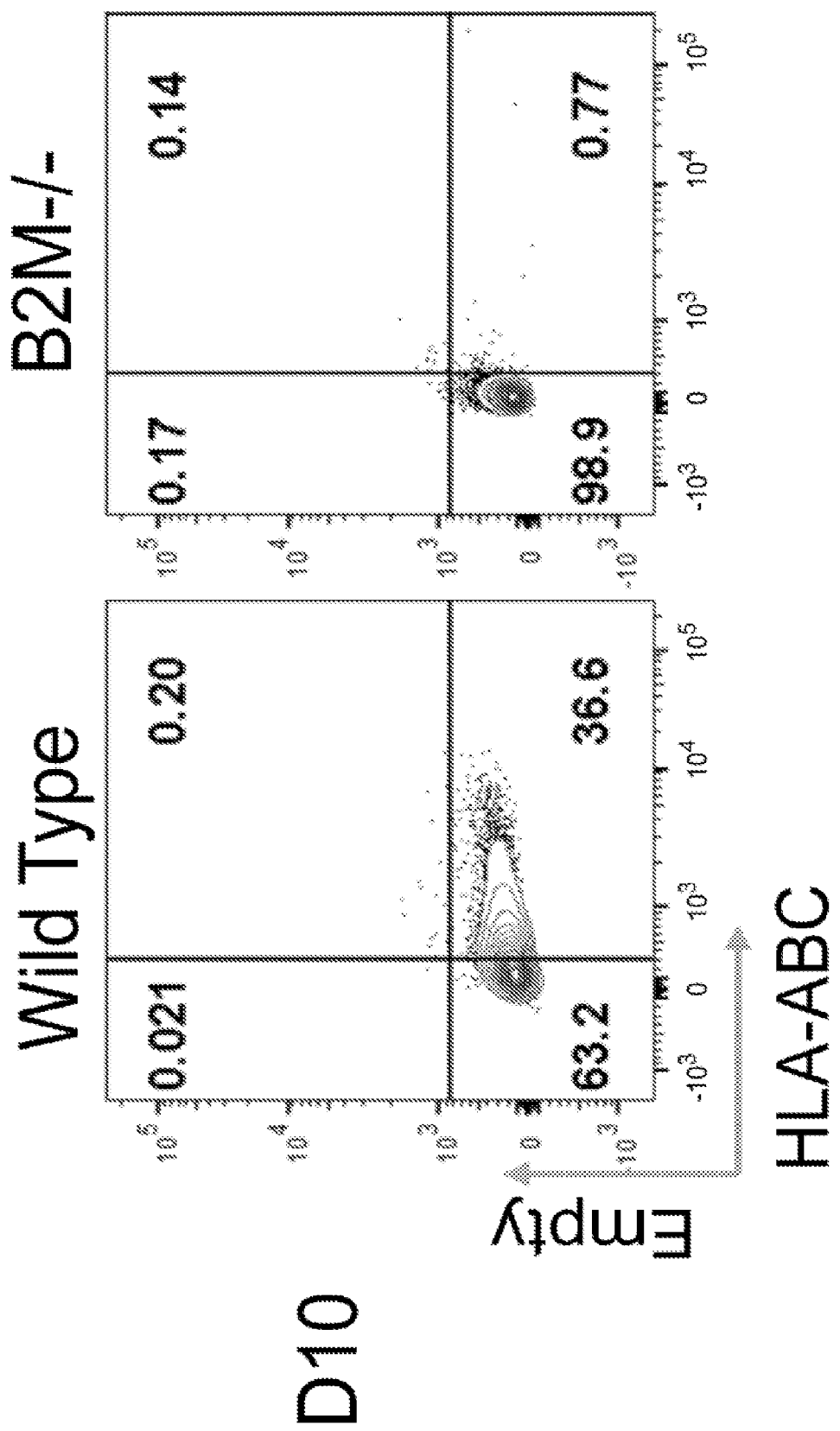
FIG. 33 shows that CD34+CD43−HE differentiated from B2M−/− iPSC remains HLA class I null.

The effect of 32M deletion on the differentiation capacity of iPSC was then assessed using the differentiation platform and methods as disclosed herein. B2M−/− iPSC and wildtype iPSC were differentiated for 10 days to generate HE and analyzed for the expression of CD34+CD43− HE cells by flow cytometry. FIGS. 32A and 32B show that the B2M−/− iPSCs can differentiate into CD34+HE at a similar frequency as wildtype controls. FIG. 33 shows that CD34+CD43− HE differentiated from B2M−/− iPSC remains HLA class I null.

Figure 32C:
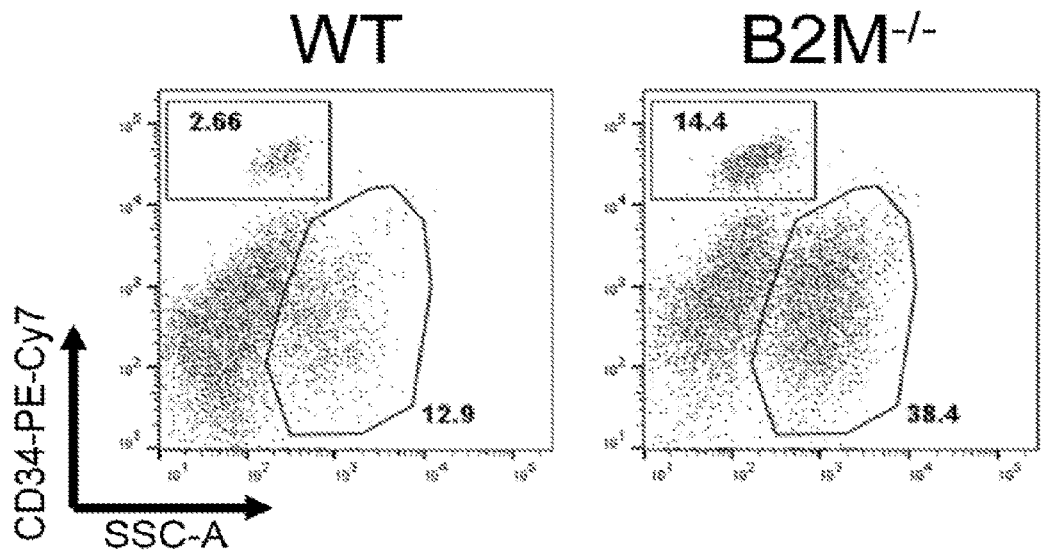

To demonstrate the hematopoietic potential of the B2M−/− iPSC-derived HE, cells were sorted using FACS and assessed for their ability to undergo the endothelial to hematopoietic transition to generate CD45+ hematopoietic progenitors as described in the multipotent progenitor assay (iMPP) in FIG. 1. FIG. 32C illustrates that B2M−/− HE can generate CD45+ pan-hematopoietic progenitors with similar efficiency as wildtype HE.

Figure 32D:
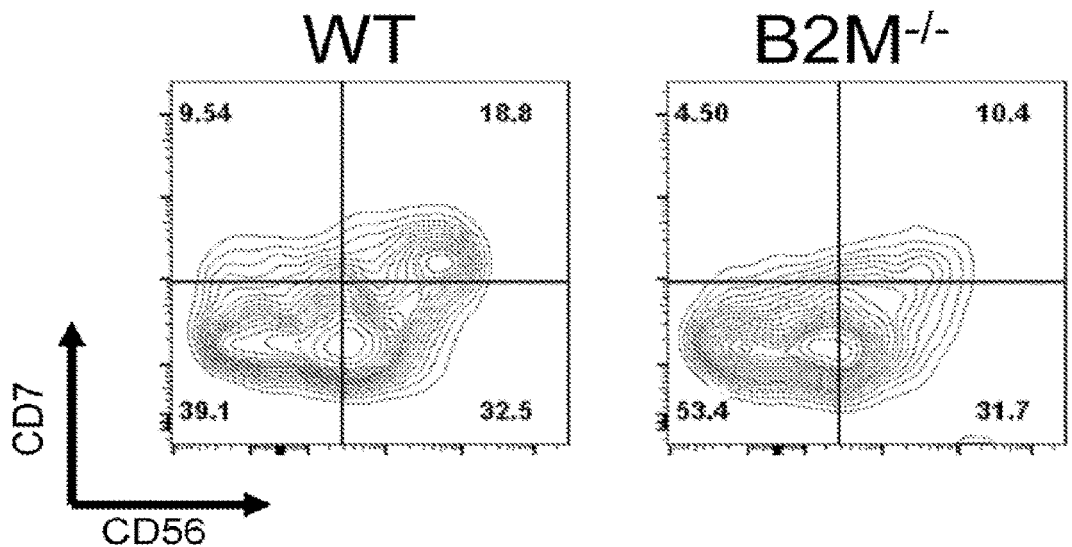

Lastly, the lymphoid potential of the B2M−/− iPSC-derived HE was assessed. FACS sorted CD34+CD43− HE cells were further differentiated toward NK cell progenitors as described in FIG. 3. After approximately 10 days of differentiation the cultures were assessed for the presence of NK progenitor cells by the expression of CD56 and CD7 using flow cytometry based on a CD45+ gating strategy (FIG. 32D). B2M−/− iPSC-derived HE has been shown to have an equivalent capacity to generate iNK progenitors cells when compared to wildtype iPSC-derived HE.

This example illustrated that the differentiation potential of iPSC is unaffected by its retained genetic imprint through genomic editing, that the differentiation platform disclosed herein is capable of differentiating genetically imprinted iPSCs at a comparable level as iPSCs without genetic imprint, and that the genetic imprint of the iPSC is retained in its differentiated cells.

Figure 34A:
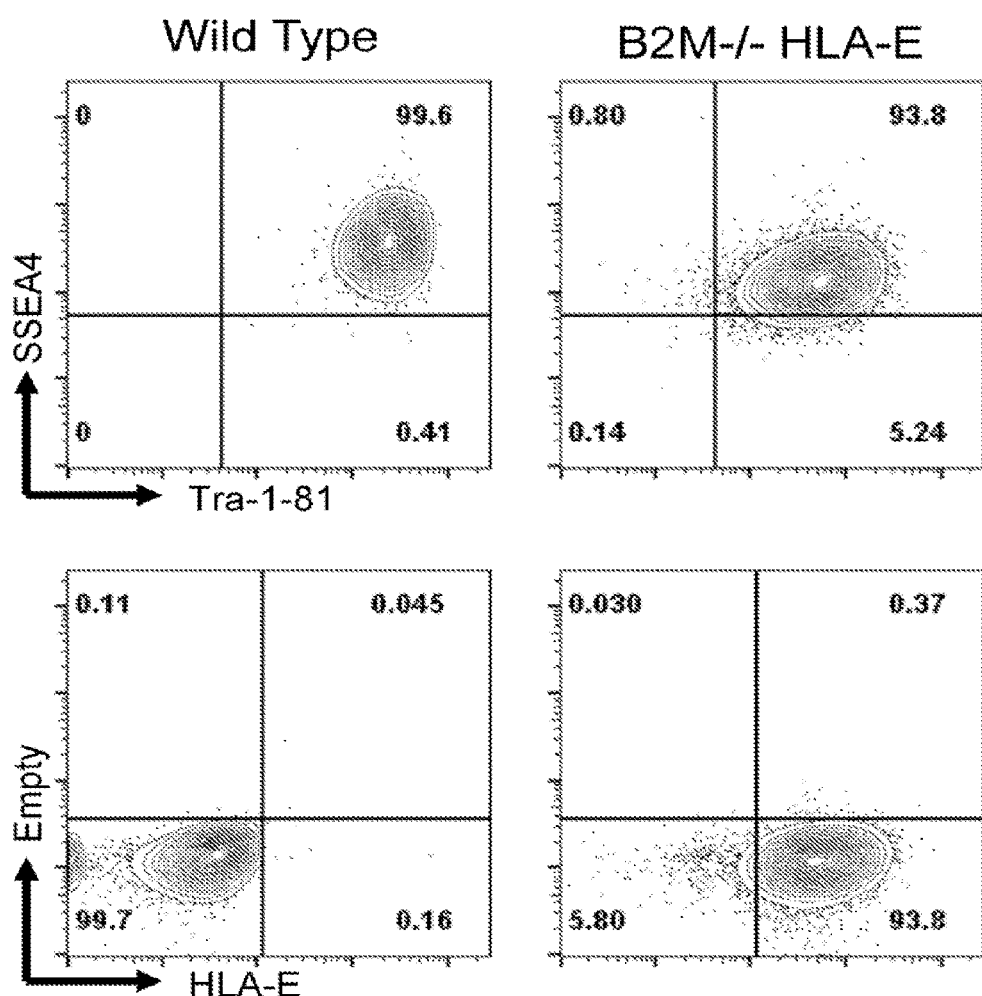
FIG. 34A-B shows Modulation of HLA class I on iPSC increases persistence of iPSC in immune-competent recipients. A. the transduced HLA-modified iPSCs express HLA-E on the cell surface and maintain a pluripotent phenotype. B. In vivo luciferin imaging of teratomas at 72-hour post injection with the B2M−/−HLAE iPSC showing increased persistence compared to wildtype iPSC.

2. Modulation of HLA Class I on iPSC and Differentiation of the Modulated iPSC to Increase Persistence of iPSC and Derivative Cells Thereof in Immune-Competent Recipients To further improve the immune-resistance and persistence of HLA class I modified iPSCs (B2M−/− iPSCs or HLA I-modified iPSCs), the B2M−/− iPSCs were transduced with lentivirus containing a HLA-E/B2M fusion protein. The quality (i.e., the pluripotency state) of the transduced HLA I-modified iPSCs (B2M−/− HLA-E iPSCs) was assessed by flow cytometry for the pluripotency markers TRA-181 and SSEA4 as well as the expression of HLA-E. FIG. 34A shows that the transduced HLA I-modified iPSCs express HLA-E on the cell surface and maintain a pluripotent phenotype.

Figure 34B:
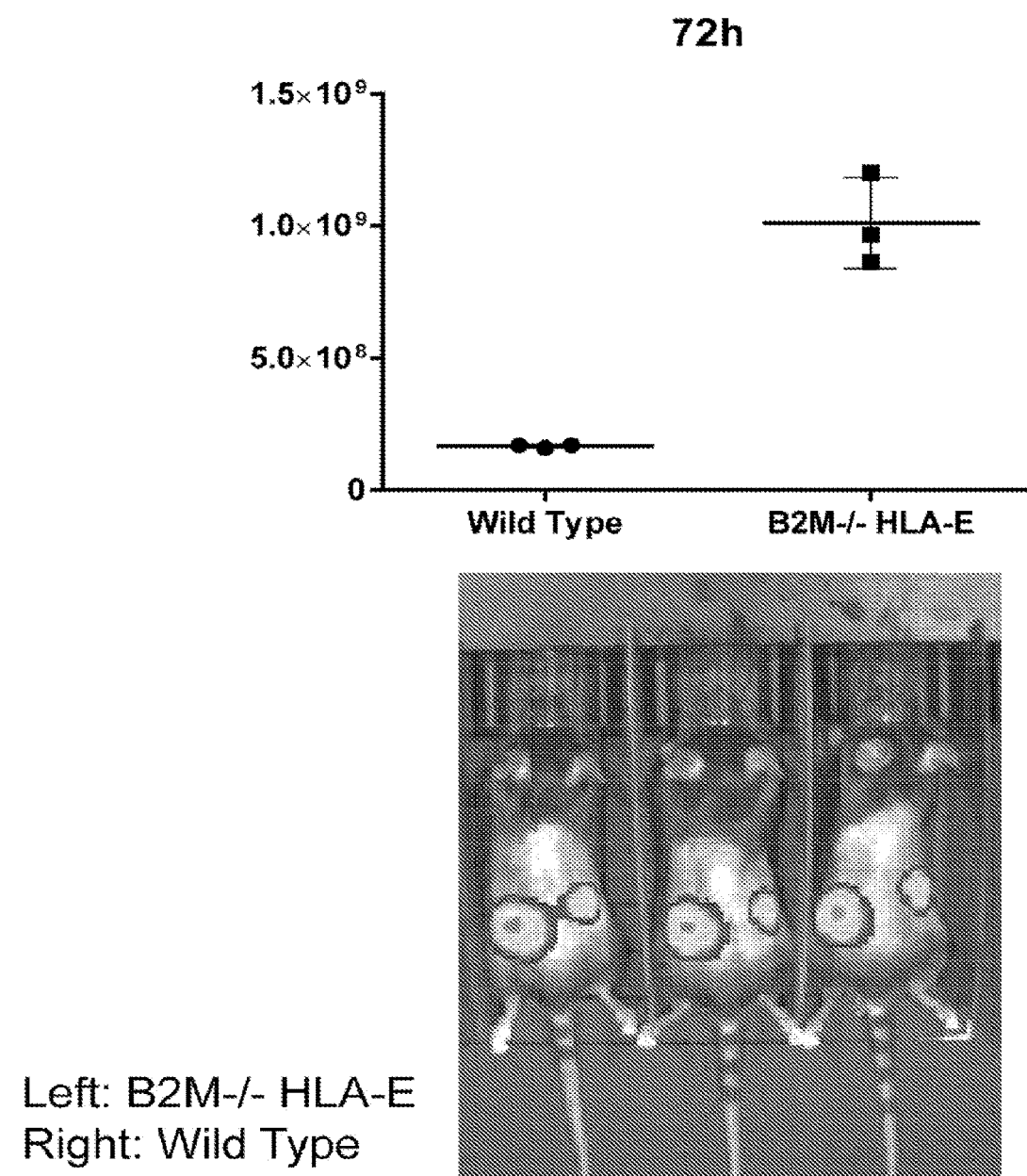

To determine if the transduced HLA I-modified iPSC have increased persistence in vivo, luciferized wildtype and the B2M−/− HLA-E iPSCs were injected subcutaneously on opposing flanks of immune-competent C57BL/6 recipients in a teratoma assay. Mice were analyzed daily by IVIS imaging in conjunction with luciferin injection to visualize the developing teratoma. FIG. 34B demonstrates that at 72-hour post injection the B2M−/−HLA-E iPSCs show increased quantitative persistence of about 6 fold compared to wildtype iPSC. Three representative mice depicting increased luciferin imaging with the B2M−/−HLA-E iPSC teratomas were also presented in FIG. 34B.

Figure 35:
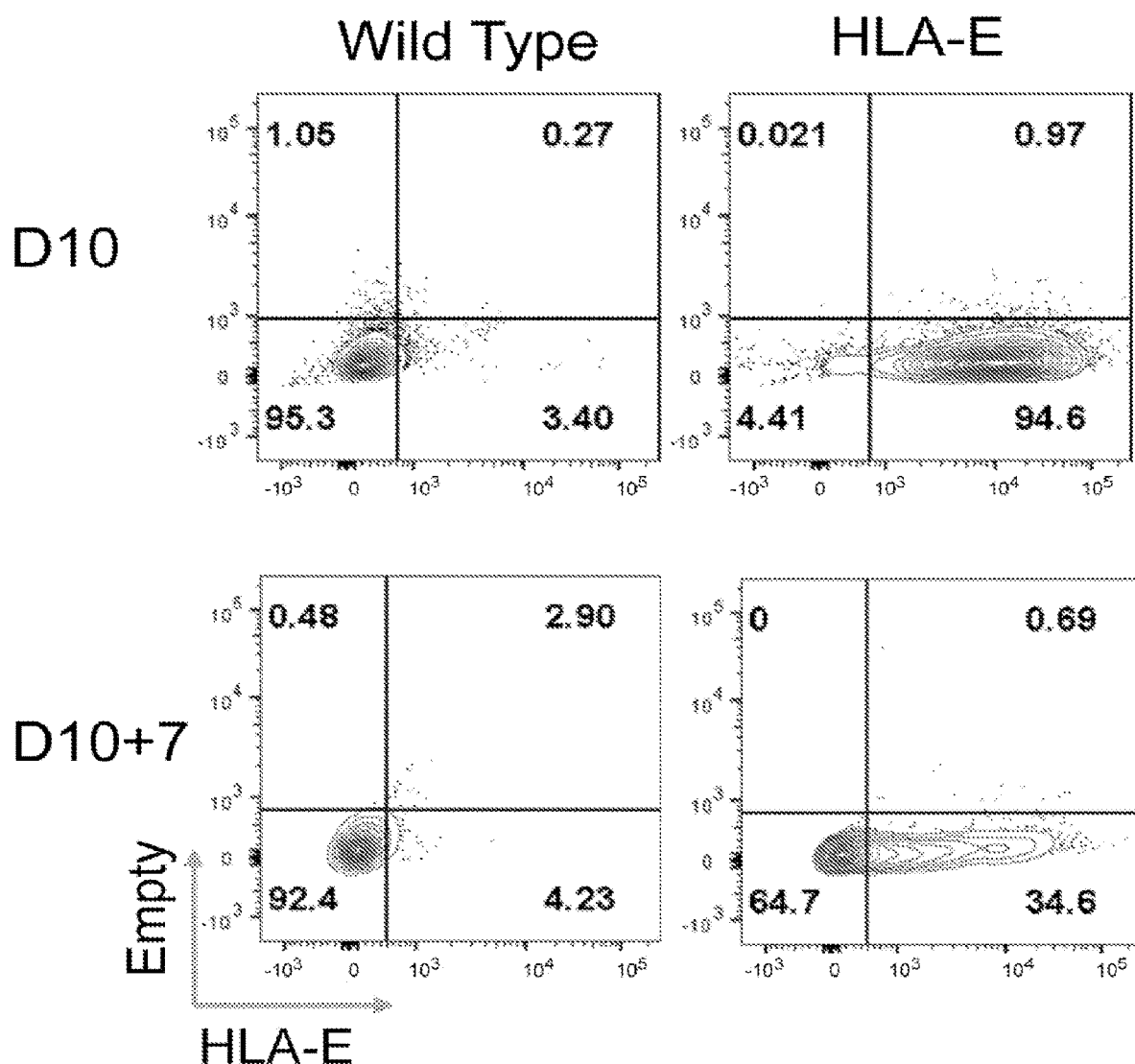
FIG. 35 shows that HLA-E expression is retained in both D10 (CD34+CD43− HE cells) and D17 (CD45+ pan-hematopoietic progenitors) differentiated cells from the B2M−/− HLA-E iPSCs.

To assess the differentiation capacity of the modulated HLA I-modified iPSCs, the B2M−/− HLA-E and wildtype iPSCs were differentiated for 10 days to generate HE and analyzed for the expression of CD34+CD43− HE cells by flow cytometry. FIG. 35 shows that HLA-E expression is retained in both D10 (CD34+CD43− HE cells) and D17 (CD45+ pan-hematopoietic progenitors generated in the iMPP assay) differentiated cells from the B2M−/− HLA-E iPSCs.

Figure 36A:
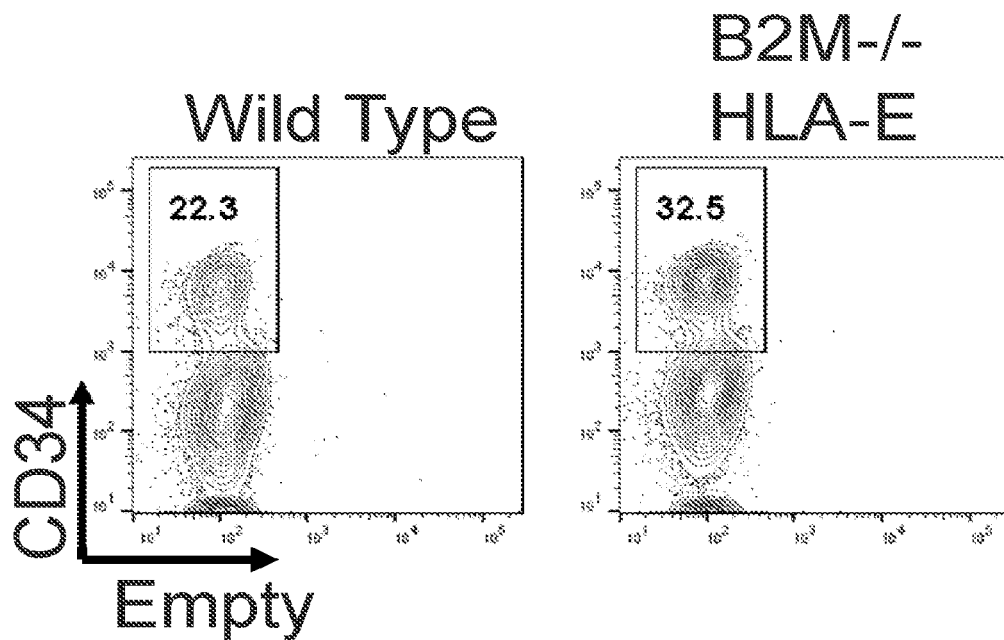
FIG. 36A-C shows that HLA class I modulated iPSC can generate functional CD34+HE. A. shows that the B2M−/− HLA-E iPSC can differentiate to CD34+HE at a similar frequency as wildtype controls. B. shows that the B2M−/− HLA-E iPSC can differentiate to CD34+HE in a comparable number as wildtype control. C. the B2M−/− HLA-E HE can generate CD45+ pan-hematopoietic progenitors with similar efficiency as wildtype HE.
Figure 36B:
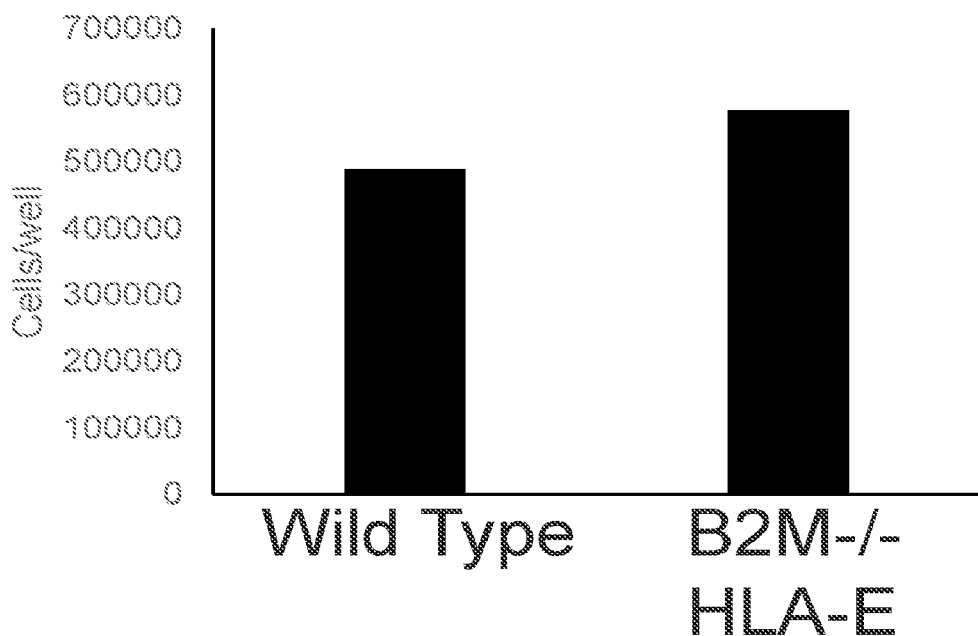
Figure 36C:
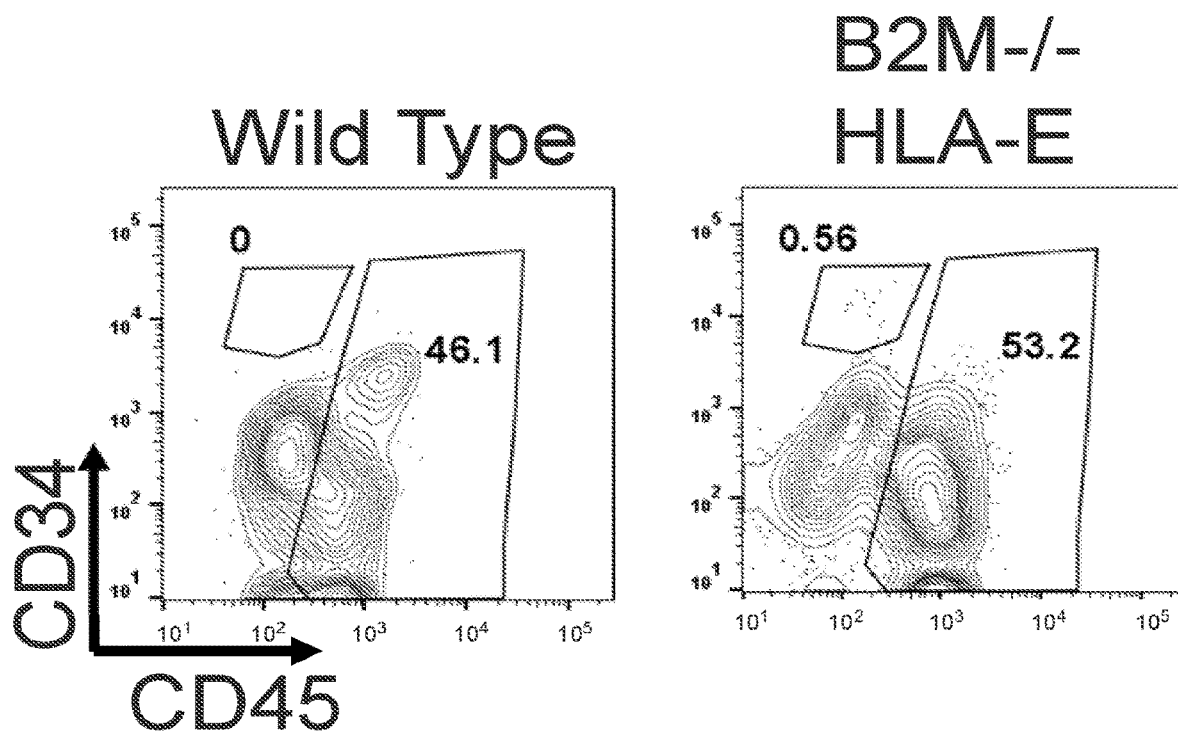

FIG. 36A and FIG. 36B show that the B2M−/− HLA-E iPSC can differentiate to CD34+HE at a similar frequency as wildtype controls. To demonstrate the hematopoietic potential of the B2M−/− HLA-E iPSC-derived HE, the cells were sorted using FACS and assessed for their ability to undergo the endothelial to hematopoietic transition to generate CD45+ hematopoietic progenitors as described in the multipotent progenitor assay (iMPP) in FIG. 1. FIG. 36C illustrates that the B2M−/− HLA-E HE can generate CD45+ pan-hematopoietic progenitors with similar efficiency as wildtype HE. As such, the immune resistance conveyed by B2M−/− HLA-E is retained in the derivative cells differentiated from the iPSCs having the same genetic imprint. The HE cells comprising B2M−/− HLA-E are shown to have increased persistence. A similar improvement in persistence was observed when HLA-G was used instead of HLA-E. Additionally, a modified version of HLA-E or HLA-G to avoid cleavage is applied to further enhance in vivo persistence of HLA class I modified iPSCs.

3. Generation of iPSCs and Derivative Cells with Enhanced Properties Through Expression of Targeted Exogenous Molecules and/or Modification of Endogenous Genes Molecules that are modified or modulated at iPSC level may be used to enhance properties desirable in immune therapies using the derivative lymphocytes obtained through the present differentiation platform. These molecules may include safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the iPSCs or derivative cells thereof. In addition to B2M/HLA-I and HLA-E/G, the targeted molecules contributing to desirable properties further include, but are not limited to, CD16 receptor and 41BBL costimulatory molecule, CD3, CD4, CD8, CD47, CD137, CD80, PDL1, $A_{2A}R$, CAR (chimeric antigen receptor), TCR (T cell receptor), TAP1, TAP2, Tapasin, NLRC5, PD1, LAG3, TIM3, RFXANK, CITTA, RFX5, RFXAP, and surface triggering receptor for coupling bi- or multi-specific engagers. More specifically, the genetic modification of the targeted molecules in iPSC include one or more of: deletion or reduced expression of B2M, TAP1, TAP2, Tapasin, NLRC5, PD1, LAG3, TIM3, RFXANK, CITTA, RFX5, RFXAP; introduced or increased expression of HLA-E, HLA-G, HACD16, 41BBL, CD3, CD4, CD8, CD47, CD137, CD80, PDL1, $A_{2A}R$, CAR, TCR or surface triggering receptors for coupling with bi- or multi-specific engagers. The increased or reduced expression of the targeted molecules can be permanent, transient, temporal or inducible, and can be controlled by endogenous or exogenous promoters.

Figure 37A:
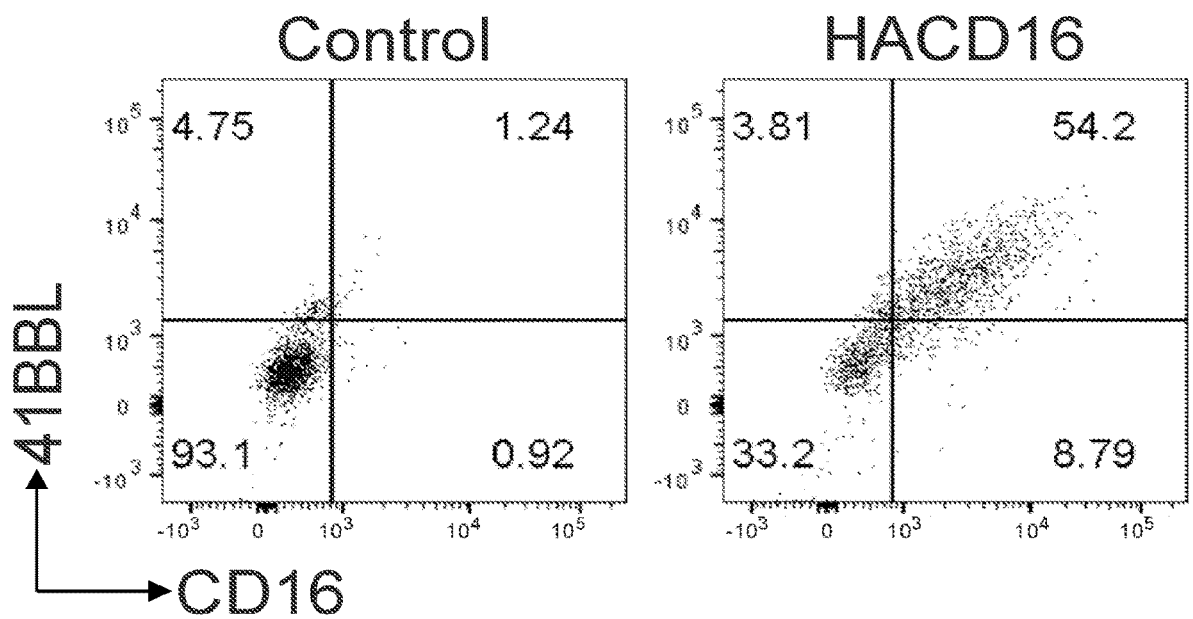
FIG. 37A-B shows that iPSC genetically engineered to express the high-affinity CD16 receptor and 41BBL co-stimulatory molecule retain expression throughout differentiation to iCD34 cells. A. Day 0 undifferentiated cells B. Day 10 differentiated cells.
Figure 37B:
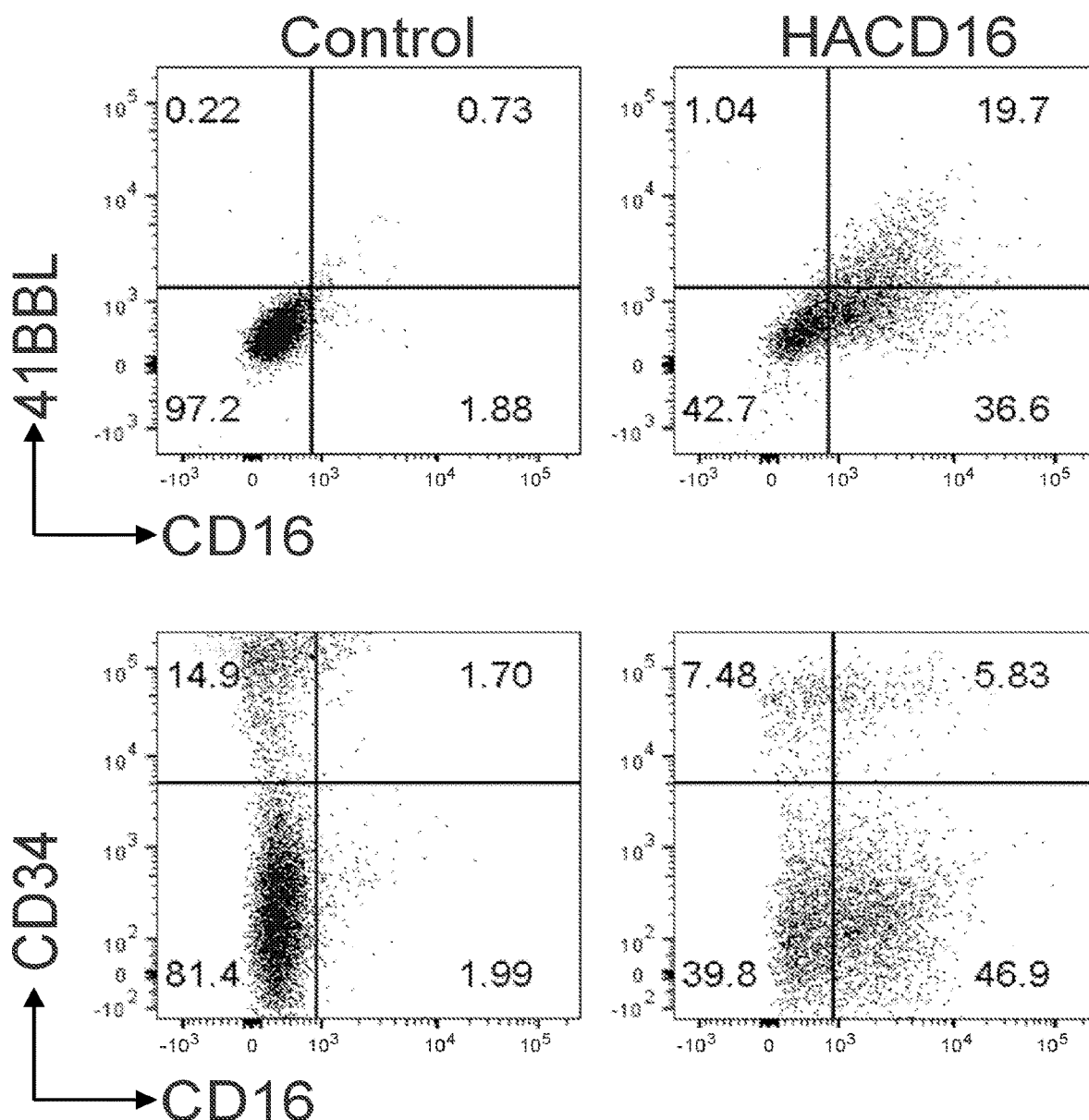
Figure 41:
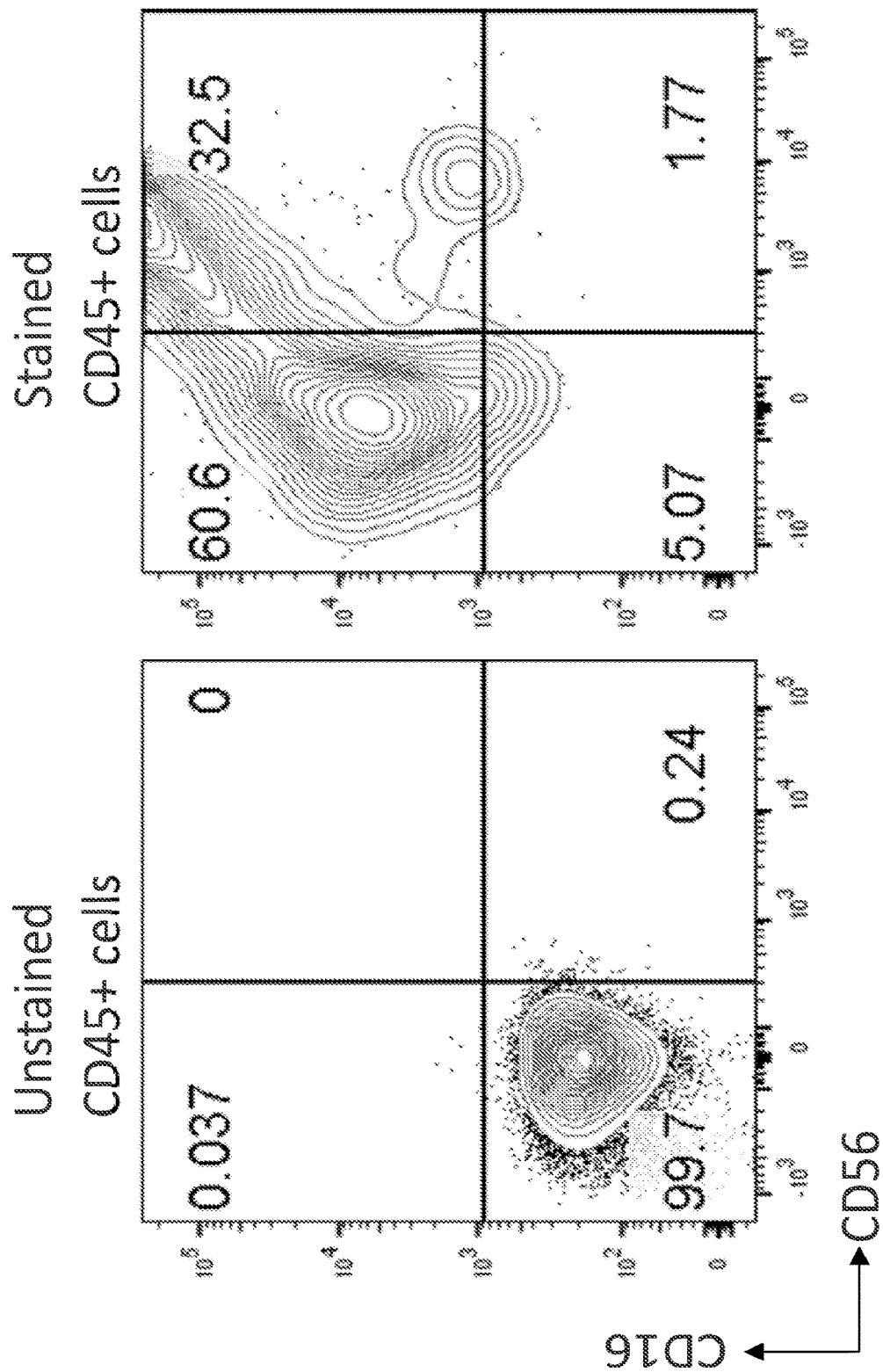
FIG. 41 shows that iPSC genetically engineered to express the HACD16 receptor retain the expression through differentiation to Day 20 iNK cells.

To optimize iPSC-derived lymphoid effector cells, the desired modality may be introduced into iPSC using various delivery methods known in the art. In this exemplary illustration, iPSCs were transduced with lentivirus containing the non-cleavable high-affinity CD16 receptor (HACD16) and 41BBL co-stimulatory molecules to generate iPSC and derivative cells having enhanced cytotoxicity. FIG. 37A demonstrates the efficient expression of HACD16 and 41BBL on the surface of iPSC following lenti-viral transduction by flow cytometric analysis. FIG. 37B demonstrates that the expression of HACD16 and 41BBL expression is maintained and does not perturb the ability of iPSC to generate CD34+HE cells following 10 days of differentiation using the platform provided herein. Further, FIG. 41 demonstrates that the expression of HACD16 is maintained and does not perturb the ability of iPSC to generate Day 10 CD56+ iNK cells using a CD45+ gating strategy.

The cellular cytotoxicity of iPSC-derived effector cells, including T, NK, NKT cells, macrophages, and neutrophils, can be further enhanced by coupling bi- or multi-specific engagers that are capable of redirecting the effector cells to targeted tumor cells. In general, the concept of the bi- or multi-specific engagement focus on retargeting of effector cells to specific tumor cells using bi- or multi-specific antibodies that simultaneously target a tumor-associated antigen and an activating receptor at the surface of effector cells. This bispecific binding also stimulates effector cell function, leading to effective effector cell activation and ultimately to tumor cell destruction. Because effector cell activation and tumor cell killing occur only when effector and target cells are crosslinked by the bispecific engager, it provides a safety control mechanism. Furthermore, through this retargeting engager, major histocompatibility complex (MHC)-restricted activation is bypassed.

Figure 39:
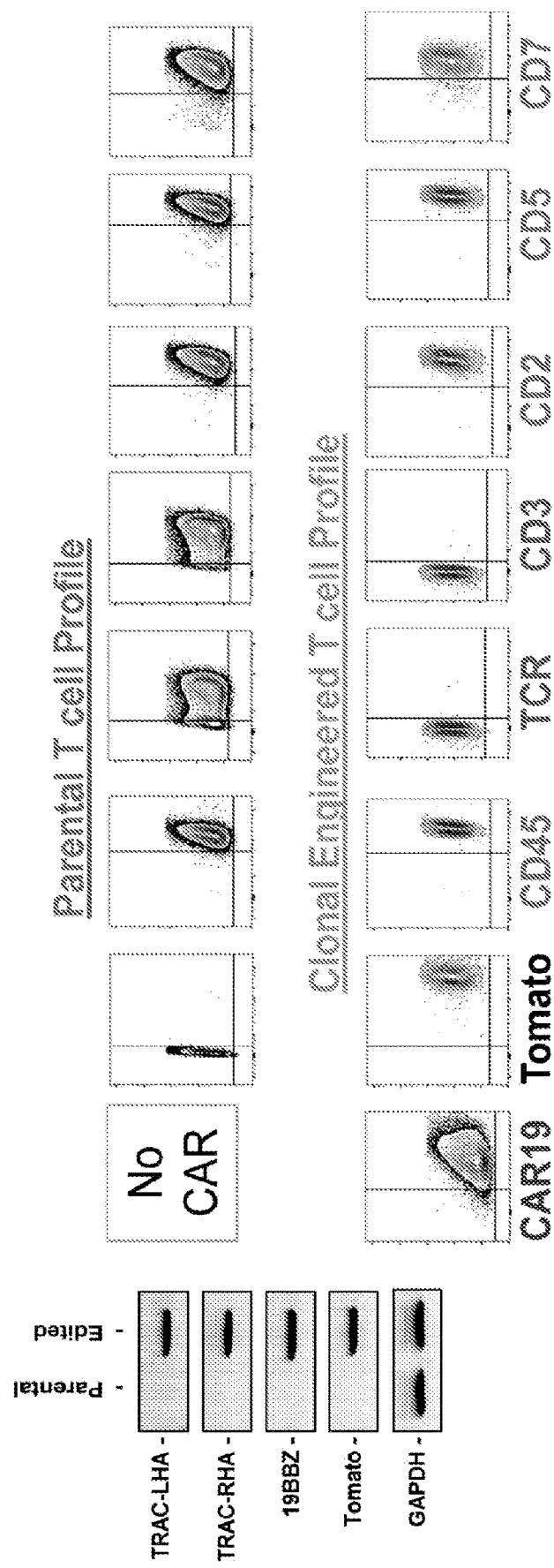
FIG. 39 shows the cell type specific expression of CAR driven by the endogenous TCR promoter, and the expression and function knock-out of TCR due to the locus specific insertion of CAR.

Bispecific engager mediated effector cell retargeting involves coupling of the surface receptors on the side of effector cells. Naturally existing surface receptors include, but not limited to, CD3, FcgRIII (CD16), FcgRI (CD64), and FcaR (CD89), expressed on T cells, NKT cells, NK cells, macrophages, and neutrophils, respectively (FIG. 39A). Additionally, engineered surface triggering receptors can be introduced to express on effector cell surface for the purpose of retargeting engager coupling. The genetically engineered surface triggering receptor facilitates bi- or multi-specific antibody engagement between the effector cells and specific target cell independent of their natural receptors and cell types. Using this approach, one may generate iPSCs comprising a universal surface triggering receptor, and then differentiate such iPSCs into populations of various effector cell types that express the universal surface triggering receptor. During cell therapies, one or more types of effector cells can be used, all of which can couple with the same bi- or multi-specific engager through the universal surface triggering receptor (FIG. 39B) to target one or more tumor cells. The universal triggering receptor can be introduced to iPSC through genomic editing using the methods described in U.S. Application No. 62/366,503. Generally, an engineered universal surface triggering receptor contains an anti-epitope, and a co-stimulatory domain. The anti-epitope of the surface triggering receptor directs the coupling of any effector cell expressing the receptor with a bi- or multi-specific engager having matching epitope on one end. The targeting specificity of the engager on the other end directs the coupled effector cell to one or more types of tumor cells having specific antigens for killings. For a universal surface triggering receptor, in one example, the co-stimulatory domain may comprise IL2 protein or part thereof to achieve canonical or noncononical cellular activation and/or enhance effector cell function irrespective of the effector cell type.

On the side of the tumor cell, established tumor-associated antigens that can be used for bispecific engager coupling include, but not limited to, CD19, CD20 or CD30 of hematologic malignancies; EGFR (epidermal growth factor receptor), HER2/ERBB2/neu (human epidermal growth factor receptor 2), EPCAM (epithelial cell adhesion molecule), EphA2 (erythropoietin-producing hepatocellular carcinoma A2) and CEA (carcinoembrantigen) for solid tumors. Additionally, the surface bispecific antibodies/engagers may further comprise additional features, such as biotinylated protein(s) to enhance bispecific engagement and binding, surface membrane anchor domain(s) for long-term surface presentation, costimulatory domain(s) to enhance signaling upon bispecific interaction, and on and off-switch mechanism for inducible or temporal expression control of the engager.

Different types of iPSC derived effector cell, including T cells, NK cells, NKT cells, macrophages and neutrophils, recognizable by the bi- or multi-specific engagers may be applied individually or in combination in cancer immune therapies for targeting one or more liquid and solid tumors upon the coupling of the engager specific to tumor targets.

4. Differentiation of CAR-T Derived iPSC that Retains the CAR

Chimeric antigen receptors (CARs) are engineered transmembrane receptors that serve to apply specificity onto an immune effector cell such as a T or NK cell. CARs are fusion proteins typically consisting of a single-chain variable fragment (scFV) derived from monoclonal antibodies to provide antigen recognition and a combination of intracellular signaling domains to provide activation signals to the immune effector cell. CARs hold great potential as a potent universal cancer immunotherapy as CAR-immune effector cells can be engineered to recognize any tumor associated antigen and thus target the engineered immune effector cells only to the tumor cells without the requirement for HLA matching.

Figure 24:
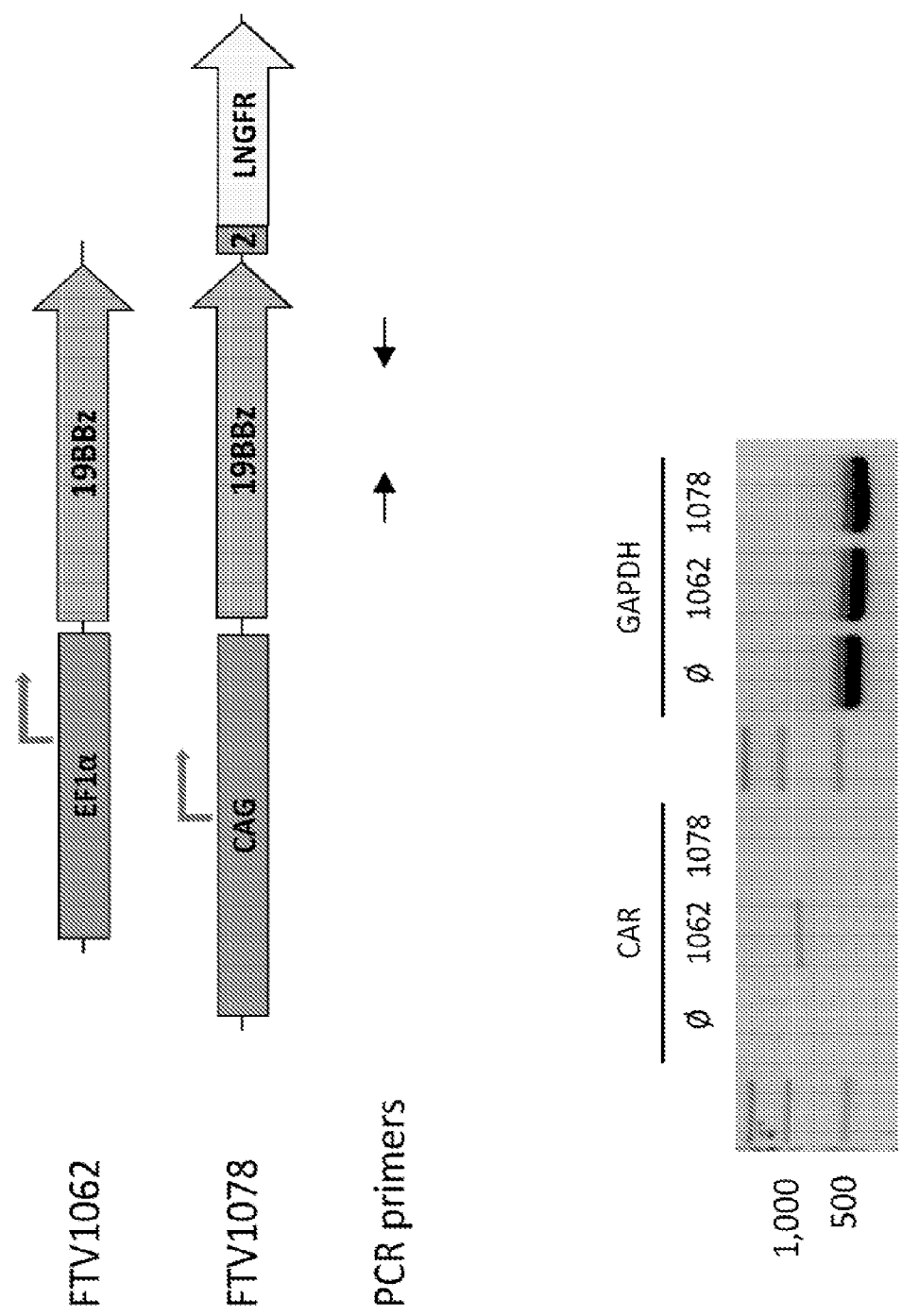
FIG. 24 shows reprogramming of a CAR-T cell to iPSCs (TiPSCs) which retain the same genetic imprint of the source T cell by PCR analysis of CAR (FTV106) integration in iPSCs derived from T cells transduced with FTV106.
Figure 38A:
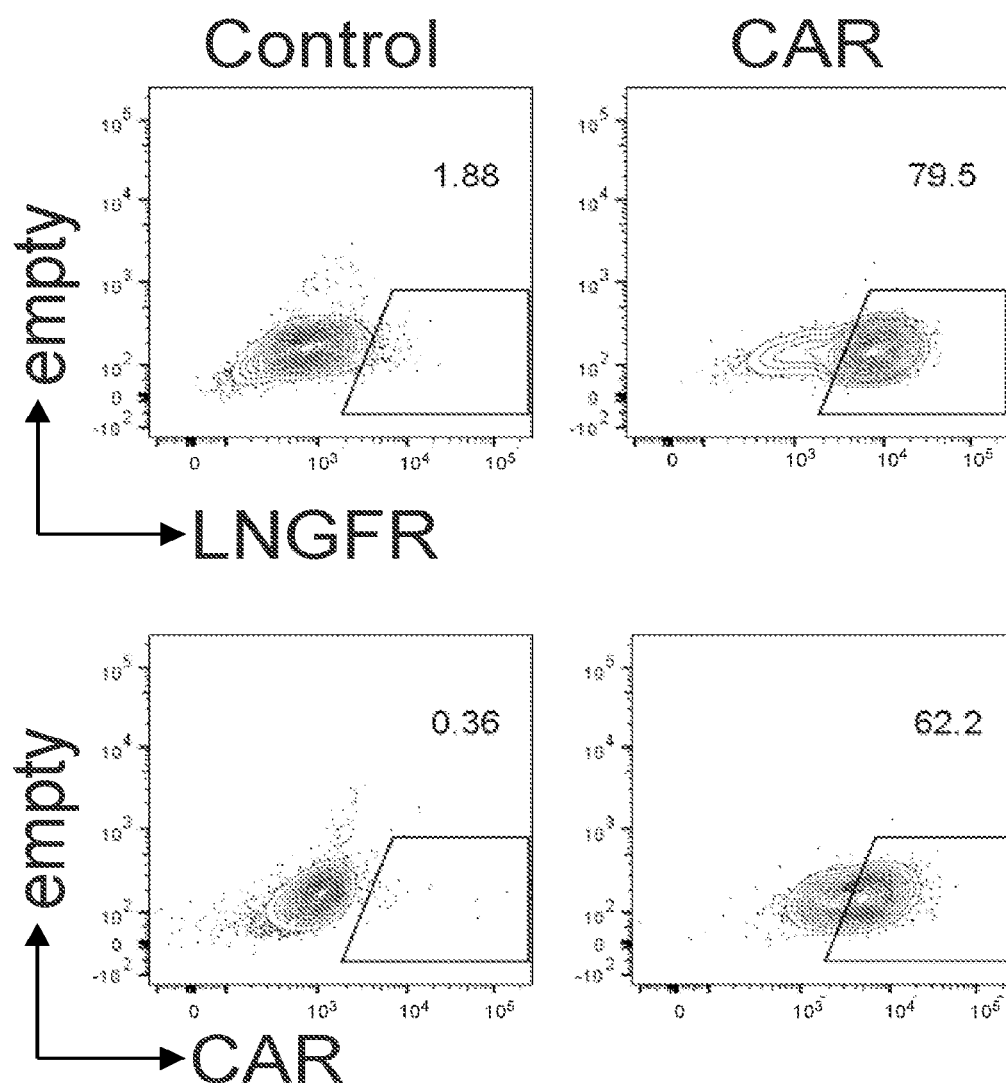
FIG. 38A-B shows that iPSC genetically engineered to express the CD19 chimeric antigen receptor (CAR) and truncated LNGFR cell surface marker as an co-identifier for the CAR retain expression through differentiation to iCD34 cells. A. Day 0 undifferentiated cells B. Day 10 differentiated cells.
Figure 38B:
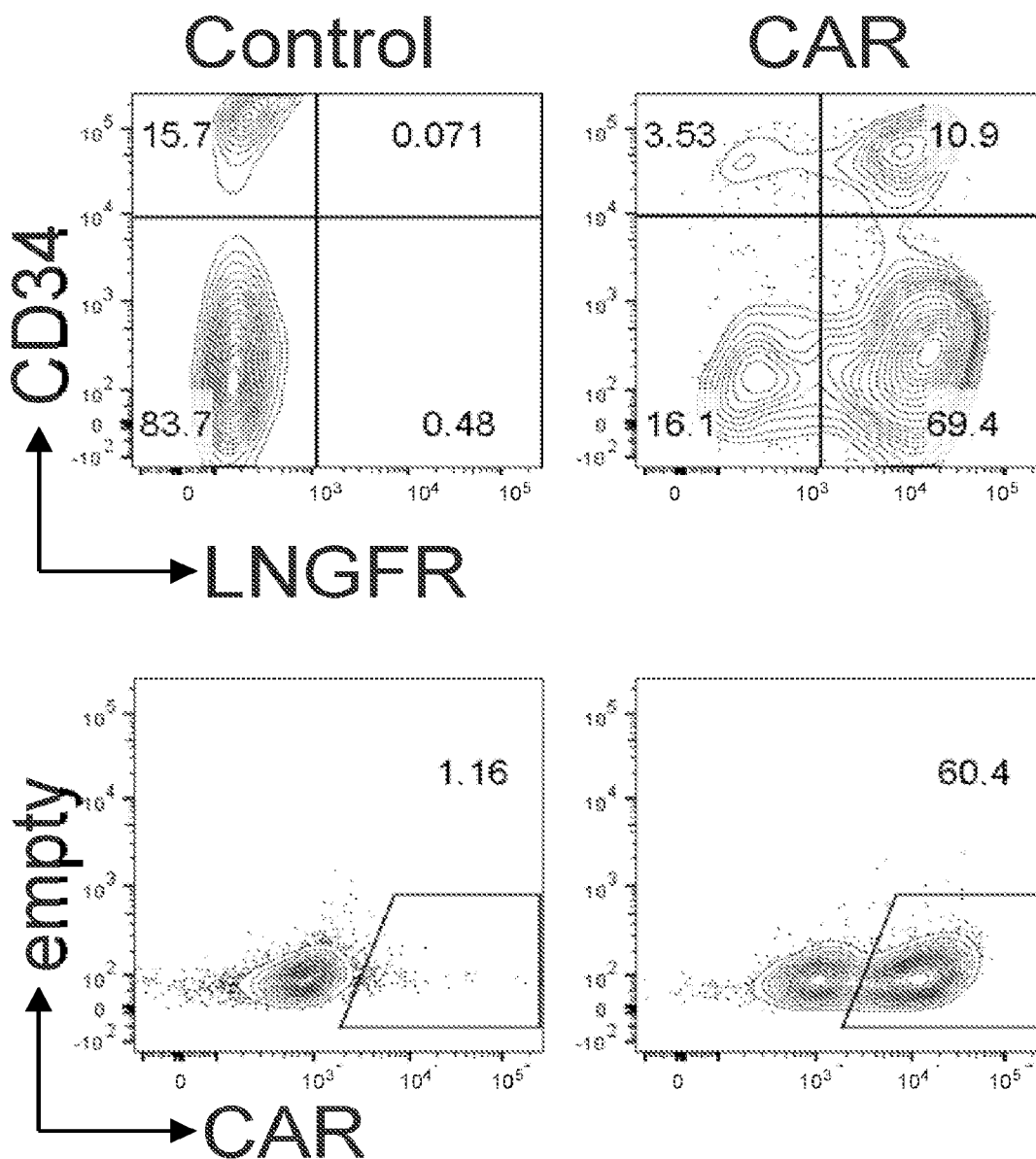

We have shown the reprogramming of a CAR-T cell to iPSCs which retain the same genetic imprint of the source cell, i.e., the same chimeric antigen receptor (FIG. 24). The iPSCs genetically engineered to express the CD19 chimeric antigen receptor (CAR) and truncated LNGFR cell surface marker as a co-identifier for the CAR retain expression through differentiation to iCD34 cells (FIG. 38). Therefore, using the presently disclosed differentiation platform, methods and compositions, the iPSCs having desired genetic imprint can be differentiated to various immune cell types that retain the same genetic imprints comprised in the iPSCs and source immune cell thereof.

Also provided herein are derivative T cells differentiated from an iPSC comprising a CAR at an endogenous TCR locus. The locus specific insertion of CAR was achieved at the level of T cell, which is subsequently reprogrammed into iPSC comprising the targeted insertion of CAR. Alternatively, the locus specific insertion of CAR can take place at the iPSC level. Because there is only one expressive TCR locus, the copy number of CAR insertion that is expressive is under control through the locus specific insertion. Further, the CAR is inserted in the constant region of TCR. The truncation of TCR constant region leads to TCR knock-out, which eliminates the HLA matching requirement in cell therapies. Moreover, the CAR expression is controlled by the TCR endogenous promoter, and thus is at the same level and in the same developmental stage as TCR. The controlled CAR expression mimicking the endogenous TCR avoids potential impact to differentiation potency during the course of iPSC differentiation. FIG. 40 shows the expression of CAR at a comparable level compared to TCR expression in the parental line, and the elimination of both expression and function of TCR in the engineered cell lines. The engineered T cell is then reprogrammed to iPSC which is subsequently differentiated into CAR expressing T cells that are TCR null.

5. Generation of Effector Lymphoid Cells with Enhanced Properties Using iPSCs Containing Donor-, Disease-, or Condition-Specific Genetic Imprints Other than guided integration of genetic imprints through genome editing of iPSCs, genetic imprints existing in immune cells from specific donor, disease, or condition (such as treatment responsiveness) may also be utilized in iPSC-based cell therapies in view of the presently disclosed differentiation platform. Certain genetic imprints in immune cells such as T cells originated from selected sources translates to unique attributes that are preferential in treating various diseases. These preferential attributes include, but are not limited to, unique antigen targeting receptor expression; unique HLA presentation or lack thereof, resistance to tumor microenvironment; induction of bystander immune cells and immune modulations; improved on-target specificity with reduced off-tumor effect; resistance to treatment such as chemotherapy; improved homing, persistence, and cytotoxicity. The genetically imprinted immune cells can be collected from preferred sources, and reprogrammed into induced pluripotent stem cells, preferably to a ground state pluripotency using the methods disclosed for example in PCT/US2011/065900.

As such, also provided herein are approaches, methods and utility of generating induced pluripotent stem cells (iPSC), progenitor T cells or rejuvenated T cells from antigen-specific T lymphocytes of a specific donor or patient. The donor may be healthy, with a disease condition, or may be sensitive or resistant to a treatment. For example, a patient who is treated with a population of a cell comprising programmed/modulated/engineered T cells, and who experienced disease elimination as a result, is expected to have naturally selected and expanded through disease elimination an effective subpopulation of said T cells due to its advantages in eliminating the disease burden conveyed by its donor specific imprint. By obtaining these T cells from a donor after disease elimination and reprogramming them to iPSCs, an unlimited quantity of T cells with desirable disease elimination related imprints can be created.

The antigen-specificity associated with the donor or patient-derived T-cell feedstock cell population is maintained during iPSC derivation, dedifferentiation, and subsequent differentiation. Such derivative cells may be further modified to enhance safety, efficacy, persistence or specificity.

To carry out the method, primary antigen specific T cells are first isolated from a selected donor. The donor may be healthy, with a disease condition, or may be sensitive or resistant to a treatment. The isolated primary antigen-specific cells are then, optionally, enriched by various methods, for example: by co-culturing polyclonal T cells with tumor cells expressing the antigen(s) of interest or non-transformed cells bearing antigen(s) of interest in a permissive culture medium such that antigen-specific T cells proliferate faster than T cells that do not recognize the cell-expressed antigen of interest. The isolated primary antigen-specific cells may also be enriched by co-culturing polyclonal T cells in a permissive medium with dendritic cells, thymic epithelial cell, endothelial cells or artificial antigen presenting cells or plasma particles or peptides expressing or encoding the antigen(s) of interest such that antigen-specific T cells proliferate faster than T cells that do not recognize the cell-expressed antigen of interest. The isolated primary antigen-specific cells may also be enriched by immunoflourescent or immunomagnetic sorting methods employing T cell receptor-specific streptamers, or T cell receptor-specific fusion peptides or antibodies or other macromolecular binding agents. In one example, the T cell receptor-specific streptamers target cancer testis (CT) antigens. Additionally, the isolated primary antigen-specific cells may be modulated or rejuvenated using one or more agents including transcription factors and small molecules.

Next, induced pluripotent stem cells (iPSCs) are generated from the isolated and/or enriched primary antigen-specific T cells, preferably, to a ground state pluripotency using the methods disclosed for example in PCT/US2011/065900. The iPSC derived from the primary antigen-specific T cells may be genetically edited to contain a secondary or tertiary antigen specificity, or activating or inhibitory modalities relating to safety, efficacy and persistence, through the introduction of transgene(s) that can be permanent, transient, temporal or inducible.

The iPSCs with or without genetic editing are then cultured, expanded, and differentiated into a population of iPSC derived antigen-specific T cells using the present differentiation platform, methods and compositions. The iPSC derived antigen-specific T cells comprise subsets including TSCM, TCM, and/or regulatory T cells, among others. Preferably, the antigen-specificity associated with the donor or patient-derived primary antigen-specific T cells is maintained and retained not only during iPSC derivation or dedifferentiation, but also the subsequent differentiation.

The iPSC derived antigen-specific T cells can be further modified to enhance safety, efficacy, persistence or specificity either at the level of iPSC or iPSC-derived T cells. For example, the iPSC derived antigen-specific T cells are augmented by expression of a transgene encoding a T cell receptor or chimeric antigen receptor. Or, the iPSC derived antigen-specific T cells are augmented by expression of transgene/s encoding one or more cytokine receptors. Further, the iPSC derived antigen-specific T cells are augmented by expression of transgene/s contributing to persistence, cell dosage requirement, or safety switches. Alternatively, the iPSC derived antigen-specific T cells are augmented by expression of transgene/s encoding one or more co-stimulatory molecules including CD137 or CD80. The iPSC derived antigen-specific T cells are augmented by deletion, insertion or reduction in expression of human leukocyte antigens. The iPSC derived antigen-specific T cells are augmented by deletion, or reduction in expression of checkpoint molecules including, but not limited to, PD1, LAG3, and TIM3. The iPSC derived antigen-specific T cells are augmented by expressing CD3, CD8, and/or CD4. The modified expression of pertinent molecule in the iPSC derived antigen-specific T cells can be permanent, transient, temporal or inducible.

The above iPSC derived antigen-specific T cells with or without genetic enhancement are suitable for adoptive cell transfer to treat various diseases or conditions including, but not limited to, autoimmune disorders, hematological malignancies, solid tumors, cancers, or infections. For the purpose of treating hematological malignancies or solid tumors, the iPSC derived antigen-specific T cells may be transferred before, during or after additional treatments involving anti-tumor agent or hematopoietic stem cell transplant procedures.

6. Genetic Imprint Serving as a Marker of Clonality or Clonal Detection of iPSCs and Derivative Cells Thereof Induced pluripotent stem cell (iPSC)-based therapies are gaining traction as effective treatment options for patients suffering from a variety of diseases. However, the technical practicality of producing and utilizing iPSC-based therapies are yet to address the consistency and safety issues of such products in view of the heterogeneous nature of iPSCs and derivative cells thereof. Currently used methods include single cell sorting and cloning, and cloning by limiting dilution, all of which can be laborious, inefficient and often unsuccessful, particularly if the heterogeneity is great in a given population. Here provided is a novel technique to characterize clonality of iPSC-derived cell populations utilizing genetic imprint(s) retainable at any intermediate stage of the differentiation carried out using the presently disclosed differentiation platform, methods and compositions.

T and B lymphocytes are unique amongst mammalian cell populations in that during normal maturation they undergo specific and irreversible genomic sequence alteration by virtue of V(D)J recombination, this process is also known as somatic rearrangement. This is a unique mechanism of genetic recombination that occurs only in developing lymphocytes during the early stages of T and B cell maturation. The process results in the highly diverse repertoire of antibodies/immunoglobulins (Igs) and T cell receptors (TCRs) found on B cells and T cells, respectively. V(D)J recombination occurs in the primary lymphoid organs (bone marrow for B cells and thymus for T cells) and in a nearly random fashion rearranges variable (V), joining (J), and in some cases, diversity (D) gene segments. The process ultimately results in novel amino acid sequences in the antigen-binding regions of Igs and TCRs that allow for the recognition of antigens from nearly all pathogens including bacteria, viruses, parasites, and worms as well as "altered self cells" as seen in cancer. The unique diversity of alpha/beta TCR receptors is estimated to be in excess of 2E7 distinct combinations and immunoglobulin diversity is estimated to be in excess of 1E11 distinct combinations.

Given the permanency of the genetic rearrangement that occurs during B and T cell maturation, the iPSC population derived from such cells would comprise iPSCs containing Ig and TCR sequences that are unique to the individual starting lymphocyte. Therefore by sequencing or homology comparison of the specific TCR or Ig gene in putatively clonal populations of iPSC derived from mature lymphocytes, it can be determined whether the population is truly clonal or not. Similarly, after differentiating the imprinted iPSC using the present platform and methods, the clonality of the differentiated progenies can also be assessed by gene sequencing or homology comparison of the retained somatic rearrangement in the iPSC derived differentiated cells. The identified somatic rearrangement can also be used to track adoptive cell homing, persistence and expansion in vivo by sampling and analyzing patient blood, tissue or tumor biopsy for unique genetic recombination signature, and matching that signature to the somatic rearrangement in the starting T cell population, derived iPSC and iPSC differentiated cell types in order to make corresponding assessment to address consistency and safety issues germane to therapy efficacy and regulatory compliance.

One skilled in the art would readily appreciate that the methods, compositions, and products described herein are representative of exemplary embodiments, and not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated as incorporated by reference.

The present disclosure illustratively described herein suitably may be practiced in the absence of any element or elements, limitation or limitations that are not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for directing differentiation of pluripotent stem cells to hematopoietic lineage cells, comprising:
   (i) contacting the pluripotent stem cells with a composition comprising a BMP pathway activator, and optionally bFGF, to obtain mesodermal cells;
   (ii) contacting the mesodermal cells with a composition comprising a BMP pathway activator, bFGF, and a WNT pathway activator, to obtain mesodermal cells having definitive hemogenic endothelium (HE) potential, wherein the mesodermal cells having definitive hemogenic endothelium (HE) potential are capable of providing hematopoietic lineage cells; and
   (iii) contacting the mesodermal cells having definitive HE potential with a composition comprising bFGF and a ROCK inhibitor to obtain definitive HE Cells;
   wherein the hematopoietic lineage cells comprise hematopoietic stem and progenitor cells (HSC), pre-HSC, hematopoietic multipotent progenitor cell (MPP), pre-T cell progenitor cells, pre-NK cell progenitor cells, T cell progenitor cells, NK cell progenitor cells, T cells, NK cells, NKT cells, or B cells; and
   wherein mesodermal cells and mesodermal cells having definitive HE potential are obtained in steps (i) and (ii) without the step of forming embryoid bodies.

2. The method of claim 1, wherein the composition comprising bFGF and a ROCK inhibitor, further comprises one or more of a Wnt pathway activator, IGF and EPO.

3. The method of claim 1, further comprising: contacting the definitive HE cells with a composition comprising a BMP activator, and optionally a ROCK inhibitor, and one or more growth factors and cytokines selected from the group consisting of TPO, IL3, GMCSF, EPO, bFGF, VEGF, SCF, IL6, Flt3L and IL11 to obtain hematopoietic multipotent progenitor cells (MPP).

4. The method of claim 1, further comprising: contacting the definitive HE cells with a composition comprising one or more growth factors and cytokines selected from the group consisting of SCF, Flt3L, TPO, and IL7; and optionally one or more of a BMP activator, a ROCK inhibitor, VEGF and bFGF to obtain pre-T cell progenitors, T cell progenitors, and/or T cells.

5. The method of claim 1, further comprising: contacting the definitive HE cells with a composition comprising one or more growth factors and cytokines selected from the group consisting of SCF, Flt3L, TPO, IL7 and IL15, and optionally one or more of a BMP activator, a ROCK inhibitor, VEGF and bFGF to obtain pre-NK cell progenitors, NK cell progenitors, and/or NK cells.

6. The method of claim 1, further comprising:
   (a) prior to step (i), contacting the pluripotent stem cells with a composition comprising a MEK inhibitor, a GSK3 inhibitor, and a ROCK inhibitor, to seed and expand the cells; or
   (b) subjecting the pluripotent stem cells, the mesodermal cells, and/or the mesodermal cells having definitive hemogenic endothelium potential under low oxygen tension between about 2% to about 10%.

7. The method of claim 1, wherein
   (i) the pluripotent stem cell differentiation to hematopoietic lineage cells is free of, or essentially free of, TGFβ receptor/ALK inhibitors;
   (ii) the pluripotent stem cell differentiation to hematopoietic lineage cells is under feeder-free condition or stromal-free condition;
   (iii) the pluripotent stem cells comprise induced pluripotent stem cells (iPSCs) or naïve iPSCs;
   (iv) the WNT pathway activator is a GSK3 inhibitor;
   (v) the WNT pathway activator is CHIR99021;
   (vi) the BMP pathway activator is BMP4; or
   (vii) the ROCK inhibitor is Thiazovivin or Y-27632.

8. The method of claim 1, further comprising:
   contacting pluripotent stem cell-derived pre-T cell progenitors with a composition comprising one or more growth factors and cytokines selected from the group consisting of SCF, Flt3L, and IL7, to obtain pluripotent stem cell-derived T cell progenitors or T cells, wherein the composition is free of one or more of VEGF, bFGF, TPO, BMP activators and ROCK inhibitors;
   wherein the pluripotent stem cell-derived pre-T cell progenitors are obtained by contacting the definitive hemogenic endothelium with a composition comprising a ROCK inhibitor, and one or more growth factors and cytokines selected from the group consisting of VEGF, bFGF, SCF, Flt3L, TPO, and IL7, to allow cell differentiation and expansion; and
   wherein the composition comprising bFGF and a ROCK inhibitor is free of TGFβ receptor/ALK inhibitor.

9. The method of claim 1, further comprising:
   contacting pluripotent stem cell-derived pre-NK cell progenitors with a composition comprising one or more growth factors and cytokines selected from the group consisting of SCF, Flt3L, IL3, IL7, and IL15, to obtain pluripotent stem cell-derived NK cell progenitors or NK cells, wherein the composition is free of one or more of VEGF, bFGF, TPO, BMP activators and ROCK inhibitors; and
   wherein the pluripotent stem cell-derived pre-NK cell progenitors are obtained by contacting the definitive hemogenic endothelium with a composition comprising a ROCK inhibitor; one or more growth factors and cytokines selected from the group consisting of VEGF, bFGF, SCF, Flt3L, TPO, IL3, IL7 and IL15; and optionally, a BMP activator, to allow cell differentiation and expansion.

10. The method of claim 1, further comprising:
    contacting pluripotent stem cell-derived pre-HSC with a composition comprising a BMP activator, and one or more growth factors and cytokines selected from the group consisting of TPO, IL3, GMCSF, EPO, bFGF, VEGF, SCF, IL6 and IL11, to obtain pluripotent stem cell-derived hematopoietic multipotent progenitors, wherein the composition is free of ROCK inhibitor;
    wherein the pluripotent stem cell-derived pre-HSC are obtained by contacting the definitive hemogenic endothelium with a composition comprising a BMP activator, a ROCK inhibitor, and one or more growth factors and cytokines selected from the group consisting of TPO, IL3, GMCSF, EPO, bFGF, VEGF, SCF, IL6, Flt3L and IL11, to allow cell differentiation and expansion; and
    wherein the composition comprising bFGF and a ROCK inhibitor is free of TGFβ receptor/ALK inhibitor.

11. The method of claim 1, wherein the hematopoietic lineage cells are:

(i) pluripotent stem cell-derived definitive hemogenic endothelium (iHE), wherein the iHE cell line or clonal cells are CD34+, and at least one of CD43−, CD93−, CXCR4−, CD73−, and CXCR4−CD73−;
(ii) pluripotent stem cell-derived multipotent progenitor cells, wherein the iMPP cells are CD34+CD45+;
(iii) pluripotent stem cell-derived T cell progenitors, wherein the T cell progenitors are CD34+CD45+CD7+ or CD34−CD45+CD7+;
(iv) pluripotent stem cell-derived T cells, wherein the T cells are CD45+CD3+CD4+ or CD45+CD3+CD8+;
(v) pluripotent stem cell derived NK cell progenitors, wherein the NK cell progenitors are CD3−CD45+CD56+CD7+;
(vi) pluripotent stem cell-derived NK cells, wherein the NK cells are CD3−CD45+CD56+, and optionally further defined by NKp46+, CD57+, and CD16+;
(vii) pluripotent stem cell-derived NKT, wherein the NKT cells are CD45+Vα24Jα18+CD3+; or
(viii) pluripotent stem cell-derived B cells, wherein the B cells are CD45+CD19+.

12. A pharmaceutical composition comprising the hematopoietic lineage cells made by the method of claim 1 and a pharmaceutically acceptable medium.

13. Therapeutic use of the pharmaceutical composition of claim 12 by introducing the composition to a subject suitable for adoptive cell therapy, wherein the subject has an autoimmune disorder; a hematological malignancy; a solid tumor; cancer, or an infection associated with HIV, RSV, EBV, CMV, adenovirus, or BK polyomavirus.

14. The method of claim 1, wherein the hematopoietic lineage cells comprise T cells or T cell progenitors, and the method further comprises administering the T cells or T cell progenitors to a subject.

15. The method of claim 14, wherein (a) the administered T cell or T cell progenitors rejuvenate thymus and reconstitute T cells in vivo, and (b) the subject:
(i) is a candidate for bone marrow or stem cell transplantation, or the subject has received chemotherapy or irradiation therapy;
(ii) has received bone marrow ablative or non-myeloablative chemotherapy or radiation therapy;
(iii) has a hyperproliferative disorder or a cancer of hematopoietic system;
(iv) has a solid tumor;
(v) has a virus infection or a disease associated with virus infection; or
(vi) has an autoimmune disorder.

16. The method of claim 1, wherein (a) the composition comprising bFGF and a ROCK inhibitor further comprises a Wnt pathway agonist, and (b) the obtained definitive HE cells:
(i) are increased in numbers and percentage in cell population
(ii) have increased potency in differentiation; and/or
(iii) improved HE cellularity,
as compared to culturing without the Wnt pathway activator.

17. The method of claim 16, wherein (a) the medium further comprises one or more growth factors and cytokines selected from the group consisting of bFGF, VEGF, SCF, IGF, EPO, IL6, and IL11; or (b) the pluripotent stem cells comprise naïve iPSCs.

18. The method of claim 1, wherein the pluripotent stem cells are iPSCs obtained by reprogramming immune cells.

19. The method of claim 18, wherein the immune cells are obtained by enriching primary antigen-specific T cells from a selected source that are donor-, disease-, or treatment response-specific.

20. The method of claim 19, wherein enriching the primary antigen-specific T cells comprises:
(i) co-culturing the primary antigen specific T cells with (a) tumor cells expressing antigen(s) of interest; (b) non-transformed cells expressing antigen(s) of interest, (c) dendritic cells, thymic epithelial cells, endothelial cells, or artificial antigen presenting cells expressing antigen(s) of interest, or (d) plasma particles or peptides comprising antigen(s) of interest, to proliferate antigen-specific T cells that recognize the antigen of interest; or
(ii) sorting the primary antigen specific T cells using T cell receptor-specific binding agents that are specific to antigen(s) of interest.

\* \* \* \* \*